US010100050B2

(12) United States Patent
Capaldi et al.

(10) Patent No.: US 10,100,050 B2
(45) Date of Patent: Oct. 16, 2018

(54) KINASE INHIBITORS

(71) Applicant: CHIESI FARMACEUTICI S.P.A., Parma (IT)

(72) Inventors: Carmelida Capaldi, Parma (IT); Elisabetta Armani, Parma (IT); Andrew Steven Robert Jennings, Harlow (GB); Christopher Hurley, Harlow (GB)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

(21) Appl. No.: 15/388,350

(22) Filed: Dec. 22, 2016

(65) Prior Publication Data
US 2017/0183345 A1   Jun. 29, 2017

(30) Foreign Application Priority Data

Dec. 23, 2015   (EP) ..................... 15202348

(51) Int. Cl.
*C07D 471/04*   (2006.01)
(52) U.S. Cl.
CPC .................. *C07D 471/04* (2013.01)
(58) Field of Classification Search
CPC .................................................... C07D 471/04
See application file for complete search history.

(56) References Cited

U.S. PATENT DOCUMENTS

| 8,450,483 B2 * | 5/2013 | Gorgens | A01N 43/36 |
| | | | 544/325 |
| 9,145,413 B2 * | 9/2015 | Van Niel | C07D 401/12 |
| 9,315,503 B2 * | 4/2016 | Van Niel | C07D 471/04 |

FOREIGN PATENT DOCUMENTS

WO   2013/083604   6/2013

OTHER PUBLICATIONS

Schönherr "Profound Methyl Effects in Drug Discovery and a Call for New C—H Methylation Reactions" Angew. Chem. Int. Ed. 2013, 52, 12256-12267.*
Wisclicenus, J. "Adolph Strecker's Short Textbook of Organic Chemistry" 1881, Spottiswoode: London, pp. 38-39.*
Maria Gabriella Matera, Luigino Calzetta, Andrea Segreti & Mario Cazzola (2012) Emerging drugs for chronic obstructive pulmonary disease, Expert Opinion on Emerging Drugs, 17:1, 61-82.*
Chung "p38 Mitogen-Activated Protein Kinase Pathways in Asthma and COPD" Chest Jun. 2011 vol. 139, Issue 6, pp. 1470-1479 (abstract only).*
European Search Report in Application No. 15202348.7 dated Mar. 17, 2016.
International Search Report issued in Application No. PCT/EP2016/081837 dated Feb. 22, 2017.

* cited by examiner

*Primary Examiner* — David K O'Dell
(74) *Attorney, Agent, or Firm* — Oblon, McClelland, Maier & Neustadt, L.L.P.

(57) ABSTRACT

Compounds of formula (I) defined herein are p38 MAPK inhibitors and are useful as anti-inflammatory agents in the treatment of, inter alia, diseases of the respiratory tract.

16 Claims, No Drawings

KINASE INHIBITORS

CROSS REFERENCES TO RELATED APPLICATIONS

This application claims priority to European Patent Application No. 15202348.7 filed on Dec. 23, 2015, which is incorporated herein by reference in its entirety.

BACKGROUND OF THE INVENTION

Field of the Invention

The present invention relates to compounds and compositions that are p38 MAPK inhibitors and are useful as anti-inflammatory agents in the treatment of, inter alia, diseases of the respiratory tract.

Discussion of the Background

Mitogen activated protein kinases (MAPK) constitute a family of proline-directed serine/threonine kinases that activate their substrates by dual phosphorylation. There are four known human isoforms of p38 MAP kinase, p38α, p38β, p38γ, and p38δ. The p38 kinases, which are also known as cytokine suppressive anti-inflammatory drug binding proteins (CSBP), stress activated protein kinases (SAPK) and RK, are responsible for phosphorylating (see Stein et al., Ann. Rep. Med Chem., 1996, 31, 289-298, which is incorporated herein by reference in its entirety) and activating transcription factors (such as ATF-2, MAX, CHOP and C/ERPb) as well as other kinases (such as MAPKAP-K2/3 or MK2/3), and are themselves activated by physical and chemical stress (e.g. UV, osmotic stress), pro-inflammatory cytokines and bacterial lipopolysaccharide (LPS) (see Herlaar E. & Brown Z., Molecular Medicine Today, 1999, 5, 439-447, which is incorporated herein by reference in its entirety). The products of p38 phosphorylation have been shown to mediate the production of inflammatory cytokines, including tumor necrosis factor alpha (TNFα) and interleukin-(IL)-1, and cyclooxygenase-2 (COX-2). IL-1 and TNFα are also known to stimulate the production of other proinflammatory cytokines such as IL-6 and IL-8.

IL-1 and TNFα are biological substances produced by a variety of cells, such as monocytes or macrophages. IL-1 has been demonstrated to mediate a variety of biological activities thought to be important in immunoregulation and other physiological conditions such as inflammation (see, e.g. Dinarello et al., Rev. Infect. Disease, 1984, 6, 51, which is incorporated herein by reference in its entirety). Excessive or unregulated TNF production (particularly TNFα) has been implicated in mediating or exacerbating a number of diseases, and it is believed that TNF can cause or contribute to the effects of inflammation in general. IL-8 is a chemotactic factor produced by several cell types including mononuclear cells, fibroblasts, endothelial cells, and keratinocytes. Its production from endothelial cells is induced by IL-1, TNF, or lipopolysaccharide (LPS). IL-8 stimulates a number of functions in vitro. It has been shown to have chemoattractant properties for neutrophils, T-lymphocytes and basophils. Increase in IL-8 production is also responsible for chemotaxis of neutrophils into the inflammatory site in vivo.

Inhibition of signal transduction via p38, which in addition to IL-1, TNF and IL-8 described above is also required for the synthesis and/or action of several additional pro-inflammatory proteins (e.g., IL-6, GM-CSF, COX-2, collagenase and stromelysin), is expected to be a highly effective mechanism for regulating the excessive and destructive activation of the immune system. This expectation is supported by the potent and diverse anti-inflammatory activities described for p38 kinase inhibitors (see Badger et al., J. Pharm. Exp. Thera., 1996, 279, 1453-1461; Griswold et al, Pharmacol. Comm., 1996, 7, 323-229, both of which are incorporated herein by reference in their entireties). In particular, p38 kinase inhibitors have been described as potential agents for treating rheumatoid arthritis. In addition to the links between p38 activation and chronic inflammation and arthritis, there is also data implicating a role for p38 in the pathogenesis of airway diseases in particular COPD and asthma. Stress stimuli (including tobacco smoke, infections or oxidative products) can cause inflammation within the lung environment. Inhibitors of p38 have been shown to inhibit LPS and ovalbumin induced airway TNF-α, IL-β, IL-6, IL-4, IL-5 and IL-13 (see Haddad et al, Br. J. Pharmacol., 2001, 132 (8), 1715-1724; Underwood et al, Am. J. Physiol. Lung Cell. Mol. 2000, 279, 895-902; Duan et al., 2005 Am. J. Respir. Crit. Care Med., 171, 571-578; Escott et al Br. J. Pharmacol., 2000, 131, 173-176; Underwood et al., J. Pharmacol. Exp. Ther. 2000, 293, 281-288, all of which are incorporated herein by reference in their entireties). Furthermore, they significantly inhibit neutrophilia and the release of MMP-9 in LPS, ozone or cigarette smoke animal models. There is also a significant body of preclinical data highlighting the potential benefits of inhibition of the p38 kinase that could be relevant in the lung (see Lee et al., Immunopharmacology, 2000, 47, 185-200, which is incorporated herein by reference in its entirety). Thus, therapeutic inhibition of p38 activation may be important in the regulation of airway inflammation.

The implication of the p38MAPK pathway in various diseases has been reviewed by P. Chopra et al. (Expert Opinion on Investigational Drugs, 2008, 17(10), 1411-1425, which is incorporated herein by reference in its entirety). It is believed that the compounds of the present invention can be used to treat p38 mediated diseases such as: chronic obstructive pulmonary disease (COPD), asthma, chronic or acute bronchoconstriction, bronchitis, acute lung injury and bronchiectasis, pulmonary artery hypertension, tuberculosis, lung cancer, inflammation generally (e.g. inflammatory bowel disease), arthritis, neuroinflammation, pain, fever, fibrotic diseases, pulmonary disorders and diseases (e.g., hyperoxic alveolar injury), cardiovascular diseases, post-ischemic reperfusion injury and congestive heart failure, cardiomyopathy, stroke, ischemia, reperfusion injury, renal reperfusion injury, brain edema, neurotrauma and brain trauma, neurodegenerative disorders, central nervous system disorders, liver disease and nephritis, gastrointestinal conditions, ulcerative diseases, Crohn's disease, ophthalmic diseases, ophthalmological conditions, glaucoma, acute injury to the eye tissue and ocular traumas, diabetes, diabetic nephropathy, skin-related conditions, myalgias due to infection, influenza, endotoxic shock, toxic shock syndrome, autoimmune disease, graft rejection, bone resorption diseases, multiple sclerosis, psoriasis, eczema, disorders of the female reproductive system, pathological (but non-malignant) conditions, such as hemangiomas, angiofibroma of the nasopharynx, and avascular necrosis of bone, benign and malignant tumors/neoplasia including cancer, leukaemia, lymphoma, systemic lupus erythematosus (SLE), angiogenesis including neoplasia, haemorrhage, coagulation, radiation damage, and/or metastasis. Chronic release of active TNF can cause cachexia and anorexia, and TNF can be lethal. TNF has also been implicated in infectious diseases. These include, for example, malaria, mycobacterial infection and meningitis. These also include viral infections, such as HIV, influenza virus, and herpes virus, including herpes simplex virus type-1 (HSV-1), herpes simplex virus type-2 (HSV-2), cytomegalovirus (CMV), varicella-zoster virus (VZV), Epstein-Barr virus, human herpes virus-6 (HHV-6), human herpesvirus-7 (HHV7), human herpesvirus-8 (HHV-8), pseudorabies and rhinotracheitis, among others.

Known P38 kinase inhibitors have been reviewed by G. J. Hanson (Expert Opinions on Therapeutic Patents, 1997, 7, 729-733, which is incorporated herein by reference in its entirety) J Hynes et al. (Current Topics in Medicinal Chemistry, 2005, 5, 967-985, which is incorporated herein by reference in its entirety), C. Dominguez et al (Expert Opinions on Therapeutics Patents, 2005, 15, 801-816, which is incorporated herein by reference in its entirety) and L. H. Pettus & R. P. Wurtz (Current Topics in Medicinal Chemistry, 2008, 8, 1452-1467, which is incorporated herein by reference in its entirety). P38 kinase inhibitors are known in the art, for example WO 2014/195400 and WO 2013/083604, which are incorporated herein by reference in their entireties.

However, there remains a need for improved compounds that are p38 MAPK inhibitors and are useful as anti-inflammatory agents in the treatment of, inter alia, diseases of the respiratory tract.

SUMMARY OF THE INVENTION

Accordingly, it is one object of the present invention to provide novel compounds which are kinase inhibitors.

It is another object of the present invention to provide novel compounds and compositions that are p38 MAPK inhibitors.

It is another object of the present invention to provide novel methods of treating diseases of the respiratory tract by administering such a compound.

These and other objects, which will become apparent during the following detailed description, have been achieved by the inventors' discovery of the compounds of formula (I) described below.

The compounds of the present invention are inhibitors of p38 mitogen activated protein kinase ("p38 MAPK," "p38 kinase," or "p38"), including p38α kinase, and are inhibitors of cytokine and chemokine production including TNFα and IL-8 production. They have a number of therapeutic applications, in the treatment of inflammatory diseases, particularly allergic and non-allergic airways diseases, more particularly obstructive or inflammatory airways diseases such as chronic obstructive pulmonary disease ("COPD") and asthma. They are therefore particularly suited for pulmonary delivery, by inhalation by nose or mouth.

Thus one object of the present invention is to identify more potent anti-inflammatory agents to be used in the treatment of diseases of the respiratory tract.

The BEAS-2B cells are Bronchial Epithelial cells and it is known in the literature that this cell line releases IL-8 upon stimulation with TNFα (see King E M, Holden N S, Gong W, Rider C F, Newton R. J Biol Chem. 2009; 284(39): 26803-15, which is incorporated herein by reference in its entirety) and p38 inhibitors inhibit the release of IL-8 in TNFα stimulated BEAS-2B cells (see Chmura K, Bai X, Nakamura M, Kandasamy P, McGibney M, Kuronuma K, Mitsuzawa H, Voelker D R, Chan E D. Am J Physiol Lung Cell Mol Physiol. 2008; 295(1):L220-30, which is incorporated herein by reference in its entirety).

Another object of the present invention is to identify novel potent p38 mitogen activated protein kinase inhibitors which show an appropriate developability profile on inhalatory administration to effectively treat respiratory obstructive or inflammatory diseases. It is to be understood that such profile may be achieved in a number of different ways by modulation of specific properties; by way of example, it could be achieved by administration of a low effective dose of the drug thus limiting side effects or via along duration of action in the lungs which may reduce the frequency of administration.

DETAILED DESCRIPTION OF THE PREFERRED EMBODIMENTS

According to the invention there is provided a compound of formula (I)

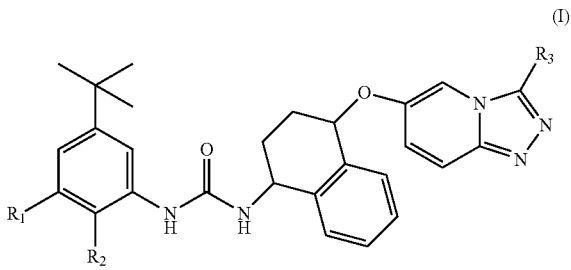

(I)

wherein $R_1$ is H or selected from the group consisting of $(C_1-C_4)$alkyl-, $(C_3-C_7)$cycloalkyl-, $(C_4-C_7)$heterocycloalkyl-, $R^AO-$, $R^CSO_2(R^A)N-$, $R^CSO_2-$, $(R^AR^B)NC(O)-$, $R^CCO(R^A)N-$, $R^AO(C_1-C_4)$alkylene-, $(R^AR^B)N-$, $R^CO(O)C-$, $(R^AR^B)NSO_2-$, $R^CSO_2(C_1-C_4)$alkylene-, $R^C(O)CO(C_1-C_4)$alkylene-, $R^CSO_2(R^A)N(C_1-C_4)$alkylene-, $R^COC(O)(R^A)N-$, $(R^AR^B)NCO(R^D)N-$, $(R^AR^B)N(C_1-C_6)$alkylene-, wherein any of such alkyl, alkylene, cycloalkyl, heterocycloalkyl or heteroaryl may be optionally substituted by one or more groups selected from $(C_1-C_3)$alkyl, $(C_3-C_6)$cycloalkyl, $(C_4-C_7)$heterocycloalkyl, $-OR^A$, halo and CN;

$R_2$ is H or selected from the group consisting of halo, $(C_1-C_6)$alkyl, $R^AO-$, $(R^AR^B)N(C_1-C_6)$alkylene- and $R^AO(C_1-C_4)$alkylene-;

$R^A$ and $R^B$ are at each occurrence independently H or selected from the group consisting of $(C_1-C_4)$alkyl-, $(C_3-C_7)$cycloalkyl- and $(C_4-C_7)$heterocycloalkyl-, wherein any of such alkyl, alkylene, cycloalkyl or heterocycloalkyl may be optionally substituted; or $R^A$ and $R^B$ may form together with the nitrogen atom to which they are attached an optionally substituted 5-11-membered saturated heterocyclic monocyclic ring system optionally containing a further heteroatom which is oxygen or nitrogen;

$R^C$ is selected from the group consisting of $(C_1-C_4)$alkyl-, $(C_3-C_7)$cycloalkyl- and $(C_4-C_7)$heterocycloalkyl-, wherein any of such alkyl, alkylene, cycloalkyl, heterocycloalkyl may be optionally substituted;

R$^D$ is H or is selected from the group consisting of (C$_1$-C$_4$)alkyl-, (C$_3$-C$_7$)cycloalkyl- and (C$_4$-C$_7$)heterocycloalkyl-, wherein any of such alkyl, alkylene, cycloalkyl or heterocycloalkyl may be optionally substituted;

R$_3$ is selected from (IIa)-(IIf)

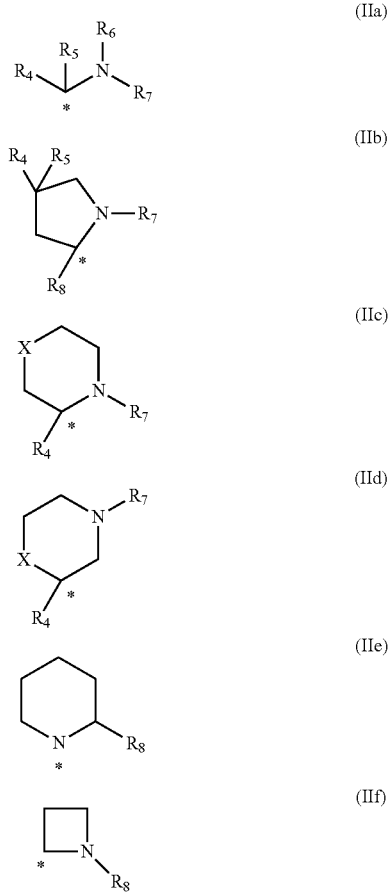

R$_4$ and R$_5$ are at each occurrence independently H or optionally substituted (C$_1$-C$_4$)alkyl-; or R$_4$ and R$_5$ may form together with the carbon atom to which they are attached an optionally substituted 3-6-membered saturated heterocyclic monocyclic ring system; R$_6$ and R$_7$ are at each occurrence independently H or optionally substituted (C$_1$-C$_4$)alkyl-; or R$_6$ and R$_7$ may form together with the nitrogen atom to which they are attached an optionally substituted 4-6-membered saturated heterocyclic monocyclic ring system optionally containing a further heteroatom which is oxygen or nitrogen, wherein said nitrogen may be optionally substituted with (C$_1$-C$_6$)alkyl-; R$_8$ is H or optionally substituted (C$_1$-C$_4$)alkyl-; X is selected from —CH$_2$, —O— and —NR$_8$; and wherein for "optionally substituted" is intended a susbtitution by one or more groups selected from (C$_1$-C$_3$) alkyl, (C$_3$-C$_6$)cycloalkyl, (C$_4$-C$_7$)heterocycloalkyl, OH, (C$_1$-C$_6$)alkyl-O, —NH$_2$, (C$_1$-C$_4$)HN—, (C$_1$-C$_4$)alkyl(C$_1$-C$_4$)alkyl(N)—, halo and CN; with the proviso that when R$_1$ is CH$_3$SO$_2$(H)N—, then R$_2$ is not CH$_3$O— or C$_2$H$_5$O— and when R$_1$ is H, then R$_2$ is not H, halo or CH$_3$;

and pharmaceutically acceptable salts thereof.

As used herein, the terms "halogen" or "halo" include fluorine, chlorine, bromine and iodine atoms.

As used herein, the term "C$_x$-C$_y$alkyl" wherein x and y are integers, refers to a straight or branched chain alkyl radical having from x to y carbon atoms. Thus when x is 1 and y is 6, for example, the term includes methyl, ethyl, n-propyl, isopropyl, n-butyl, isobutyl, sec-butyl, t-butyl, n-pentyl and n-hexyl.

As used herein, the term "C$_x$-C$_y$alkylene" wherein x and y are integers, refers to a C$_x$-C$_y$alkyl radical having in total two unsatisfied valencies, such as a divalent methylene radical.

As used herein, the term "C$_z$-C$_k$cycloalkyl" wherein z and k are integers refers to a monocyclic saturated carbocyclic radical having from z to k carbon atoms and includes, for example, cyclopropyl, cyclobutyl, cyclopentyl, cyclohexyl, cycloheptyl and cyclooctyl. Comprised within the scope of the term "C$_z$-C$_k$cycloalkyl" are those radicals having two unsatisfied valencies on the same carbon atom which will link to any C$_x$-C$_y$alkyl, C$_x$-C$_y$alkylene C$_z$-C$_k$cycloalkyl C$_z$-C$_k$cycloalkylene, C$_z$-C$_k$heterocycloalkyl, C$_z$-C$_k$heterocycloalkylC$_x$-C$_y$alkyl, C$_z$-C$_k$heterocycloalkylC$_z$-C$_k$cycloalkyl or (C$_z$-C$_k$)heterocycloalkylcarbonyl group by replacement of two hydrogen atoms placed on the same carbon. In such circumstances, this radical forms a gem-disubstituted or spiro system together with the C$_x$-C$_y$alkyl, C$_x$-C$_y$alkylene C$_z$-C$_k$cycloalkyl C$_z$-C$_k$cycloalkylene, C$_z$-C$_k$heterocycloalkyl, C$_z$-C$_k$heterocycloalkylC$_x$-C$_y$alkyl, C$_z$-C$_k$heterocycloalkylC$_z$-C$_k$cycloalkyl or (C$_z$-C$_k$)heterocycloalkylcarbonyl group it is linked to.

As used herein, the term "heteroaryl" refers to a mono- or bi-cyclic aromatic radical containing one or more heteroatoms selected from S, N and O, and includes radicals having two such monocyclic rings, or one such monocyclic ring and one monocyclic aryl ring, which are fused through a common bond. Illustrative examples of 5 and 6-membered heteroaryl are: are thienyl, furyl, pyrrolyl, imidazolyl, thiazolyl, isothiazolyl, pyrazolyl, oxazolyl, isoxazolyl, isothiazolyl, triazolyl, thiadiazolyl, oxadiazolyl, pyridinyl, pyridazinyl, pyrimidinyl, pyrazinyl, and triazinyl. Illustrative examples of 8-10-membered heteroaryl are: benzothienyl, benzofuryl, benzimidazolyl, benzothiazolyl, benzisothiazolyl, benzoxazolyl, benzisoxazolyl, benzotriazolyl, indolyl and indazolyl.

As used herein, the terms "heterocyclyl" and "heterocycli" relate to a saturated mono-, bi- or tri-cyclic non-aromatic radical containing one or more heteroatoms selected from S, N and O. In the case of bicyclic heterocyclic systems, included within the scope of the term are fused, spiro and bridged bicyclic systems. In particular, the term "C$_z$-C$_k$heterocycloalkyl" refers to monocyclic (C$_z$-C$_k$)cycloalkyl groups, in which at least one ring carbon atom is replaced by a heteroatom (e.g. N, NH, S or O). Examples of (C$_z$-C$_k$)heterocycloalkyl include pyrrolidinyl, thiazolidinyl, piperazinyl, piperidinyl, morpholinyl, thiomorpholinyl.

By analogy, the term "C$_z$-C$_k$heterocycloalkylene" refers to a divalent C$_z$-C$_k$heterocycloalkyl radical, wherein C$_z$-C$_k$heterocycloalkyl is as above defined.

In another aspect, the invention includes pharmaceutical compositions comprising a compound of the invention, together with one or more pharmaceutically acceptable carriers and/or excipients. Particularly preferred are compositions adapted for inhalation for pulmonary administration.

In another aspect, the invention includes the use of a compound of the invention for the treatment of diseases or conditions which benefit from inhibition of p38 MAP kinase activity. The treatment of obstructive or inflammatory airways diseases is a preferred use. All forms of obstructive or inflammatory airways diseases are potentially treatable with the compounds of the present invention, in particular an obstructive or inflammatory airways disease that is a member selected from the group consisting of chronic eosinophilic pneumonia, asthma, COPD, COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension, chronic inflammatory diseases including cystic fibrosis, bronchiectasis and pulmonary fibrosis (Idiopathic). Efficacy is anticipated when p38 kinase inhibitors are administered either locally to the lung (for example by inhalation and intranasal delivery) or via systemic routes (for example, oral, intravenous and subcutaneous delivery).

Compounds of the invention may exist in one or more geometrical, optical, enantiomeric, diastereomeric and tautomeric forms, including but not limited to cis- and trans-forms, E- and Z-forms, R-, S- and meso-forms, keto-, and enol-forms. Unless otherwise stated a reference to a particular compound includes all such isomeric forms, including racemic and other mixtures thereof. Where appropriate such isomers can be separated from their mixtures by the application or adaptation of known methods (e.g. chromatographic techniques and recrystallisation techniques). Where appropriate such isomers may be prepared by the application of adaptation of known methods (e.g. asymmetric synthesis).

Throughout the specification the use of an asterisk "*" in the definition of a structural formula, indicates the point of attachment for the radical group to the rest of the molecule.

It is expected that compounds of the invention may be prepared in the form of hydrates, and solvates. Any reference herein, including the claims herein, to "compounds with which the invention is concerned" or "compounds of the invention" or "the present compounds", and the like, includes reference to salts hydrates, and solvates of such compounds. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Individual compounds of the invention may exist in several polymorphic forms and may be obtained in different crystal or co-crystal habits, and they are intended to be included within the meaning of the term "compounds of the invention".

The compounds may also be administered in the form of prodrugs thereof. Thus certain derivatives of the compounds which may be active in their own right or may have little or no pharmacological activity themselves can, when administered into or onto the body, be converted into compounds of the invention having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and V. J. Stella) and *Bioreversible Carriers in Drug Design*, Pergamon Press, 1987 (ed. E. B. Roche, American Pharmaceutical Association; C. S. Larsen and J. Østergaard, Design and application of prodrugs, In Textbook of Drug Design and Discovery, 3$^{rd}$ Edition, 2002, Taylor and Francis), which are incorporated herein by reference in their entireties.

Prodrugs in accordance with the invention can, for example, be produced by replacing appropriate functionalities present in the compounds of formula (I) with certain moieties known to those skilled in the art as 'pro-moieties' as described, for example, in *Design of Prodrugs* by H. Bundgaard (Elsevier, 1985), which is incorporated herein by reference in its entirety. Such examples could be a prodrug of a carboxyl group (such as —CO—O—CH$_2$—O—CO-tBu as used in the pivampicillin prodrug of ampicillin), an amide (—CO—NH—CH$_2$—NAlk$_2$) or an amidine (—C(=N—O—CH$_3$)—NH$_2$).

In one embodiment, compounds of formula (Ia) are provided, which are compounds of formula (I) as above defined wherein carbon stereogenic center on the cycloalkylene portion linked to group —NH and —O— and identified, respectively, with numbers (1) and (2) herebelow, possess the absolute configuration herebelow represented

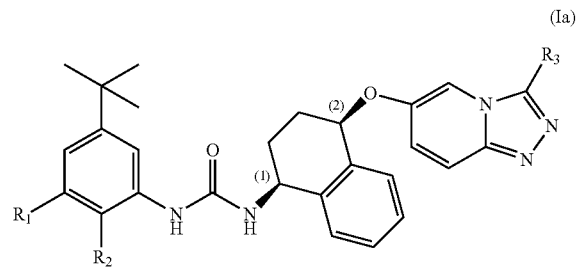

(Ia)

It is to be understood that all preferred groups or embodiments described herebelow for compounds of formula (I) may be combined among each other and apply as well to compounds of formula (Ia) mutatis mutandis.

In one embodiment R$_1$ is H or selected from the group consisting of (C$_1$-C$_4$)alkyl-, R$^C$SO$_2$(R$^A$)N—, R$^C$SO$_2$—, (R$^A$R$^B$)NC(O)—, R$^C$CO(R$^A$)N—, R$^A$O(C$_1$-C$_4$)alkylene-, (R$^A$R$^B$)N—, R$^C$O(O)C—, (R$^A$R$^B$)NSO$_2$—, R$^C$SO$_2$(C$_1$-C$_4$) alkylene-, R$^C$(O)CO(C$_1$-C$_4$)alkylene-, R$^C$SO$_2$(R$^A$)N(C$_1$-C$_4$) alkylene-, R$^C$OC(O)(R$^A$)N—, wherein any of such alkyl, alkylene or heterocycloalkyl may be optionally substituted by one or more groups —OR$^A$; wherein R$^A$ and R$^B$ are at each occurrence independently H or (C$_1$-C$_4$)alkyl-, which may be optionally substituted by —OH or R$^A$ and R$^B$ may form together with the nitrogen atom to which they are attached an optionally substituted 6 membered saturated heterocyclic monocyclic ring system optionally containing a further heteroatom which is oxygen; R$^C$ is selected from the group consisting of (C$_1$-C$_4$)alkyl- and (C$_3$-C$_7$)cycloalkyl-, wherein any of such alkyl or cycloalkyl may be optionally substituted by one or more groups selected from (C$_1$-C$_6$) alkyl-O— and halo.

In another embodiment R$_2$ is H or selected from the group consisting of (C$_1$-C$_6$)alkyl and R$^A$O—; wherein R$^A$ is H or (C$_1$-C$_4$)alkyl-.

In another embodiment R$_3$ is (IIb)

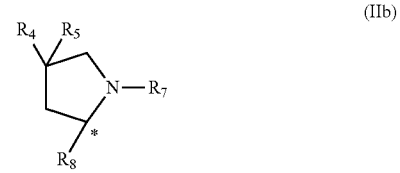

(IIb)

wherein R$_4$ and R$_5$ are at each occurrence independently H or (C$_1$-C$_4$)alkyl- optionally substituted by —OH; R$_7$ is H or (C$_1$-C$_4$)alkyl-; R$_8$ is H or (C$_1$-C$_4$)alkyl- optionally substituted by —OH.

In another embodiment $R_3$ is (IIa)

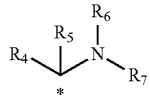
(IIa)

wherein $R_4$ and $R_5$ are $(C_1$-$C_4)$alkyl-; $R_6$ and $R_7$ are $(C_1$-$C_4)$alkyl-.

In another embodiment $R_3$ is (IIc)

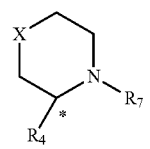
(IIc)

wherein $R_4$ is H; $R_7$ is $(C_1$-$C_4)$alkyl-; X is —CH$_2$ or —O—.

In another embodiment $R_3$ is (IId)

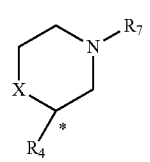
(IId)

wherein $R_4$ is H; $R_7$ is $(C_1$-$C_4)$alkyl-; X is —CH$_2$.

In one embodiment $R_1$ is H or selected from the group consisting of $(C_1$-$C_4)$alkyl-, $R^CSO_2(R^A)N$—, $R^CSO_2$—, $(R^AR^B)NC(O)$—, $R^CCO(R^A)N$—, $(R^AR^B)N$—, $R^CO(O)C$—, $(R^AR^B)NSO_2$—, $R^CSO_2(C_1$-$C_4)$alkylene-, $R^C(O)CO(C_1$-$C_4)$alkylene-, $R^CSO_2(R^A)N(C_1$-$C_4)$alkylene-, $R^COC(O)(R^A)N$—, $(R^AR^B)N(C_1$-$C_6)$alkylene- wherein any of such alkyl, alkylene or heterocycloalkyl may be optionally substituted by one or more groups —OR$^A$; $R_2$ is H or selected from the group consisting of $(C_1$-$C_6)$alkyl-, $R^AO$— and $R^AO(C_1$-$C_4)$alkylene-; wherein $R^A$ and $R^B$ are at each occurrence independently H or $(C_1$-$C_4)$alkyl-, wherein any of such alkyl may be optionally substituted by $(C_1$-$C_4)$alkyl $(C_1$-$C_4)$alkyl(N)—; $R^C$ is selected from the group consisting of $(C_1$-$C_4)$alkyl- and $(C_3$-$C_7)$cycloalkyl-, wherein any of such alkyl may be optionally substituted by $(C_1$-$C_6)$alkyl-O—; $R_3$ is selected from (IIa), (III)), (IIIe) and (IIe)

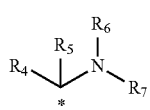
(IIa)

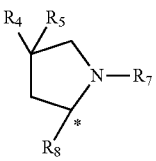
(IIb)

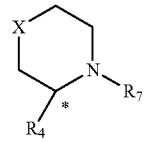
(IIc)

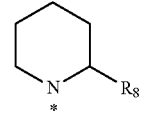
(IIe)

wherein X is —CH$_2$,
$R_4$ and $R_5$ are at each occurrence independently H or $(C_1$-$C_4)$alkyl-;
$R_6$ and $R_7$ are at each occurrence $(C_1$-$C_4)$alkyl-;
$R_8$ is H or $(C_1$-$C_4)$alkyl-.

In one embodiment $R_1$ is H or selected from the group consisting of $R^CSO_2(R^A)N$—, $(R^AR^B)NC(O)$—, $R^CCO(R^A)N$—, $R^AO(C_1$-$C_4)$alkylene-, $(R^AR^B)N$—, $(R^AR^B)NSO_2$—, $(R^AR^B)N(C_1$-$C_6)$alkylene-; $R_2$ is H or selected from the group consisting of $R^AO$— and $(R^AR^B)N(C_1$-$C_6)$alkylene-; wherein $R^A$ and $R^B$ are at each occurrence independently H or $(C_1$-$C_4)$alkyl-, wherein any of such alkyl may be optionally substituted by —OH, $(C_1$-$C_4)$alkyl$(C_1$-$C_4)$alkyl(N)— and $(C_4$-$C_7)$heterocycloalkyl; or $R^A$ and $R^B$ may form together with the nitrogen atom to which they are attached an optionally substituted 6 membered saturated heterocyclic monocyclic ring system optionally containing a further heteroatom which is oxygen; $R^C$ is selected from the group consisting of $(C_1$-$C_4)$alkyl- and $(C_3$-$C_7)$cycloalkyl-; $R_3$ is selected from (IIa), (IIb), (IIc), and (IIe)

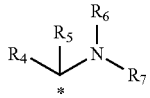
(IIa)

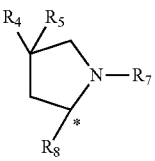
(IIb)

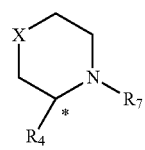
(IIe)

wherein X is —CH$_2$;
$R_4$ and $R_5$ are at each occurrence independently H or $(C_1$-$C_4)$alkyl-;
$R_6$ and $R_7$ are at each occurrence $(C_1$-$C_4)$alkyl-;
$R_8$ is H or $(C_1$-$C_4)$alkyl- which may be optionally substituted by —OH.

In one embodiment R₁ is selected from the group consisting of $R^CSO_2(R^A)N—$, $(R^AR^B)NC(O)—$, $R^CCO(R^A)N—$, $(R^AR^B)N(C_1-C_6)$alkylene-; R₂ is H or selected from the group consisting of $(C_1-C_6)$alkyl and $R^AO—$; wherein $R^A$ and $R^B$ are at each occurrence independently H or $(C_1-C_4)$ alkyl-, wherein any of such alkyl may be optionally substituted by —OH; or $R^A$ and $R^B$ may form together with the nitrogen atom to which they are attached an optionally substituted 6 membered saturated heterocyclic monocyclic ring system optionally containing a further heteroatom which is nitrogen; $R^C$ is $(C_1-C_4)$alkyl-; R₃ is selected from (IIa), (IIb), (IIc), (IIe) and (IIf)

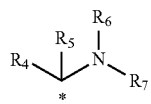
(IIa)

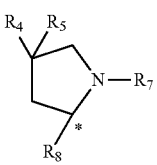
(IIb)

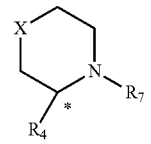
(IIc)

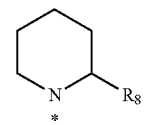
(IIe)

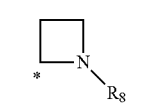
(IIf)

wherein X is selected from —CH₂ and —O—;
R₄ and R₅ are at each occurrence independently H or $(C_1-C_4)$alkyl-; R₇ is $(C_1-C_4)$alkyl- which may be optionally substituted by —OH; or R₆ and R₇ may form together with the nitrogen atom to which they are attached an optionally substituted 4-6-membered saturated heterocyclic monocyclic ring system optionally containing a further heteroatom which is nitrogen wherein said nitrogen may be optionally substituted with $(C_1-C_6)$alkyl-; R₈ is H or $(C_1-C_4)$alkyl-.

In one embodiment, the invention is directed to compounds of formula (IB)

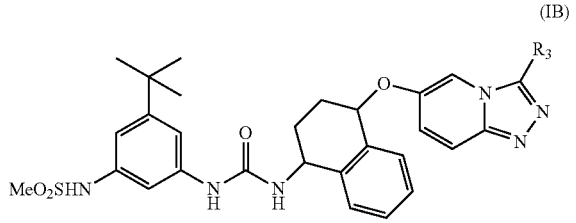
(IB)

wherein R₃ is selected from (IIa)-(IIf).

In one embodiment, the invention is directed to compounds of formula (I)

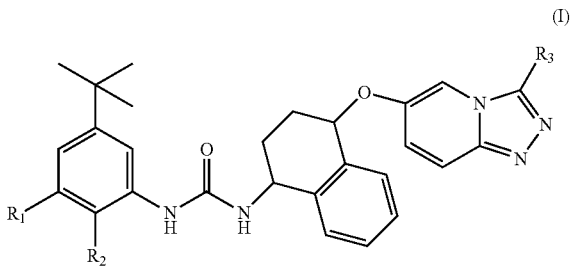
(I)

wherein R₈ is H or selected in the group consisting of $R^AO(C_1-C_4)$alkylene-, $(R^AR^B)N(C_1-C_6)$alkylene- and $R^CSO_2(R^A)N—$;

R₂ is H, or selected from the group consisting of $(R^AR^B)N(C_1-C_6)$alkylene- and $R^AO—$;

wherein $R^A$ and $R^B$ are at each occurrence independently H or $(C_1-C_4)$alkyl-, wherein any of such alkyl may be optionally substituted by $(C_1-C_4)$alkyl$(C_1-C_4)$alkyl(N)— and OH;

or $R^A$ and $R^B$ may form together with the nitrogen atom to which they are attached an optionally substituted 5-11-membered saturated heterocyclic monocyclic ring system optionally containing a further heteroatom which is oxygen; $R^C$ is $(C_1-C_4)$alkyl-;

R₃ is (IIe)

(IIe)

wherein R₈ is H or $(C_1-C_4)$alkyl-.

In one embodiment, a compound of formula (I) is selected from the group consisting of 1-(5-tert-Butyl-2-methyl-2H-pyrazol-3-yl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea hydrochloride salt;

1-(5-tert-Butyl-3-hydroxymethyl-2-methoxy-phenyl)-3-{(1S,4R)-4-[-3-((S)-1-methyl-pyrrolidin-2-yl)-[1,2,4]triazolo[4,3-a]pyridin-6-yloxy]-1,2,3,4-tetrahydro-naphthalen-1-yl}-urea;

1-(5-tert-Butyl-3-hydroxymethyl-2-methoxy-phenyl)-3-{(1S,4R)-4-[-3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea hydrochloride salt;

1-(5-tert-Butyl-3-hydroxymethyl-2-methoxy-phenyl)-3-{(1S,4R)-4-[3-(1-dimethylamino-1-methyl-ethyl)-[1,2,4]triazolo[4,3-a]pyridin-6-yloxy]-1,2,3,4-tetrahydro-naphthalen-1-yl}-urea hydrochloride salt;

1-(5-tert-Butyl-3-hydroxymethyl-2-methoxy-phenyl)-3-{(1S,4R)-4-[3-((S)-1-methyl-piperidin-2-yl)-[1,2,4]triazolo[4,3-a]pyridin-6-yloxy]-1,2,3,4-tetrahydro-naphthalen-1-yl}-urea;

1-(5-tert-Butyl-3-hydroxymethyl-2-methoxy-phenyl)-3-{(1S,4R)-4-[3-((S)-1-isopropyl-pyrrolidin-2-yl)-[1,2,4]triazolo[4,3-a]pyridin-6-yloxy]-1,2,3,4-tetrahydro-naphthalen-1-yl}-urea;

5-tert-Butyl-2-methoxy-N-methyl-3-(3-{(1S,4R)-4-[-3-((S)-1-methyl-pyrrolidin-2-yl)-[1,2,4]triazolo[4,3-a]pyridin-6-yloxy]-1,2,3,4-tetrahydro-naphthalen-1-yl}-ureido)-benzamide hydrochloride salt;

N-[5-tert-Butyl-3-(3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido)-2-methoxy-phenyl]-acetamide;

N-[5-tert-Butyl-3-(3-{(1S,4R)-4-[3-((S)-1-isopropyl-pyrrolidin-2-yl)-[1,2,4]triazolo[4,3-a]pyridin-6-yloxy]-1,2,3,4-tetrahydro-naphthalen-1-yl}-ureido)-2-methoxy-phenyl]-acetamide;

N-[5-tert-Butyl-3-(3-{(1S,4R)-4-[3-(1-dimethylamino-1-methyl-ethyl)-[1,2,4]triazolo[4,3-a]pyridin-6-yloxy]-1,2,3,4-tetrahydro-naphthalen-1-yl}-ureido)-2-methoxy-phenyl]-acetamide;

N-[5-tert-Butyl-2-methoxy-3-(3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-ureido)-phenyl]-acetamide;

N-[5-tert-Butyl-2-methoxy-3-(3-{(1S,4R)-4-[3-((S)-1-methyl-piperidin-2-yl)-[1,2,4]triazolo[4,3-a]pyridin-6-yloxy]-1,2,3,4-tetrahydro-naphthalen-1-yl}-ureido)-phenyl]-acetamide;

Ethanesulfonic acid [5-tert-butyl-3-(3-{(1S,4R)-4-[3(1-dimethylamino-1-methyl-ethyl)-[1,2,4]triazolo[4,3-a]pyridin-6-yloxy]-1,2,3,4-tetrahydro-naphthalen-1-yl}-ureido)-2-methoxy-phenyl]-amide hydrochloride salt;

Cyclopropanesulfonic acid [5-tert-butyl-3-(3-{(1S,4R)-4-[3(1-dimethylamino-1-methyl-ethyl)-[1,2,4]triazolo[4,3-a]pyridin-6-yloxy]-1,2,3,4-tetrahydro-naphthalen-1-yl}-ureido)-2-methoxy-phenyl]-amide partial formate salt;

2-Methoxy-ethanesulfonic acid [5-tert-butyl-3-(3-{(1S,4R)-4-[3(1-dimethylamino-1-methyl-ethyl)-[1,2,4]triazolo[4,3-a]pyridin-6-yloxy]-1,2,3,4-tetrahydro-naphthalen-1-yl}-ureido)-2-methoxy-phenyl]-amide hydrochloride salt;

2-Methyl-propane-1-sulfonic acid [5-tert-butyl-3-(3-{(1S,4R)-4-[3-(1-dimethylamino-1-methyl-ethyl)-[1,2,4]triazolo[4,3-a]pyridin-6-yloxy]-1,2,3,4-tetrahydro-naphthalen-1-yl}-ureido)-2-methoxy-phenyl]-amide hydrochloride salt;

N-[5-tert-Butyl-2-methoxy-3-(3-{(1S,4R)-4-[3-((S)-1-methyl-pyrrolidin-2-1)-[1,2,4]triazolo[4,3-a]pyridin-6-yloxy]-1,2,3,4-tetrahydro-naphthalen-1-yl}-ureido)-phenyl]-N-(2-hydroxy-ethyl)-methanesulfonamide formate salt;

1-(3-Amino-5-tert-butyl-2-methoxyphenyl-3-{(1S,4R)-4-[3-(1-dimethylamino-1-methyl-ethyl)-[1,2,4]triazolo[4,3-a]pyridin-6-yloxy]-1,2,3,4-tetrahydro-naphthalen-1-yl}-urea;

1-(3-Amino-5-tert-butyl-2-methoxyphenyl-3-{(1S,4R)-4-[3-(1-dimethylamino-1-methyl-ethyl)-[1,2,4]triazolo[4,3-a]pyridin-6-yloxy]-1,2,3,4-tetrahydro-naphthalen-1-yl}-urea;

N-[3-tert-Butyl-5-(3-{(1S,4R)-4-[3-(1-dimethylamino-1-methyl-ethyl)-[1,2,4]triazolo[4,3-a]pyridin-6-yloxy]-1,2,3,4-tetrahydro-naphthalen-1-yl}-ureido)-phenyl]-methanesulfonamide;

N-[3-tert-Butyl-5-(3-{(1S,4R)-4-[3((R)-1,2-dimethyl-pyrrolidin-2-yl)-[1,2,4]triazolo[4,3-a]pyridin-6-yloxy]-1,2,3,4-tetrahydro-naphthalen-1-yl}-ureido)-phenyl]-methanesulfonamide;

N-[3-tert-Butyl-5-(3-{(1S,4R)-4-[3((S)-1-methyl-pyrrolidin-2-yl)-[1,2,4]triazolo[4,3-a]pyridin-6-yloxy]-1,2,3,4-tetrahydro-naphthalen-1-yl}-ureido-phenyl]-methanesulfonamide;

N-[3-tert-Butyl-5-(3-{(1S,4R)-4-[3((R)-1-methyl-pyrrolidin-2-yl)-[1,2,4]triazolo[4,3-a]pyridin-6-yloxy]-1,2,3,4-tetrahydro-naphthalen-1-yl}-ureido-phenyl]-methanesulfonamide;

N-[3-tert-Butyl-5-(3-{(1S,4R)-4-[3((S)-1-isopropyl-piperidin-2-yl)-[1,2,4]triazolo[4,3-a]pyridin-6-yloxy]-1,2,3,4-tetrahydro-naphthalen-1-yl}-ureido-phenyl]-methanesulfonamide;

N-[3-tert-Butyl-5-(3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido)-phenyl]-methanesulfonamide;

N-[3-tert-Butyl-5-(3-{(1S,4R)-4-[3-((R)-4-methyl-morpholin-3-yl)-[1,2,4]triazolo[4,3-a]pyridin-6-yloxy]-1,2,3,4-tetrahydro-naphthalenyl}-ureido)-phenyl]-methanesulfonamide;

N-[3-tert-Butyl-5-(3-{(1S,4R)-4-[3-((S)-1,4,4-trimethyl-pyrrolidin-2-yl)-[1,2,4]triazolo[4,3-a]pyridin-6-yloxy]-1,2,3,4-tetrahydro-naphthalenyl}-ureido)-phenyl]-methanesulfonamide;

N-[3-tert-Butyl-5-(3-{(1S,4R)-4-[3-((S)-1-ethyl-2-methyl-pyrrolidin-2-yl)-[1,2,4]triazolo[4,3-a]pyridin-6-yloxy]-1,2,3,4-tetrahydro-naphthalen-1-yl}-ureido)-phenyl]-methanesulfonamide;

N-[3-tert-Butyl-5-(3-{(1S,4R)-4-[3-((S)-1-isopropyl-2-methyl-pyrrolidin-2-yl)-[1,2,4]triazolo[4,3-a]pyridin-6-yloxy]-1,2,3,4-tetrahydro-naphthalen-1-yl}-ureido)-phenyl]-methanesulfonamide;

N-[3-tert-Butyl-5-(3-{(1S,4R)-4-[3-((S)-2-methyl-pyrrolidin-2-yl)-[1,2,4]triazolo[4,3-a]pyridin-6-yloxy]-1,2,3,4-tetrahydro-naphthalen-1-yl}-ureido)-phenyl]-methanesulfonamide;

N-[3-tert-Butyl-5-(3-{(1S,4R)-4-[3-((R)-1-methyl-piperidin-3-yl)-[1,2,4]triazolo[4,3-a]pyridin-6-yloxy]-1,2,3,4-tetrahydro-naphthalen-1-yl}-ureido)-phenyl]-methanesulfonamide;

N-{3-tert-Butyl-5-[3-((1S,4R)-4-{3-[(S)-1-(2-hydroxy-ethyl)-pyrrolidin-2-yl]-[1,2,4]triazolo[4,3-a]pyridin-6-yloxy}-1,2,3,4-tetrahydro-naphthalen-1-yl)-ureido]-phenyl}-methanesulfonamide;

N-{3-tert-Butyl-5-[3-((1S,4R)-4-{3-[(S)-1-(2-hydroxy-ethyl)-2-methyl-pyrrolidin-2-yl]-[1,2,4]triazolo[4,3-a]pyridin-6-yloxy}-1,2,3,4-tetrahydro-naphthalen-1-yl)-ureido]-phenyl}-methanesulfonamide;

N-{3-tert-Butyl-5-[3-((1S,4R)-4-{3-[(S)-1-(2-hydroxy-ethyl)-pyrrolidin-2-yl]-[1,2,4]triazolo[4,3-a]pyridin-6-yloxy}-1,2,3,4-tetrahydro-naphthalen-1-yl)-ureido]-phenyl}-methanesulfonamide;

1-(3-Amino-5-tert-butyl-phenyl-3-{(1S,4R)-4-[3-(1-dimethylamino-1-methyl-ethyl)-[1,2,4]triazolo[4,3-a]pyridin-6-yloxy]-1,2,3,4-tetrahydro-naphthalen-1-yl}-urea;

1-(3-Amino-5-tert-butyl-phenyl-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea;

Cyclopropanesulfonic acid [3-tert-butyl-5-(3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-ureido)-phenyl]-amide;

Cyclopropanesulfonic acid [3-tert-butyl-5-(3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido)-phenyl]-amide;

3-tert-Butyl-N-methyl-5-(3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-ureido)-benzenesulfonamide;

3-tert-Butyl-5-(3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido)-N-methyl-benzenesulfonamide;

3-tert-Butyl-5-(3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-ureido)-benzoic acid methyl ester;

3-tert-Butyl-5-(3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido)-benzoic acid methyl ester;

1-(3-tert-Butyl-5-methanesulfonylmethyl-phenyl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea;

Acetic acid 3-tert-butyl-5-(3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-ureido)-benzyl ester;

Acetic acid 3-tert-butyl-5-(3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido)-benzyl ester;

N-[3-tert-Butyl-5-(3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido)-benzyl]-methanesulfonamide;

[3-tert-Butyl-5-(3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido)-phenyl]-carbamic acid methyl ester;

1-(3-tert-Butyl-5-methanesulfonyl-phenyl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea;

1-(3-tert-Butyl-5-morpholin-4-yl-phenyl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea;

1-(3-tert-Butyl-5-hydroxymethyl-phenyl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea;

3-tert-Butyl-N-(2-hydroxy-ethyl)-5-(3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-ureido)-benzamide;

3-tert-Butyl-5-(3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido)-N-(2-hydroxy-ethyl)-benzamide;

3-tert-Butyl-5-(3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-ureido)-benzamide;

3-tert-Butyl-5-(3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido-benzamide;

3-tert-Butyl-N-methyl-5-(3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-ureido)-benzamide;

3-tert-Butyl-5-(3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido)-N-methyl-benzamide;

N-[5-tert-Butyl-3-(3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido)-2-methyl-phenyl]-methanesulfonamide;

N-[5-tert-Butyl-2-methyl-3-(3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-ureido)-phenyl]-methanesulfonamide;

1-(3-tert-Butyl-5-morpholin-4-yl-phenyl)-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea;

1-(5-tert-Butyl-2-hydroxymethyl-phenyl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea;

N-(5-tert-Butyl-2-methoxy-3-{3-[(1S,4R)-4-(3-piperidin-1-yl-[1,2,4]triazolo[4,3-a]pyridin-6-yloxy)-1,2,3,4-tetrahydro-naphthalen-1-yl]-ureido}-phenyl-N-(2-dimethyl-amino-ethyl)-methanesulfonamide formate salt;

N-[3-tert-Butyl-5-(3-{(1S,4R)-4-[3-((S)-1-methyl-piperidin-2-yl)-[1,2,4]triazolo[4,3-a]pyridin-6-yloxy]-1,2,3,4-tetrahydro-naphthalen-1-yl}-ureido)-phenyl]-methanesulfonamide;

N-{3-tert-Butyl-5-[3-((1S,4R)-4-{3-[1-methyl-1-(4-methyl-piperazin-1-yl)-ethyl]-[1,2,4]triazolo[4,3-a]pyridin-6-yloxy}-1,2,3,4-tetrahydro-naphthalen-1-yl)-ureido]-phenyl}-methanesulfonamide;

N-[3-tert-Butyl-5-(3-{(1S,4R)-4-[3-((S)-1-methyl-azetidin-2-yl)-[1,2,4]triazolo[4,3-a]pyridin-6-yloxy]-1,2,3,4-tetrahydro-naphthalen-1-yl}-ureido)-phenyl]-methanesulfonamide;

1-(3-tert-Butyl-5-piperazin-1-yl-phenyl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea;

1-(3-tert-Butyl-5-dimethylaminomethyl-phenyl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea;

1-(3-tert-Butyl-5-dimethylaminomethyl-phenyl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-(3-tert-Butyl-5-{[(2-hydroxy-ethyl)-methyl-amino]-methyl}-phenyl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea;

1-(3-tert-Butyl-5-{[(2-hydroxy-ethyl)-methyl-amino]-methyl}-phenyl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-[3-tert-Butyl-5-(2-dimethylamino-ethoxymethyl)-phenyl]-3-{1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea;

1-[3-tert-Butyl-5-(2-dimethylamino-ethoxymethyl)-phenyl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-[3-tert-Butyl-5-(2-piperidin-1-yl-ethoxymethyl)-phenyl]-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea;

1-[3-tert-Butyl-5-(2-morpholin-4-yl-ethoxymethyl)-phenyl]-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea;

1-(5-tert-Butyl-2-morpholin-4-ylmethyl-phenyl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea;

1-(5-tert-Butyl-2-morpholin-4-ylmethyl-phenyl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-(3-{[Bis-(2-hydroxy-ethyl)-amino]-methyl}-5-tert-butyl-phenyl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea;

1-(3-{[Bis-(2-hydroxy-ethyl)-amino]-methyl}-5-tert-butyl-phenyl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

and pharmaceutically acceptable salts thereof.

As mentioned above the compounds of the invention are p38MAPK inhibitors, and thus may have utility for the treatment of diseases or conditions which benefit from inhibition of the p38 enzyme. Such diseases and conditions are known from the literature and several have been mentioned above. However, the compounds are generally of use as anti-inflammatory agents, particularly for use in the treatment of respiratory disease. In particular, the compounds may be used in the treatment of chronic obstructive pulmonary disease (COPD), chronic bronchitis, lung fibrosis, pneumonia, acute respiratory distress syndrome (ARDS), pulmonary emphysema, or smoking-induced emphysema, intrinsic (non-allergic asthma and extrinsic (allergic) asthma, mild asthma, moderate asthma, severe asthma, steroid resistant asthma, neutrophilic asthma, bronchitic asthma, exercise induced asthma, occupational asthma and asthma induced following bacterial infection, cystic fibrosis, pulmonary fibrosis and bronchiectasis.

The present invention provides the use of the compounds of the invention for the prevention and/or treatment of any disease or condition which benefit from inhibition of the p38 enzyme.

In a further aspect the present invention provides the use of compounds of the invention for the preparation of a medicament for the prevention and/or treatment of any disease or condition which benefit from inhibition of the p38 enzyme.

Moreover the present invention provides a method for prevention and/or treatment of any disease which benefit from inhibition of the p38 enzyme, said method comprises administering to a patient in need of such treatment a therapeutically effective amount of a compound of the invention.

As mentioned above, the compounds with which the invention is concerned are p38 kinase inhibitors, and are useful in the treatment of several diseases for example inflammatory diseases of the respiratory tract. Examples of such diseases are referred to above, and include asthma, rhinitis, allergic airway syndrome, bronchitis and chronic obstructive pulmonary disease.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial, as is required in the pharmaceutical art. In general, the daily dose range for oral administration will lie within the range of from about 0.001 mg to about 100 mg per kg body weight of a human, often 0.01 mg to about 50 mg per kg, for example 0.1 to 10 mg per kg, in single or divided doses. In general, the daily dose range for inhaled administration will lie within the range of from about 0.1 µg to about 1 mg per kg body weight of a human, preferably 0.1 µg to 50 µg per kg, in single or divided doses. On the other hand, it may be necessary to use dosages outside these limits in some cases. For the purpose of the invention, inhaled administration is preferred.

The compounds with which the invention is concerned may be prepared for administration by any route consistent with their pharmacokinetic properties. Orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavoring or coloring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia, which is incorporated herein by reference in its entirety.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

However, for treatment of an inflammatory disease of the respiratory tract, compounds of the invention may also be formulated for inhalation, for example as a nasal spray, or dry powder or aerosol inhalers. For delivery by inhalation, the active compound is preferably in the form of microparticles. They may be prepared by a variety of techniques, including spray-drying, freeze-drying and micronization. Aerosol generation can be carried out using, for example, pressure-driven jet atomizers or ultrasonic atomizers, preferably using propellant-driven metered aerosols or propellant-free administration of micronized active compounds from, for example, inhalation capsules or other "dry powder" delivery systems.

By way of example, a composition of the invention may be prepared as a suspension for delivery from a nebulizer or as an aerosol in a liquid propellant, for example for use in a pressurised metered dose inhaler (PMDI). Propellants suitable for use in a PMDI are known to the skilled person, and include CFC-12, HFA-134a, HFA-227, HCFC-22 and HFA-152.

In a preferred embodiment of the invention, a composition of the invention is in dry powder form, for delivery using a dry powder inhaler (DPI).

Microparticles for delivery by administration may be formulated with excipients that aid delivery and release. For example, in a dry powder formulation, microparticles may be formulated with large carrier particles that aid flow from the DPI into the lung. Suitable carrier particles are known, and include lactose particles; they may have a mass median aerodynamic diameter of greater than 90 μm.

In the case of an aerosol-based formulation, an example is:

| | |
|---|---|
| Compound of the invention | 24 mg/canister |
| Lecithin, NF Liq. Conc. | 1.2 mg/canister |
| Trichlorofluoromethane, NF | 4.025 g/canister |
| Dichlorodifluoromethane, NF | 12.15 g/canister. |

The active compounds may be dosed as described depending on the inhaler system used. In addition to the active compounds, the administration forms may additionally contain excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described EP-A-0 505 321, which is incorporated herein by reference in its entirety). Additionally, compounds of the invention may be delivered in multi-chamber devices thus allowing for delivery of combination agents.

Other compounds may be combined with compounds with which the invention is concerned for the prevention and treatment of inflammatory diseases, in particular respiratory diseases. Thus the present invention is also concerned with pharmaceutical compositions comprising a therapeutically effective amount of a compound of the invention and one or more other therapeutic agents. Suitable therapeutic agents for a combination therapy with compounds of the invention include, but are not limited to: (1) corticosteroids, such as fluticasone propionate, fluticasone furoate, mometasone furoate, beclometasone dipropionate, ciclesonide, budesonide, GSK 685698, GSK 870086, QAE 397, QMF 149, TPI-1020; (2) β2-adrenoreceptor agonists such as salbutamol, albuterol, terbutaline, fenoterol, and long acting β-adrenoreceptor agonists such as salmeterol, indacaterol, formoterol (including formoterol fumarate), arformoterol, carmoterol, GSK 642444, GSK 159797, GSK 159802, GSK 597501, GSK 678007, AZD3199; (3) corticosteroid/long acting β2 agonist combination products such as salmeterol/fluticasone propionate (Advair/Seretide), formoterol/budesonide (Symbicort), formoterol/fluticasone propionate (Flutiform), formoterol/ciclesonide, formoterol/mometasone furoate, formoterol/beclometasone dipropionate, indacaterol/mometasone furoate, Indacaterol/QAE 397, GSK 159797/GSK 685698, GSK 159802/GSK 685698, GSK 642444/GSK 685698, GSK 159797/GSK 870086, GSK 159802/GSK 870086, GSK 642444/GSK 870086, arformoterol/ciclesonide; (4) anticholinergic agents, for example muscarinic-3 (M3) receptor antagonists such as ipratropium bromide, tiotropium bromide, Aclidinium (LAS-34273), NVA-237, GSK 233705, Darotropium, GSK 573719, GSK 961081, QAT 370, QAX 028, EP-101; (5) dual pharmacology M3-anticholinergic/p2-adrenoreceptor agonists such as GSK961081, AZD2115 and LAS190792; (6) leukotriene modulators, for example leukotriene antagonists such as montelukast, zafirulast or pranlukast or leukotriene biosynthesis inhibitors such as Zileuton or BAY-1005, or LTB4 antagonists such as Amelubant, or FLAP inhibitors such as GSK 2190914, AM-103; (7) phosphodiesterase-IV (PDE-IV) inhibitors (oral or inhaled), such as roflumilast, cilomilast, Oglemilast, ONO-6126, Tetomilast, Tofimilast, UK 500,001, GSK 256066; (8) antihistamines, for example selective histamine-1 (H1) receptor antagonists, such as fexofenadine, citirizine, loratidine or astemizole or dual H1/H3 receptor antagonists such as GSK 835726, GSK 1004723, or selective histamine-4 (H4) receptor antagonists, such as ZPL3893787; (9) antitussive agents, such as codeine or dextramorphan; (10) a mucolytic, for example N acetyl cysteine or fudostein; (11) a expectorant/mucokinetic modulator, for example ambroxol, hypertonic solutions (e.g. saline or mannitol) or surfactant; (12) a peptide mucolytic, for example recombinant human deoxyribonoclease I (dornase-alfa and rhDNase) or helicidin; (13) antibiotics, for example azithromycin, tobramycin and aztreonam; (14) non-selective COX-1/COX-2 inhibitors, such as ibuprofen or ketoprofen; (15) COX-2 inhibitors, such as celecoxib and rofecoxib; (16) VLA-4 antagonists, such as those described in WO 97/03094 and WO9 7/02289, which are incorporated herein by reference in their entireties; (17) TACE inhibitors and TNF-α inhibitors, for example anti-TNF monoclonal antibodies, such as Remicade and CDP-870 and TNF receptor immunoglobulin molecules, such as Enbrel; (18) inhibitors of matrix metalloprotease, for example MMP-12; (19) human neutrophil elastase inhibitors, such as ONO-6818 or those described in WO 2005/026124, WO 2003/053930 and WO 06/082412, which are incorporated herein by reference in their entireties; (20) A2b antagonists such as those described in WO 2002/42298, which is incorporated herein by reference in its entirety; (21) modulators of chemokine receptor function, for example antagonists of CCR3 and CCR8; (22) compounds which modulate the action of other prostanoid receptors, for example a thromboxane $A_2$ antagonist; DP1 antagonists such as MK-0524, CRTH2 antagonists such as ODC9101 and OC000459 and AZD1981 and mixed DP1/CRTH2 antagonists such as AMG 009 and AMG853; (23) PPAR agonists including PPAR alpha agonists (such as fenofibrate), PPAR delta agonists, PPAR gamma agonists such as Pioglitazone, Rosiglitazone and Balaglitazone; (24) methylxanthines such as theophylline or aminophylline and methylxanthine/corticosteroid combinations such as theophylline/budesonide, theophylline/fluticasone propionate, theophylline/ciclesonide, theophylline/mometasone furoate and theophylline/beclometasone dipropionate; (25) A2a agonists such as those described in EP1052264 and EP1241176; (26) CXCR2 or IL-8 antagonists such as SCH 527123 or GSK 656933; (27) IL-R signalling modulators such as kineret and ACZ 885; and (28) MCP-1 antagonists such as ABN-912.

The invention is also directed to a kit comprising the pharmaceutical compositions of compounds of the invention alone or in combination with or in admixture with one or more pharmaceutically acceptable carriers and/or excipients and a device which may be a single- or multi-dose dry powder inhaler, a metered dose inhaler or a nebulizer.

In one aspect of the present invention, a process for the preparation of compounds of the invention is provided, according to general synthetic routes described in this section. In the following reaction schemes, unless otherwise indicated, the groups mentioned assume the same meaning as those reported for compounds of formula (I), (II) and (III).

The skilled person may introduce, where appropriate, suitable variations to the conditions specifically described in the examples in order to adapt the synthetic routes to the provision of further compounds of the invention. Such variations may include, but are not limited to, use of appropriate starting materials to generate different compounds, changes in the solvent and temperature of reactions, replacements of reactants with analogous chemical role, introduction or removal of protection/deprotection stages of functional groups sensitive to reaction conditions and reagents, as well as introduction or removal of specific synthetic steps oriented to further functionalization of the chemical scaffold.

Processes which can be used and are described and reported in Examples and Schemes, should not be viewed as limiting the scope of the synthetic methods available for the preparation of the compounds of the invention.

The process described is particularly advantageous as it is susceptible of being properly modulated, through any proper variant known to the skilled person, so as to obtained any of the desired compounds of the invention. Such variants are comprised within the scope of the present invention.

From all of the above, it should be clear to the skilled person that any of the described groups may be present as such or in any properly protected form.

In particular, functional groups present in the intermediate and compounds and which could generate unwanted side reaction and by-products, need to be properly protected before the alkylation, acylation, coupling or sulfonylation takes place. Likewise, subsequent deprotection of those same protected groups may follow upon completion of the said reactions.

In the present invention, unless otherwise indicated, the term "protecting group" designates a protective group adapted to preserve the function of the group it is bound to. Typically, protective groups are used to preserve amino, hydroxyl, or carboxyl functions. Appropriate protecting groups may thus include, for example, benzyl, benzyloxycarbonyl, t-butoxycarbonyl, alkyl or benzyl esters or the like, which are well known to those skilled in the art (see, for a general reference, T. W. Green; Protective Groups in Organic Synthesis (Wiley, N.Y. 1981), which is incorporated herein by reference in its entirety).

Likewise, selective protection and deprotection of any of the said groups, for instance including carbonyl, hydroxyl or amino groups, may be accomplished according to very well-known methods commonly employed in organic synthetic chemistry.

Optional salification of the compounds of formula (I) may be carried out by properly converting any of the free acidic or amino groups into the corresponding pharmaceutically acceptable salts. In this case too, the operative conditions being employed for the optional salification of the compounds of the invention are all within the ordinary knowledge of the skilled person.

From all of the above, it should be clear that the above process, comprehensive of any variant thereof for the preparation of suitable compounds of the invention, may be conveniently modified so that to adapt the reaction conditions to the specific needs, for instance by choosing appropriate condensing agents, solvents and protective groups, as the case may be.

For example compounds of the invention of formula (I) may be prepared according to the route illustrated in Scheme 1.

Scheme 1
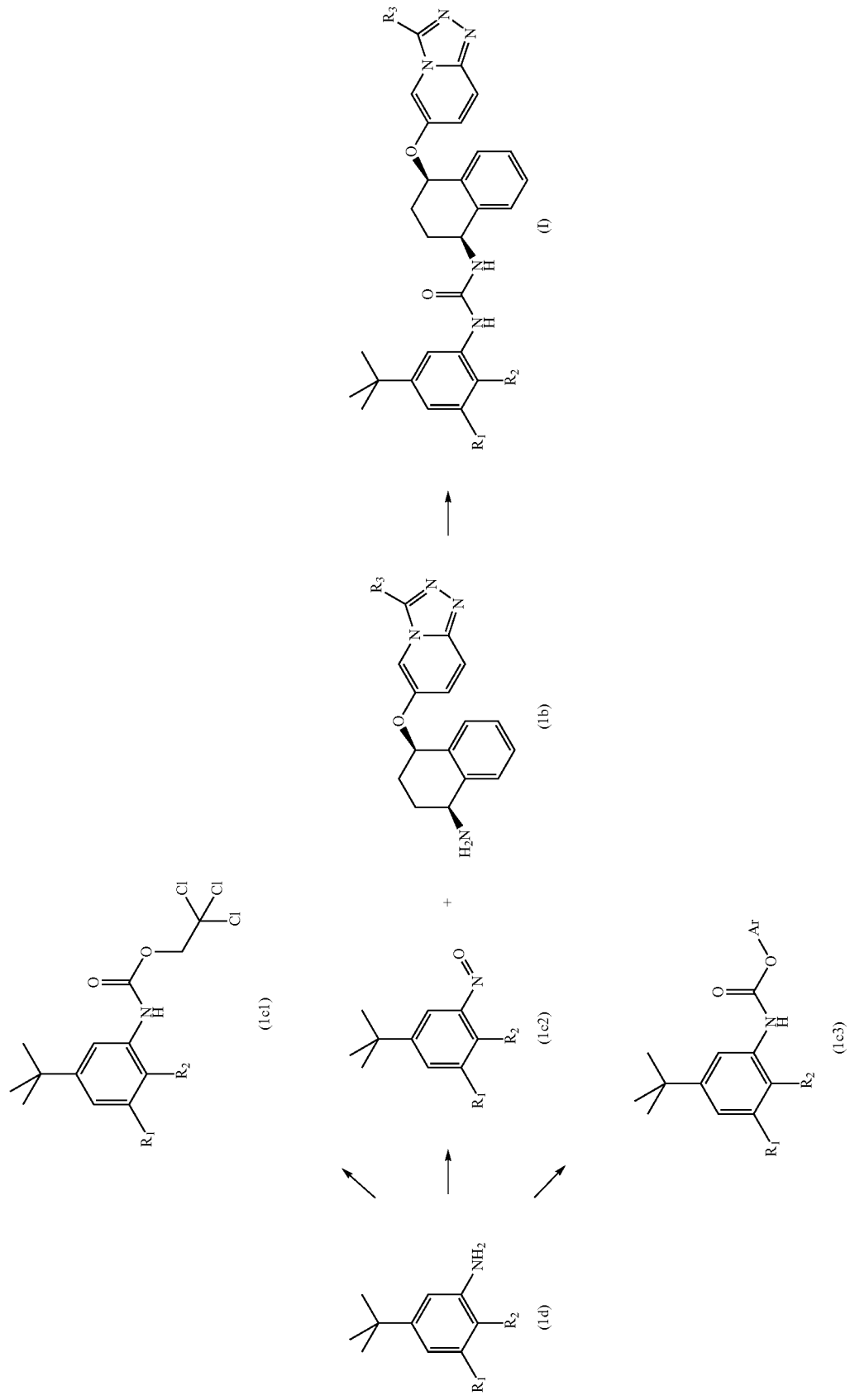

Compounds of general formula (I) may be prepared from compounds of general formula (1b) by reaction with a compound of general formula (1c1), or (1c2) in a suitable solvent such as dimethyl sulfoxide, 1,4-dioxane, DMF, 2-methylTHF, THF or acetonitrile, in the presence of a base such as diisopropylethylamine or sodium hydroxide at a range of temperatures, preferably between RT and 100° C.

Alternatively compounds of general formula (I) may be prepared from compounds of general formula (1b) by reaction with a compound of general formula (1c3) wherein Ar is a suitable aryl group such as phenyl or 4-nitrophenyl in a suitable solvent such as EtOAc, DCM, 1,4-dioxane, DMF, 2-methylTHF, THF or acetonitrile, in the presence of a base such as diisopropylethylamine, sodium bicarbonate or sodium hydroxide at a range of temperatures, preferably between RT and 100° C.

Compounds of general formula (1c1), (1c2) and (1c3) are either known in the literature or may be prepared from amines of general formula (1d) according to known literature procedures (e.g. WO 2006009741, EP 1 609 789, J. Org. Chem. 2013, 78, 3159-3169, which are incorporated herein by reference in their entireties).

Compounds of general formula (1d) are either commercially available or are known in the literature or may be prepared from compounds of formula (1e):

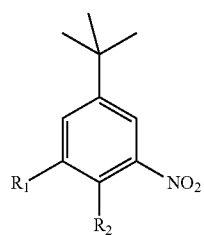

(1e)

by reduction of the nitro group by hydrogenation in the presence of hydrogen gas in the presence of a suitable catalyst such as palladium on carbon or Raney nickel in a suitable solvent such as ethanol or methanol at a range of temperatures, preferably between RT and 50° C. Alternatively transfer hydrogenation using a suitable source of hydrogen such as ammonium formate or cyclohexadiene in the presence of a suitable catalyst such as palladium on carbon in a suitable solvent such as ethanol or methanol at a range of temperatures, preferably between 50° C. and the reflux temperature of the solvent may be used. Alternatively a suitable metal such as iron or zinc powder can be used in a solvent such as methanol, water, DMF or acetic acid optionally with an additive such as HCl or ammonium chloride at a range of temperatures, preferably between RT and the reflux temperature of the solvent may be used.

Alternatively compounds of formula (1d) can be prepared from compounds of formula (2a) as illustrated in Scheme 2.

Scheme 2

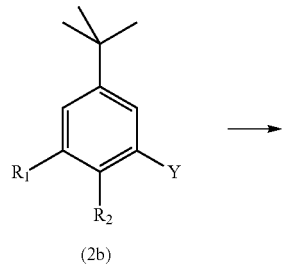

(2b)

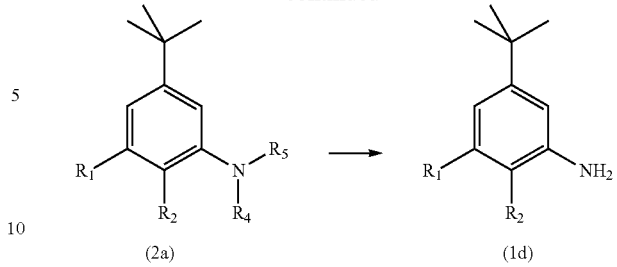

(2a) (1d)

in which $R_4$ or $R_5$ or both together are a protecting group such as Boc, Cbz, or phthalimides that can be removed by methods know to those skilled in the art. Compounds of formula (2a) can be prepared by compounds of formula (2b) in which Y is a suitable chemical group known to those skilled in the art selected such that it can facilitate a suitable coupling reaction such as metal catalysed cross coupling; for example Y may include halogen or a suitable leaving group such as mesylate or triflate; by reaction with a compound such as (2c)

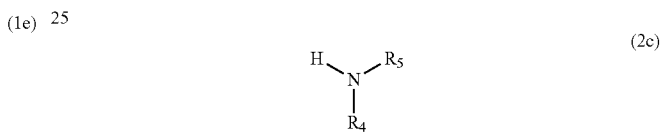

(2c)

For example compound (2c) could be tert-butyl carbamate. Examples of the coupling conditions used may include a catalyst such as palladium acetate or $Pd_2(dba)_3$, a ligand such as xantphos or X-phos in a suitable solvent such as 1,4-dioxane, 2-methylTHF, THF or toluene, in the presence of a base such as cesium carbonate, potassium carbonate, potassium tert-butoxide or potassium phosphate at a range of temperatures, preferably between RT and 100° C.

Compounds of foiinula (2b) are commercially available or are known in the literature or may be prepared by literature methods by those skilled in the art. Compounds of general formula (1b), may be prepared according to the route illustrated in Scheme 3.

Scheme 3

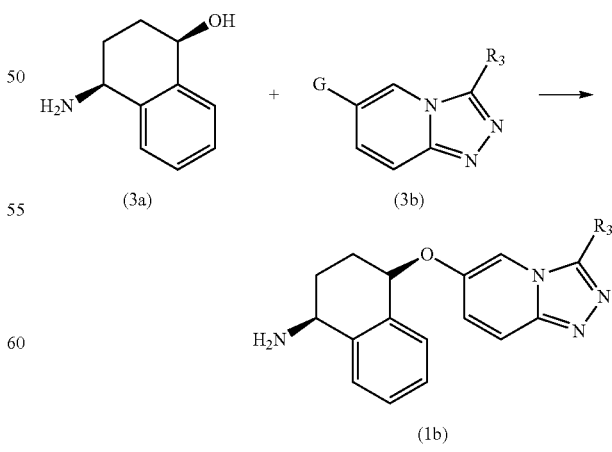

Compounds of general formula (1b) may be prepared from compounds of general formula (3b) by reaction with compound (3a), wherein G is a suitable chemical group known to those skilled in the art selected such that it can facilitate a suitable coupling reaction such as nucleophilic displacement or metal catalysed cross coupling. For example G may include halogen or a suitable leaving group such as mesylate or triflate. Examples of the coupling conditions used may include using a base such as sodium hydride or potassium tert-butoxide and 18-crown-6 or 1,3-dimethyl-3,4,5,6-tetrahydro-2(1H)-pyrimidinone in a suitable solvent such as N,N-dimethylformamide, toluene, 1,4-dioxane or acetonitrile at a range of temperatures, preferably between RT and 150° C.

Compounds of formula (3b) may be prepared according to the route in Scheme 4.

acid or Mitsunobu conditions (diethylazodicarboxylate/triphenylphosphine/trimethylsilylazide), in the absence or presence of a suitable solvent such as tetrahydrofuran, toluene or NMP, at a range of temperatures, preferably between RT and 120° C.

Compounds of formula (4d) may be prepared from compounds of formula (4a) by reaction with a compound of general formula (4b1) using a suitable acylating/dehydrating agent such as triphenylphosphine/trichloroacetonitrile/HOBt/2-(7-aza-1H-benzotriazole-1-yl)-1,1,3,3-tetramethyluronium hexafluorophosphate or 1-ethyl-3-(3-dimethylaminopropyl)carbodiimide in the presence of a base such as diisopropylethylamine, in a suitable solvent such as dichlo- Scheme 4

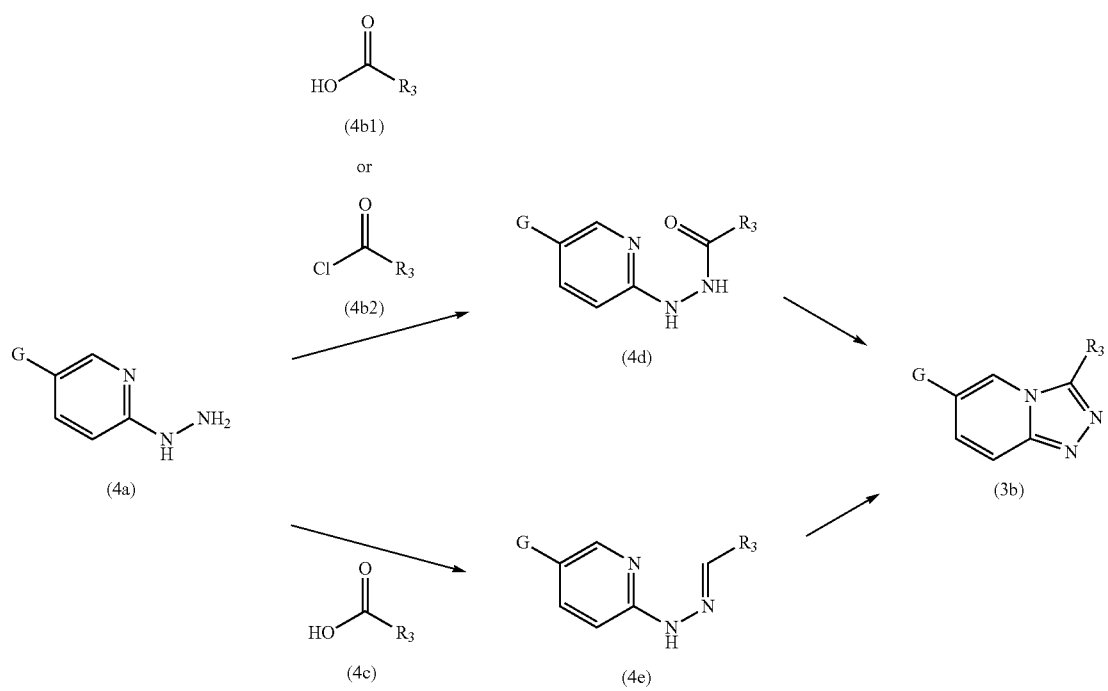

Compounds of general formula (3b) may be prepared from compounds of general formula (4e) as above reported using a suitable oxidant such as chloramine T, lead tetracetate or phenyliodine(III) diacetate, in a suitable solvent such as dichloromethane or ethanol at a range of temperatures, preferably between RT and 100° C. Compounds of general formula (4e) may be prepared from compounds of general formula (4a) by reaction with an aldehyde of general formula (4c) in a suitable solvent such as ethanol or tetrahydrofuran at a range of temperatures, preferably between RT and 80° C.

Compounds of formula (4a) and (4c) are commercially available, known in the literature or may be prepared by literature methods by those skilled in the art.

Alternatively, compounds of formula (3b) may be prepared from compounds of formula (4d) using a suitable dehydrating agent such as Burgess' reagent, triphenyl phosphine and hexachloroethane, phosphorus oxychloride, acetic romethane or acetonitrile, at a range of temperatures, preferably between RT and 150° C.

Alternatively, compounds of formula (4d) may be prepared from compounds of formula (4a) by reaction with a compound of general formula (4b2) in the presence of a base such as diisopropylethylamine, in a suitable solvent such as dichloromethane or THF at a range of temperatures preferably between −10° C. and the boiling point of the solvent.

Compounds of formulae (4b1) and (4b2) are commercially available, known in the literature or may be prepared by adapting appropriate literature methods by those skilled in the art.

Compound (3a) is known in the literature (WO 2014/195402, which is incorporatd herein by reference in its entirety).

Alternatively compounds of general formula (I) may be prepared from compounds of general formula (5a) by reaction with a compound of general formula (2b) as illustrated in Scheme 5.

Scheme 5

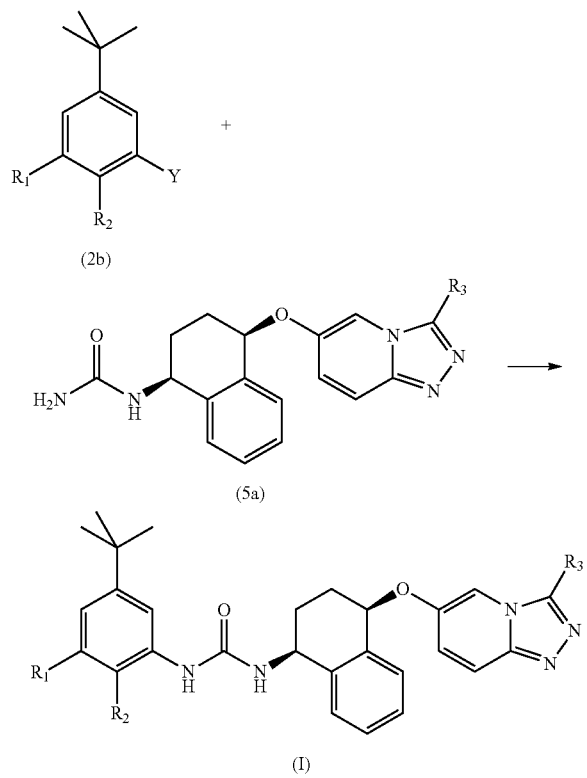

wherein Y is a suitable chemical group known to those skilled in the art selected such that it can facilitate a suitable coupling reaction such as metal catalysed cross coupling. For example Y may include halogen or a suitable leaving group such as mesylate or triflate. Examples of the coupling conditions used may include a catalyst such as palladium acetate or $Pd_2(dba)_3$, a ligand such as xantphos or X-phos in a suitable solvent such as 1,4-dioxane, 2-methylTHF, THF or toluene, in the presence of a base such as cesium carbonate, potassium carbonate, potassium tert-butoxide or potassium phosphate at a range of temperatures, preferably between RT and 100° C.

Compounds of general formula (5a) may be prepared from compounds of general formula (1b) by reaction with phosgene or triphosgene in a suitable solvent such as DCM or THF in the presence of a suitable base such as TEA or DIPEA at a range of temperatures, preferably between 0° C. and RT; followed by adding the mixture to a solution of ammonia in a suitable solvent such as methanol or water.

Other features of the invention will become apparent in the course of the following descriptions of exemplary embodiments which are given for illustration of the invention and are not intended to be limiting thereof.

EXAMPLES

Abbreviations used in the experimental section:
aq.=aqueous;
DCM=dichloromethane;
DEAD=Diethyl azodicarboxylate;
DIPEA=diisopropylethylamine;
DMF=N,N-dimethylformamide;
DMSO=dimethyl sulfoxide;
EDC=1-ethyl-3-(3'-dimethylaminopropyl)carbodiimide hydrochloride;
EtOAc=ethyl acetate;
EtOH=ethanol;
$Et_2O$=diethyl ether;
FCC=flash column chromatography;
h=hour;
$H_2O$=water;
HOBt=1-hydroxy-benzotriazole;
HPLC=high performance liquid chromatography;
IMS=industrial methylated spirit; LCMS=liquid chromatography mass spectrometry;
m-CPBA=meta-chloroperbenzoic acid;
MDAP=mass-directed auto-purification;
MeCN=acetonitrile; MeOH=methanol;
min=minutes;
NaOH=sodium hydroxide;
$NH_3$=ammonia;
NMR=nuclear magnetic resonance;
$PPh_3$=triphenylphosphine;
RT=room temperature;
Rt=retention time;
sat.=saturated;
SCX-2=strong cation exchange chromatography;
TBAF=tetrabutylammonium fluoride;
TFA=trifluoroacetic acid;
TFAA=Trifluoroacetic anhydride;
THF=Tetrahydrofuran.

In the procedures that follow, after each starting material, reference to an Intermediate/Example number is usually provided. This is provided merely for assistance to the skilled chemist. The starting material may not necessarily have been prepared from the batch referred to.

When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

The nomenclature of structures was assigned using Autonom 2000 Name software from MDL Inc. When the nomenclature of structures could not be assigned using Autonom, ACD/Name software utility part of the ACD/Labs Release 12.00 Product Version 12.5 (Build 45133, 16 Dec. 2010) was used. Stereochemical assignments of compounds are based on comparisons with data reported in WO 2008/043019, which is incorporated herein by reference in is entirety, for key intermediates. All reactions were carried out under anhydrous conditions and an atmosphere of nitrogen or argon unless specified otherwise.

NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz. Shifts are given in ppm relative to tetramethylsilane ($\delta$=0 ppm). J values are given in Hz through-out. NMR spectra were assigned using DataChord Spectrum Analyst Version 4.0.b21 or SpinWorks version 3.

Where products were purified by flash column chromatography, 'flash silica' refers to silica gel for chromatography, 0.035 to 0.070 mm (220 to 440 mesh) (e.g. Fluka silica gel 60), and an applied pressure of nitrogen up to 10 p.s.i accelerated column elution or use of the CombiFlash®

Companion purification system or use of the Biotage SP1 purification system. All solvents and commercial reagents were used as received.

Compounds purified by preparative HPLC were purified using a C18-reverse-phase column (100×22.5 mm i.d. Genesis column with 7 μm particle size), or a Phenyl-Hexyl column (250×21.2 mm i.d. Gemini column with 5 μm particle size), UV detection between 220-254 nm, flow 5-20 mL/min), eluting with gradients from 100-0 to 0-100% water/acetonitrile (containing 0.1% TFA or 0.1% formic acid) or a C18-reverse-phase column (19×250 mm, XBridge OBD, with 5 μm particle size), eluting with gradients from 100-0 to 0-100% water/acetonitrile (containing 0.1% NH$_4$OH); or a ChiralPak IC column (10×250 mm i.d., with 5 μm particle size), unless otherwise indicated. Fractions containing the required product (identified by LCMS analysis) were pooled, the organic solvent removed by evaporation, and the remaining aqueous residue lyophilized, to give the final product. Products purified by preparative HPLC were isolated as free base, formate or TFA salts, unless otherwise stated.

The Liquid Chromatography Mass Spectroscopy (LCMS) and MDAP systems used are:

Method 1

Waters ZMD quadrupole mass spectrometer with a C18-reverse-phase column (30×4.6 mm Phenomenex Luna 3 μm particle size), elution with A: water+0.1% formic acid; B: acetonitrile+0.1% formic acid. Gradient:

| Gradient - Time | flow mL/min | % A | % B |
| --- | --- | --- | --- |
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (2004 split to MS with in-line HP1100 DAD detector). MS ionization method—Electrospray (positive and negative ion).

Method 2

Acquity i-Class (quaternary pump/PDA detector)+Quattro Micro Mass Spectrometer with an ACQUITY UPLC BEH C$_{18}$ 1.7 μm, 100×2.1 mm, maintained at 40° C. Elution with A: water+0.1% formic acid; B: acetonitrile+0.1% formic acid. Gradient:

| Gradient - Time | flow mL/min | % A | % B |
| --- | --- | --- | --- |
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—MS, UV PDA. MS ionization method—Electrospray (positive and negative ion).

Method 3

Waters micromass ZQ2000 quadrupole mass spectrometer with an Acquity BEH C18 1.7 um 100×2.1 mm, Acquity BEH Shield RP18 1.7 um 100×2.1 mm or Acquity HSST3 1.8 um 100×2.1 mm, maintained at 40° C. Elution with A: water+0.1% formic acid; B: acetonitrile+0.1% formic acid. Gradient:

| Gradient - Time | flow mL/min | % A | % B |
| --- | --- | --- | --- |
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—MS, UV PDA. MS ionization method—Electrospray (positive and negative ion).

Method 4

Acquity H-Class (quaternary pump/PDA detector)+QDa Mass Spectrometer, Acquity UPLC BEH C18 1.7μ, 50×2.1 mm at 50° C. Elution with A: water+0.1% formic acid; B: acetonitrile+0.1% formic acid. Gradient:

| Gradient - Time | flow mL/min | % A | % B |
| --- | --- | --- | --- |
| 0.00 | 1.0 | 97 | 3 |
| 1.50 | 1.0 | 1 | 99 |
| 1.90 | 1.0 | 1 | 99 |
| 2.00 | 1.0 | 97 | 3 |
| 2.50 | 1.0 | 97 | 3 |

Detection—MS, UV diode array 190-450 nm. MS ionization method—Electrospray (positive and negative ion).

Method 5

Acquity H-Class (quaternary pump/PDA detector)+QDa Mass Spectrometer, Acquity UPLC BEH C18 1.7μ, 50×2.1 mm at 50° C. or XBridge BEH C18 2.5μ, 50×2.1 mm at 50° C. Elution with A: water+0.1% aqueous ammonia; B: acetonitrile+0.1% aqueous ammonia. Gradient:

| Gradient - Time | flow mL/min | % A | % B |
| --- | --- | --- | --- |
| 0.00 | 1.0 | 97 | 3 |
| 1.50 | 1.0 | 1 | 99 |
| 1.90 | 1.0 | 1 | 99 |
| 2.00 | 1.0 | 97 | 3 |
| 2.50 | 1.0 | 97 | 3 |

Detection—MS, UV diode array 190-450 nm. MS ionization method—Electrospray (positive and negative ion).

Method 6

Agilent 1260 infinity purification system. Column: XSELECT CSH Prep C18 OBD, particle size 5 μm, 30×150 mm, RT. Elution with A: water+0.1% formic acid; B: CH3CN+0.1% formic acid. Gradient—90% A/10% B to 2% A/95% B over 22 min—flow rate 60 mL/min. Detection—In-line Agilent 6100 series single Quadrupole LC/MS.

Method 7

Agilent 1260 infinity purification system. Column: XBridge Prep C18 OBD, particle size 5 μm, 30×150 mm, RT. Elution with A: water+0.1% ammonia; B: CH$_3$CN+0.1% ammonia. Gradient—90% A/10% B to 2% A/95% B over 22 min—flow rate 60 mL/min. Detection—In-line Agilent 6100 series single Quadrupole LC/MS.

Example 1. 1-(5-tert-Butyl-2-methyl-2H-pyrazol-3-yl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea hydrochloride salt

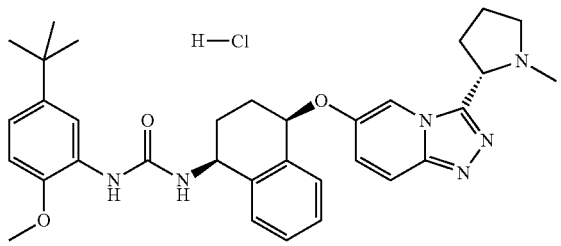 [SMILES: COc1ccc(C(C)(C)C)cc1NC(=O)N[C@H]1CC[C@@H](Oc2ccc3nnc([C@@H]4CCCN4C)n3c2)c2ccccc21 ; Cl]

To a solution of (1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-ylamine (WO 2014/195402, which is incorporated herein by reference in its entirety, 198 mg, 0.55 mmol) and DIPEA (0.29 ml, 1.67 mmol) in 2-methyltetrahydrofuran (4 ml) at 0° C. was added 4-tert-butyl-2-isocyanato-1-methoxy-benzene (CAS: 284462-77-7, 115 mg, 0.59 mmol). The reaction mixture was warmed at RT, stirred for 4 h and then it was diluted with H$_2$O. The two phases were separated and the aqueous phase was extracted with EtOAc (×2) and the combined organic phases were washed with brine, dried with Na$_2$SO$_4$ and the solvent was removed under reduced pressure. The crude mixture was purified by FCC eluting with 0-10% 2M NH$_3$ in MeOH/DCM. The resulting product was further purified by HPLC (Gemini C18, 5-95% MeCN in H$_2$O, 0.1% HCO$_2$H). The obtained solid was dissolved in MeCN (1 ml) and H$_2$O (1 ml) and an aqueous HCl solution (1M, 1 eq) was added. The mixture was lyophilised to afford the title compound (114 mg, 36%)

NB. The hydrochloride salt presented two different stereoisomers due to formation of a stereogenic centre on the ammonium and the stereoisomers have been labelled with [#].

LCMS (Method 3): Rt 3.83 min, m/z 569 [MH$^+$]. $^1$H NMR (400 MHz, d$_6$-DMSO): 1.22 (9H, s), 1.80-1.90 (1H, m), 1.95-2.44 (6H, m), 2.65-2.78 (1H, m), 2.89 (2H, s), 3.23-3.35 (1H, m), 3.66-3.81 (1H, m), 3.77 (3H, s), 4.86-4.95 (1H, m), 5.38-5.50 (0.7H[#], m), 5.55-5.71 (1.3H[#], m), 6.81-6.89 (2H, m), 7.24-7.43 (6H, m), 7.84 (1H, d, J=10 Hz), 7.89-7.94 (1H, m), 8.28 (1H, d, J=1.6 Hz), 8.54 (0.7H[#], br s), 8.88 (0.3H[#], br s), 10.78 (0.7H[#], br s), 11.98 (0.3H[#], br s) plus one proton obscured by the solvent peak.

Intermediate A. (5-tert-Butyl-3-isocyanato-2-methoxy-phenyl)-methanol

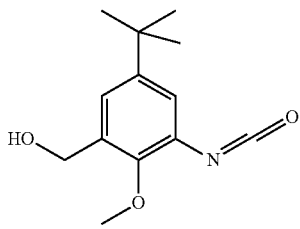 [SMILES: COc1c(CO)cc(C(C)(C)C)cc1N=CC=O]

To a stirred solution of (3-amino-5-tert-butyl-2-methoxy-phenyl)-methanol (WO 2011/040509, 103 mg, 0.49 mmol) in DCM (7.5 ml) and saturated aqueous NaHCO$_3$ solution (5 ml) at 0° C. was added phosgene (20% solution in toluene, 0.78 ml, 1.48 mmol). The reaction mixture was stirred at 0° C. for 1 h and then the two phases were separated. The aqueous phase was extracted with DCM (×2) and the combined organic phases were dried with Na$_2$SO$_4$ and the solvent was removed under reduced pressure.

The resulting solid was triturated with cyclohexane to give the title compound (129 mg, quant.).

$^1$H NMR (300 MHz, CDCl$_3$): 1.29 (9H, s), 1.92 (1H, t, J=6.0 Hz), 3.89 (3H, s), 4.73 (2H, d, J=6.0 Hz), 7.01 (1H, d, J=2.5 Hz), 7.21 (1H, d, J=2.5 Hz).

Intermediate B. 1-[5-tert-Butyl-3-(tert-butyl-dimethyl-silanyloxymethyl)-2-methoxy-phenyl]-3-{(1S,4R)-4-[3-(1-dimethylamino-1-methyl-ethyl)-[1,2,4]triazolo[4,3-a]pyridin-6-yloxy]-1,2,3,4-tetrahydro-naphthalen-1-yl}-urea

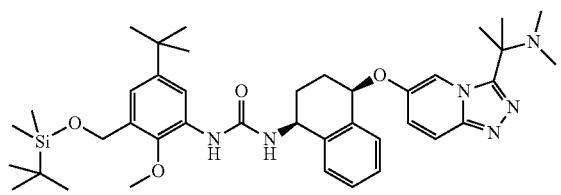 [SMILES: COc1c(CO[Si](C)(C)C(C)(C)C)cc(C(C)(C)C)cc1NC(=O)N[C@H]1CC[C@@H](Oc2ccc3nnc(C(C)(C)N(C)C)n3c2)c2ccccc21]

a. tert-Butyl-(5-tert-butyl-2-methoxy-3-nitro-benzyloxy)-dimethyl-silane (Intermediate Ba)

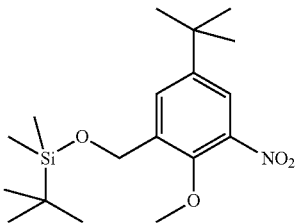 [SMILES: COc1c(CO[Si](C)(C)C(C)(C)C)cc(C(C)(C)C)cc1[N+](=O)[O-]]

To a stirred solution of (5-tert-butyl-2-methoxy-3-nitro-phenyl)-methanol (WO 2015/092423, which is incorporated herein by reference in its entirety, 209 mg, 0.87 mmol) in DMF (2 ml) under nitrogen was added imidazole (148 mg, 2.18 mmol) and tert-butyldimethylchlorosilane (158 mg, 1.05 mmol). The reaction mixture was stirred at RT for 3 days, diluted with H$_2$O and Et$_2$O and the two phases were separated. The aqueous phase was extracted with Et$_2$O and the combined organic phases were washed with a citric acid solution (10%), aqueous NaOH 1M and brine, dried with Na$_2$SO$_4$ and the solvent was removed under reduced pressure. The crude mixture was purified by FCC eluting with 0-20% EtOAc/cyclohexane to afford the title compound (276 mg, 90%).

$^1$H NMR (300 MHz, CDCl$_3$): 0.13 (6H, s), 0.96 (9H, s), 1.33 (911, s), 3.74 (3H, s), 4.82 (2H, br s), 7.71 (1H, d, J=2.4 Hz), 7.79-7.81 (1H, m).

b. 5-tert-Butyl-3-(tert-butyl-dimethyl-silanyloxymethyl)-2-methoxy-phenylamine (Intermediate Bb)

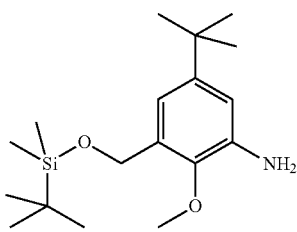 [SMILES: COc1c(N)cc(C(C)(C)C)cc1CO[Si](C)(C)C(C)(C)C]

To a stirred solution of Intermediate Ba (278 mg, 079 mmol) in ethanol (5 ml) under nitrogen were added palladium on activated charcoal (10% Pd, 111 mg) and ammonium formate (248 mg, 3.94 mmol). The resulting mixture was stirred at 50° C. for 2 h. The reaction mixture was filtered through a pad of Celite® and the ethanol was removed under reduced pressure. The residue was partitioned between DCM and H₂O. The aqueous phase was extracted with DCM (×2) and the combined organic phases were washed with brine, dried with Na₂SO₄ and the solvent removed under reduced pressure to give the title compound (260 mg, quant.).

¹H NMR (300 MHz, CDCl₃): 0.11 (6H, s), 0.95 (9H, s), 1.28 (911, s), 3.70 (2H, br s), 3.74 (3H, s), 4.77 (2H, s), 6.68-6.70 (1H, m), 6.88-6.91 (1H, m).

c. tert-Butyl-(5-tert-butyl-3-isocyanato-2-methoxy-benzyloxy)-dimethyl-silane (Intermediate Bc)

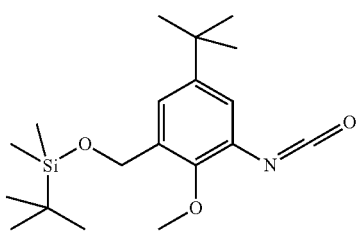 [SMILES: COc1c(CO[Si](C)(C)C(C)(C)C)cc(C(C)(C)C)cc1N=CC=O]

To a stirred solution of Intermediate Bb (256 mg, 0.79 mmol) in DCM (14 ml) and a saturated aqueous NaHCO₃ solution (9 ml) at 0° C. was added phosgene (20% solution in toluene, 1.25 ml, 2.38 mmol). The reaction mixture was stirred at 0° C. for 1 h and then the two phases were separated. The aqueous phase was extracted with DCM (×2). The combined organic phases were washed with brine, dried with Na₂SO₄ and the solvent was removed under reduced pressure to afford the title compound (264 mg, 96%).

¹H NMR (400 MHz, CDCl₃): 0.11 (6H, s), 0.95 (9H, s), 1.28 (9H, s), 3.82 (3H, s), 4.78 (2H, s), 6.92-6.98 (1H, m), 7.31-7.36 (1H, m).

d. 1-[5-tert-Butyl-3-(tert-butyl-dimethyl-silanyloxymethyl)-2-methoxy-phenyl]-3-{(1S,4R)-4-[3-(1-dimethylamino-1-methyl-ethyl)-[1,2,4]triazolo[4,3-a]pyridin-6-yloxy]-1,2,3,4-tetrahydro-naphthalen-1-yl}-urea (Intermediate B)

The title compound was prepared starting from (1S,4R)-4-[3-(1-dimethylamino-1-methyl-ethyl)-[1,2,4]triazolo[4,3-a]pyridin-6-yloxy]-1,2,3,4-tetrahydro-naphthalen-1-ylamine (WO 2013/083604, which is incorporated herein by reference in its entirety, 250 mg, 0.68 mmol) and Intermediate Bc (263 mg, 0.75 mmol) using the procedure described to make Example 1. The crude was purified by FCC eluting with 0-10% MeOH/EtOAc to afford the title compound (372 mg, 76%).

LCMS (Method 1): Rt 4.28 min, m/z 715 [MH⁺].

Intermediate C. 1-[5-tert-Butyl-3-(tert-butyl-dimethyl-silanyloxymethyl)-2-methoxy-phenyl]-3-{(1S,4R)-4-[3-((S)-1-methyl-piperidin-2-yl)-[1,2,4]triazolo[4,3-a]pyridin-6-yloxy]1,2,3,4-tetrahydro-naphthalen-1-yl}-urea

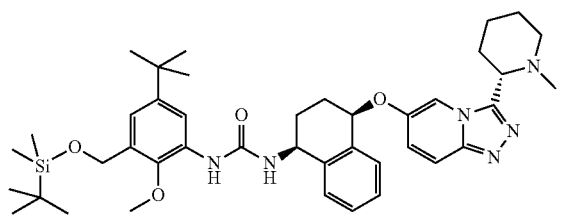 [SMILES: COc1c(CO[Si](C)(C)C(C)(C)C)cc(C(C)(C)C)cc1NC(=O)N[C@H]1CC[C@@H](Oc2ccc3nnc([C@@H]4CCCCN4C)n3c2)c2ccccc21]

The title compound was prepared starting from (1S,4R)-4-[3-((S)-1-methyl-piperidin-2-yl)-[1,2,4]triazolo[4,3-a]pyridin-6-yloxy]-1,2,3,4-tetrahydro-naphthalen-1-ylamine (WO 2013/083604, which is incorporated herein by reference in its entirety, 186 mg, 0.49 mmol) and Intermediate Bc (215 mg, 0.62 mmol) using the procedure described to make Example 1. The crude was purified by FCC eluting with 0-20% MeOH/EtOAc to afford the title compound (271 mg, 61%).

¹H NMR (300 MHz, CDCl₃): 0.10 (6H, s), 0.94 (9H, s), 1.30 (9H, s), 1.50-1.91 (6H, m), 2.02 (3H, s), 2.05-2.38 (4H, m), 2.98-3.08 (1H, m), 3.74 (3H, s), 3.78-3.85 (1H, m), 4.76 (2H, s), 5.17-5.23 (2H, m), 5.45 (1H, d, J=8.5 Hz), 6.82 (1H, s), 7.01 (1H, dd, J=9.5, 2.1 Hz), 7.20-7.39 (5H, m), 7.52 (1H, d, J=7.7 Hz), 7.6 (1H, d, J=9.8 Hz), 7.81 (1H, d, J=2.3 Hz), 8.48 (1H, d, J=1.4 Hz).

Intermediate D. 1-[5-tert-Butyl-3-(tert-butyl-dimethyl-silanyloxymethyl)-2-methoxy-phenyl]-3-{(1S,4R)-4-[3-((S)-1-isopropyl-pyrrolidin-2-yl)-[1,2,4]triazolo[4,3-a]pyridin-6yloxy]-1,2,3,4-tetrahydro-naphthalen-1-yl}-urea

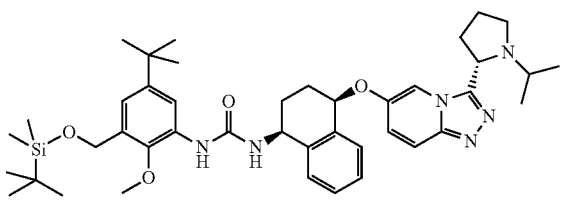 [SMILES: COc1c(CO[Si](C)(C)C(C)(C)C)cc(C(C)(C)C)cc1NC(=O)N[C@H]1CC[C@@H](Oc2ccc3nnc([C@@H]4CCCN4C(C)C)n3c2)c2ccccc21]

The title compound was prepared starting from (1S,4R)-4-[3-(S)-1-isopropyl-pyrrolidin-2-yl)-[1,2,4]triazolo[4,3-a]pyridin-6-yloxy]-1,2,3,4-tetrahydro-naphthalen-1-ylamine (WO 2013/083604, which is incorporated herein by reference in its entirety, 214 mg, 0.55 mmol) and Intermediate Bc (239 mg, 0.69 mmol) using the procedure described to make Example 1. The crude was purified by FCC eluting with 0-10% MeOH/EtOAc to afford the title compound (164 mg, 32%).

$^1$H NMR (300 MHz, CDCl$_3$): 0.10 (6H, s), 0.92-1.00 (15H, m), 1.30 (9H, s), 1.86-1.99 (3H, m), 2.05-2.34 (4H, m), 2.59-2.77 (2H, m), 3.07-3.15 (1H, m), 3.74 (3H, s), 4.51-4.59 (1H, m), 4.75 (2H, s), 5.11-5.23 (3H, m), 6.60 (1H, s), 7.01 (1H, dd, J=10.0, 2.4 Hz), 7.27-7.39 (5H, m), 7.49 (1H, m), 7.64 (1H, dd, J=9.8, 0.6 Hz), 7.76 (1H, d, J=2.4 Hz), 8.50 (1H, d, J=2.0 Hz).

Examples 2-6 a. General Procedure for the Examples 2-3

A solution of Intermediate A (0.30 mmol) and an appropriate Intermediate (see Table 1) (0.27 mmol) in 2-methyl-tetrahydrofuran (2 ml) was stirred at RT for 16 h. The reaction mixture was diluted with H$_2$O. The two phases were separated and the aqueous phase was extracted with EtOAc (×2) and the combined organic phases were washed with brine, dried with Na$_2$SO$_4$ and the solvent was removed under reduced pressure.

For obtaining Example 2, the resulting residue was purified by FCC, eluting with 0-10% MeOH/DCM or MDAP (Method 7) to afford Example 2 (25%).

For obtaining Example 3, after the FCC purification the obtained solid was dissolved in MeCN (2 ml) and H$_2$O (2 ml) and an aqueous HCl solution (1M, 1 eq) was added. The mixture was lyophilised to afford Example 3 (10%).

b. General Procedure for the Examples 4-6

To a stirred solution of the relevant Intermediate (see Table 1) (0.20 mmol) in THF (3 ml) was added tetrabutylammonium fluoride (1 M in THF, 0.30 ml, 0.30 mmol). The resulting mixture was stirred at RT for 5 hours and then it was diluted with EtOAc and a saturated aqueous NaHCO$_3$ solution. The two phases were separated and the aqueous phase was extracted with EtOAc. The combined organic phases were washed with brine, dried with Na$_2$SO$_4$ and the solvent was removed under reduced pressure.

For obtaining Example 5-6, the resulting residue was purified by FCC, eluting with 0-10% 2M NH$_3$ in MeOH/DCM or eluting with 0-20% MeOH/EtOAc to afford the title compounds (Examples 5-6, 20-67%).

For obtaining Example 4, after the FCC purification the obtained solid was dissolved in MeCN (2 ml) and H$_2$O (2 ml) and an aqueous HCl solution (1M, 1 eq) was added. The mixture was lyophilized to afford Example 4 (87%).

TABLE 1

| Ex. | Intermediate | Structure | NMR (400 MHz) δ | LC-MS |
|---|---|---|---|---|
| 2 | (1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-ylamine (WO 2014/195402, which is incorporated herein by reference in its entirety) | 1-(5-tert-Butyl-3-hydroxymethyl-2-methoxy-phenyl)-3-{(1S,4R)-4-[-3-((S)-1-methyl-pyrrolidin-2-yl)-[1,2,4]triazolo[4,3-a]pyridin-6-yloxy]-1,2,3,4-tetrahydro-naphthalen-1-yl}-urea | $^1$H NMR (400 MHz, d$_6$-DMSO): 1.23 (9H, s), 1.82-2.23 (11H, m), 2.32 (1H, q, J = 8.4 Hz), 3.10-3.14 (1H, m), 3.61 (3H, s), 3.97 (1H, t, J = 8.0 Hz), 4.48 (2H, d, J = 5.0 Hz), 4.86-4.92 (1H, m), 5.01 (1H, t, J = 5.0 Hz), 5.40 (1H, t, J = 4.6 Hz), 6.99 (1H, d, J = 2.6 Hz), 7.24-7.40 (6H, m), 7.74 (1H, d, J = 9.8 Hz), 7.92 (1H, s), 8.22 (1H, d, J = 2.3 Hz), 8.25 (1H, d, J = 1.6 Hz) | (Method 3): Rt 3.28 min, m/z 599 [MH$^+$] |
| 3 | (1S,4R)-4-[3-((S)-1,2-Dimethyl-pyrrolidin-2-yl)-[1,2,4]triazolo[4,3-a]pyridin-6-yloxy]-1,2,3,4-tetrahydro-naphthalen-1-ylamine (WO 2013/083604, which is incorporated herein by reference in its entirety) | 1-(5-tert-Butyl-3-hydroxymethyl-2-methoxy-phenyl)-3-{(1S,4R)-4-[-3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea hydrochloride salt | The hydrochloride salt presented two different stereoisomers due to formation of a stereogenic centre on the ammonium and the stereoisomers have been labelled with#  $^1$H NMR (400 MHz, d$_6$-DMSO): 1.24 (9H, s), 1.77 (2H, br s), 1.82-2.43(8H, m), 2.57 (1H, d, J = 4.08 Hz), 2.67-3.15 (3H, br s), 3.62 (3H, s), 3.61-3.94 (3H, m), 4.48 (2H, s), 4.85- | (Method 3): Rt 3.35 min, m/z 613 [MH$^+$] |

TABLE 1-continued

| Ex. | Intermediate | Structure | NMR (400 MHz) δ | LC-MS |
|---|---|---|---|---|
| | | | 4.94 (1H, m), 5.66 (0.7H#, br s), 5.83 (0.3H#, br s), 6.99 (1H, d, J = 2.2 Hz), 7.23-7.46 (6H, m), 7.82-7.90 (1H, m), 9.91-8.01 (1H, m), 8.22 (0.7H#, br s), 8.22 (1H, d, J = 2.2Hz), 8.79 (0.3H#, br s), 10.79 (0.7H#, br s), 12.18 (0.3H#, br s) | |
| 4 | Intermediate B | 1-(5-tert-Butyl-3-hydroxymethyl-2-methoxy-phenyl)-3-{(1S,4R)-4-[3-(1-dimethylamino-1-methyl-ethyl)-[1,2,4]triazolo[4,3-a]pyridin-6-yloxy]-1,2,3,4-tetrahydro-naphthalen-1-yl}-urea hydrochloride salt | $^1$H NMR (400 MHz, d-$_6$-DMSO): 1.18-1.26 (10H, m), 1.79-2.21 (10H, m), 2.64-2.89 (4H, m), 3.61 (3H, s), 4.48 (2H, s), 4.85-4.93 (1H, m), 5.79 (1H, s), 6.99 (1H, d, J = 2.1 Hz), 7.25-7.31 (1H, m), 7.33-7.44 (5H, m), 7.86 (1H, d, J = 10.0 Hz), 7.94 (1H, s), 8.21 (1H, d, J = 2.3 Hz), 8.54-8.62 (1H, m), 11.00 (1H, s) plus 2 protons obscured by water | (Method 3): Rt 3.41 min, m/z 601 [MH$^+$] |
| 5 | Intermediate C | 1-(5-tert-Butyl-3-hydroxymethyl-2-methoxy-phenyl)-3-{(1S,4R)-4-[3-((S)-1-methyl-piperidin-2-yl)-[1,2,4]triazolo[4,3-a]pyridin-6-yloxy]-1,2,3,4-tetrahydro-naphthalen-1-yl}-urea | $^1$H NMR (400 MHz, d-$_6$-DMSO): 1.27 (9H, m), 1.35-1.48 (1H, m), 1.55-1.75 (3H, m), 1.78-1.98 (6H, m), 2.00-2.09 (1H, m), 2.11-2.24 (2H, m), 3.00 (2H, dt, J = 11.5, 3.2 Hz), 3.65 (3H, s), 3.80 (1H, dd, J = 11.0, 2.7 Hz), 4.51 (2H, d, J = 5.6 Hz), 4.88-4.97 (1H, m), 5.04 (1H, t, J = 5.6 Hz), 5.44 (1H, t, J = 4.5 Hz), 7.02 (1H, d, J = 2.5 Hz), 7.26-7.46 (6H, m), 7.76 (1H, d, J = 10.0 Hz), 7.95 (1H, s), 8.25 (1H, d, J = 2.5 Hz), 8.43 (1H, d, J = 1.5 Hz) | (Method 2): Rt 3.34 min, m/z 613 [MH$^+$] |

TABLE 1-continued

| Ex. | Intermediate | Structure | NMR (400 MHz) δ | LC-MS |
|---|---|---|---|---|
| 6 | Intermediate D | 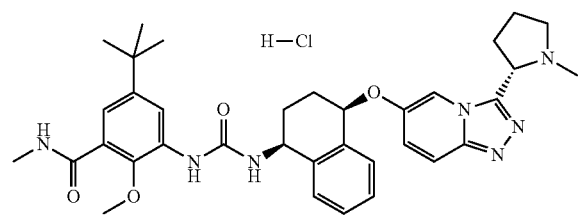<br>1-(5-tert-Butyl-3-hydroxymethyl-2-methoxy-phenyl)-3-{(1S,4R)-4-[3-((S)-1-isopropyl-pyrrolidin-2-yl)-[1,2,4]triazolo[4,3-a]pyridin-6-yloxy]-1,2,3,4-tetrahydro-naphthalen-1-yl}-urea | $^1$H NMR (400 MHz, d$_6$-DMSO): 0.90 (6H, t J = 6.5 Hz), 1.26 (9H, s), 1.83-2.24 (8H, m), 2.55-2.65 (2H, m), 3.05-3.13 (1H, m), 3.65 (3H, s), 4.42-4.48 (1H, m), 4.51 (2H, d, J = 2.7 Hz), 4.88-4.96 (1H, m), 5.04 (1H, t, J = 5.4 Hz), 5.37 (1H, t, J = 4.6 Hz), 7.02 (1H, d, J = 1.3 Hz), 7.27-7.45 (6H, m), 7.76 (1H, d, J = 10.4 Hz), 7.90 (1H, s), 8.24 (1H, d, J = 2.2 Hz), 8.41 (1H, d, J = 1.7 Hz). | (Method 2): Rt 3.44 min, m/z 627 [MH$^+$] |

Example 7. 5-tert-Butyl-2-methoxy-N-methyl-3-(3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-ureido)-benzamide hydrochloride salt

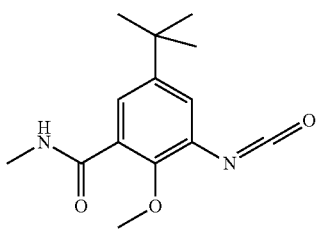 [SMILES: CNC(=O)c1cc(C(C)(C)C)cc(N=CC=O)c1OC]

a. 5-tert-Butyl-3-isocyanato-2-methoxy-N-methyl-benzamide (Intermediate 7a)

The title compound (277 mg, 95%) was prepared starting from 3-amino-5-tert-butyl-2-methoxy-N-methyl-benzamide (US 2014/0296208, 238 mg, 1.01 mmol) using the procedure described to make Intermediate A.

$^1$H NMR (300 MHz, CDCl$_3$): 1.30 (9H, s), 3.04 (3H, d, J=5.0 Hz), 3.86 (3H, s), 7.17 (1H, d, J=2.7 Hz), 7.37 (1H, br s), 7.86 (1H, d, J=2.7 Hz).

b. Example 7

The title compound was prepared starting from (1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-ylamine (WO 2014/195402, 134 mg, 0.37 mmol) and Intermediate 7a (134 mg, 0.44 mmol) using the procedure described to make Example 1. The crude was purified by FCC eluting with 0-10% MeOH/DCM. The obtained solid was dissolved in MeCN (3 ml) and H$_2$O (3 ml) and an aqueous HCl solution (1M, 1 eq) was added. The mixture was lyophilised to afford the title compound (197 mg, 81%).

The hydrochloride salt presented two different stereoisomers due to formation of a stereogenic centre on the ammonium and the stereoisomers have been labelled with [#].

LCMS (Method 3): Rt 3.24 min, m/z 626 [MH$^+$]. $^1$H NMR (400 MHz, d$_6$-DMSO): 1.24 (9H, s), 1.82-1.94 (1H, m), 1.97-2.07 (1H, m), 2.08-2.54 (6H, m), 2.65-2.96 (4H, m), 2.75 (3H, d, J=4.8 Hz), 3.64 (3H, s), 3.64-3.80 (1H, br s), 4.87-4.96 (1H, m), 5.18-5.74 (2H, m), 7.00 (1H, d, J=2.3 Hz), 7.26-7.43 (5H, m), 7.53 (1H, d, J=8.0 Hz), 7.84 (1H, d, J=10.0 Hz), 8.01-8.11 (2H, m), 8.42 (1H, d, J=2.6 Hz), 8.48 (0.7H[#], br s), 8.82 (0.3H[#], br s), 10.67 (0.7H[#], br s), 11.65 (0.3H[#], br s).

Example 8. N-[5-tert-Butyl-3-(3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido)-2-methoxy-phenyl]-acetamide

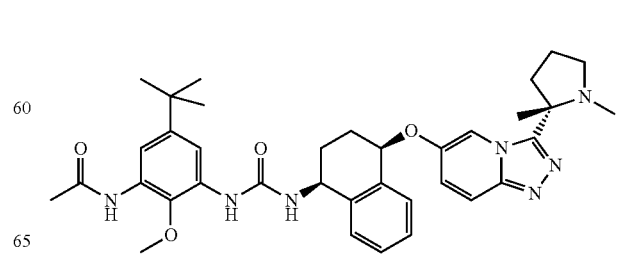

a. N-(5-tert-Butyl-3-isocyanato-2-methoxy-phenyl)-acetamide (Intermediate 8a)

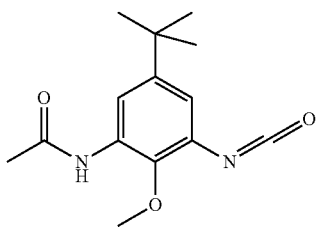 [SMILES: COc1c(N=CC=O)cc(C(C)(C)C)cc1NC(C)=O]

The title compound (4.80 g, 96%) was prepared starting from N-(3-amino-5-tert-butyl-2-methoxy-phenyl)-acetamide ((Bioorg. Med. Chem. Lett., 2009, 19, 2386-2391, which is incorporated herein by reference in its entirety), 4.50 g, 19.1 mmol) using the procedure described to make Intermediate A.

$^1$H NMR (300 MHz, CDCl$_3$): 1.28 (9H, s), 2.22 (3H, s), 3.85 (3H, s), 6.80 (1H, d, J=2.2 Hz), 7.56 (1H, br s), 8.22 (1H, br s).

b. Example 8

The title compound was prepared starting from (1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-ylamine (WO 2013/083604, 463 mg, 1.23 mmol) and Intermediate 8a (402 mg, 1.53 mmol) using the procedure described to make Example 1. The crude was purified by FCC eluting with 0-10% MeOH/DCM. The resulting solid was triturated with ether and dried under vacum to give the title compound (347 mg, 44%).

LCMS (Method 2): Rt 3.37 min, m/z 640 [MH$^+$]. $^1$H NMR (400 MHz, d-$_6$-DMSO): 1.24 (9H, s), 1.52 (3H, s), 1.79-1.89 (1H, m), 1.89-2.01 (3H, m), 2.04 (3H, s), 2.09 (3H, s), 2.11-2.26 (3H, m), 2.66 (1H, q, J=8.7 Hz), 3.13-3.21 (1H, m), 3.63 (3H, s), 4.89-4.97 (1H, m), 5.37 (1H, t, J=4.4 Hz), 7.26-7.46 (6H, m), 7.49 (1H, s), 7.77 (1H, d, J=9.8 Hz), 8.00 (1H, s), 8.11 (1H, d, J=1.7 Hz), 8.48 (1H, d, J=1.7 Hz), 9.24 (1H, s) plus one proton obscured by solvent.

Examples 9-12 a. General Procedure for the Examples 9-12

The title compounds were prepared starting from Intermediate 8a and an appropriate amine [See Table 2] using the procedure described to make Example 8. The crude was purified by FCC eluting with 0-5% 2M NH$_3$ in MeOH/DCM or FCC eluting with 0-20% MeOH/EtOAc afforded the title compounds (16-92%).

TABLE 2

| Ex. | Intermediate | Structure | NMR (400 MHz) δ | LC-MS |
|---|---|---|---|---|
| 9 | (1S,4R)-4-[3-((S)-1-isopropyl-pyrrolidin-2-yl)-[1,2,4]triazolo[4,3-a]pyridin-6-yloxy]-1,2,3,4-tetrahydro-naphthalen-1-ylamine (WO 2013/083604, which is incorporated herein by reference in its entirety) | N-[5-tert-Butyl-3-(3-{(1S,4R)-4-[3-((S)-1-isopropyl-pyrrolidin-2-yl)-[1,2,4]triazolo[4,3-a]pyridin-6-yloxy]-1,2,3,4-tetrahydro-naphthalen-1-yl}-ureido)-2-methoxy-phenyl]-acetamide | $^1$H NMR (400 MHz, d-$_6$-DMSO): 0.90 (6H, t, J = 6.7 Hz), 1.24 (9H, m), 1.84-1.97 (4H, m), 1.98-2.24 (6H, m), 2.56-2.65 (2H, m), 3.06-3.13 (1H, m), 3.63 (3H, s), 4.43-4.49 (1H, m), 4.88-4.96 (1H, m), 5.38 (1H, t, J = 3.9 Hz), 7.28-7.46 (6H, m), 7.49 (1H, s), 7.76 (1H, d, J = 10.0 Hz), 8.00 (1H, s), 8.10 (1H, d, J = 1.8 Hz), 8.42 (1H, d, J = 1.8 Hz), 9.24 (1H, s) plus one proton obscured by solvent | (Method 3): Rt 3.52 min, m/z 654 [MH$^+$]. |
| 10 | (1S,4R)-4-[3-(1-dimethylamino-1-methyl-ethyl)-[1,2,4]triazolo[4,3-a]pyridin-6-yloxy]-1,2,3,4-tetrahydro-naphthalen-1-ylamine (WO 2013/083604, which is incorporated herein by reference in its entirety) | N-[5-tert-Butyl-3-(3-{(1S,4R)-4-[3-(1-dimethylamino-1-methyl-ethyl)-[1,2,4]triazolo[4,3-a]pyridin-6-yloxy]-1,2,3,4-tetrahydro-naphthalen-1-yl}-ureido)-2-methoxy-phenyl]-acetamide | $^1$H NMR (400 MHz, CDCl$_3$): 1.30 (9H, s), 1.59 (6H, s), 1.97-2.24 (12H, m), 2.24-2.33 (1H, m), 3.77 (3H, s), 5.14-5.22 (2H, m), 5.38 (1H, d, J = 8.6 Hz), 6.62 (1H, s), 7.00 (1H, dd, J = 9.9, 2.1 Hz), 7.25-7.40 (3H, m), 7.48-7.58 (3H, m), 7.62 (1H, d, J = 10.2 Hz), 8.14 (1H, s), 8.65 (1H, d, J = 1.7 Hz) | (Method 2): Rt 3.35 min, m/z 628 [MH$^+$]. |

TABLE 2-continued

| Ex. | Intermediate | Structure | NMR (400 MHz) δ | LC-MS |
|---|---|---|---|---|
| 11 | (1S,4R)-4-[3-((S)-1-Methyl-pyrrolidin-2-yl)-[1,2,4]triazolo[4,3-a]pyridin-6-yloxy]-1,2,3,4-tetrahydro-naphthalen-1-ylamine (WO 2014/195402, which is incorporated herein by reference in its entirety) | N-[5-tert-Butyl-2-methoxy-3-(3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-ureido)-2-methoxy-phenyl]-acetamide | ¹H NMR (400 MHz, d-₆-DMSO): 1.21 (9H, s), 1.83-2.23 (14H, m), 2.33 (1H, q, J = 8.4 Hz), 3.10-3.15 (1H, m), 3.60 (3H, s), 3.98 (1H, t, J = 8.0 Hz), 4.86-4.93 (1H, m), 5.41 (1H, t, J = 4.2 Hz), 7.25-7.47 (7H, m), 7.73-7.76 (1H, m), 7.97 (1H, br s), 8.08 (1H, br s), 8.26 (lH, d, J = 1.4 Hz), 9.21 (1H, br s) | (Method 2): Rt 3.27 min, m/z 626 [MH⁺]. |
| 12 | (1S,4R)-4-[3-((S)-1-methyl-piperidin-2-yl)-[1,2,4]triazolo[4,3-a]pyridin-6-yloxy]-1,2,3,4-tetrahydro-naphthalen-1-ylamine (WO 2013/083604 | N-[5-tert-Butyl-2-methoxy-3-(3-{(1S,4R)-4-[3-((S)-1-methyl-piperidin-2-yl)-[1,2,4]triazolo[4,3-a]pyridin-6-yloxy]-1,2,3,4-tetrahydro-naphthalen-1-yl}-ureido)-phenyl]-acetamide | ¹H NMR (400 MHz, d-₆-DMSO): 1.24 (9H, s), 1.37-1.48 (1H, m), 1.59-2.22 (15H, m), 2.97-3.03 (1H, m), 3.62 (3H, s), 3.77-3.82 (1H, m), 4.90-4.96 (1H, m), 5.44 (1H, t, J = 4.5 Hz), 7.28-7.50 (7H, m), 7.77 (1H, dd, J = 9.8, 0.5 Hz), 8.01 (1H, br s), 8.11 (1H, d, J = 2.0 Hz), 8.44 (1H, d, J = 1.5 Hz), 9.25 (1H, br s), plus one proton obscured by solvent | (Method 2): Rt 3.33 min, m/z 640 [MH⁺]. |

Intermediate E. Ethanesulfonic acid (5-tert-butyl-3-isocyanato-2-methoxy-phenyl)-amide

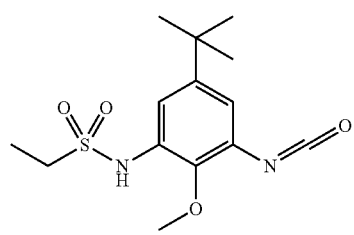 [SMILES: CCS(=O)(=O)Nc1cc(C(C)(C)C)cc(N=C=O)c1OC]

a. 5-tert-Butyl-2-methoxy-3-nitro-phenylamine (Intermediate Ea)

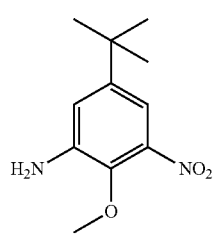 [SMILES: COc1c(N)cc(C(C)(C)C)cc1[N+](=O)[O-]]

A solution of 5-tert-butyl-2-methoxy-1,3-dinitro-benzene (CAS: 77055-30-2, 25.0 g, 98.4 mmol) in IMS (250 ml) was treated with palladium on activated charcoal (10% Pd, 2.50 g) and 4-methyl-cyclohexene (28.3 g, 295 mmol). The reaction mixture was heated at reflux for 5 h, then it was cooled at RT, filtered through a pad of celite and the solvent was removed under reduced pressure. The residue was partitioned in Et₂O and an aqueous 1M HCl solution and the two phases were separated. The organic phase was washed with water and brine, dried with Na₂SO₄ and the solvent was removed under reduced pressure to afford the title compound (21.6 g, 98%).

¹H NMR (300 MHz, CDCl₃): 1.29 (9H, s), 3.88 (3H, s), 4.01 (2H, br s), 6.97 (1H, d, J=2.3 Hz), 7.21 (1H, d, J=2.3 Hz).

b. Ethanesulfonic acid (5-tert-butyl-2-methoxy-3-nitro-phenyl)-amide (Intermediate Eb)

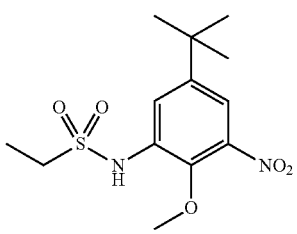 [SMILES: CCS(=O)(=O)Nc1cc(C(C)(C)C)cc([N+](=O)[O-])c1OC]

A stirred solution of Intermediate Ea (0.93 g, 4.15 mmol) and pyridine (0.93 ml, 11.5 mmol) in toluene (10 ml) was treated with ethanesulfonyl chloride (0.47 ml, 4.98 mmol) and heated at 80° C. overnight. The reaction mixture was cooled at RT, diluted with EtOAc and washed with an aqueous 1M HCl solution (×2), a saturated aqueous NaHCO$_3$ solution (×2) and brine (×2). The organic phase was dried with MgSO$_4$ and the solvent was removed under reduced pressure. Purification by FCC, eluting with DCM afforded the title compound (0.72 g, 55%).

LCMS (Method 1): Rt 3.96 min, m/z 317 [MH$^+$].

c. Ethanesulfonic acid (3-amino-5-tert-butyl-2-methoxy-phenyl)-amide (Intermediate Ec)

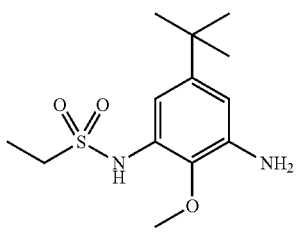 [SMILES: CCS(=O)(=O)Nc1cc(C(C)(C)C)cc(N)c1OC]

A stirred solution of Intermediate Eb (0.72 g, 2.28 mmol) in IMS (14 ml) was treated with palladium on activated charcoal (10% Pd, 80 mg) and ammonium formate (0.72 g, 11.38 mmol) and heated at 40° C. for 1 day. Another aliquot of ammonium formate (0.72 g, 11.4 mmol) was added and the reaction mixture was heated at 50° C. for 1 day. Further aliquots of ammonium formate (1.00 g, 15.9 mmol) and palladium on activated charcoal (10% Pd, 100 mg) were added and the reaction mixture was heated at 50° C. for 4 hours. The reaction mixture was cooled at RT, diluted with EtOAc and filtered through a pad of Celite®. The solvent was removed under reduced pressure and the residue was partitioned between EtOAc and H$_2$O. The two phases were separated and the organic phase was washed with H$_2$O and brine. The organic phase was dried with MgSO$_4$ and the solvent was removed under reduced pressure to afford the title compound (333 mg, 51%).

$^1$H NMR (300 MHz, CDCl$_3$): 1.26 (9H, s), 1.36 (3H, t, J=7.4 Hz), 3.16 (2H, q, J=7.4 Hz), 3.75 (2H, bs), 3.76 (3H, s), 6.53 (1H, d, J=2.2 Hz), 6.74 (1H, bs), 6.97 (1H, d, J=2.2 Hz).

d. Ethanesulfonic acid (5-tert-butyl-3-isocyanato-2-methoxy-phenyl)-amide (Intermediate E)

The title compound (206 mg, 95%) was prepared starting from Intermediate Ec (200 mg, 0.70 mmol) using the procedure described to make Intermediate A.

$^1$H NMR (300 MHz, CDCl$_3$): 1.28 (911, s), 1.38 (3H, t, J=7.4 Hz), 3.16 (2H, q, J=7.4 Hz), 3.88 (3H, s), 6.74 (1H, bs), 6.83 (1H, d, J=2.2 Hz), 7.41 (1H, d, J=2.2 Hz).

Intermediate F. Cyclopropanesulfonic acid (5-tert-butyl-3-isocyanato-2-methoxy-phenyl)-amide

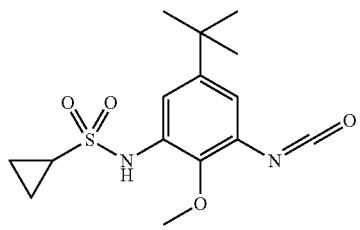 [SMILES: COc1c(N=C=O)cc(C(C)(C)C)cc1NS(=O)(=O)C1CC1]

The title compound (251 mg, quant.) was prepared starting from N-[3-amino-5-(1, 1-dimethylethyl)-2-methoxyphenyl]-cyclopropanesulfonamide (WO 2010/026095, which is incorporated herein by reference in its entirety, 200 mg, 0.67 mmol) using the procedure described to make Intermediate A. $^1$H NMR (300 MHz, d$_6$-DMSO): 0.88-1.04 (4H, m), 1.23 (9H, s), 2.67-2.78 (1H, m), 3.85 (3H, s), 6.98 (1H, d, J=2.2 Hz), 7.30 (1H, d, J=2.2 Hz), 9.35 (1H, br s).

Intermediate G. 2-Methoxy-ethanesulfonic acid (5-tert-butyl-3-isocyanato-2-methoxy-phenyl)-amide

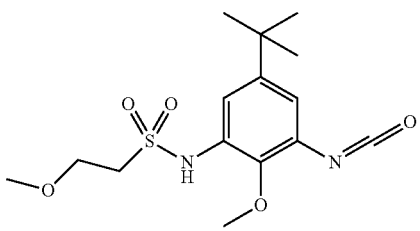 [SMILES: COCCS(=O)(=O)Nc1cc(C(C)(C)C)cc(N=C=O)c1OC]

a. 2-Methoxy-ethanesulfonic acid (5-tert-butyl-2-methoxy-3-nitro-phenyl)-amide (Intermediate Ga)

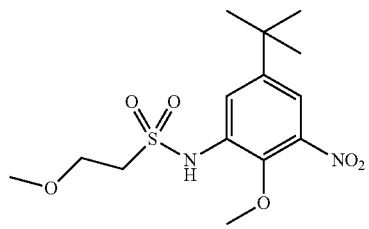 [SMILES: COCCS(=O)(=O)Nc1cc(C(C)(C)C)cc([N+](=O)[O-])c1OC]

The title compound (820 mg, 57%) was prepared starting from Intermediate Ea (930 mg, 4.15 mmol) and 2-Methoxy-ethanesulfonyl chloride (790 mg, 4.98 mmol) using the procedure described to make Intermediate Eb.

LCMS (Method 1): Rt 3.95 min, m/z 347 [MH$^+$].

b. 2-Methoxy-ethanesulfonic acid (3-amino-5-tert-butyl-2-methoxy-phenyl)-amide (Intermediate Gb)

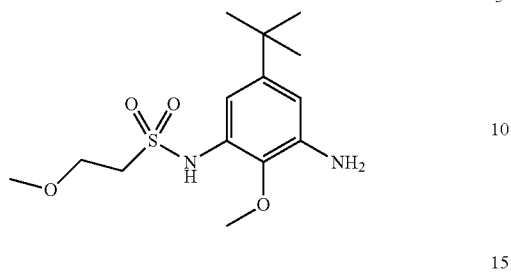

The title compound (335 mg, 45%) was prepared starting from Intermediate Gb (820 mg, 2.37 mmol) using the procedure described to make Intermediate Ec.

$^1$H NMR (300 MHz, CDCl$_3$): 1.26 (9H, s), 3.32 (3H, s), 3.39 (2H, t, J=6.0 Hz), 3.74 (2H, bs), 3.75 (3H, s), 3.80 (2H, t, J=6.0 Hz), 6.53 (1H, d, J=2.2 Hz), 6.89 (1H, bs), 7.01 (1H, d, J=2.2 Hz).

c. Cyclopropanesulfonic acid (5-tert-butyl-3-isocyanato-2-methoxy-phenyl)-amide (Intermediate G)

The title compound (174 mg, 81%) was prepared starting from Intermediate Gb (200 mg, 0.63 mmol) using the procedure described to make Intermediate A.

$^1$H NMR (300 MHz, CDCl$_3$): 1.28 (9H, s), 3.34 (3H, s), 3.38 (2H, t, J=5.8 Hz), 3.82 (2H, t, J=5.8 Hz), 3.86 (3H, s), 6.82 (1H, d, J=2.2 Hz), 6.97 (1H, bs), 7.47 (1H, d, J=2.2 Hz).

Intermediate H. 2-Methyl-propane-1-sulfonic acid (5-tert-butyl-3-isocyanato-2-methoxy-phenyl)-amide

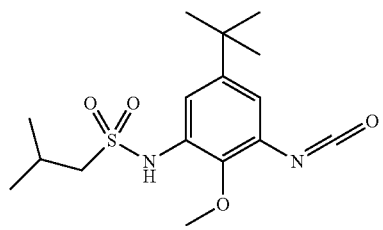 [SMILES: COc1c(N=C=O)cc(C(C)(C)C)cc1NS(=O)(=O)CC(C)C]

a. 2-Methyl-propane-1-sulfonic acid (5-tert-butyl-2-methoxy-3-nitro-phenyl)-amide (Intermediate Ha)

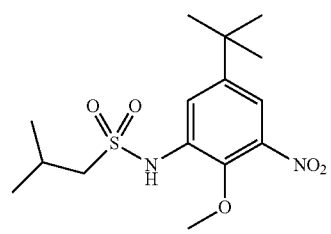

The title compound (631 mg, 44%) was prepared starting from Intermediate Ea (940 mg, 4.19 mmol) and 2-methyl-1-propanesulfonyl chloride (0.98 ml, 6.29 mmol), using the procedure described to make Intermediate Eb.

$^1$H NMR (300 MHz, CDCl$_3$): 1.11 (6H, d, J=6.7 Hz), 1.34 (9H, s), 2.25-2.39 (1H, m), 3.01 (2H, d, J=6.5 Hz), 3.92 (3H, s), 6.95 (1H, br s), 7.61 (1H, d, J=2.3 Hz), 7.85 (1H, d, J=2.3 Hz).

b. 2-Methyl-propane-1-sulfonic acid (3-amino-5-tert-butyl-2-methoxy-phenyl)-amide (Intermediate Hb)

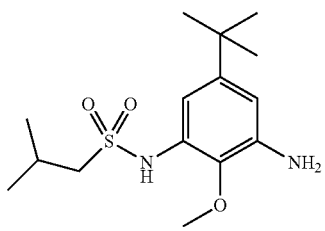 [SMILES: COc1c(NS(=O)(=O)CC(C)C)cc(C(C)(C)C)cc1[N+](=O)[O-]]

The title compound (535 mg, 92%) was prepared starting from Intermediate Hb (630 mg, 1.83 mmol) using the procedure described to make Intermediate Ec.

LCMS (Method 1): Rt 3.78 min, m/z 315 [MH$^+$].

c. 2-Methyl-propane-1-sulfonic acid (5-tert-butyl-3-isocyanato-2-methoxy-phenyl)-amide (Intermediate H)

The title compound (670 mg, quant., containing ~2.0 mol % of toluene) was prepared starting from Intermediate Hb (530 mg, 1.69 mmol) using the procedure described to make Intermediate A.

$^1$H NMR (300 MHz, CDCl$_3$): 1.10 (6H, d, J=6.7 Hz), 1.28 (9H, s), 2.25-2.35 (1H, m), 3.02 (2H, d, J=6.5 Hz), 3.86 (3H, s), 6.76 (1H, br s), 6.82 (1H, d, J=2.3 Hz), 7.40 (1H, d, J=2.3 Hz).

Examples 13-16

General Procedure for the Examples 13-16

A solution of (1S,4R)-4-[3-(1-dimethylamino-1-methyl-ethyl)-[1,2,4]triazolo[4,3-a]pyridin-6-yloxy]-1,2,3,4-tetrahydro-naphthalen-1-ylamine (WO 2013/083604, which is incorporated herein by reference in its entirety, 0.27 mmol) and an appropriate isocyanate (see Table 3) (0.30 mmol) in 2-methyltetrahydrofuran (2 ml) was stirred at RT for 1 day. The reaction mixture was diluted with DCM and washed with H$_2$O (×2) and brine. The organic phase was passed through a phase separator and the solvent was removed under reduced pressure. The resulting residue was purified by FCC, eluting with 0-5% 2M NH$_3$ in MeOH/DCM or MDAP (Method 6) to afford the title compound (Example 14, 30%). For obtaining Examples 13, 15 and 16, after purification the obtained solid was dissolved in MeCN (1 ml) and H$_2$O (1 ml) and an aqueous HCl solution (1M, 1 equivalent) was added. The mixture was lyophilised to afford the title compounds (Examples 13, 15 and 16, 12-23%).

| Ex. | Intermediate | Structure | NMR (400 MHz) δ | LC-MS |
|---|---|---|---|---|
| 13 | Intermediate E | H—Cl<br><br>Ethanesulfonic acid [5-tert-Butyl-3-(3-{(1S,4R)-4-[3(1-dimethylamino-1-methyl-ethyl)-[1,2,4]triazolo[4,3-a]pyridin-6-yloxy]-1,2,3,4-tetrahydro-naphthalen-1-yl}-ureido)-2-methoxy-phenyl]-amide hydrochloride salt | $^1$H NMR (400 MHz, d$_6$-DMSO): 1.25 (9H, s), 1.27 (3H, t, J = 7.4 Hz), 1.82-2.23 (12H, m), 2.65-2.90 (4H, m), 3.13 (2H, q, J = 7.4 Hz), 3.69 (3H,s), 4.88-4.97 (1H, m), 5.83 (1H, bs), 6.92 (1H, d, J = 2.2 Hz), 7.32 (1H, td, J = 7.4, 1.4 Hz), 7.36-7.46 (4H, m), 7.89 (1H, d, J = 9.6 Hz), 8.10 (1H, s), 8.18 (1H, d, J = 2.2 Hz), 8.62 (1H, bs), 8.99 (1H, s), 11.06 (1H, bs). | (Method 3): Rt 3.71 min, m/z 678 [MH$^+$] |
| 14 | Intermediate F | 0.75eq. Formic Acid<br><br>Cyclopropanesulfonic acid [5-tert-butyl-3-(3-{(1S,4R)-4-[3(1-dimethylamino-1-methyl-ethyl)-[1,2,4]triazolo[4,3-a]pyridin-6-yloxy]-1,2,3,4-tetrahydro-naphthalen-1-yl}-ureido)-2-methoxy-phenyl]-amide partial formate salt | $^1$H NMR (400 MHz, d$_6$-DMSO): 0.91-1.02 (4H, m), 1.25 (9H, s), 1.51 (3H, s), 1.52 (3H, s), 1.84-2.22 (4H, m), 2.13 (6H, s), 2.65-2.73 (1H, m), 3.70 (3H, s), 4.88-4.97 (1H, m), 5.44 (1H, t, J = 4.5 Hz), 7.01 (1H, d, J = 2.4 Hz), 7.28-7.46 (6H, m), 7.75 (1H, dd, J = 9.9, 0.6 Hz), 8.06 (1H, s), 8.16 (0.75H, s), 8.18 (1H, d, J = 2.3 Hz), 8.58 (1H, d, J = 1.8 Hz), 9.03 (1H, br s). | (Method 2): Rt 3.74 min, m/z 690 [MH$^+$]. |
| 15 | Intermediate G | H—Cl<br><br>2-Methoxy-ethanesulfonic acid [5-tert-butyl-3-(3-{(1S,4R)-4-[3(1-dimethylamino-1-methyl-ethyl)-[1,2,4]triazolo[4,3-a]pyridin-6-yloxy]-1,2,3,4-tetrahydro-naphthalen-1-yl}-ureido)-2-methoxy-phenyl]-amide hydrochloride salt | $^1$H NMR (400 MHz, d$_6$-DMSO): 1.25 (9H, s), 1.83-2.24 (12H, m), 2.64-2.91 (4H, m), 3.24 (3H, s), 3.41 (2H, m, partially obscured by H$_2$O), 3.68 (3H, s), 3.73 (2H, t, J = 6.2 Hz), 4.88-4.97 (1H, m), 5.84 (1H, bs), 6.95 (1H, d, J = 2.4 Hz), 7.32 (1H, td, J = 7.4, 1.3 Hz), 7.36-7.48 (4H, m), 7.89 (1H, d, J = 9.8 Hz), 8.10 (1H, s), 8.19 (1H, d, J = 2.2 | (Method 3): Rt 3.69 min, m/z 708 [MH$^+$]. |

TABLE 3-continued

| Ex. | Intermediate | Structure | NMR (400 MHz) δ | LC-MS |
|---|---|---|---|---|
| 16 | Intermediate H | 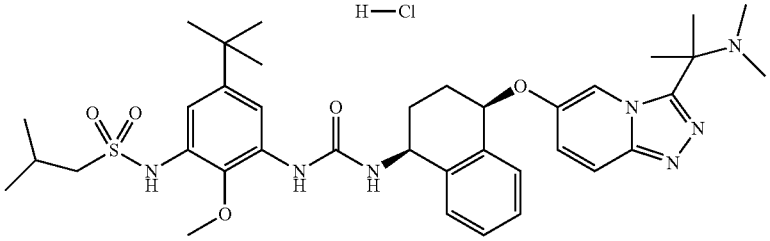<br>2-Methyl-propane-1-sulfonic acid [5-tert-Butyl-3-(3-{(1S,4R)-4-[3(1-dimethylamino-1-methyl-ethyl)-[1,2,4]triazolo[4,3-a]pyridin-6-yloxy]-1,2,3,4-tetrahydro-naphthalen-1-yl}-ureido)-2-methoxy-phenyl]-amide hydrochloride salt | Hz), 8.64 (1H, d, J = 1.1 Hz), 9.01 (1H, s), 11.10 (1H, bs) plus one proton not observed.<br>$^1$H NMR (400 MHz, d$_6$-DMSO): 1.03 (6H, d, J = 6.7 Hz), 1.25 (9H, s), 1.86-2.23 (4H, m), 2.66-2.94 (1H, m), 3.04 (2H, d, J = 6.4 Hz), 3.68 (3H, s), 4.89-4.96 (2H, m), 5.82 (1H, bs), 6.92 (1H, d, J = 2.3 Hz), 7.30-7.45 (6H, m), 7.86-7.91 (1H, br s), 8.10 (1H, s), 8.18 (1H, d, J = 2.4 Hz), 8.60 (1H, br s), 9.02 (1H, s), 11.00 (1H, bs), plus six protons obscured by water | (Method 3): Rt 4.12 min, m/z 706 [MH$^+$]. |

Example 17. N-[5-tert-Butyl-2-methoxy-3-(3-{(1S,4R)-4-[3-((S)-1-methyl-pyrrolidin-2-1)-[1,2,4]triazolo[4,3-a]pyridin-6-yloxy]-1,2,3,4-tetrahydro-naphthalen-1-yl}-ureido)-phenyl]-N-(2-hydroxy-ethyl)-methanesulfonamide formate salt

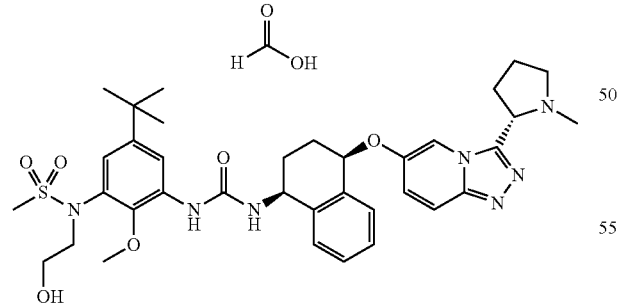

a. N-(3-Amino-5-tert-butyl-2-methoxy-phenyl)-N-[2-(tetrahydro-pyran-2-yloxy)-ethyl]-methanesulfonamide (Intermediate 17a)

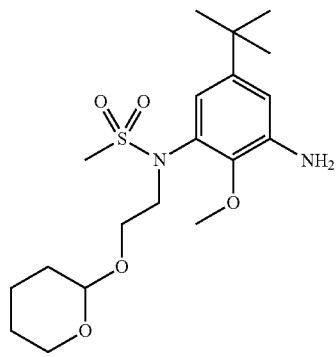 [SMILES: COc1c(N)cc(C(C)(C)C)cc1N(CCOC1CCCCO1)S(C)(=O)=O]

To a stirred solution of N-(3-amino-5-tert-butyl-2-methoxy-phenyl)-methanesulfonamide (WO 2013/083604, which is incorporated herein by reference in its entirety, 500 mg, 1.84 mmol) in DMF was added K$_2$CO$_3$ (381 mg, 2.75 mmol) and 2-(2-bromoethoxy)tetrahydro-2H-pyran (277 μl, 1.84 mmol). The reaction mixture was heated at 80° C. for 18 hours, cooled at RT and partitioned between EtOAc and H$_2$O. The aqueous phase was extracted with EtOAc (×2) and the combined organic phases were washed with brine (×2), dried with MgSO$_4$ and the solvent was removed under reduced pressure. Purification by FCC, eluting with 0-100% EtOAc/cyclohexane afforded the title compound (393 mg, 53%).

LCMS (Method 1): Rt 3.85 min, m/z 401 [MH$^+$].

b. N-(5-tert-Butyl-3-isocyanato-2-methoxy-phenyl)-N-[2-(tetrahydro-pyran-2-yloxy)-ethyl]-methanesulfonamide (Intermediate 17b)

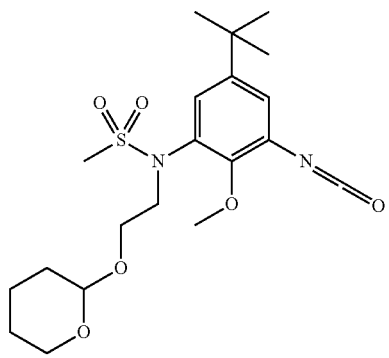 [SMILES: COc1c(N=CC=O)cc(C(C)(C)C)cc1N(CCOC1CCCCO1)S(C)(=O)=O]

The title compound (360 mg, 89%) was prepared starting from Intermediate 17a (378 mg, 0.94 mmol) using the procedure described to make Intermediate A.

LCMS (Method 1): Rt 4.59 min, m/z 449 [MNa$^+$].

c. N-[5-tert-Butyl-2-methoxy-3-(3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-ureido)-phenyl]-N-[2-(tetrahydro-pyran-2-yloxy)-ethyl]-methanesulfonamide (Intermediate 17c)

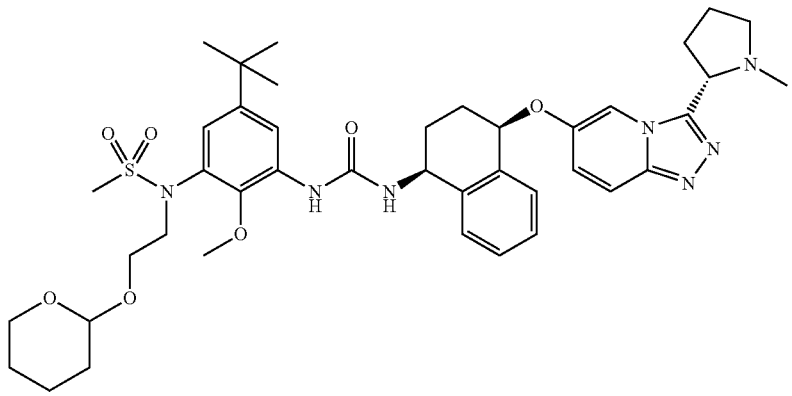 [SMILES: COc1c(NC(=O)N[C@H]2CC[C@@H](Oc3ccc4nnc([C@@H]5CCCN5C)n4c3)c3ccccc32)cc(C(C)(C)C)cc1N(CCOC1CCCCO1)S(C)(=O)=O]

To a stirred solution of Intermediate 17b (360 mg, 0.84 mmol) in dioxane (4 ml) at 0° C. was added DIPEA (440 μl, 2.53 mmol) and (1S,4R)-4-[3-(S)-1-methyl-pyrrolidin-2-yl)-[1,2,4]triazolo[4,3-a]pyridin-6-yloxy]-1,2,3,4-tetrahydro-naphthalen-1-ylamine (WO 2014/195402, 307 mg, 0.84 mmol). The reaction mixture was stirred at 0° C. for 1 hour, warmed at RT overnight and then partitioned between EtOAc and brine.

The two phases were separated and the aqueous phase was extracted with EtOAc. The combined organic phases were washed with brine, dried with MgSO$_4$ and the solvent was removed under reduced pressure. Purification by FCC, eluting with 0-10% 2M NH$_3$ in MeOH/DCM afforded the title compound (340 mg, 51%).

LCMS (Method 1): Rt 3.08 min, m/z 790 [MH$^+$].

d. N-[5-tert-Butyl-2-methoxy-3-(3-{(1S,4R)-4-[3-((S)-1-methyl-pyrrolidin-2-1)-[1,2,4]triazolo[4,3-a]pyridin-6-yloxy]-1,2,3,4-tetrahydro-naphthalen-1-yl}-ureido)-phenyl]-N-(2-hydroxy-ethyl)-methanesulfonamide formate salt (Example 17)

A stirred solution of Intermediate 17c (220 mg, 0.28 mmol) in MeOH (5 ml) was treated with pyridinium p-toluene sulfonate (210 mg, 0.84 mmol) and heated at 45° C. overnight. A further aliquot of pyridinium p-toluene sulfonate (210 mg, 0.84 mmol) was added and the reaction mixture was stirred at 45° C. for other 24 hours. The volatiles were removed under reduced pressure and the residue was partitioned between DCM and a saturated aqueous NaHCO$_3$ solution. The two phases were separated and the aqueous phase was extracted with DCM. The combined organic phases were washed with a saturated aqueous NaHCO$_3$ solution, passed through a phase separator and the solved was removed under reduced pressure. Purification by MDAP (Method 6) afforded the title compound (116 mg, 59%).

LCMS (Method 3): Rt 3.21 min, m/z 706 [MH$^+$]. $^1$H NMR (400 MHz, d$_6$-DMSO): 1.24 (9H, s), 1.83-2.23 (12H, m), 2.33 (1H, q, J=8.7 Hz), 3.10-3.63 (8H, m, partially covered by H$_2$O signal), 3.75 (3H, s), 3.97 (1H, t, J=7.9 Hz), 4.86-4.93 (1H, m), 5.40 (1H, t, J=4.4 Hz), 6.89 (1H, d, J=2.3 Hz), 7.24-7.41 (6H, m), 7.73 (1H, d, J=10.0 Hz), 8.03 (1H, br s), 8.13 (1H, br s), 8.25 (1H, br s), 8.30 (1H, d, J=2.6 Hz).

Example 18. 1-(3-Amino-5-tert-butyl-2-methoxy-phenyl-3-{(1S,4R)-4-[3-(1-dimethylamino-1-methyl-ethyl)-[1,2,4]triazolo[4,3-a]pyridin-6-yloxy]-1,2,3,4-tetrahydro-naphthalen-1-yl}-urea

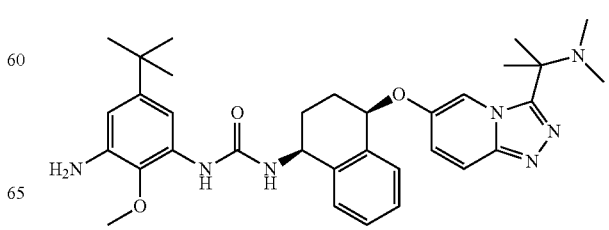

a. N-(5-tert-Butyl-2-methoxy-3-nitro-phenyl)-2,2,2-trifluoro-acetamide (Intermediate 18a)

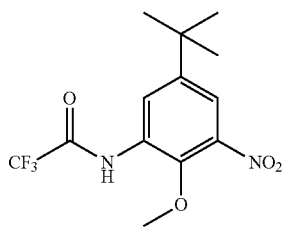 [SMILES: COc1c(NC(=O)C(F)(F)F)cc(C(C)(C)C)cc1[N+](=O)[O-]]

A stirred solution of Intermediate Ea (2.24 g, 10.0 mmol) and pyridine (2.0 ml, 25.0 mmol) in DCM (25 ml) at 0° C. was treated with TFAA (1.74 ml, 12.5 mmol). The reaction mixture was warmed at RT, diluted with DCM and washed with an aqueous 1M HCl solution (×2), a saturated aqueous NaHCO$_3$ solution (×2) and brine. The organic phase was passed through a phase separator and the solvent was removed under reduced pressure. Purification by FCC, eluting with 0-20% EtOAc/cyclohexane afforded the title compound (2.87 g, 90%).

LCMS (Method 1): Rt 4.20 min, m/z 321 [MH$^+$].

b. N-(3-Amino-5-tert-butyl-2-methoxy-phenyl)-2,2,2-trifluoro-acetamide (Intermediate 18b)

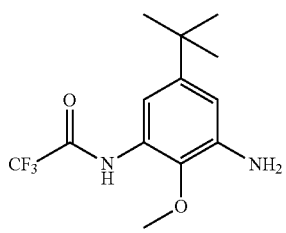

A stirred solution of Intermediate 18a (1.50 g, 4.68 mmol) in IMS (20 ml) was treated with palladium on activated charcoal (10% Pd, 150 mg). The vessel was evacuated and filled with argon (×3) and then it was evacuated and filled with hydrogen. The reaction mixture was stirred at RT for 18 hours, diluted with EtOAc and filtered through a pad of Celite®. The solvent was removed under reduced pressure to give the title compound (1.34 g, 99%).

LCMS (Method 1): Rt 3.73 min, m/z 291 [MH$^+$].

c. N-(5-tert-Butyl-3-isocyanato-2-methoxy-phenyl)-2,2,2-trifluoro-acetamide (Intermediate 18c)

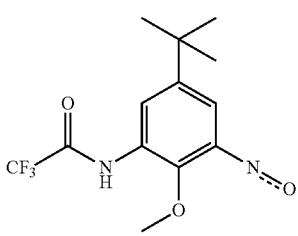

The title compound (1.22 g, 84%) was prepared starting from Intermediate 18b (1.34 mg, 4.62 mmol) using the procedure described to make Intermediate A.

$^1$H NMR (300 MHz, CDCl$_3$): 1.30 (9H, s), 3.90 (3H, s), 6.93 (1H, d, J=2.2 Hz), 8.16 (1H, d, J=2.2 Hz), 8.35 (1H, br s).

d. N-[5-tert-Butyl-3-(3-{(1S,4R)-4-[3-(1-dimethyl-amino-1-methyl-ethyl)-[1,2,4]triazolo[4,3-a]pyridin-6-yloxy]-1,2,3,4-tetrahydro-naphthalen-1-yl}-ureido)-2-methoxy-phenyl]-2,2,2-trifluoro-acetamide (Intermediate 18d)

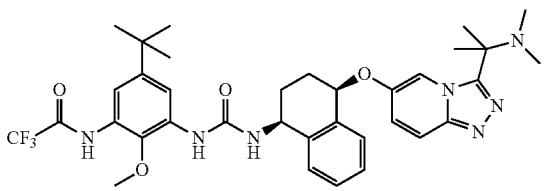 [SMILES: COc1c(NC(=O)N[C@H]2CC[C@@H](Oc3ccc4nnc(C(C)(C)N(C)C)n4c3)c3ccccc32)cc(C(C)(C)C)cc1NC(=O)C(F)(F)F]

A solution of (1S,4R)-4-[3-(1-dimethyl amino-1-methyl-ethyl)-[1,2,4]triazolo[4,3-a]pyridin-6-yloxy]-1,2,3,4-tetrahydro-naphthalen-1-ylamine (WO 2013/083604, 1.11 g, 3.04 mmol) and Intermediate 18c (1.20 g, 3.79 mmol) in 2-methyltetrahydrofuran (20 ml) was stirred at RT for 18 hours. The solvent was removed under reduced pressure. The resulting residue was purified by FCC, eluting with 0-5% 2M NH$_3$ in MeOH/DCM to afford the title compound (1.46 g, 71%).

LCMS (Method 1): Rt 3.25 min, m/z 682 [MH$^+$].

A solution of Intermediate 18d (1.46 g, 2.14 mmol) in MeOH (70 ml) and H$_2$O (4.5 ml) was treated with K$_2$CO$_3$ (1.48 g, 2.14 mmol). The reaction mixture was heated at reflux for 12 hours, cooled at RT and diluted with DCM and H$_2$O. The two phases were separated and the aqueous phase was extracted with DCM. The combined organic phases were washed with a saturated aqueous NaHCO$_3$ solution (×2) and brine, passed through a phase separator and the solvent was removed under reduced pressure. Purification by FCC, eluting with 0-10% 2M NH$_3$ in MeOH/DCM afforded the title compound (1.24 g, 99%).

LCMS (Method 3): Rt 3.49 min, m/z 586 [MH$^+$]. $^1$H NMR (400 MHz, d$_6$-DMSO): 1.20 (9H, s), 1.51 (3H, s), 1.52 (3H, s), 1.83-2.20 (4H, m), 2.13 (6H, s), 3.58 (3H, s), 4.70 (2H, bs), 4.86-4.94 (1H, m), 5.44 (1H, t, J=4.4 Hz), 6.34 (1H, d, J=2.3 Hz), 7.27-7.45 (6H, m), 7.58 (1H, d, J=2.3 Hz), 7.75 (1H, d, J=10.0 Hz), 7.83 (1H, bs), 8.58 (1H, d, J=1.9 Hz).

Intermediate I. (1S,4R)-4-[3-((R)-1,2-Dimethyl-pyrrolidin-2-yl)-[1,2,4]triazolo[4,3-a]pyridin-6-yloxy]-1,2,3,4-tetrahydro-naphthalen-1-ylamine

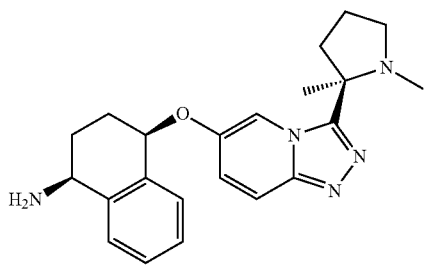 [SMILES: CN1CCC[C@]1(C)c1nnc2ccc(O[C@@H]3CC[C@H](N)c4ccccc43)cn12]

a. (R)-1,2-Dimethyl-pyrrolidine-2-carboxylic acid hydrochloride salt (Intermediate Ia)

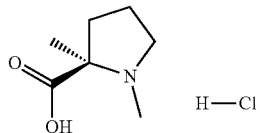

To a solution of 2-methyl-D-proline hydrochloride salt (10.0 g, 60.4 mmol) in EtOH (150 ml) was added formaldehyde (37% in water, 12.0 ml, 148 mmol) and palladium on carbon (10% Pd, 1.5 g). The vessel was evacuated and filled with hydrogen (×3) and the reaction mixture was stirred overnight at RT under hydrogen. The reaction mixture was filtered through a pad of celite and the solvent was removed under reduced pressure. The residue was triturated with ether to give the title compound (10.7 g, 99%).

$^1$H NMR (300 MHz, d$_6$-DMSO): 1.54 (3H, br s), 1.86-2.14 (3H, m), 2.28 (1H, br s), 2.76 (3H, s), 3.22-3.64 (3H, m).

b. (R)-1,2-Dimethyl-pyrrolidine-2-carboxylic acid N'-(5-Fluoro-pyridine-2-yl)-hydrazide (Intermediate Ib)

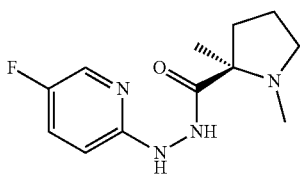 [SMILES: CN1CCC[C@]1(C)C(=O)NNc1ccc(F)cn1]

A solution of Intermediate Ia (10.6 g, 59.1 mmol), (5-fluoro-pyridin-2-yl)-hydrazine (WO 2014/195402, 7.50 g, 59.1 mmol), HOBt (0.90 g, 5.91 mmol) and DIPEA (10.1 ml, 59.1 mmol) in DCM (150 ml) was treated with EDC (11.3 g, 59.1 mmol). The reaction mixture was stirred at RT for 2 hours. The volatiles were removed under reduced pressure and the residue was partitioned between EtOAc and H$_2$O. The organic phase was washed with H$_2$O and brine, dried with Na$_2$SO$_4$ and the solvent was removed under reduced pressure. The crude was purified by FCC eluting with DCM, followed by 10% acetone/DCM and finally 0-5% 2M NH$_3$ in MeOH/DCM. The resulting solid was triturated with petrol ether to give the title compound (7.60 g, 51%).

$^1$H NMR (300 MHz, CDCl$_3$): 1.24 (3H, s), 1.73-1.92 (311, m), 2.12-2.30 (1H, m), 2.38 (3H, s), 2.50-2.63 (1H, m), 3.07-3.18 (1H, m), 6.53 (1H, br s), 6.60 (1H, dd, J=9.0, 3.6 Hz), 7.22-7.33 (1H, m), 8.03 (1H, d, J=2.7 Hz), 9.33 (1H, br s).

c. 3-((R)-1,2-Dimethyl-pyrrolidin-2-yl)-6-fluoro-[1,2,4]triazolo[4,3-a]pyridine (Intermediate Ic)

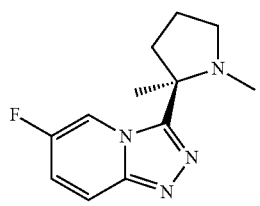 [SMILES: CN1CCC[C@]1(C)c1nnc2ccc(F)cn12]

Hexachloroethane (2.22 g, 9.40 mmol) was added portion-wise to a stirred solution of Intermediate Ib (7.50 g, 29.8 mmol), triphenylphosphine (15.6 g, 59.5 mmol) and TEA (16 ml, 118.9 mmol) in 2-methyltetrahydrofuran (150 ml) and the reaction mixture was stirred at 80° C. for 1 h. The reaction mixture was cooled at RT, diluted with H$_2$O and the two phases were separated. The organic phase was washed with H$_2$O and extracted with an aqueous 0.5 M citric acid solution. The aqueous phase was washed with 2-methyltetrahydrofuran and then basified with solid K$_2$CO$_3$. The resulting aqueous phase was extracted with DCM (×3) and the combined organic phases were dried with Na$_2$SO$_4$ and the solvent was removed under reduced pressure to afford the title compound (6.74 g, 97%).

$^1$H NMR (300 MHz, CDCl$_3$): 1.65 (3H, s), 1.85-2.28 (7H, m), 2.74 (1H, q, J=8.7 Hz), 3.20-3.30 (1H, m), 7.17 (1H, ddd, J=9.9, 7.3, 2.1 Hz), 7.73 (1H, dd, J=9.9, 5.0 Hz), 8.82 (1H, m).

d. (1S,4R)-4-[3-((R)-1,2-Dimethyl-pyrrolidin-2-yl)-[1,2,4]triazolo[4,3-a]pyridin-6-yloxy]-1,2,3,4-tetrahydro-naphthalen-1-ylamine (Intermediate I)

To a stirred solution of Intermediate Ic (6.50 g, 27.8 mmol), (1R,4S)-4-amino-1,2,3,4-tetrahydro-naphthalen-1-ol (WO 2014/195402, 4.53 g, 27.8 mmol) and 18-crown-6 (750 mg, 2.8 mmol) in 2-methyltetrahydrofuran (100 ml) at 0° C. under nitrogen was added potassium tert-butoxide (3.58 g, 32.0 mmol). The reaction mixture was warmed at RT, stirred overnight and quenched with H$_2$O. The two phases were separated and the organic phase was washed with H$_2$O and extracted with an aqueous 0.5M citric acid solution. The aqueous phase was washed with Et$_2$O and then basified with solid K$_2$CO$_3$. The resulting aqueous phase was extracted with DCM. The organic phase was dried with Na$_2$SO$_4$ and the solvent was removed under reduced pressure to afford the title compound (8.32 g, 79%).

$^1$H NMR (300 MHz, CDCl$_3$): 1.65 (3H, s), 1.84-2.13 (10H, m), 2.18-2.39 (2H, m), 2.73 (1H, q, J=8.9 Hz), 3.11-3.21 (1H, m), 3.98 (1H, dd, J=8.4, 5.1 Hz), 5.17 (1H, t, J=4.5 Hz), 7.11 (1H, dd, J=9.9, 2.3 Hz), 7.29 (1H, d, J=7.2 Hz), 7.33-7.43 (2H, m), 7.60 (1H, d, J=7.7 Hz), 7.68 (1H, dd, J=9.9, 0.8 Hz), 8.57 (1H, d, J=2.2 Hz) plus one proton obscured by water.

Intermediate J. (1S,4R)-4-[3-((S)-1-Dimethylamino-2-methyl-propyl)-[1,2,4]triazolo[4,3-a]pyridin-6-yloxy]-1,2,3,4-tetrahydro-naphthalen-1-ylamine

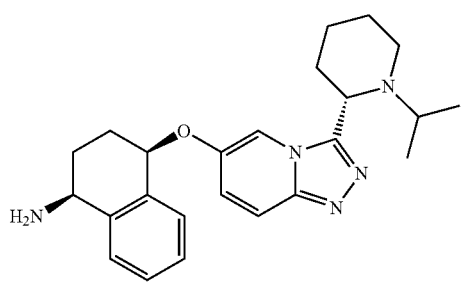 [SMILES: CC(C)N1CCCC[C@H]1c1nnc2ccc(O[C@@H]3CC[C@H](N)c4ccccc43)cn12]

a. 1-Isopropyl-piperidine-2-carboxylic acid N'-(5-fluoro-pyridin-2-yl)-hydrazide (Intermediate Ja)

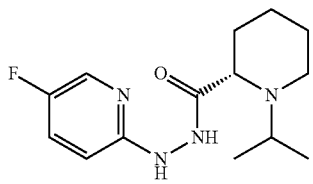 [SMILES: CC(C)N1CCCC[C@H]1C(=O)NNc1ccc(F)cn1]

The title compound was prepared starting from 1-isopropyl-L-pipecolinic acid (CAS: 1141826-51-8, 1.41 g, 8.23 mmol) and (5-fluoro-pyridin-2-yl)-hydrazine (WO 2014/195402, which is incorporated herein by reference in its entirety, 7.50 g, 59.1 mmol) using the procedure described to make Intermediate Ib.
LCMS (Method 1): Rt 0.45 min, m/z 281 [MH⁺].

b. 6-Fluoro-3-((S)-1-isopropyl-piperidin-2-yl)-[1,2,4]triazolo[3,4-a]pyridine (Intermediate Jb)

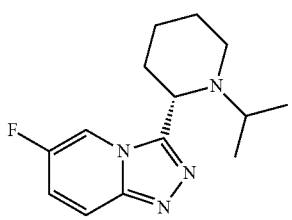 [SMILES: CC(C)N1CCCC[C@H]1c1nnc2ccc(F)cn12]

The title compound was prepared starting from Intermediate Ja (1.14 g, 4.03 mmol) using the procedure described to make Intermediate Ic. The crude mixture was purified by FCC eluting with 0-10% 2M NH₃ in MeOH/DCM to give the title compound (655 mg, 62%, cointaining 0.15 eq of triphenylphosphine oxide).
$^1$H NMR (300 MHz, CDCl₃): 0.89 (3H, d, J=6.5 Hz), 1.02 (3H, d, J=6.7 Hz), 1.33-1.92 (6H, m), 2.20-2.36 (2H, m), 2.99-3.10 (1H, m), 4.32-4.42 (1H, m), 7.17 (1H, ddd, J=10.0, 7.5, 2.3 Hz), 7.41-7.76 (1H, m, NB: this signal was partially obscured by the presence of triphenylphosphine oxide impurity), 8.78 (1H, ddd, J=4.1, 2.3, 0.8 Hz).

c. (1S,4R)-4-[3-((S)-1-Dimethylamino-2-methyl-propyl)-[1,2,4]triazolo[4,3-a]pyridin-6-yloxy]-1,2,3,4-tetrahydro-naphthalen-1-ylamine (Intermediate J)

To a stirred solution of (1R,4S)-4-amino-1,2,3,4-tetrahydro-naphthalen-1-ol (WO 2014/195402, 405 mg, 2.48 mmol) in DMF (3 ml) under nitrogen was added sodium hydride (60% dispersion in mineral oil, 298 mg, 7.45 mmol). The reaction mixture was stirred at RT for 20 minutes and then a solution of Intermediate Jb (0.652 g, 2.48 mmol) in DMF (3 ml) was added. The resulting mixture was stirred at 40° C. for 16 h, cooled at 0° C. and quenched with a saturated aqueous NH₄Cl solution. The reaction mixture was diluted with EtOAc and brine and the two phases were separated. The aqueous phase was extracted with EtOAc (×2), the combined organic phases were dried with Na₂SO₄ and the solvent was removed under pressure. Purification by FCC, eluting with 0-20% 2M NH₃ in MeOH/DCM afforded the title compound (747 mg, 74%).
$^1$H NMR (300 MHz, CDCl₃): 0.90 (3H, d, J=6.5 Hz), 1.03 (3H, d, J=6.5 Hz), 1.35-2.47 (13H, m), 2.95-3.05 (1H, m), 3.98 (1H, dd, J=8.5, 5.1 Hz), 4.30-4.40 (1H, m), 5.18 (1H, t, J=4.4 Hz), 7.11 (1H, dd, J=10.7, 2.3 Hz), 7.21-7.45 (4H, m), 7.59-7.67 (2H, m), 8.45 (1H, d, J=2.0 Hz).

Intermediate K. N-(3-tert-Butyl-5-isocyanato-phenyl)-methanesulfonamide

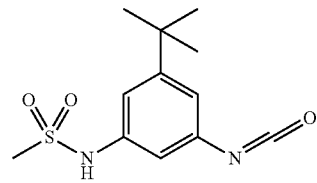 [SMILES: CC(C)(C)c1cc(N=C=O)cc(NS(C)(=O)=O)c1]

The title compound (6.20 g, quant.) was prepared starting from N-(3-amino-5-tert-butyl-phenyl)-methanesulfonamide (WO 2008/089034, which is incorporated herein by reference in its entirety, 5.50 g, 22.7 mmol) using the procedure described to make Intermediate A.
$^1$H NMR (300 MHz, CDCl₃): 1.29 (9H, s), 3.04 (3H, s), 6.66 (1H, br), 6.85 (1H, d, J=2.0 Hz), 6.91 (1H, d, J=1.7 Hz), 6.99 (1H, d, J=1.8 Hz).

Intermediate L. (1S,4R)-4-[3-((R)-4-Methyl-morpholin-3-yl)-[1,2,4]triazolo[4,3-a]pyridin-6-yloxy]-1,2,3,4-tetrahydro-naphthalen-1-ylamine

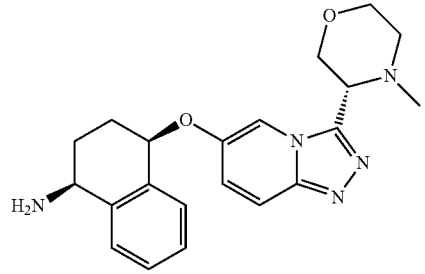 [SMILES: CN1CCOC[C@H]1c1nnc2ccc(O[C@@H]3CC[C@H](N)c4ccccc43)cn12]

a. (S)-3-[N'-(5-Fluoro-pyridin-2-yl)-hydrazinocarbonyl]-morpholine-4-carboxylic acid tert-butyl ester (Intermediate La)

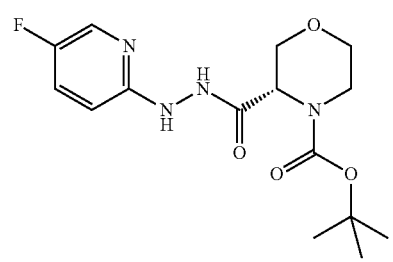 [SMILES: CC(C)(C)OC(=O)N1CCOC[C@H]1C(=O)NNc1ccc(F)cn1]

The title compound (6.37 g, 85%) was prepared starting from (3S)-4-(tert-butoxycarbonyl)morpholine-3-carboxylic acid (CAS: 783350-37-8, 5.09 g, 22.0 mmol) and (5-fluoro-pyridin-2-yl)-hydrazine (WO 2014/195402, which is incorporated herein by reference in its entirety, 2.80 g, 22.0 mmol) using the procedure described to make Intermediate Ib.

LCMS (Method 4): Rt 1.11 min, m/z 341 [MH$^+$].

b. (S)-3-[N'-(5-Fluoro-pyridin-2-yl)-hydrazinocarbonyl]-morpholine-4-carboxylic acid tert-butyl ester (Intermediate Lb)

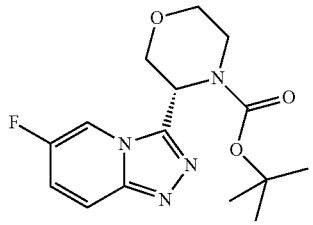 [SMILES: CC(C)(C)OC(=O)N1CCOC[C@H]1c1nnc2ccc(F)cn12]

The title compound (2.91 g, 48%) was prepared starting from Intermediate La (6.35 g, 18.7 mmol) using the procedure described to make Intermediate Ic.

LCMS (Method 4): Rt 1.15 min, m/z 323 [MH$^+$].

c. 6-Fluoro-3((R)-4-methyl-morpholin-3-yl)-[1,2,4]triazolo[4,3-a]pyridine (Intermediate Lc)

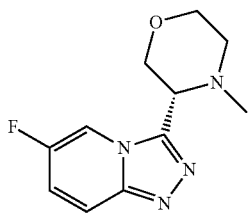 [SMILES: CN1CCOC[C@H]1c1nnc2ccc(F)cn12]

To a stirred solution of Intermediate Lb (2.91 g, 9.03 mmol) in DCM (75 ml) at 0° C. was added TFA (10 ml). The reaction mixture was warmed at RT and stirred for 18 hours. The volatiles were removed under reduced pressure and the residue was partitioned between DCM and a saturated aqueous NaHCO$_3$ solution. The two phases were separated and the aqueous phase was extracted with DCM (×3). The combined organic phases were dried with MgSO$_4$ and the solvent was removed under reduced pressure. The solid was dissolved in DCM (40 ml) and MeOH (2 ml) and the solution was treated with formaldehyde (37% in water, 2.2 ml, 30 mmol). The reaction mixture was stirred for 30 minutes at RT and then sodium triacetoxyborohydride (3.78 g, 18 mmol) was added over 15 minutes. The reaction mixture was stirred at RT for 18 hours, diluted with DCM and H$_2$O and the two phases were separated. The organic phase was washed with H$_2$O and brine, dried with MgSO$_4$ and the solvent was removed under reduced pressure. Purification by FCC, eluting with 0-10% 2M NH$_3$ in MeOH/DCM gave the title compound (1.07 g, 50%, purity ~90%).

LCMS (Method 4): Rt 0.34 min, m/z 237 [MH$^+$].

d. (1S,4R)-4-[3-((R)-4-Methyl-morpholin-3-yl)-[1,2,4]triazolo[4,3-a]pyridin-6-yloxy]-1,2,3,4-tetrahydro-naphthalen-1-ylamine (Intermediate L)

The title compound was prepared starting from Intermediate Lc (1.06 g, 4.49 mmol) and (1R,4S)-4-amino-1,2,3,4-tetrahydro-naphthalen-1-ol (WO 2014/195402, which is incorporated herein by reference in its entirety, 0.73 g, 4.49 mmol) using the procedure described to make Intermediate I. Purification by FCC, eluting with 0-10% 2M NH$_3$ in MeOH/DCM gave the title compound (682 mg, 40%).

LCMS (Method 4): Rt 0.42 min, m/z 380 [MH$^+$].

Intermediate M. (1S,4R)-4-[3-((S)-1-Isopropyl-2-methyl-pyrrolidin-2-yl)-[1,2,4]triazolo[4,3-a]pyridin-6-yloxy]-1,2,3,4-tetrahydro-naphthalen-1-ylamine

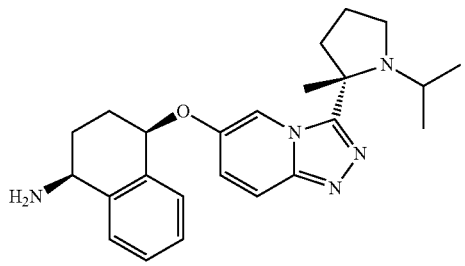 [SMILES: CC(C)N1CCC[C@@]1(C)c1nnc2ccc(O[C@@H]3CC[C@H](N)c4ccccc43)cn12]

a. (S)-1-Isopropyl-2-methyl-pyrrolidine-2-carboxylic acid benzyl ester (Intermediate Ma)

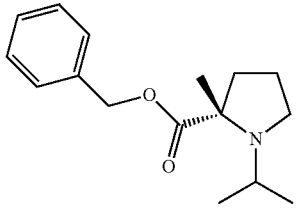 [SMILES: CC(C)N1CCC[C@@]1(C)C(=O)OCc1ccccc1]

A stirred solution of (S)-2-methyl-pyrrolidine-2-carboxylic acid benzyl ester (DE 3536446, 1.40 g, 6.50 mmol) in acetone (50 ml) was treated with molecular sieves (4 Å, 500 mg). The reaction mixture was stirred at RT for 3 days. Sodium triacetoxyborohydride (3.40 g, 16.0 mmol) was added in two portions and the reaction mixture was stirred for 1 hour, quenched with H$_2$O and extracted with EtOAc. The organic phase was washed with a saturated aqueous NaHCO$_3$ solution and brine, passed through a phase separator and the solvent was removed under reduced pressure to afford the title compound (1.60 g, 94%).

LCMS (Method 4): Rt 0.82 min, m/z 262 [MH$^+$].

b. (S)-1-Isopropyl-2-methyl-pyrrolidine-2-carboxylic acid N'-(5-fluoro-pyridin-2-yl)-hydrazide (Intermediate Mb)

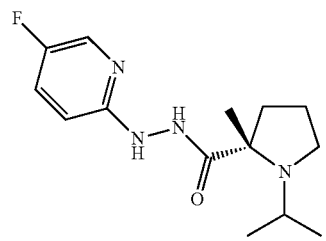 [SMILES: CC(C)N1CCC[C@@]1(C)C(=O)NNc1ccc(F)cn1]

To a solution of Intermediate Ma (1.60 g, 6.13 mmol) in EtOH (50 ml) was added palladium on charcoal (10% Pd, 600 mg). The vessel was evacuated and filled with hydrogen (×3) and the reaction mixture was stirred at RT for 3 hours under hydrogen. The reaction mixture was filtered through a pad of celite and the solvent was removed under reduced pressure to give (S)-1-isopropyl-2-methyl-pyrrolidine-2-carboxylic acid (1.15 g, quant.). The residue was dissolved in DMF (40 ml) and (5-fluoro-pyridin-2-yl)-hydrazine (WO 2014/195402, which is incorporated herein by reference in its entirety, 1.02 g, 8.04 mmol), HOBt (108 mg, 0.80 mmol) and EDC (1.70 g, 8.80 mmol) were added. The reaction mixture was stirred at RT for 18 hours and then it was partitioned between EtOAc and $H_2O$. The two phases were separated and the aqueous phase was extracted with EtOAc (×2). The organic phase was washed with brine (×3), passed through a phase separator and the solvent was removed under reduced pressure. The crude was purified by FCC eluting with 0-10% 2M $NH_3$ in MeOH/DCM to give the title compound (1.87 g, quant.).

LCMS (Method 4): Rt 0.60 min, m/z 281 [MH$^+$].

c. 6-Fluoro-3-((S)-1-isopropyl-2-methyl-pyrrolidin-2-yl)-[1,2,4]triazolo[4,3-a]pyridine (Intermediate Mc)

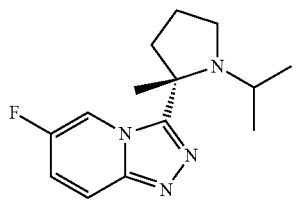 [SMILES: CC(C)N1CCC[C@@]1(C)c1nnc2ccc(F)cn12]

The title compound (1.72, 98%) was prepared starting from Intermediate Mb (1.87 g, 6.70 mmol) using the procedure described to make Intermediate Ic.

LCMS (Method 4): Rt 0.65 min, m/z 263 [MH$^4$].

d. (1S,4R)-4-[3-((S)-1-Isopropyl-2-methyl-pyrrolidin-2-yl)-[1,2,4]triazolo[4,3-a]pyridin-6-yloxy]-1,2,3,4-tetrahydro-naphthalen-1-ylamine (Intermediate M)

The title compound was prepared starting from Intermediate Mc (950 mg, 3.60 mmol) and (1R,4S)-4-amino-1,2,3,4-tetrahydro-naphthalen-1-ol (WO 2014/195402, which is incorporated herein by reference in its entirety, 886 mg, 5.40 mmol) using the procedure described to make Intermediate J. Purification by FCC, eluting with 0-10% 2M $NH_3$ in MeOH/DCM gave the title compound (800 mg, 55%).

LCMS (Method 4): Rt 0.57 min, m/z 406 [MH$^+$].

Intermediate N. (1S,4R)-4-[3-((S)-2-Methyl-pyrrolidin-2-yl)-[1,2,4]triazolo[4,3-a]pyridin-6-yloxy]-1,2,3,4-tetrahydro-naphthalen-1-ylamine

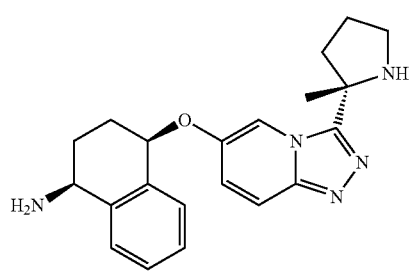 [SMILES: C[C@@]1(c2nnc3ccc(O[C@@H]4CC[C@H](N)c5ccccc54)cn23)CCCN1]

a. (S)-2-[N'-(5-Fluoro-pyridin-2-yl)-hydrazinocarbonyl]-2-methyl-pyrrolidine-1-carboxylic acid tert-butyl ester (Intermediate Na)

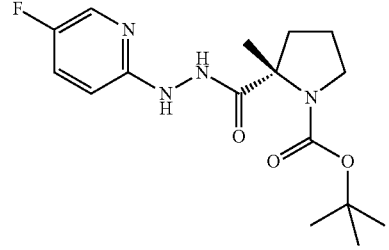 [SMILES: CC(C)(C)OC(=O)N1CCC[C@@]1(C)C(=O)NNc1ccc(F)cn1]

The title compound (8.14 g) was prepared starting from (2S)-1-[(tert-butoxy) carbonyl]-2-methylpyrrolidine-2-carboxylic acid (CAS: 103336-06-7, 5.0 g, 21.8 mmol) and (5-fluoro-pyridin-2-yl)-hydrazine (WO 2014/195402, which is incorporated herein by reference in its entirety, 2.52 g, 19.8 mmol) using the procedure described to make Intermediate Ib.

LCMS (Method 1): Rt 3.07 min, m/z 361 [MNa$^+$].

b. (S)-2-(6-Fluoro-[1,2,4]triazolo[4,3-a]pyridin-3-yl)-2-methyl-pyrrolidine-1-carboxylic acid tert-butyl ester (Intermediate Nb)

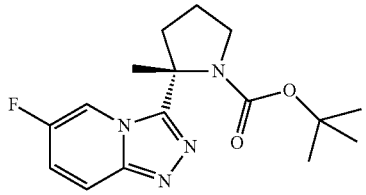 [SMILES: CC(C)(C)OC(=O)N1CCC[C@@]1(C)c1nnc2ccc(F)cn12]

The title compound (4.35 g, 69% over two steps) was prepared starting from Intermediate Na (8.14 g, 24.1 mmol) using the procedure described to make Intermediate Ic.

LCMS (Method 1): Rt 2.81 min, m/z 343 [MNa$^+$].

c. 6-Fluoro-3-((S)-2-methyl-pyrrolidin-2-yl)-[1,2,4]triazolo[4,3-a]pyridine (Intermediate Nc)

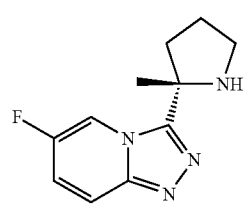 [SMILES: C[C@@]1(c2nnc3ccc(F)cn23)CCCN1]

A solution of Intermediate Nb (0.72 g, 2.3 mmol) in DCM (4 ml) was treated with TFA (4 ml). The reaction mixture was stirred at RT for 90 minutes and then the volatiles were removed under reduced pressure. The crude mixture was poured in a SCX-2 SPE cartridge, washed with MeOH and the product eluted with 2M $NH_3$ in MeOH to give the title compound (0.47 g, 94%).

¹H NMR (300 MHz, DMSO): 1.56 (3H, s), 1.65-1.91 (3H, m), 2.52-2.59 (1H, m), 2.75-2.86 (2H, m), 3.04-3.12 (1H, m), 7.46 (1H, ddd, J=10.0, 5.4, 2.5 Hz), 7.82 (1H, ddd, J=10.0, 4.8, 1.0 Hz), 9.01 (1H, ddd, J=4.8, 2.5, 1.0 Hz).

d. (1S,4R)-4-[3-((S)-2-Methyl-pyrrolidin-2-yl)-[1,2,4]triazolo[4,3-a]pyridin-6-yloxy]-1,2,3,4-tetrahydro-naphthalen-1-ylamine (Intermediate N)

The title compound was prepared starting from Intermediate Nc (470 mg, 2.10 mmol) and (1R,4S)-4-amino-1,2,3,4-tetrahydro-naphthalen-1-ol (WO 2014/195402, which is incorporated herein by reference in its entirety, 350 mg, 2.10 mmol) using the procedure described to make Intermediate J. Purification by FCC, eluting with 0-10% 2M NH₃ in MeOH/DCM gave the title compound (490 mg, 61%).

LCMS (Method 1): Rt 0.66 min, m/z 386 [MNa⁺].

Examples 19-30 a. General Procedure for the Examples 19-23

A solution of (3-tert-butyl-5-methanesulfonylamino-phenyl)-carbamic acid phenyl ester (US 2014/0296208, which is incorporated herein by reference in its entirety, 8.27 mmol), an appropriate amine (see Table 4) (8.27 mmol) and DIPEA (12.4 mmol) in dioxane (40 ml) was stirred at 60° C. for 18 hours. The volatiles were removed under reduced pressure and the residue was partitioned between 2-methyltetrahydrofuran and H₂O. The two phases were separated and the organic phase was washed with an aqueous 0.5M citric acid solution, H₂O, a saturated aqueous NaHCO₃ solution, H₂O and brine. The organic phase was dried with Na₂SO₄ and the solvent was removed under reduced pressure. The resulting residue was purified by FCC, eluting with 0-7.5% 2M NH₃ in MeOH/DCM or MDAP (Method 6) or MDAP (Method 7) or crystallisation from 2-methyltetrahydrofuran to afford the title compounds (5-89%).

b. General Procedure for the Examples 24-30

A solution of Intermediate K (22.8 mmol) and an appropriate amine (see Table 4) (22.8 mmol) in 2-methyltetrahydrofuran (100 ml) was stirred at RT for 4 hours. The volatiles were removed under reduced pressure and the residue was purified by FCC, eluting with 0-10% 2M NH₃ in MeOH/DCM or crystallisation from IMS or MDAP (Method 6) or MDAP (Method 7) or HPLC (Gemini C18, 5-95% MeCN in H₂O, 0.1% HCO₂H, 18 ml/min) afforded the title compounds (39-77%).

TABLE 4

| Ex. | Amine | Structure | NMR (400 MHz) δ | LC-MS |
|---|---|---|---|---|
| 19 | (1S,4R)-4-[3-(1-Dimethyl-amino-1-methyl-ethyl)-[1,2,4]triazolo[4,3-a]pyridin-6-yloxy]-1,2,3,4-tetrahydro-naphthalen-1-ylamine (WO 2013/083604, which is incorporated herein by reference in its entirety) | N-[3-tert-Butyl-5-(3-{(1S,4R)-4-[3-(1-dimethylamino-1-methyl-ethyl)-[1,2,4]triazolo[4,3-a]pyridin-6-yloxy]-1,2,3,4-tetrahydro-naphthalen-1-yl}-ureido)-phenyl]-methanesulfonamide | ¹H NMR (400 MHz, d₆-DMSO): 1.24 (9H,s), 1.51 (3H, s), 1.52 (3H, s), 1.84-1.96 (1H,m), 1.96-2.05 (1H, m), 2.05-2.23 (8H, m), 2.97 (3H, s), 4.86-4.95 (1H, m), 5.43 (1H, t, J = 4.2 Hz), 6.57 (1H, d, J = 8.8 Hz), 6.81 (1H, t, J = 1.8 Hz), 7.20 (1H, t, J = 1.8 Hz), 7.26 (1H, t, J = 1.7 Hz), 7.28-7.45 (5H, m), 7.75 (1H, d, J = 9.9 Hz), 8.48 (1H, s), 8.58 (1H, d, J = 2.1 Hz), 9.57 (1H, s) | (Method 3): Rt 3.52 min, m/z 634 [MH⁺] |
| 20 | Intermediate I | N-[3-tert-Butyl-5-(3-{(1S,4R)-4-[3((R)-1,2-dimethyl-pyrrolidin-2-yl)-[1,2,4]triazolo[4,3-a]pyridin-6-yloxy]-1,2,3,4-tetrahydro-naphthalen-1-yl}-ureido)-phenyl]-methanesulfonamide | ¹H NMR (400 MHz, d₆-DMSO): 1.24 (9H, s), 1.51 (3H,s), 1.78-2.30 (8H, m), 2.01 (3H, s), 2.67 (1H, q, J = 8.4 Hz), 2.97 (3H, s), 3.18 (1H, td, J = 9.0 Hz, 3.6 Hz), 4.84-4.95 (1H, m), 5.41 (1H, t, J = 4.3 Hz), 6.56 (1H, d, J = 8.5 Hz), 6.81 (1H, dd, J = 1.8, 1.3 Hz), 7.20 (1H, t, J = 1.8 Hz), 7.26 (1H, t, J = 1.8 Hz), 7.28-7.45 (5H, m), | (Method 3): Rt 3.47 min, m/z 646 [MH⁺]. |

| Ex. | Amine | Structure | NMR (400 MHz) δ | LC-MS |
|---|---|---|---|---|
| | | | 7.76 (1H, dd, J = 9.8, 0.5 Hz), 8.46-8.51 (2H, m), 9.53 (1H, br s) | |
| 21 | (1S,4R)-4-[3-((S)-1-Methyl-pyrrolidin-2-yl)-[1,2,4]triazolo[4,3-a]pyridin-6-yloxy]-1,2,3,4-tetrahydro-naphthalen-1-ylamine (WO 2014/195402, which is incorporated herein by reference in its entirety) | N-[3-tert-Butyl-5-(3-{(1S,4R)-4-[3((S)-1-methyl-pyrrolidin-2-yl)-[1,2,4]triazolo[4,3-a]pyridin-6-yloxy]-1,2,3,4-tetrahydro-naphthalen-1-yl}-ureido-phenyl]-methanesulfonamide | ¹H NMR (400 MHz, d₆-DMSO): 1.24 (9H, s), 1.84-2.27 (8H, m), 2.14 (3H, s), 2.31-2.40 (1H, m), 2.94 (3H, s), 3.10-3.18 (1H, m), 4.00 (1H, t, J = 8.3 Hz), 4.86-4.95 (1H, m), 5.42 (1H, t, J = 4.4 Hz), 6.57 (1H, d, J = 8.6 Hz), 6.79 (1H, t, J = 1.8 Hz), 7.17 (1H, br t, J = 1.8 Hz), 7.24 (1H, t, J = 1.8 Hz), 7.26-7.44 (5H, m), 7.77 (1H, dd, J = 9.8, 0.6 Hz), 8.27 (1H, d, J = 2.2 Hz), 8.46 (1H, s), 9.55 (1H, bs) | (Method 3): Rt 3.44 min, m/z 632 [MH⁺] |
| 22 | (1S,4R)-4-[3-((R)-1-Methyl-pyrrolidin-2-yl)-[1,2,4]triazolo[4,3-a]pyridin-6-yloxy]-1,2,3,4-tetrahydro-naphthalen-1-ylamine (WO 2013/083604, which is incorporated herein by reference in its entirety) | N-[3-tert-Butyl-5-(3-{(1S,4R)-4-[3((R)-1-methyl-pyrrolidin-2-yl)-[1,2,4]triazolo[4,3-a]pyridin-6-yloxy]-1,2,3,4-tetrahydro-naphthalen-1-yl}-ureido-phenyl]-methanesulfonamide | ¹H NMR (400 MHz, d₆-DMSO): 1.24 (9H, s), 1.82-2.27 (8H, m), 2.12 (3H, s), 2.31-2.40 (1H, m), 2.92 (3H, s), 3.13-3.20 (1H, m), 3.99 (1H, t, J = 8.0 Hz), 4.85-4.94 (1H, m), 5.45 (1H, t, J = 4.0 Hz), 6.56 (1H, d, J = 8.5 Hz), 6.77 (1H, t, J = 1.7 Hz), 7.14 (1H, br t, J = 1.8 Hz), 7.23 (1H, t, J = 1.8 Hz), 7.28-7.45 (5H, m), 7.76 (1H, dd, J = 9.9, 0.6 Hz), 8.31 (1H, d, J = 2.2 Hz), 8.45 (1H, s), 9.45 (1H, bs) | (Method 3): Rt 3.41 min, m/z 632 [MH⁺]. |
| 23 | Intermediate J | N-[3-tert-Butyl-5-(3-{(1S,4R)-4-[3((S)-1-isopropyl-piperidin-2-yl)-[1,2,4]triazolo[4,3-a]pyridin-6-yloxy]-1,2,3,4-tetrahydro-naphthalen-1-yl}-ureido-phenyl]-methanesulfonamide | ¹H NMR (400 MHz, d₆-DMSO): 0.82 (3H, d, J = 6.2 Hz), 0.99 (3H, d, J = 6.2 Hz), 1.24 (9H, s), 1.34-1.59 (2H, m), 1.62-2.30 (10H, m), 2.92 (3H, s), 2.94-3.03 (1H, m), 4.21-4.29 (1H, m), 4.86-4.95 (1H, m), 5.36 (1H, t, J = 4.0 Hz), 6.57 (1H, d, J = 8.8 Hz), 6.74-6.78 (1H, m), 7.12-7.16 (1H, m), 7.21- | (Method 3): Rt 3.60 min, m/z 674 [MH⁺]. |

TABLE 4-continued

| Ex. | Amine | Structure | NMR (400 MHz) δ | LC-MS |
|---|---|---|---|---|
| | | | 7.25 (1H, m), 7.27-7.34 (1H, m), 7.35-7.44 (4H, m), 7.77 (1H, d, J = 10.0 Hz), 8.43-8.51 (2H, m), 9.55 (1H, bs) | |
| 24 | (1S,4R)-4-[3-((S)-1,2-Dimethyl-pyrrolidin-2-yl)-[1,2,4]triazolo[4,3-a]pyridin-6-yloxy]-1,2,3,4-tetrahydro-naphthalen-1-ylamine (WO 2013/083604, which is incorporated herein by reference in its entirety) | N-[3-tert-Butyl-5-(3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido)-phenyl]-methanesulfonamide | ¹H NMR (400 MHz, d₆-DMSO): 1.24 (9H, s), 1.52 (3H, s), 1.77-2.25 (8H, m), 2.00 (3H, s), 2.61-2.70 (1H, m), 2.97 (3H, s), 3.13-3.20 (1H, m), 4.86-4.96 (1H, m), 5.35 (1H, t, J = 4.2 Hz), 6.53 (1H, d, J = 8.6 Hz), 6.81 (1H, t, J = 1.7 Hz), 7.20 (1H, t, J = 1.7 Hz), 7.25-7.44 (6H, m), 7.76 (1H, d, J = 9.8 Hz), 8.44-8.51 (2H, m), 9.57 (1H, s) | (Method 3): Rt 3.54 min, m/z 646 [MH⁺] |
| 25 | Intermediate L | N-[3-tert-Butyl-5-(3-{(1S,4R)-4-[3-((R)-4-methyl-morpholin-3-yl)-[1,2,4]triazolo[4,3-a]pyridin-6-yloxy]-1,2,3,4-tetrahydro-naphthalenyl}-ureido)-phenyl]-methanesulfonamide | ¹H NMR (400 MHz, d₆-DMSO): 1.24 (9H, s), 1.85-1.96 (1H, m), 2.01 (3H, s), 2.06-2.23 (3H, m), 2.41 (1H, dt, J = 11.2, 3.3 Hz), 2.91 (1H, d, J = 11.5 Hz), 2.96 (3H, s), 3.65-3.89 (4H, m), 3.99 (1H, dd, J = 10, 3.9 Hz), 4.86-4.94 (1H, m), 5.49 (1H, t, 3 = 4.2 Hz), 6.56 (1H, d, J = 8.5 Hz), 6.80 (1H, t, J = 1.7 Hz), 7.19 (1H, t, J = 1.8 Hz), 7.26 (1H, t, J = 1.7 Hz), 7.27-7.43 (5H, m), 7.77 (1H, d, J = 9.8 Hz), 8.48 (1H, s), 8.53 (1H, d, J = 1.6 Hz), 9.51 (1H, br) | (Method 3): Rt 3.53 min, m/z 648 [MH⁺]. |

TABLE 4-continued

| Ex. | Amine | Structure | NMR (400 MHz) δ | LC-MS |
|---|---|---|---|---|
| 26 | (1S,4R)-4-[3-((S)-1,4,4-Trimethyl-pyrrolidin-2-yl)-[1,2,4]triazolo[4,3-a]pyridin-6-yloxy]-1,2,3,4-tetrahydro-naphthalen-1-ylamine (WO 2013/083604, which is incorporated herein by reference in its entirety) | N-[3-tert-Butyl-5-(3-{(1S,4R)-4-[3-((S)-1,4,4-trimethyl-pyrrolidin-2-yl)-[1,2,4]triazolo[4,3-a]pyridin-6-yloxy]-1,2,3,4-tetrahydro-naphthalenyl}-ureido)-phenyl]-methanesulfonamide | $^1$H NMR (400 MHz, d$_6$-DMSO): 1.14 (3H, s), 1.12 (3H, s), 1.24 (9H, s), 1.85-1.01 (4H, m), 2.08 (3H, s), 2.09-2.22 (3H, m), 2.92 (1H, d, J = 9.1 Hz), 2.96 (3H, s), 4.10 (1H, t, J = 8.8 Hz), 4.90-4.94 (1H, m), 5.37 (1H, t, J = 4.2 Hz), 6.61 (1H, d, J = 8.7 Hz), 6.81 (1H, t, J = 1.8 Hz), 7.02 (1H, t, J = 1.9 Hz), 7.26 (1H, t, J = 1.8 Hz), 7.27-7.43 (5H, m), 7.77 (1H, d, J = 9.9 Hz), 8.40 (1H, d, J = 1.5 Hz), 8.52 (1H, s) plus one hydrogen not observed | (Method 3): Rt 3.57 min, m/z 660 [MH$^+$]. |
| 27 | (1S,4R)-4-[3-((S)-1-Ethyl-pyrrolidin-2-yl)-[1,2,4]triazolo[4,3-a]pyridin-6-yloxy]-1,2,3,4-tetrahydro-naphthalen-1-ylamine (WO 2013/083604, which is incorporated herein by reference in its entirety) | N-[3-tert-Butyl-5-(3-{(1S,4R)-4-[3-((S)-1-ethyl-2-methyl-pyrrolidin-2-yl)-[1,2,4]triazolo[4,3-a]pyridin-6-yloxy]-1,2,3,4-tetrahydro-naphthalen-1-yl}-ureido)-phenyl]-methanesulfonamide | $^1$H NMR (400 MHz, d$_6$-DMSO): 0.87 (3H, t, J = 7.2 Hz), 1.24 (9H, s), 1.52 (3H, s), 1.76-2.22 (9H, m), 2.26-2.37 (1H, m), 2.96 (3H, s), 4.85-4.94 (1H, m), 5.29-5.34 (1H, m), 6.57 (1H, d, J = 8.6 Hz), 6.80 (1H, t, J = 1.7 Hz), 7.17-7.21 (1H, m), 7.25 (1H, t, J = 1.7 Hz), 7.27-7.44 (5H, m), 7.77 (1H, dd, J = 9.8, 0.6 Hz), 8.48 (1H, s), 8.57-8.60 (1H, m), 9.56 (1H, br s), plus two protons obscured by solvent | (Method 3): Rt 3.53 min, m/z 660 [MH$^+$] |
| 28 | Intermediate M | N-[3-tert-Butyl-5-(3-{(1S,4R)-4-[3-((S)-1-isopropyl-2-methyl-pyrrolidin-2-yl)-[1,2,4]triazolo[4,3-a]pyridin-6-yloxy]-1,2,3,4-tetrahydro-naphthalen-1-yl}-ureido)-phenyl]-methanesulfonamide | NB. The compounds presented two different stereoisomers which have been labelled with #. $^1$H NMR (400 MHz, d$_6$-DMSO): 0.5 (0.7H#, d, J = 6.5 Hz), 0.58 (2.3H#, d, J = 6.5 Hz), 0.99-1.03 (3H, m), 1.25 (2.7H#, s), 1.26 (6.3H#, s), 1.63-1.65 (3H, m), 1.77-2.25 (6H, m), 2.64-2.73 (1H, m), 2.94 (0.7H#, s), 2.95 (2.3H#, s) 3.13-3.28 (2H, m), | (Method 3): Rt 3.76 min, m/z 674 [MH$^+$]. |

TABLE 4-continued

| Ex. | Amine | Structure | NMR (400 MHz) δ | LC-MS |
|---|---|---|---|---|
| | | | 4.88-5.04 (1H#, m), 5.27-5.45 (1H#, m), 6.36 (0.3H#, d, J = 8.4 Hz), 6.44 (0.7 H#, d, J = 8.6 Hz), 6.83-6.85 (1H, m), 7.17-7.44 (8H, m), 7.66-7.71 (1H, m), 8.27 (0.3H#, br s), 8.32 (0.7 H#, br s), 8.45-8.51 (1H#, m), plus two protons obscured by slovent | |
| 29 | Intermediate N | N-[3-tert-Butyl-5-(3-{(1S,4R)-4-[3-((S)-2-methyl-pyrrolidin-2-yl)-[1,2,4]triazolo[4,3-a]pyridin-6-yloxy]-1,2,3,4-tetrahydro-naphthalen-1-yl}-ureido)-phenyl]-methanesulfonamide | ¹H NMR (400 MHz, d₆-DMSO): 1.24 (9H, s), 1.50 (3H, s), 1.66-2.22 (5H, m), 2.54-2.59 (1H, m), 2.77-2.89 (1H, m), 2.97 (3H, s), 3.05-3.12 (1H, m), 4.87-4.93 (1H, m), 5.42 (1H, t, J = 4.0 Hz), 6.57 (1H, d, J = 8.6 Hz), 6.81 (1H, t, J = 1.8 Hz), 7.20(1H, t, J = 1.9 Hz), 7.26-7.43 (6H, m), 7.71 (1H, dd, J = 9.8, 0.6 Hz), 8.65 (1H, d, J = 1.6 Hz), 9.56 (1H, br s), plus three protons obscured by solvent | (Method 3): Rt 3.36 min, m/z 632 [MH⁺]. |
| 30 | (1S,4R)-4-[3-((R)-1-Methyl-piperidin-3-yl)-{1,2,4]triazolo[4,3-a]pyridin-6-yloxy]-1,2,3,4-tetrahydro-naphthalen-1-ylamine (WO 2013/083604, which is incorporated herein by reference in its entirety) | N-[3-tert-Butyl-5-(3-{(1S,4R)-4-[3-((R)-1-methyl-piperidin-3-yl)-[1,2,4]triazolo[4,3-a]pyridin-6-yloxy]-1,2,3,4-tetrahydro-naphthalen-1-yl}-ureido)-phenyl]-methanesulfonamide | ¹H NMR (400 MHz, d₆-DMSO): 1.23 (9H, s), 1.50-1.79 (3H, m), 1.84-2.24 (8H, m), 2.81-2.88 (4H, m), 2.98-3.02 (1H, m), 3.50-3.58 (1H, m), 4.86-4.94 (1H, m), 5.59 (1H, t, J = 4.2 Hz), 6.53 (1H, d, J = 8.6 Hz), 6.72 (1H, br s), 7.08 (1H, br s), 7.18-7.42 (6H, m), 7.70 (1H, d, J = 9.8 Hz), 8.32 (1H, d, J = 1.4 Hz), 8.40 (1H, br s), plus three protons not observed | (Method 3): Rt 3.40 min, m/z 646 [MH⁺]. |

Example 31. N-{3-tert-Butyl-5-[3-((1S,4R)-4-{3-[(S)-1-(2-hydroxy-ethyl)-pyrrolidin-2-yl]-[1,2,4]triazolo[4,3-a]pyridin-6-yloxy}-1,2,3,4-tetrahydronaphthalen-1-yl)-ureido]-phenyl}-methanesulfonamide

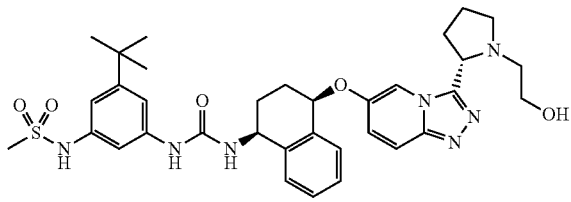 [SMILES: CC(C)(C)c1cc(NC(=O)N[C@H]2CC[C@@H](Oc3ccc4nnc([C@@H]5CCCN5CCO)n4c3)c3ccccc32)cc(NS(C)(=O)=O)c1]

a. (S)-1-tert-Butoxycarbonylmethyl-pyrrolidine-2-carboxylic acid (Intermediate 31a)

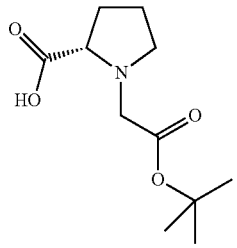 [SMILES: CC(C)(C)OC(=O)CN1CCC[C@H]1C(=O)O]

To a solution of (S)-1-tert-butoxycarbonylmethyl-pyrrolidine-2-carboxylic acid benzyl ester (WO 2010/136493, which is incorporated herein by reference in its entirety, 22.5 g, 70.4 mmol) in IMS (400 ml) was added palladium on carbon (10% Pd, 2.25 g). The vessel was evacuated and filled with hydrogen (×3) and the reaction mixture was stirred at RT under hydrogen for 3 hours. The reaction mixture was filtered through a pad of Celite® and the solvent was removed under reduced pressure to give the title compound (16.2 g, quant.).

$^1$H NMR (300 MHz, CDCl$_3$): 1.48 (9H, s), 1.73-1.85 (1H, m), 1.89-1.96 (1H, m), 2.14-2.31 (2H, m), 2.72-2.78 (1H, m), 3.30-3.34 (1H, m), 3.47 (2H, d, J=2.9 Hz), 3.55 (1H, dd, J=7.3, 2.0 Hz).

b. {(S)-2-[N-(5-Fluoro-pyridin-2-yl)-hydrazinocarbonyl]-pyrrolidin-1-yl}-acetic acid tert-butyl ester (Intermediate 31b)

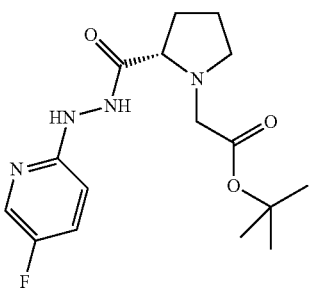 [SMILES: CC(C)(C)OC(=O)CN1CCC[C@H]1C(=O)NNc1ccc(F)cn1]

The title compound was prepared starting from Intermediate 31a (9.02 g, 39.3 mmol) and (5-fluoro-pyridin-2-yl)-hydrazine (WO 2014/195402, which is incorporated herein by reference in its entirety, 5.00 g, 39.3 mmol) in DMF (180 ml) using the procedure described to make Intermediate Ib. Purification by FCC, eluting with 0-10% 2M NH$_3$ in MeOH/DCM gave the title compound (9.48 g, 71%).

$^1$H NMR (300 MHz, CDCl$_3$): 1.47 (9H, s), 1.83-1.94 (2H, m), 2.01-2.08 (1H, m), 2.22-2.32 (1H, m), 2.66-2.72 (1H, m), 3.25-3.29 (1H, m), 3.39 (1H, AB system, d, J=12.9 Hz), 3.51-3.55 (2H, m), 6.60-6.64 (2H, m), 7.24-7.29 (1H, m), 8.02 (1H, d, J=2.2 Hz), 9.52 (1H, d, J=3.3 Hz).

c. [(S)-2-(6-Fluoro-[1,2,4]triazolo[4,3-a]pyridin-3-yl)-pyrrolidin-1-yl]-acetic acid tert-butyl ester (Intermediate 31c)

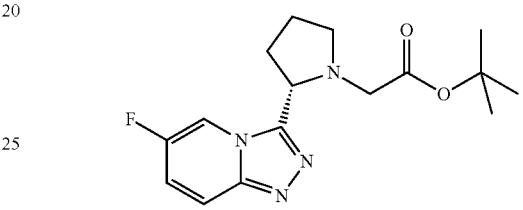

The title compound was prepared starting from Intermediate 31b (8.47 g, 25.0 mmol) using the procedure described to make Intermediate Ic. The crude mixture was poured in a SCX-2 SPE cartridge, washed with 33% MeOH/DCM and the product eluted with 2M NH$_3$ in MeOH to give the title compound (6.21 g, 77%).

$^1$H NMR (300 MHz, CDCl$_3$): 1.38 (9H, s), 1.99-2.16 (2H, m), 2.29-2.35 (1H, m), 2.64-2.70 (1H, m), 3.06 (1H, AB system, d, J=12.4 Hz), 3.24 (1H, AB system, d, J=12.4 Hz), 3.42-3.49 (1H, m), 4.53-4.57 (1H, m), 7.19 (1H, ddd, J=7.5, 5.6, 1.7 Hz), 7.73 (1H, ddd, J=7.2, 4.0, 0.6 Hz), 8.71-8.72 (1H, m).

d. 2-[(S)-2-(6-Fluoro-[1,2,4]triazolo[4,3-a]pyridin-3-yl)-pyrrolidin-1-yl]-ethanol (Intermediate 31d)

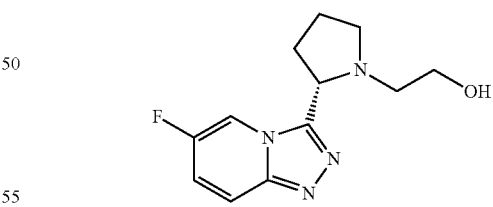

To a stirred solution of Intermediate 31c (3.00 g, 9.4 mmol) in THF (60 ml) at −5° C. under nitrogen was added lithium aluminium hydride (1M in THF, 18.7 ml, 18.7 mmol) over 15 minutes. The reaction mixture was stirred at −5° C. for 1 hour, carefully quenched with H$_2$O and the reaction mixture was filtered through a pad of Centel). The crude mixture was poured in a SCX-2 SPE cartridge, washed with MeOH and the product eluted with 2M NH$_3$ in MeOH to give the title compound (1.76 g, 75%, purity ~70%).

LCMS (Method 5): Rt 1.14 min, m/z 273 [MNa$^+$].

e. 6-Fluoro-3-[(S)-1-(2-triisopropylsilanyloxy-ethyl)-pyrrolidin-2-yl]-[1,2,4]triazolo[4,3-a]pyridine (Intermediate 31e)

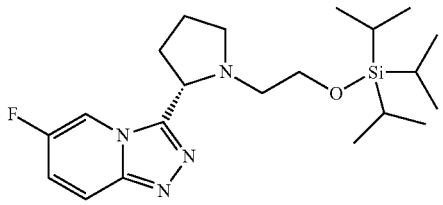 [SMILES: CC(C)[Si](OCCN1CCC[C@H]1c1nnc2ccc(F)cn12)(C(C)C)C(C)C]

To a stirred solution of Intermediate 31d (1.55 g, 6.2 mmol) in DCM (40 ml) at −5° C. was added TEA (2.6 ml, 18.6 mmol) and triisopropylsilyl trifluoromethanesulfonate (2.5 ml, 9.3 mmol) over 15 minutes. The reaction mixture was stirred at −5° C. for 15 minutes, warmed at RT and stirred for other 3 hours. A saturated aqueous NaHCO₃ solution was added and the two phases were separated. The aqueous phase was extracted with DCM (×2) and the combined organic phases were dried with MgSO₄ and the solvent was removed under reduced pressure. Purification by FCC, eluting with 0-8% 2M NH₃ in MeOH/DCM gave the title compound (1.14 g, 45%).

LCMS (Method 5): Rt 2.50 min, m/z 407 [MH⁺].

f. (1S,4R)-4-{3-[(S)-1-(2-Triisopropylsilanyloxy-ethyl)-pyrrolidin-2-yl]-[1,2,4]triazolo[4,3-a]pyridin-6-yloxy}-1,2,3,4-tetrahydro-naphthalen-1-ylamine (Intermediate 31f)

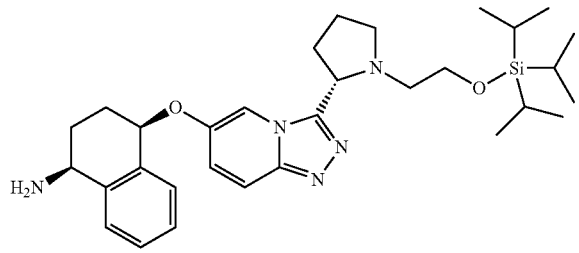 [SMILES: CC(C)[Si](OCCN1CCC[C@H]1c1nnc2ccc(O[C@@H]3CC[C@H](N)c4ccccc43)cn12)(C(C)C)C(C)C]

The title compound was prepared starting from Intermediate 31e (1.14 g, 2.80 mmol) and (1R,4S)-4-amino-1,2,3,4-tetrahydro-naphthalen-1-ol (WO 2014/195402, which is incorporated herein by reference in its entirety, 0.46 g, 2.80 mmol) using the procedure described to make Intermediate I. Purification by FCC, eluting with 0-8% 2M NH₃ in MeOH/DCM gave the title compound (671 mg, 40%).

LCMS (Method 5): Rt 2.37 min, m/z 550 [MH⁺].

g. N-{3-tert-Butyl-5-[3-((1S,4R)-4-{3-[(S)-1-(2-triisopropylsilanyloxy-ethyl)-pyrrolidin-2-yl]-[1,2,4]triazolo[4,3-a]pyridin-6-yloxy}-1,2,3,4-tetrahydro-naphthalen-1-yl)-ureido]-phenyl}-methanesulfonamide (Intermediate 31g)

The title compound was prepared starting from Intermediate 31f (0.30 g, 0.55 mmol) and Intermediate K (0.25 g, 0.93 mmol) using the procedure described to make Intermediate 18d. The volatiles were removed under reduced pressure and the residue was used in the following step without any other purification.

LCMS (Method 5): Rt 2.45 min, m/z 819 [MH⁺].

h. Example 31

To a stirred solution of Intermediate 31g (675 mg, of which 450 mg of Intermediate 31g, 0.55 mmol) in THF (7 ml) was added TBAF (1M in THF, 2.8 ml, 2.8 mmol) and the reaction mixture was stirred at RT for 15 hours. A further aliquot of TBAF (1M in THF, 2.8 ml, 2.8 mmol) was added and the reaction mixture was stirred for 7 hours. The crude mixture was poured in a SCX-2 SPE cartridge, washed with MeOH and the product eluted with 2M NH₃ in MeOH. The solvent was removed under reduced pressure and the residue was further purified by MDAP (Method 7) to give the title compound (43 mg, 12% over two steps).

LCMS (Method 3): Rt 3.39 min, m/z 662 [MH⁺]. ¹H NMR (400 MHz, d-₆-DMSO): 1.24 (9H, s), 1.82-2.25 (8H, m), 2.30-2.40 (2H, m), 2.41-2.48 (1H, m), 2.90 (3H, s), 3.25-3.31 (1H, m), 3.35-3.42 (2H, m), 4.16-4.24 (1H, m), 4.45 (1H, t, J=5.1 Hz), 4.85-4.94 (1H, m), 5.44 (1H, t, J=4.2 Hz), 6.55 (1H, d, J=8.9 Hz), 6.73-6.76 (1H, m), 7.11 (1H, s), 7.21 (1H, s), 7.27-7.33 (2H, m), 7.35-7.44 (3H, m), 7.74 (1H, d, J=10.0 Hz), 8.43 (1H, s), 8.48 (1H, d, J=1.6 Hz), 9.50 (1H, s).

Example 32. N-{3-tert-Butyl-5-[3-((1S,4R)-4-{3-[(S)-1-(2-hydroxy-ethyl)-2-methyl-pyrrolidin-2-yl]-[1,2,4]triazolo[4,3-a]pyridin-6-yloxy}-1,2,3,4-tetrahydro-naphthalen-1-yl)-ureido]-phenyl}-methanesulfonamide

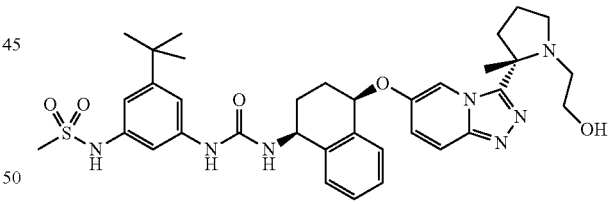

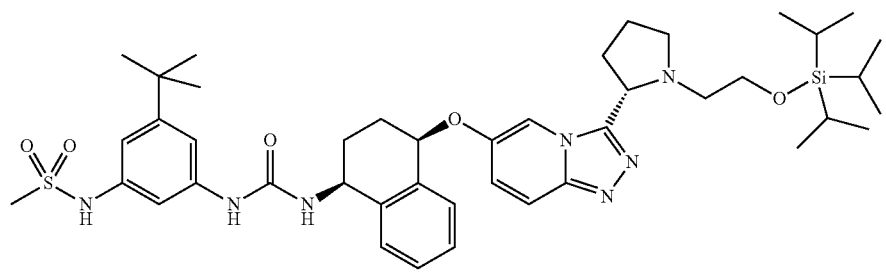 [SMILES: CC(C)[Si](OCCN1CCC[C@H]1c1nnc2ccc(O[C@@H]3CC[C@H](NC(=O)Nc4cc(NS(C)(=O)=O)cc(C(C)(C)C)c4)c4ccccc43)cn12)(C(C)C)C(C)C]

a. (S)-1-tert-Butoxycarbonylmethyl-2-methyl-pyrrolidine-2-carboxylic acid benzyl ester (Intermediate 32a)

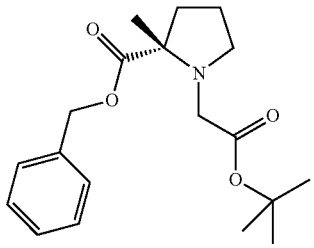 [SMILES: CC(C)(C)OC(=O)CN1CCC[C@@]1(C)C(=O)OCc1ccccc1]

A stirred solution of (S)-2-methyl-pyrrolidine-2-carboxylic acid benzyl ester (DE 3536446, 1.08 g, 5.00 mmol) in DMF (11 ml) was treated with $K_2CO_3$ (2.00 g, 14.4 mmol) and tert-butyl-bromoacetate (0.90 g, 6.12 mmol). The reaction mixture was stirred at 35° C. for 5 hours, cooled at RT and diluted with $H_2O$ and EtOAc. The two phases were separated and the organic phase was washed with brine, passed through a phase separator and the solvent was removed under reduced pressure. Purification by FCC, eluting with 0-10% 2M $NH_3$ in MeOH/DCM gave the title compound (1.83 g, quant.).

LCMS (Method 4): Rt 1.16 min, m/z 334 [MH$^+$].

b. (S)-1-tert-Butoxycarbonylmethyl-2-methyl-pyrrolidine-2-carboxylic acid (Intermediate 32b)

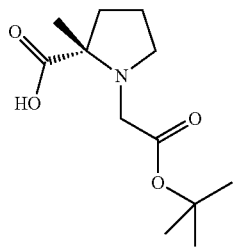 [SMILES: CC(C)(C)OC(=O)CN1CCC[C@@]1(C)C(=O)O]

To a solution of Intermediate 32a (1.83 g, 5.50 mmol) in EtOH (30 ml) was added palladium on charcoal (10% Pd, 500 mg). The vessel was evacuated and filled with hydrogen (×3) and the reaction mixture was stirred at RT under hydrogen for 30 hours. The reaction mixture was filtered through a pad of Celite® and the solvent was removed under reduced pressure to give the title compound (1.21 g, 93%).

$^1$H NMR (300 MHz, CDCl$_3$): 1.27 (3H, s), 1.42 (9H, s), 1.69-1.87 (2H, m), 2.11-2.20 (1H, m), 2.49-2.51 (2H, m), 2.94-3.14 (2H, m), 3.45-3.50 (2H, m).

c. {(S)-2-[N'-(5-Fluoro-pyridin-2-yl)-hydrazinocarbonyl]-2-methyl-pyrrolidin-1-yl}-acetic acid tert-butyl ester (Intermediate 32c)

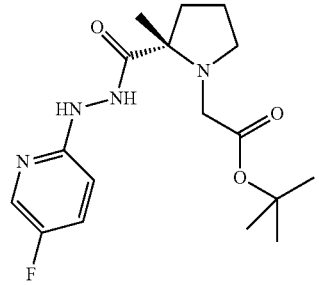 [SMILES: CC(C)(C)OC(=O)CN1CCC[C@@]1(C)C(=O)NNc1ccc(F)cn1]

The title compound was prepared starting from Intermediate 32b (1.21 g, 4.90 mmol) and (5-fluoro-pyridin-2-yl)-hydrazine (WO 2014/195402, which is incorporated herein by reference in its entirety, 762 mg, 6.00 mmol) in DMF (5 ml) using the procedure described to make Intermediate Ib. Purification by FCC, eluting with 0-100% EtOAc/cyclohexane gave the title compound (1.33 g, 77%).

LCMS (Method 4): Rt 1.02 min, m/z 353 [MH$^+$].

d. [(S)-2-(6-Fluoro-[1,2,4]triazolo[4,3-a]pyridin-3-yl)-2-methyl-pyrrolidin-1-yl]-acetic acid tert-butyl ester (Intermediate 32d)

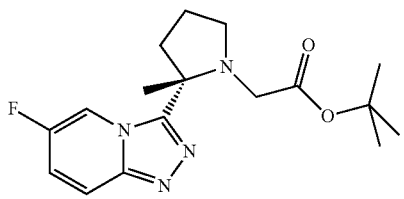 [SMILES: CC(C)(C)OC(=O)CN1CCC[C@@]1(C)c1nnc2ccc(F)cn12]

The title compound was prepared starting from Intermediate 32c (1.33 g, 3.80 mmol) using the procedure described to make Intermediate Ic. The crude mixture was poured in a SCX-2 SPE cartridge, washed with MeOH and the product eluted with 2M $NH_3$ in MeOH to give the title compound (558 mg, 44%).

LCMS (Method 4): Rt 1.21 min, m/z 335 [MH$^+$].

e. 2-[(S)-2-(6-Fluoro-[1,2,4]triazolo[4,3-a]pyridin-3-yl)-2-methyl-pyrrolidin-1-yl]-ethanol (Intermediate 32e)

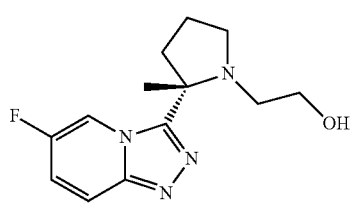 [SMILES: C[C@@]1(c2nnc3ccc(F)cn23)CCCN1CCO]

The title compound (420 mg, 96%) was prepared starting from Intermediate 32d (558 mg, 1.67 mmol) using the procedure described to make Intermediate 31d.

LCMS (Method 4): Rt 0.56 min, m/z 265 [MH$^+$].

f. 6-Fluoro-3-[(S)-2-methyl-1-(2-triisopropylsilanyloxy-ethyl)-pyrrolidin-2-yl]-[1,2,4]triazolo[4,3-a]pyridine (Intermediate 32f)

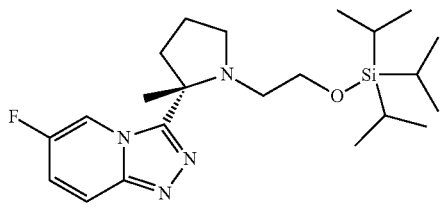 [SMILES: CC(C)[Si](OCCN1CCC[C@@]1(C)c1nnc2ccc(F)cn12)(C(C)C)C(C)C]

The title compound was prepared starting from Intermediate 32e (422 mg, 1.60 mmol) using the procedure described to make Intermediate 31e. Purification by FCC, eluting with 0-100% EtOAc/cyclohexane gave the title compound (301 mg, 56%).

¹H NMR (300 MHz, CDCl₃): 0.91-0.99 (21H, m), 1.68 (3H, s), 1.84-1.93 (1H, m), 2.05-2.21 (3H, m), 2.36-2.55 (2H, m), 2.70 (1H, q, J=8.9 Hz), 3.45-3.67 (3H, m), 7.16 (1H, ddd, J=10.0, 7.5, 2.4 Hz), 7.73 (1H, ddd, J=10.0, 5.0, 0.8 Hz), 8.83 (1H, ddd, J=4.4, 2.4, 0.8 Hz).

g. (1S,4R)-4-{3-[(S)-2-Methyl-1-(2-triisopropylsilanyloxy-ethyl)-pyrrolidin-2-yl]-[1,2,4]triazolo[4,3-a]pyridin-6-yloxy}-1,2,3,4-tetrahydro-naphthalen-1-ylamine (Intermediate 32g)

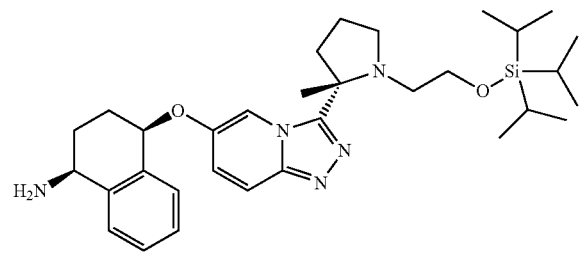 [SMILES: CC(C)[Si](OCCN1CCC[C@@]1(C)c1nnc2ccc(O[C@@H]3CC[C@H](N)c4ccccc43)cn12)(C(C)C)C(C)C]

The title compound was prepared starting from Intermediate 32f (100 mg, 0.30 mmol) and (1R,4S)-4-amino-1,2,3,4-tetrahydro-naphthalen-1-ol (WO 2014/195402, which is incorporated herein by reference in its entirety, 97 mg, 0.60 mmol) using the procedure described to make Intermediate J. Purification by FCC, eluting with 0-10% 2M NH₃ in MeOH/DCM afforded the title compound (44 mg, 26%).

LCMS (Method 1): Rt 2.81 min, m/z 586 [MNa⁺].

h. N-{3-tert-Butyl-5-[3-((1S,4R)-4-{3-[(S)-2-methyl-1-(2-triisopropylsilanyloxy-ethyl)-pyrrolidin-2-yl]-[1,2,4]triazolo[4,3-a]pyridin-6-yloxy}-1,2,3,4-tetrahydro-naphthalen-1-yl)-ureido]-phenyl}-methanesulfonamide (Intermediate 32h)

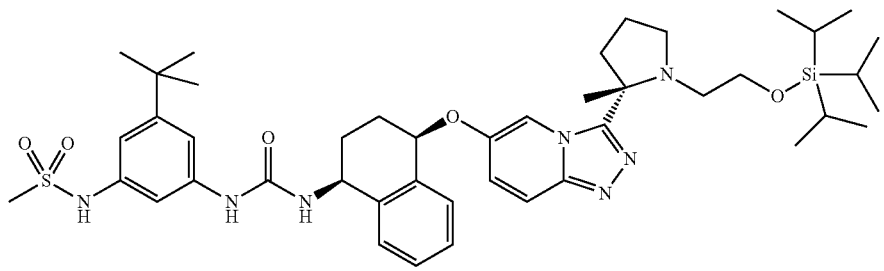 [SMILES: CC(C)[Si](OCCN1CCC[C@@]1(C)c1nnc2ccc(O[C@@H]3CC[C@H](NC(=O)Nc4cc(NS(C)(=O)=O)cc(C(C)(C)C)c4)c4ccccc43)cn12)(C(C)C)C(C)C]

The title compound was prepared starting from Intermediate 32g (44 mg, 0.08 mmol) and Intermediate K (0.31 mg, 0.12 mmol) using the procedure described to make Intermediate 18d. Purification by FCC, eluting with 0-100% EtOAc/cyclohexane, followed by 0-10% 2M NH₃ in MeOH/DCM afforded the title compound (44 mg, 66%).

LCMS (Method 4): Rt 1.48 min, m/z 832 [MH⁺].

The title compound was prepared starting from Intermediate 32h (44 mg, 0.05 mmol) using the procedure described to make Example 31. Purification by HPLC (Gemini C18, 5-95% MeCN in H₂O, 0.1% HCO₂H, 18 ml/min) gave the product as a formate salt. The solid was dissolved in DCM and a saturated aqueous NaHCO₃ solution. The two phases were separated and the aqueous phase was extracted with DCM (×2). The organic phase was dried with MgSO₄ and the solvent was removed under reduced pressure to afford the title compound as a free base (20 mg, 59%).

LCMS (Method 3): Rt 3.47 min, m/z 676 [MH⁺]. ¹H NMR (400 MHz, d₆-DMSO): 1.24 (9H, s), 1.53 (3H, s), 1.76-2.38 (8H, m), 2.54-2.62 (1H, m), 2.97 (3H, s), 3.35-3.39 (2H, m), 4.40 (1H, t, J=5.4 Hz), 4.86-4.93 (1H, m), 5.42 (1H, t, J=3.8 Hz), 6.56 (1H, d, J=8.5 Hz), 6.81 (1H, t, J=1.8 Hz), 7.21 (1H, t, J=1.8 Hz), 7.27 (1H, t, J=1.8 Hz), 7.28-7.42 (6H, m), 7.74 (1H, d, J=9.9 Hz), 8.50 (1H, br s), 8.67 (1H, d, J=1.9 Hz), 9.56 (1H, br), plus two protons obscured by solvent.

Example 33. N-{3-tert-Butyl-5-[3-((1S,4R)-4-{3-[(S)-1-(2-hydroxy-ethyl)-pyrrolidin-2-yl]-[1,2,4]triazolo[4,3-a]pyridin-6-yloxy}-1,2,3,4-tetrahydro-naphthalen-1-yl)-ureido]-phenyl}-methanesulfonamide

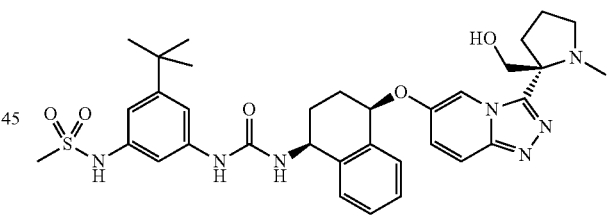

a. N-[3-tert-Butyl-5-(3-{(1S,4R)-4-[3-((S)-1-methyl-2-triisopropylsilanyloxymethyl-pyrrolidin-2-yl)-[1,2,4]triazolo[4,3-a]pyridin-6-yloxy]-1,2,3,4-tetrahydro-naphthalen-1-yl}-ureido)-phenyl]-methanesulfonamide (Intermediate 33a)

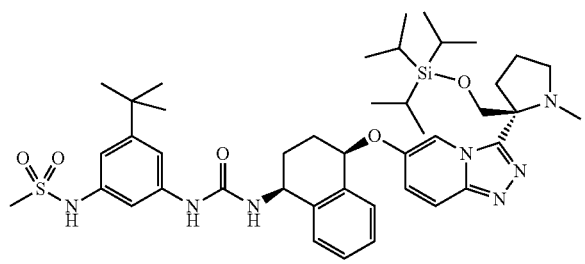

The title compound was prepared starting from (1S,4R)-4-[3-((S)-1-methyl-2-triisopropylsilanyloxymethyl-pyrrolidin-2-yl)-[1,2,4]triazolo[4,3-a]pyridin-6-yloxy]-1,2,3,4-tetrahydro-naphthalen-1-ylamine (WO 2013/083604, which is incorporated herein by reference in its entirety, 200 mg, 0.36 mmol) and Intermediate K (160 mg, 0.60 mmol) using the procedure described to make Intermediate 18d. The volatiles were removed under reduced pressure and the residue was used in the following step without any other purification.

LCMS (Method 5): Rt 2.59 min, m/z 818 [MH+].

b. Example 33

The title compound was prepared starting from Intermediate 33a (373 mg, of which 295 mg of Intermediate 33a, 0.36 mmol) using the procedure described to make Example 31. Purification by MDAP (Method 7), followed by a further MDAP (Method 6) gave the product as a formate salt. The solid was dissolved in MeOH and poured in a SCX-2 SPE cartridge, washed with MeOH and the product eluted with 2M NH3 in MeOH. The solvent was removed under reduced pressure to afford the title compound as a free base (79 mg, 33% over two steps).

LCMS (Method 3): Rt 3.38 min, m/z 662 [MH+]. $^1$H NMR (400 MHz, d$_6$-DMSO): 1.24 (9H, s), 1.83-2.29 (8H, m), 2.25 (3H, s), 2.96 (3H, s), 2.98-3.10 (2H, m), 4.05 (1H, dd, J=11.5, 5.7 Hz), 4.18 (1H, dd, J=11.8, 5.1 Hz), 4.82-4.94 (2H, m), 5.33 (1H, t, J=4.1 Hz), 6.56 (1H, d, J=8.7 Hz), 6.81 (1H, t, J=1.8 Hz), 7.20 (1H, t, J=1.9 Hz), 7.26 (1H, t, J=1.7 Hz), 7.27-7.43 (5H, m), 7.75 (1H, d, J=9.9 Hz), 8.38 (1H, d, J=1.9 Hz), 8.48 (1H, s), 9.56 (1H, br).

Example 34. 1-(3-Amino-5-tert-butyl-phenyl-3-{(1S,4R)-4-[3-(1-dimethylamino-1-methyl-ethyl)-[1,2,4]triazolo[4,3-a]pyridin-6-yloxy]-1,2,3,4-tetrahydro-naphthalen-1-yl}-urea

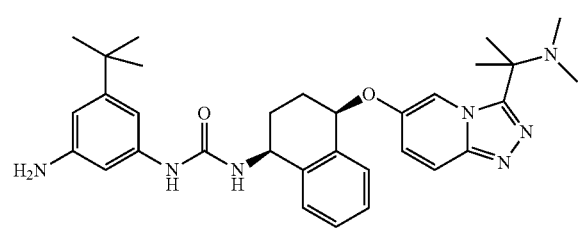 [SMILES: CN(C)C(C)(C)c1nnc2ccc(O[C@@H]3CC[C@H](NC(=O)Nc4cc(N)cc(C(C)(C)C)c4)c4ccccc43)cn12]

a. N-(3-Amino-5-tert-butyl-phenyl)-2,2,2-trifluoro-acetamide (Intermediate 34a)

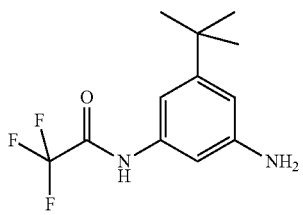 [SMILES: CC(C)(C)c1cc(N)cc(NC(=O)C(F)(F)F)c1]

To a stirred solution of 5-tert-butyl-benzene-1,3-diamine (CAS: 22503-17-9, 328 mg, 2.00 mmol) in 2-methyltetrahydrofuran (5 ml) was added trifluoro-acetic acid phenyl ester (300 µl, 2.00 mmol). The reaction mixture was stirred at RT for 3 hours, diluted with 2-methyltetrahydrofuran and washed with an aqueous 1M HCl solution, H$_2$O, an aqueous 5% K$_2$CO$_3$ solution, H$_2$O and brine, dried with Na$_2$SO$_4$ and the solvent was removed under reduced pressure. Purification by FCC eluting with 0-10% Et$_2$O/DCM gave the title compound (390 mg, 75%).

$^1$H NMR (300 MHz, CDCl$_3$): 1.27 (9H, s), 3.75 (2H, br s), 6.57 (1H, t, J=2.0 Hz), 6.72 (1H, t, J=1.7 Hz), 7.01 (1H, t, J=2.0 Hz), 7.72 (1H, br s).

b. [3-tert-Butyl-5-(2,2,2-trifluoro-acetylamino)-phenyl]-carbamic acid phenyl ester (Intermediate 34b)

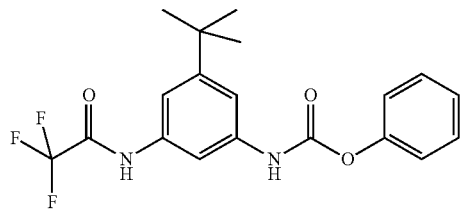 [SMILES: CC(C)(C)c1cc(NC(=O)Oc2ccccc2)cc(NC(=O)C(F)(F)F)c1]

To a stirred solution of Intermediate 34a (375 mg, 1.44 mmol) in EtOAc (10 ml) was added a solution of NaHCO$_3$ (267 mg, 3.18 mmol in 3 ml of H$_2$O) and phenyl chloroformate (290 µL, 2.30 mmol). The reaction mixture was stirred for 30 minutes, dried with Na$_2$SO$_4$ and the solvent was removed under reduced pressure. Purification by FCC, eluting with 0-2.5% Et$_2$O/DCM afforded the title compound (515 mg, 94%).

$^1$H NMR (300 MHz, CDCl$_3$): 1.32 (9H, s), 7.00 (1H, br s), 7.16-7.28 (3H, m), 7.32 (1H, t, J=2.0 Hz), 7.37-7.43 (3H, m), 7.63 (1H, t, J=2.0 Hz), 7.83 (1H, br s).

c. N-[3-tert-Butyl-5-(3-{(1S,4R)-4-[3-(1-dimethylamino-1-methyl-ethyl)-[1,2,4]triazolo[4,3-a]pyridin-6-yloxy]-1,2,3,4-tetrahydro-naphthalen-1-yl}-ureido)-phenyl]-2,2,2-trifluoro-acetamide (Intermediate 34c)

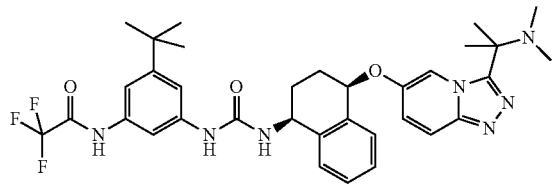 [SMILES: CN(C)C(C)(C)c1nnc2ccc(O[C@@H]3CC[C@H](NC(=O)Nc4cc(NC(=O)C(F)(F)F)cc(C(C)(C)C)c4)c4ccccc43)cn12]

To a stirred solution of Intermediate 34b (670 mg, 1.76 mmol) in dioxane (10 ml) was added DIPEA (450 µl, 2.64 mmol) and (1S,4R)-4-[3-(1-dimethylamino-1-methyl-ethyl)-[1,2,4]triazolo[4,3-a]pyridin-6-yloxy]-1,2,3,4-tetrahydro-naphthalen-1-ylamine (WO 2013/083604, 640 mg, 1.75 mmol). The reaction mixture was heated at 60° C. for 18 hours. The solvent was removed under reduced pressure and the residue was partitioned between 2-methyltetrahydrofuran and H₂O. The two phases were separated and the organic phase was washed with an aqueous 0.5M citric acid solution, H₂O, a saturated aqueous NaHCO₃ solution, water and brine. The organic phase was dried with Na₂SO₄ and the solvent was removed under reduced pressure. Purification by FCC, eluting with 0-7.5% 2M NH₃ in MeOH/DCM gave the title compound (660 mg, 58%).

¹H NMR (300 MHz, CDCl₃): 1.30 (9H, s), 1.52 (3H, s), 1.53 (3H, s), 2.05-2.30 (10H, m), 5.15-5.23 (2H, m), 6.81 (1H, d, J=9.0 Hz), 6.88 (1H, dd, J=10.0, 2.0 Hz), 7.22-7.36 (5H, m), 7.44 (1H, t, J=1.7 Hz), 7.54 (1H, d, J=7.5 Hz), 7.72 (1H, t, J=2.0 Hz), 8.15 (1H, br s), 8.26 (1H, br s), 8.67 (1H, d, J=1.8 Hz).

The title compound was prepared starting from Intermediate 34c (900 mg, 1.38 mmol) using the procedure described to make Example 18. The crude was purified by FCC, eluting with 20% acetone/DCM followed by 2.5-7.5% 2M NH₃ in MeOH/DCM. The solid was further purified by FCC, eluting with EtOAc followed by 2.5-5.0% 2M NH₃ in MeOH/DCM to afford the title compound (345 mg, 45%).

LCMS (Method 3): Rt 2.94 min, m/z 556 [MH⁺]. ¹H NMR (400 MHz, d₆-DMSO): 1.20 (9H, s), 1.51 (3H, s), 1.52 (3H, s), 1.81-2.23 (4H, m), 2.12 (6H, s), 4.83-4.93 (1H, m), 4.88 (21-1, br s), 5.42 (1H, t, J=4.2 Hz), 6.20 (1H, t, J=1.7 Hz), 6.48 (1H, d, J=8.7 Hz), 6.56 (1H, t, J=1.7 Hz), 6.61 (1H, t, J=1.7 Hz), 7.26-7.44 (5H, m), 7.75 (1H, dd, J=9.9, 0.7 Hz), 8.05 (1H, br s), 8.58 (1H, d, J=2.2 Hz).

Example 35. 1-(3-Amino-5-tert-butyl-phenyl-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea

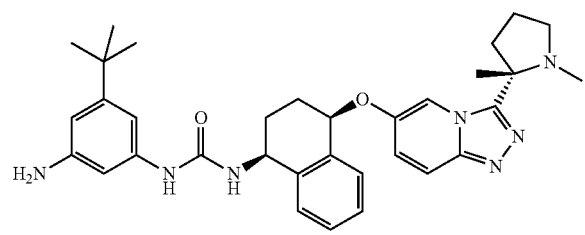 [SMILES: CN1CCC[C@@]1(C)c1nnc2ccc(O[C@@H]3CC[C@H](NC(=O)Nc4cc(N)cc(C(C)(C)C)c4)c4ccccc43)cn12]

a. N-(3-tert-Butyl-5-isocyanato-phenyl)-2,2,2-trifluoro-acetamide (Intermediate 35a)

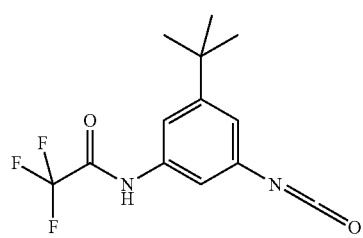 [SMILES: CC(C)(C)c1cc(N=CC=O)cc(NC(=O)C(F)(F)F)c1]

The title compound (970 mg, 92%) was prepared starting from Intermediate 34a (950 mg, 3.65 mmol) using the procedure described to make Intermediate A.

¹H NMR (300 MHz, CDCl₃): 1.31 (9H, s), 6.98 (1H, t, J=1.7 Hz), 7.27 (1H, t, J=1.7 Hz), 7.34 (1H, t, J=2.0 Hz), 7.82 (1H, br s).

b. N-[3-tert-Butyl-5-(3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido)-phenyl]-2,2,2-trifluoro-acetamide (Intermediate 35b)

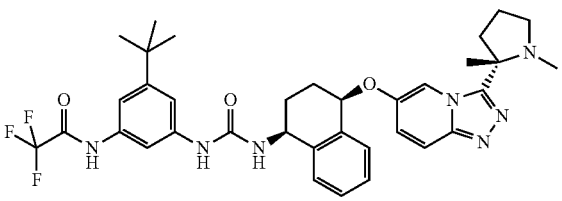 [SMILES: CN1CCC[C@@]1(C)c1nnc2ccc(O[C@@H]3CC[C@H](NC(=O)Nc4cc(NC(=O)C(F)(F)F)cc(C(C)(C)C)c4)c4ccccc43)cn12]

The title compound (1.05 g, 91%) was prepared starting from (1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-ylamine (WO 2013/083604, which is incorporated herein by reference in its entirety, 660 mg, 1.75 mmol) and Intermediate 35a (500 g, 1.75 mmol) using the procedure described to make Example 18.

¹H NMR (300 MHz, CDCl₃): 1.30 (9H, s), 1.64 (3H, s), 1.81-2.34 (11H, m), 2.71 (1H, q, J=8.5 Hz), 3.12-3.19 (1H, m), 5.14-5.23 (2H, m), 6.87 (1H, dd, J=10.0, 2.2 Hz), 6.94 (1H, d, J=8.6 Hz), 7.20-7.35 (5H, m), 7.45 (1H, t, J=1.7 Hz), 7.55 (1H, d, J=7.5 Hz), 7.72 (1H, t, J=1.8 Hz), 8.17 (1H, br s), 8.34 (1H, br s), 8.57 (1H, d, J=1.8 Hz).

c. Example 35

The title compound was prepared starting from Intermediate 35b (930 mg, 1.44 mmol) using the procedure described to make Example 18. The crude was purified by FCC, eluting with 0-5% 2M NH₃ in MeOH/DCM. The solid was further purified by HPLC (X-Bridge 18, 10-98% MeCN in H₂O, 0.1% NH₄OH, 18 ml/min) to afford the title compound (420 mg, 53%).

LCMS (Method 3): Rt 2.85 min, m/z 568 [MH⁺]. ¹H NMR (400 MHz, d₆-DMSO): 1.19 (9H, s), 1.51 (3H, s), 1.78-2.05 (5H, m), 2.03 (31-1, s), 2.06-2.24 (3H, m), 2.61-2.70 (1H, m), 3.13-3.20 (1H, m), 4.84-4.92 (3H, m), 5.34 (1H, t, J=4.0 Hz), 6.20 (1H, t, J=1.8 Hz), 6.48 (1H, d, J=8.7 Hz), 6.56 (1H, t, J=1.8 Hz), 6.61 (1H, t, J=1.8 Hz), 7.25-7.44 (5H, m), 7.76 (1H, dd, J=9.8, 0.6 Hz), 8.07 (1H, br s), 8.44-8.48 (1H, m).

Intermediate O. (3-tert-Butyl-5-cyclopropanesulfonylamino-phenyl)-carbamic acid phenyl ester

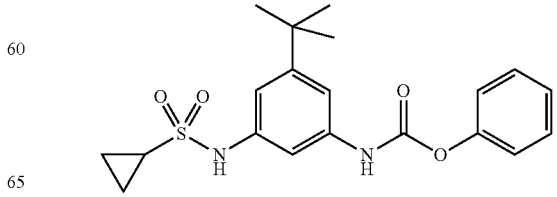

a. Cyclopropanesulfonic acid (3-amino-5-tert-butyl-phenyl)-amide (Intermediate Oa)

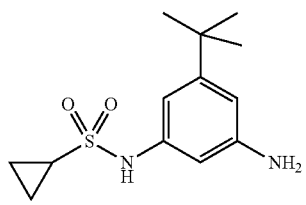 [SMILES: CC(C)(C)c1cc(N)cc(NS(=O)(=O)C2CC2)c1]

A stirred solution of 5-tert-butyl-benzene-1,3-diamine (CAS: 22503-17-9, 0.25 g, 1.52 mmol) and pyridine (0.5 ml, 6.18 mmol) in DCM (3 ml) was treated with cyclopropanesulfonyl chloride (155 µl, 1.52 mmol). The reaction mixture was stirred at RT for 3 days, diluted with DCM and washed with a saturated aqueous NaHCO$_3$ solution and brine. The organic phase was dried with MgSO$_4$ and the solvent was removed under reduced pressure. Purification by FCC, eluting with 0-30% EtOAc/DCM afforded the title compound (285 mg).

LCMS (Method 4): Purity~60%, Rt 1.06 min, m/z 269 [MH$^+$].

b. (3-tert-Butyl-5-cyclopropanesulfonylamino-phenyl)-carbamic acid phenyl ester (Intermediate 0)

The title compound was prepared starting from Intermediate Oa (285 mg, purity ~60%) using the procedure described to make Intermediate 34b. Purification by FCC, eluting with 0-40% EtOAc/cyclohexane afforded the title compound (156 mg, 74%).

LCMS (Method 4): Rt 1.52 min, m/z 389 [MH$^+$].

Intermediate P. (3-tert-Butyl-5-methylsulfamoyl-phenyl)-carbamic acid 2,2,2-trichloro-ethyl ester

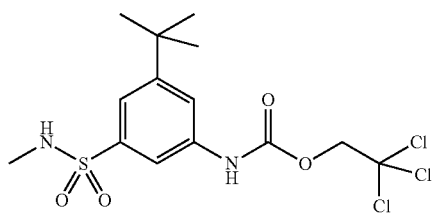 [SMILES: CNS(=O)(=O)c1cc(NC(=O)OCC(Cl)(Cl)Cl)cc(C(C)(C)C)c1]

A solution of 3-tert-butyl-5-methylsulfamoyl-benzoic acid (WO 2008/021388, which is incorporated herein by reference in its entirety, 400 mg, 1.47 mmol) in THF (10 ml) was treated with TEA (270 µl, 1.91 mmol) and DPPA (412 µl, 1.91 mmol). The reaction mixture was stirred at RT for 1 hour and then 2,2,2-trichloro-ethanol (225 µl, 2.35 mmol) was added. The reaction mixture was heated at 70° C. for 18 hours and cooled at RT. The volatiles were removed under reduced pressure and the residue was partitioned between EtOAc and an aqueous 5% citric acid solution. The two phases were separated and the aqueous phase was extracted with EtOAc. The combined organic phases were washed with a saturated aqueous NaHCO$_3$ solution and brine, dried with Na$_2$SO$_4$ and the solvent was removed under reduced pressure. Purification by FCC, eluting with 0-70% EtOAc/cyclohexane gave the title compound (429 mg, 70%).

$^1$H NMR (300 MHz, CDCl$_3$): 1.35 (9H, s), 2.69 (3H, d, J=5.4 Hz), 4.45 (1H, q, J=5.4 Hz), 4.84 (2H, s), 7.18 (1H, br s), 7.62 (1Ht, J=1.7 Hz), 7.66 (1H, br s), 7.81 (1H, br s).

Intermediate Q. 1-tert-Butyl-3-isocyanato-5-methanesulfonylmethyl-benzene

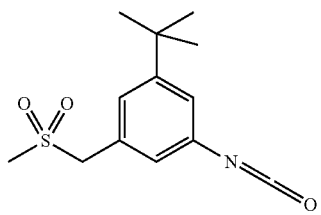 [SMILES: CC(C)(C)c1cc(CS(C)(=O)=O)cc(N=CC=O)c1]

a. 1-Bromo-3-tert-butyl-5-methanesulfonylmethyl-benzene (Intermediate Qa)

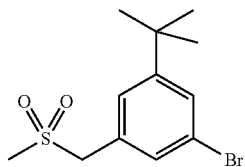 [SMILES: CC(C)(C)c1cc(Br)cc(CS(C)(=O)=O)c1]

To a solution of (3-bromo-5-tert-butyl-phenyl)-methanol (WO 2011/140936, which is incorporated herein by reference in its entirety, 200 mg, 0.82 mmol) and DIPEA (292 µl, 1.64 mmol) in DCM (7 ml) at 0° C. was added dropwise methanesulfonyl chloride (127 µl, 1.64 mmol). The reaction mixture was stirred at 0° C. for 5 minutes and at RT for 60 minutes. An aqueous 1M HCl solution was added and the two phases were separated. The aqueous phase was extracted with DCM (×2) and the combined organic phases were dried with Na$_2$SO$_4$ and the solvent was removed under reduced pressure. The residue was dissolved in DMF (10 ml) and methanesulfinate sodium salt (167 mg, 1.64 mmol) was added. The reaction mixture was heated at 60° C. for 24 hours, cooled at RT and the volatiles were removed under reduced pressure. The residue was partitioned between EtOAc and aqueous HCl 1M solution and the two phases were separated. The organic phase was washed with a saturated aqueous NaHCO$_3$ solution and brine, dried with Na$_2$SO$_4$ and the solvent was removed under reduced pressure. Purification by FCC, 0-50% EtOAc/cyclohexane afforded the title compound (210 mg, 84%).

$^1$H NMR (300 MHz, CDCl$_3$): 1.32 (9H, s), 2.78 (3H, s), 4.20 (2H, s), 7.35 (1H, t, J=1.6 Hz), 7.38 (1H, t, J=1.6 Hz), 7.55 (1H, t, J=1.6 Hz).

b. (3-tert-Butyl-5-methanesulfonylmethyl-phenyl)-carbamic acid tert-butyl ester (Intermediate Qb)

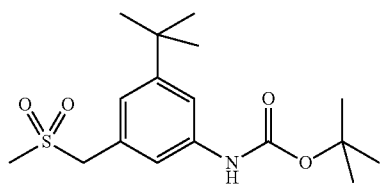 [SMILES: CC(C)(C)OC(=O)Nc1cc(CS(C)(=O)=O)cc(C(C)(C)C)c1]

A suspension of Intermediate Qa (150 mg, 0.49 mmol), tert-butyl carbamate (69 mg, 0.59 mmol), Pd$_2$(dba)$_3$ (22 mg, 0.02 mmol), XPhos (35 mg, 0.07 mmol) and sodium tert-butoxide (66 mg, 0.69 mmol) in toluene (1.5 ml) was heated at 95° C. for 18 hours. The reaction mixture was then cooled at RT, diluted with DCM and filtered through a pad of Celite®. Purification by FCC, 0-40% EtOAc/cyclohexane afforded the title compound (126 mg, 75%).

$^1$H NMR (300 MHz, CDCl$_3$): 1.31 (9H, s), 1.43 (9H, s), 2.76 (3H, s), 4.20 (2H, s), 6.62 (1H, br s), 7.09-7.10 (1H, m), 7.32-7.37 (2H, m).

c. 3-tert-Butyl-5-methanesulfonylmethyl-phenylamine (Intermediate Qc)

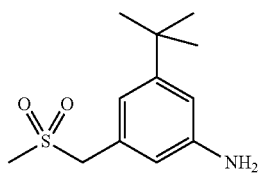

Intermediate Qb (126 mg, 0.37 mmol) was dissolved in DCM (1 ml) and TFA (1 ml) and the reaction mixture was stirred at RT for 15 hours. The volatiles were removed under reduced pressure and the residue was dissolved in DCM and a saturated aqueous NaHCO$_3$ solution. The two phases were separated and the aqueous phase was extracted with DCM (×2). The combined organic phases were dried with Na$_2$SO$_4$ and the solvent was removed under reduced pressure to afford the title compound (90 mg, quant.).

$^1$H NMR (300 MHz, CDCl$_3$): 1.20 (9H, s), 2.66 (3H, s), 4.06 (2H, s), 6.50 (1H, t, J=2.0 Hz), 6.64 (1H, t, J=2.0 Hz), 6.67 (1H, t, J=1.7 Hz) plus two protons not observed.

d. 3-tert-Butyl-5-methanesulfonylmethyl-phenylamine (Intermediate Q)

The title compound (100 mg, 76%) was prepared starting from Intermediate Qc (100 mg, 0.41 mmol) using the procedure described to make Intermediate A.

$^1$H NMR (300 MHz, CDCl$_3$): 1.24 (9H, s), 2.71 (3H, s), 4.13 (2H, s), 6.91 (1H, br s), 7.14 (1H, t, J=2.0 Hz), 7.23-7.25 (1H, m).

Intermediate R. Acetic acid 3-tert-butyl-5-isocyanato-benzyl ester

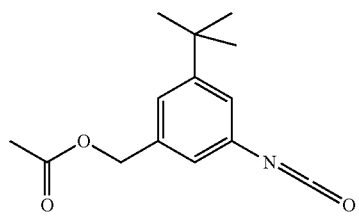 [SMILES: CC(=O)OCc1cc(N=CC=O)cc(C(C)(C)C)c1]

a. Acetic acid 3-bromo-5-tert-butyl-benzyl ester (Intermediate Ra)

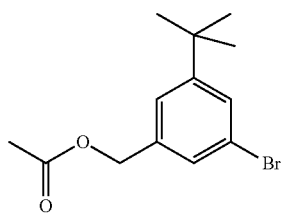 [SMILES: CC(=O)OCc1cc(Br)cc(C(C)(C)C)c1]

A solution of (3-bromo-5-tert-butyl-phenyl)-methanol (WO 2011/140936, which is incorporated herein by reference in its entirety, 200 mg, 0.82 mmol), TEA (350 µl, 2.47 mmol) and DMAP (10 mg, 0.08 mmol) in DCM (5 ml) was treated with acetic anhydride (78 µl, 0.82 mmol) and the resulting mixture was stirred at RT for 5 hours. The reaction mixture was partitioned between DCM and an aqueous 1M HCl solution and the two phases were separated. The aqueous phase was extracted with DCM (×2) and the combined organic phases were washed with brine, dried with Na$_2$SO$_4$ and the solvent was removed under reduced pressure to afford the title compound (240 mg, quant.).

$^1$H NMR (300 MHz, CDCl$_3$): 1.30 (9H, s), 2.11 (3H, s), 5.05 (2H, s), 7.27 (1H, br s), 7.33 (1H, br s), 7.47 (1H, t, J=1.6 Hz).

b. Acetic acid 3-tert-butoxycarbonylamino-5-tert-butyl-benzyl ester (Intermediate Rb)

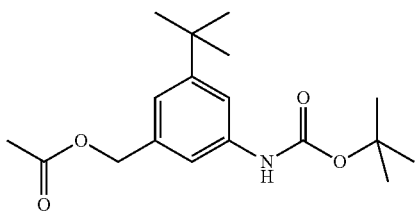 [SMILES: CC(=O)OCc1cc(NC(=O)OC(C)(C)C)cc(C(C)(C)C)c1]

A suspension of Intermediate Ra (200 mg, 0.70 mmol), tert-butyl carbamate (98 mg, 0.84 mmol), Pd(OAc)$_2$ (8 mg, 0.035 mmol), XPhos (35 mg, 0.07 mmol) and Cs$_2$CO$_3$ (319 mg, 0.98 mmol) in dioxane (5 ml) was heated at 95° C. for 18 hours. The reaction mixture was then cooled at RT, diluted with EtOAc and filtered through a pad of Celite®.

Purification by FCC, 0-40% EtOAc/cyclohexane afforded the title compound (240 mg, quant.).

$^1$H NMR (300 MHz, CDCl$_3$): 1.30 (9H, s), 1.52 (9H, s), 2.10 (3H, s), 5.06 (2H, s), 6.50 (1H, br s), 7.03 (1H, br s), 7.26-7.29 (2H, m).

c. Acetic acid 3-amino-5-tert-butyl-benzyl ester (Intermediate Rc)

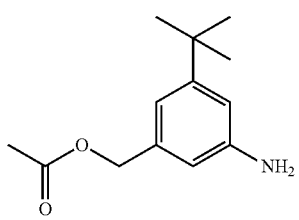 [SMILES: CC(=O)OCc1cc(N)cc(C(C)(C)C)c1]

The title compound (159 mg, 93%) was prepared starting from Intermediate Rb (248 mg, 0.77 mmol) using the procedure described to make Intermediate Qc.

$^1$H NMR (300 MHz, CDCl$_3$): 1.28 (9H, s), 2.10 (3H, s), 3.67 (2H, br s), 5.01 (2H, s), 6.53 (1H, t, J=1.8 Hz), 6.69 (1H, t, J=2.0 Hz), 6.77 (1H, br s).

d. Acetic acid 3-tert-butyl-5-isocyanato-benzyl ester (Intermediate R)

The title compound (188 mg, quant.) was prepared starting from Intermediate Re (159 mg, 0.72 mmol) using the procedure described to make Intermediate A.

$^1$H NMR (300 MHz, CDCl$_3$): 1.23 (9H, s), 2.04 (3H, s), 4.98 (2H, s), 6.84 (1H, br s), 6.97 (1H, br s), 7.10 (1H, br s).

Intermediate S. N-(3-tert-Butyl-5-isocyanato-benzyl)-methanesulfonamide

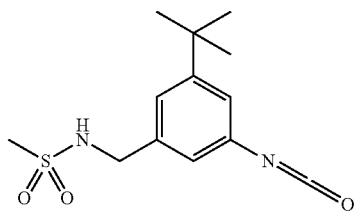 [SMILES: CC(C)(C)c1cc(CNS(C)(=O)=O)cc(N=CC=O)c1]

a. N-(3-Bromo-5-tert-butyl-benzyl)-N-tert-butoxycarbonyl-methanesulfonamide (Intermediate Sa)

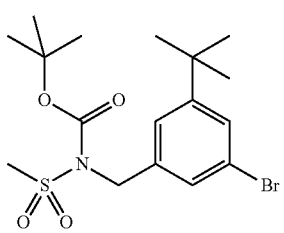 [SMILES: CC(C)(C)OC(=O)N(Cc1cc(Br)cc(C(C)(C)C)c1)S(C)(=O)=O]

A stirred solution of (3-bromo-5-tert-butyl-phenyl)-methanol (WO 2011/140936, which is incorporated herein by reference in its entirety, 350 mg, 1.44 mmol), N-(methylsulfonyl)-1,1-dimethylethyl ester carbamic acid (CAS: 147751-16-4, 337 mg, 1.73 mmol) and PPh$_3$ (454 mg, 1.73 mmol) in THF (10 ml) at 0° C. was treated with a solution of DEAD (267µ 1.70 mmol) in THF (3 ml). The reaction mixture was stirred at 0° C. for 150 minutes, warmed at RT overnight and quenched with EtOAc and a saturated aqueous NaHCO$_3$ solution. The two phases were separated and the aqueous phase was extracted with EtOAc (×2). The combined organic phases were washed with brine, dried with Na$_2$SO$_4$ and the solvent was removed under reduced pressure. Purification by FCC, eluting with 0-40% EtOAc/cyclohexane afforded the title compound (530 mg, 88%).

$^1$H NMR (300 MHz, CDCl$_3$): 1.30 (9H, s), 1.51 (9H, s), 3.21 (3H, s), 4.83 (2H, s), 7.30-7.33 (2H, m), 7.43 (1H, t, J=1.7 Hz).

b. {3-tert-Butyl-5-[(methanesulfonyl-N-tert-butoxycarbonyl-amino)-methyl]-phenyl}-carbamic acid tert-butyl ester (Intermediate Sb)

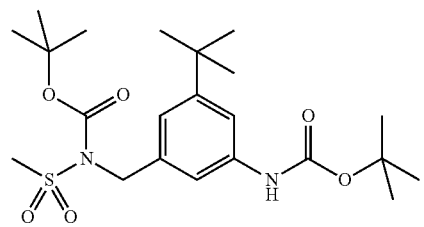 [SMILES: CC(C)(C)OC(=O)Nc1cc(CN(C(=O)OC(C)(C)C)S(C)(=O)=O)cc(C(C)(C)C)c1]

The title compound (326 mg, quant.) was prepared starting from Intermediate Sa (300 mg, 0.71 mmol) using the procedure described to make Intermediate Rb.

$^1$H NMR (300 MHz, CDCl$_3$): 1.29 (9H, s), 1.51 (18H, s), 3.21 (3H, s), 4.85 (2H, s), 6.48 (1H, br s), 7.04 (1H, t, J=1.6 Hz), 7.23 (1H, br s), 7.26-7.28 (1H, m).

c. N-(3-Amino-5-tert-butyl-benzyl)-methanesulfonamide (Intermediate Sc)

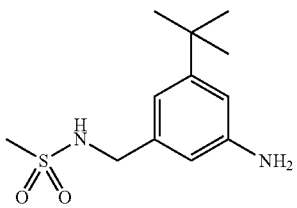 [SMILES: CC(C)(C)c1cc(N)cc(CNS(C)(=O)=O)c1]

The title compound (180 mg, 99%) was prepared starting from Intermediate Sb (326 mg, 0.71 mmol) using the procedure described to make Intermediate Qc.

$^1$H NMR (300 MHz, CDCl$_3$): 1.27 (9H, s), 2.63 (2H, br s), 2.88 (3H, s), 4.22 (2H, d, J=5.8 Hz), 4.85 (1H, br s), 6.66 (1H, s), 6.77 (1H, s), 6.80 (1H, s).

d. N-(3-tert-Butyl-5-isocyanato-benzyl)-methanesulfonamide (Intermediate S)

The title compound (208 mg, quant.) was prepared starting from Intermediate Sc (180 mg, 0.70 mmol) using the procedure described to make Intermediate A.

¹H NMR (300 MHz, CDCl₃): 1.23 (9H, s), 2.83 (3H, s), 4.21 (2H, d, J=6.3 Hz), 4.66 (1H, br s), 6.84 (1H, br s), 6.97 (1H, t, J=1.8 Hz), 7.11 (1H, br s).

Intermediate T. (3-tert-Butyl-5-isocyanato-phenyl)-carbamic acid methyl ester

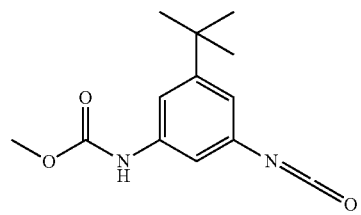 [SMILES: COC(=O)Nc1cc(N=CC=O)cc(C(C)(C)C)c1]

a. [3-tert-Butyl-5-(2,2,2-trifluoro-acetylamino)-phenyl]-carbamic acid methyl ester (Intermediate Ta)

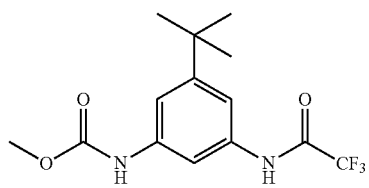 [SMILES: COC(=O)Nc1cc(NC(=O)C(F)(F)F)cc(C(C)(C)C)c1]

To a stirred solution of Intermediate 34a (200 mg, 0.77 mmol) in 2-methyltetrahydrofuran (2 ml) at 0° C. was added methyl chloroformate (59 µl, 0.77 mmol). The reaction mixture was warmed at RT and then heated at 60° C. for 18 hours. Other three aliquots of methyl chloroformate (3×30 µl) were added at regular intervals and the resulting mixture was stirred at 60° C. for 24 hours. The reaction mixture was cooled at RT and the volatiles were removed under reduced pressure. Purification by FCC, eluting with 0-100% EtOAc/cyclohexane afforded the title compound (145 mg, 59%).

LCMS (Method 4): Rt 1.23 min, m/z 319 [MH⁺].

b. (3-Amino-5-tert-butyl-phenyl)-carbamic acid methyl ester (Intermediate Tb)

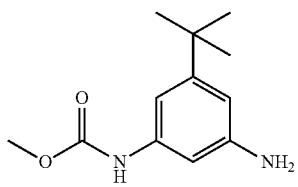 [SMILES: COC(=O)Nc1cc(N)cc(C(C)(C)C)c1]

To a stirred solution of Intermediate Ta (140 mg, 0.44 mmol) in MeOH (15 ml) was added K₂CO₃ (182 mg, 1.32 mmol) dissolved in H₂O (1 ml). The reaction mixture was heated at 60° C. for 40 hours, cooled at RT and the volatiles were removed under reduced pressure. The residue was dissolved in DCM and H₂O and the two phases were separated. The organic phase was washed with H₂O and brine, passed through a phase separator and the solvent was removed under reduced pressure to afford the title compound (77 mg, 79%).

LCMS (Method 4): Rt 0.83 min, m/z 223 [MH⁺].

c. (3-tert-Butyl-5-isocyanato-phenyl)-carbamic acid methyl ester (Intermediate T)

The title compound (85 mg, quant.) was prepared starting from Intermediate Tb (75 mg, 0.34 mmol) using the procedure described to make Intermediate A.

¹H NMR (300 MHz, CDCl₃): 1.28 (9H, s), 3.78 (3H, s), 6.58 (1H, br s), 6.80 (1H, t, J=1.7 Hz), 7.10-7.13 (2H, m).

Intermediate U. 1-tert-Butyl-3-isocyanato-5-methanesulfonyl-benzene

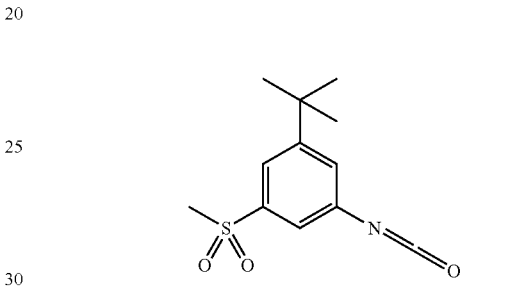

a. (3-Bromo-5-tert-butyl-phenyl)-carbamic acid benzyl ester (Intermediate Ua)

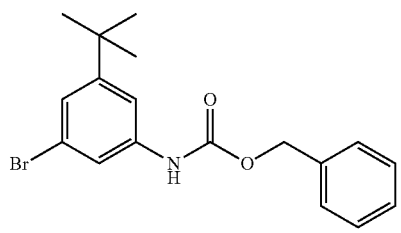 [SMILES: CC(C)(C)c1cc(Br)cc(NC(=O)OCc2ccccc2)c1]

A stirred solution of 3-bromo-5-(1,1-dimethylethyl)-benzoic acid (WO 2009/097971, which is incorporated herein by reference in its entirety, 1.50 g, 5.83 mmol) in THF (40 ml) was treated with TEA (1.1 ml, 8.11 mmol) and DPPA (1.6 ml, 7.57 mmol). The reaction mixture was stirred at RT for 20 minutes and then benzyl alcohol (783 µl, 7.57 mmol) was added. The reaction mixture was heated at 75° C. for 18 hours and cooled at RT. The volatiles were removed under reduced pressure and the residue was partitioned between EtOAc and an aqueous 1H HCl solution. The two phases were separated and the aqueous phase was extracted with EtOAc. The combined organic phases were washed with a saturated aqueous NaHCO₃ solution and brine, dried with Na₂SO₄ and the solvent was removed under reduced pressure. Purification by FCC, eluting with 0-30% EtOAc/cyclohexane gave the title compound (1.68 g, 80%).

¹H NMR (300 MHz, CDCl₃): 1.27 (9H, s), 5.19 (2H, s), 6.69 (1H, br s), 7.21 (1H, t, J=1.8 Hz), 7.25 (1H, t, J=1.8 Hz), 7.31-7.40 (5H, m), 7.48 (1H, br s).

b. (3-tert-Butyl-5-methanesulfonyl-phenyl)-carbamic acid benzyl ester (Intermediate Ub)

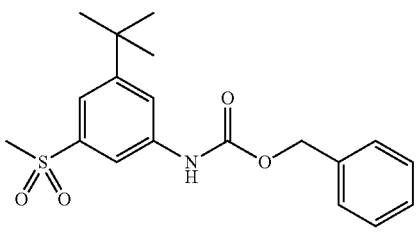 [SMILES: CC(C)(C)c1cc(NC(=O)OCc2ccccc2)cc(S(C)(=O)=O)c1]

A stirred solution of Intermediate Ua (400 mg, 1.10 mmol) in THF (10 ml) at −78° C. was treated with n-butyl lithium (2.5 M in hexane, 1.2 ml, 2.42 mmol). The reaction mixture was stirred at −78° C. for 10 minutes and then dimethyldisulfite (120 μl, 1.32 mmol) was added dropwise. The reaction mixture was stirred at −78° C. for 1 hour and at 0° C. for 1 hour. The reaction mixture was quenched with $H_2O$ and partitioned between EtOAc and an aqueous 1M HCl solution. The two phases were separated and the aqueous phase was extracted with EtOAc (×2) and the combined organic phases were dried with $Na_2SO_4$ and the solvent was removed under reduced pressure. Purification by FCC, eluting with 0-30% EtOAc/cyclohexane gave a mixture of the (3-tert-butyl-5-methylsulfanyl-phenyl)-carbamic acid benzyl ester and Intermediate Ua (ratio ~3:1, 172 mg, 47%). The mixture was dissolved in DCM (3.5 ml) and m-CPBA (320 mg, 1.85 mmol) was added. The reaction mixture was stirred at RT overnight. The volatiles were removed under reduced pressure and the residue was partitioned between EtOAc and a saturated aqueous $NaHCO_3$ solution. The two phases were separated and the aqueous phase was extracted with EtOAc (×2). The combined organic phases were washed with brine, dried with $Na_2SO_4$ and the solvent was removed under reduced pressure. Purification by FCC, eluting with 0-50% EtOAc/cyclohexane afforded the title compound (120 mg, 63%).

$^1$H NMR (300 MHz, $CDCl_3$): 1.34 (9H, s), 3.04 (3H, s), 5.22 (2H, s), 6.94 (1H, br s), 7.33-7.41 (5H, m), 7.64 (1H, t, J=1.7 Hz), 7.71 (1H, br s), 7.80 (1H, t, J=1.7 Hz).

c. 3-tert-Butyl-5-methanesulfonyl-phenylamine (Intermediate Uc)

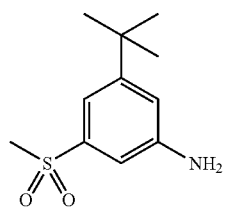

A stirred solution of Intermediate Ub (120 mg, 0.33 mmol) in EtOAc (5 ml) was treated with palladium on activated charcoal (10% Pd, 10 mg). The vessel was evacuated and filled with nitrogen (×3) and then it was evacuated and filled with hydrogen. The reaction mixture was stirred at RT for 18 hours, diluted with EtOAc and filtered through a pad of Celite®. The solvent was removed under reduced pressure to give the title compound (70 mg, 93%).

$^1$H NMR (300 MHz, $CDCl_3$): 1.31 (9H, s), 3.03 (3H, s), 4.18 (2H, br s), 6.93 (1H, t, J=1.8 Hz), 7.04 (1H, br s), 7.30 (1H, t, J=1.4 Hz).

d. 1-tert-Butyl-3-isocyanato-5-methanesulfonyl-benzene (Intermediate U)

The title compound (80 mg, quant.) was prepared starting from Intermediate Uc (70 mg, 0.31 mmol) using the procedure described to make Intermediate A.

$^1$H NMR (300 MHz, $CDCl_3$): 1.28 (9H, s), 2.99 (3H, s), 7.28 (1H, t, J=1.8 Hz), 7.42 (1H, t, J=1.8 Hz), 7.70 (1H, t, J=1.8 Hz).

Intermediate V. 4-(3-tert-Butyl-5-isocyanato-phenyl)-morpholine

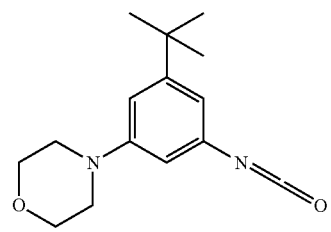 [SMILES: CC(C)(C)c1cc(N=CC=O)cc(N2CCOCC2)c1]

a. (3-tert-Butyl-5-morpholin-4-yl-phenyl)-carbamic acid benzyl ester (Intermediate Va)

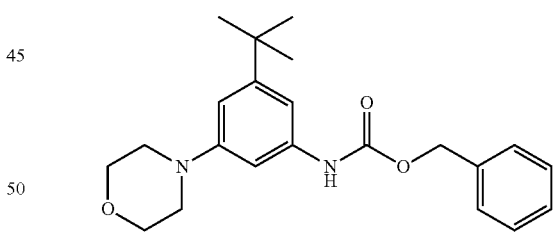

A suspension of Intermediate Ua (150 mg, 0.41 mmol), morpholine (54 μl, 0.62 mmol), $Pd_2(dba)_3$ (18 mg, 0.02 mmol), XPhos (19 mg, 0.04 mmol) and t-BuOK (70 mg, 0.62 mmol) in THF (2 ml) was purged with nitrogen for few minuted. Microwave conditions were applied (60 minutes at 100° C.) and then the reaction mixture was diluted with EtOAc and filtered through a pad of Celite®. Purification by FCC, 0-40% EtOAc/cyclohexane afforded the title compound (90 mg, 60%).

$^1$H NMR (300 MHz, $CDCl_3$): 1.28 (9H, s), 3.16 (4H, t, J=6.6 Hz), 3.83-3.86 (4H, m), 5.19 (2H, s), 6.64-6.67 (2H, m), 6.75 (1H, t, J=2.0 Hz), 7.03 (1H, br s), 7.31-7.42 (5H, m).

b. 3-tert-Butyl-5-morpholin-4-yl-phenylamine (Intermediate Vb)

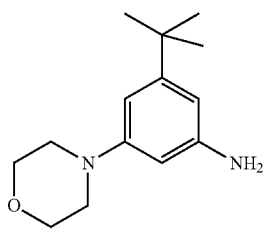 [SMILES: CC(C)(C)c1cc(N)cc(N2CCOCC2)c1]

The title compound (80 mg, 79%) was prepared starting from Intermediate Va (160 mg, 0.43 mmol) using the procedure described to make Intermediate Uc.

$^1$H NMR (300 MHz, CDCl$_3$): 1.27 (9H, s), 3.11-3.14 (4H, m), 3.83-3.86 (4H, m), 6.09 (1H, t, J=2.0 Hz), 6.30 (1H, t, J=1.7 Hz), 6.40 (1H, t, J=1.8 Hz).

c. 4-(3-tert-Butyl-5-isocyanato-phenyl)-morpholine (Intermediate V)

The title compound (100 mg, quant.) was prepared starting from Intermediate Vb (80 mg, 0.34 mmol) using the procedure described to make Intermediate A.

$^1$H NMR (300 MHz, CDCl$_3$): 1.22 (9H, s), 3.05-3.09 (4H, m), 3.76-3.80 (4H, m), 6.35 (1H, t, J=2.0 Hz), 6.57 (1H, t, J=1.7 Hz), 6.70 (1H, t, J=1.9 Hz).

Examples 36-48 a. General Procedure for Examples 36-39

A solution of an appropriate carbamate (see Table 5) (0.40 mmol), an appropriate amine (see Table 5) (0.36 mmol) and DIPEA (0.45 mmol) in dioxane (7 ml) was stirred at 60° C. until the starting materials were consumed. The volatiles were removed under reduced pressure and the residue was partitioned between EtOAc and H$_2$O. The two phases were separated and the organic phase was washed with a saturated aqueous NaHCO$_3$ solution, H$_2$O and brine. The organic phase was dried with Na$_2$SO$_4$ and the solvent was removed under reduced pressure. The resulting residue was purified by FCC, eluting with 0-7.5% 2M NH$_3$ in MeOH/DCM or MDAP (Method 6) or MDAP (Method 7) or HPLC (X-Bridge 18, 10-98% MeCN in H$_2$O, 0.1% NH$_4$OH, 18 ml/min) to afford the title compounds (12-40%).

b. General Procedure for Examples 40-41

A solution of 5-tert-butyl-isophthalic acid monomethyl ester (US 2014/0296208, which is incorporated herein by reference in its entirety, 0.50 mmol), TEA (77 µl, 0.55 mmol) and DPPA (108 µl, 0.50 mmol) in dioxane (4 ml) was stirred at RT for 45 minutes and then it was heated at 80° C. for 3 hours. The reaction mixture was cooled at RT, an appropriate amine (see Table 5) (0.36 mmol) was added and the vessel was heated at 80° C. for 15 hours. The reaction mixture was partitioned between EtOAc and a saturated aqueous NaHCO$_3$ solution. The two phases were separated and the aqueous phase was extracted with EtOAc. The combined organic phases were washed with H$_2$O and brine, dried with Na$_2$SO$_4$ and the solvent was removed under reduced pressure. The resulting residue was purified by FCC, eluting with 0-7.5% 2M NH$_3$ in MeOH/DCM or MDAP (Method 6) to afford the title compounds (20-27%).

c. General Procedure for Examples 42-48

A solution of an appropriate isocyanate (see Table 5) (0.31 mmol) and an appropiate amine (see Table 5) (0.25 mmol) in 2-methyltetrahydrofuran (4 ml) was stirred at RT for 18 hours. The reaction mixture was diluted with 2-methyltetrahydrofuran and H$_2$O and the two phases were separated. The aqueous phase was extracted with 2-methyltetrahydrofuran (×3) and the combined organic phases were dried with Na$_2$SO$_4$ and the solvent was removed under reduced pressure. The residue was purified by FCC, eluting with 0-5% 2M NH$_3$ in MeOH/DCM or HPLC (Gemini C18, 10-50% MeCN in H$_2$O, 0.1% HCO$_2$H, 18 ml/min) or HPLC (X-Bridge 18, 10-98% MeCN in H$_2$O, 0.1% NH$_4$OH, 18 ml/min) to afford the title compounds (18-50%).

TABLE 5

| Ex. | Intermediate | Amine | Structure | NMR (400 MHz) δ | LC-MS |
|---|---|---|---|---|---|
| 36 | Intermediate O | (1S,4R)-4-[3-((S)-1-Methyl-pyrrolidin-2-yl)-[1,2,4]triazolo[4,3-a]pyridin-6-yloxy]-1,2,3,4-tetrahydro-naphthalen-1-ylamine (WO 2014/195402, which is incorporated herein by reference) | Cyclopropanesulfonic acid [3-tert-butyl-5-(3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-ureido)-phenyl]-amide | $^1$H NMR (400 MHz, d$_6$-DMSO): 0.89-0.99 (4H, m), 1.24 (9H, s), 1.84-2.27 (11H, m), 2.36 (1H, q, J = 8.7 Hz), 2.54-2.62 (1H, m), 3.12-3.19 (1H, m), 4.00 (1H, t, J = 8.7 Hz), 4.86-4.95 (1H, m), 5.42 (1H, t, J = 4.2 Hz), 6.55 (1H, d, J = 8.7 Hz), 6.85 (1H, t, J = 1.9 Hz), 7.23 (2H, t, J = 1.9 Hz), 7.26-7.45 (5H, m), 7.77 (1H, d, J = 9.8 Hz), 8.27 (1H, d, J = 1.7 Hz), 8.47 (1H, s), 9.55 (1H, s). | (Method 3): Rt 3.57 min, m/z 658 [MH$^+$]. |

TABLE 5-continued

| Ex. | Intermediate | Amine | Structure | NMR (400 MHz) δ | LC-MS |
|---|---|---|---|---|---|
| 37 | Intermediate O | (1S,4R)-4-[3-((S)-1,2-Dimethyl-pyrrolidin-2-yl)-[1,2,4]triazolo[4,3-a]pyridin-6-yloxy]-1,2,3,4-tetrahydro-naphthalen-1-ylamine (WO 2013/083604, which is incorporated herein by reference) | Cyclopropanesulfonic acid [3-tert-butyl-5-(3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido)-phenyl]-amide | $^1$H NMR (400 MHz, d$_6$-DMSO): 0.89-0.99 (4H, m), 1.24 (9H, s), 1.52 (3H, s), 1.77-2.06 (8H, m), 2.06-2.24 (3H, m), 2.54-2.62 (1H, m), 2.66 (1H, q, J = 8.9 Hz), 3.12-3.21 (1H, m), 4.85-4.95 (1H, m), 5.35 (1H, t, J = 4.1 Hz), 6.57 (1H, d, J = 8.6 Hz), 6.85 (1H, t, J = 1.9 Hz), 7.27 (2H, t, J = 1.9 Hz), 7.26-7.44 (5H, m), 7.76 (1H, d, J = 9.8 Hz), 8.46 (1H, d, J = 1.7 Hz), 8.48 (1H, s), 9.55 (1H, s). | (Method 3): Rt 3.63 min, m/z 672 [MH$^+$]. |
| 38 | Intermediate P | (1S,4R)-4-[3-((S)-1-Methyl-pyrrolidin-2-yl)-[1,2,4]triazolo[4,3-a]pyridin-6-yloxy]-1,2,3,4-tetrahydro-naphthalen-1-ylamine (WO 2014/195402, which is incorporated herein by reference) | 3-tert-Butyl-N-methyl-5-(3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-ureido)-benzenesulfonamide | $^1$H NMR (400 MHz, d$_6$-DMSO): 1.30 (9H, s), 1.85-2.17 (9H, m), 2.17-2.27 (2H, m), 2.36 (1H, q, J = 8.6 Hz), 2.42 (3H, d, J = 4.9 Hz), 3.11-3.19 (1H, m), 4.00 (1H, t, J = 8.3 Hz), 4.88-4.97 (1H, m), 5.43 (1H, t, J = 4.4 Hz), 6.75 (1H, d, J = 8.5 Hz), 7.26-7.35 (3H, m), 7.35-7.44 (4H, m), 7.60 (1H, t, J = 1.8 Hz), 7.77 (1H, d, J = 9.8 Hz), 7.88 (1H, t, J = 1.8 Hz), 8.27 (1H, d, J = 1.3 Hz), 8.77 (1H, s). | (Method 3): Rt 3.47 min, m/z 632 [MH$^+$]. |
| 39 | Intermediate P | (1S,4R)-4-[3-((S)-1,2-Dimethyl-pyrrolidin-2-yl)-[1,2,4]triazolo[4,3-a]pyridin-6-yloxy]-1,2,3,4-tetrahydro-naphthalen-1-ylamine (WO 2013/083604, which is incorporated herein by reference) | 3-tert-Butyl-5-(3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido)-N-methyl-benzenesulfonamide | $^1$H NMR (400 MHz, d$_6$-DMSO): 1.30 (9H, s), 1.52 (3H, s), 1.78-2.26 (11H, m), 2.42 (3H, d, J = 4.9 Hz), 2.62-2.70 (1H, m), 3.13-3.20 (1H, m), 4.88-4.97 (1H, m), 5.35 (1H, t, J = 4.2 Hz), 6.74 (1H, d, J = 8.7 Hz), 7.26-7.45 (7H, m), 7.60 (1H, t, J = 1.9 Hz), 7.76 (1H, d, J = 9.9 Hz), 7.88 (1H, t, J = 1.7 Hz), 8.47 (1H, d, J = 1.7 Hz), 8.77 (1H, s) | (Method 3): Rt 3.54 min, m/z 646 [MH$^+$]. |

TABLE 5-continued

| Ex. | Intermediate | Amine | Structure | NMR (400 MHz) δ | LC-MS |
|---|---|---|---|---|---|
| 40 | 5-tert-Butyl-isophthalic acid monomethyl ester (US 2014/0296208, which is incorporated herein by reference) | (1S,4R)-4-[3-((S)-1-Methyl-pyrrolidin-2-yl)-[1,2,4]triazolo[4,3-a]pyridin-6-yloxy]-1,2,3,4-tetrahydro-naphthalen-1-ylamine (WO 2014/195402, which is incorporated herein by reference) | 3-tert-Butyl-5-(3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-ureido)-benzoic acid methyl ester | $^1$H NMR (400 MHz, d$_6$-DMSO): 1.29 (9H, s), 1.84-2.12 (6H, m), 2.14 (3H, s), 2.16-2.27 (2H, m), 2.31-2.40 (1H, m), 3.10-3.19 (1H, m), 3.84 (3H, s), 3.99 (1H, t, J = 8.3 Hz), 4.87-4.96 (1H, m), 5.42 (1H, t, J = 4.0 Hz), 6.69 (1H, d, J = 8.5 Hz), 7.26-7.45 (5H, m), 7.55 (1H, t, J = 1.6 Hz), 7.66 (1H, t, J = 1.8 Hz), 7.77 (1H, dd, J = 9.9 Hz), 8.02 (1H, t, J = 1.8 Hz), 8.27 (1H, d, J = 2.0 Hz), 8.65 (1H, s) | (Method 3): Rt 3.84 min, m/z 597 [MH$^+$]. |
| 41 | 5-tert-Butyl-isophthalic acid monomethyl ester (US 2014/0296208) | (1S,4R)-4-[3-((S)-1,2-Dimethyl-pyrrolidin-2-yl)-[1,2,4]triazolo[4,3-a]pyridin-6-yloxy]-1,2,3,4-tetrahydro-naphthalen-1-ylamine (WO 2013/083604, which is incorporated herein by reference) | 3-tert-Butyl-5-(3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido)-benzoic acid methyl ester | $^1$H NMR (400 MHz, d$_6$-DMSO): 1.29 (9H, s), 1.52 (3H, s), 1.79-2.25 (11H, m), 2.66 (1H, q, J = 8.5 Hz), 3.14-3.20 (1H, m), 3.85 (3H, s), 4.89-4.95 (1H, m), 5.35 (1H, t, J = 4.0 Hz), 6.71 (1H, d, J = 8.6 Hz), 7.27-7.44 (5H, m), 7.55 (1H, t, J = 1.6 Hz), 7.66 (1H, t, J = 2.0 Hz), 7.76 (1H, dd, J = 10.0, 0.6 Hz), 8.02 (1H, t, J = 1.6 Hz), 8.47 (1H, d, J = 1.4 Hz), 8.68 (1H, br s) | (Method 3): Rt 3.94 min, m/z 611 [MH$^+$]. |
| 42 | Intermediate Q | (1S,4R)-4-[3-((S)-1,2-Dimethyl-pyrrolidin-2-yl)-[1,2,4]triazolo[4,3-a]pyridin-6-yloxy]-1,2,3,4-tetrahydro-naphthalen-1-ylamine (WO 2013/083604, which is incorporated herein by reference) | 1-(3-tert-Butyl-5-methanesulfonylmethyl-phenyl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea | $^1$H NMR (400 MHz, d-$_6$-DMSO): 1.27 (9H, s), 1.52 (3H, s), 1.78-2.06 (8H, m), 2.06-2.25 (3H, m), 2.66 (1H, q, J = 8.9 Hz), 2.90 (3H, s), 3.13-3.20 (1H, m), 4.41 (2H, s), 4.87-4.96 (1H, m), 5.35 (1H, t, J = 4.2 Hz), 6.62 (1H, d, J = 8.7 Hz), 7.03 (1H, s), 7.26-7.45 (6H, m), 7.52 (1H, t, J = 1.9 Hz), 7.76 (1H, d, J = 9.8 Hz), 8.47 (1H, d, J = 1.9 Hz), 8.48 (1H, s) | (Method 3): Rt 3.42 min, m/z 645 [MH$^+$] |

TABLE 5-continued

| Ex. | Intermediate | Amine | Structure | NMR (400 MHz) δ | LC-MS |
|---|---|---|---|---|---|
| 43 | Intermediate R | (1S,4R)-4-[3-((S)-1-Methyl-pyrrolidin-2-yl)-[1,2,4]triazolo[4,3-a]pyridin-6-yloxy]-1,2,3,4-tetrahydro-naphthalen-1-ylamine (WO 2014/195402, which is incorporated herein by reference) | Acetic acid 3-tert-butyl-5-(3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-ureido)-benzyl ester | ¹H NMR (400 MHz, d-₆-DMSO): 1.27 (9H, s), 1.87-2.24 (14H, m), 2.36 (1H, q, J = 8.5 Hz), 3.12-3.18 (1H, m), 4.00 (1H, t, J = 8.0 Hz), 4.88-4.94 (1H, m), 5.02 (2H, s), 5.42 (1H, t, J = 4.0 Hz), 6.61 (1H, d, J = 8.7 Hz), 6.96 (1H, s), 7.27-7.43 (7H, m), 7.77 (1H, dd, J = 9.9, 0.6 Hz), 8.27 (1H, d, J = 1.4 Hz), 8.44 (1H, br s) | (Method 3): Rt 3.78 min, m/z 611 [MH⁺] |
| 44 | Intermediate R | (1S,4R)-4-[3-((S)-1,2-Dimethyl-pyrrolidin-2-yl)-[1,2,4]triazolo[4,3-a]pyridin-6-yloxy]-1,2,3,4-tetrahydro-naphthalen-1-ylamine (WO 2013/083604, which is incorporated herein by reference) | Acetic acid 3-tert-butyl-5-(3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido)-benzyl ester | ¹H NMR (400 MHz, d-₆-DMSO): 1.26 (9H, s), 1.51 (3H, s), 1.79-2.23 (14H, m), 2.66 (1H, q, J = 8.5 Hz), 3.14-3.19 (1H, m), 4.88-4.94 (1H, m), 5.01 (2H, s), 5.35 (1H, t, J = 4.0 Hz), 6.63 (1H, d, J = 8.7 Hz), 6.96 (1H, s), 7.27-7.43 (7H, m), 7.76 (1H, d, J = 9.9 Hz), 8.46-8.47 (2H, m) | (Method 3): Rt 3.87 min, m/z 625 [MH⁺] |
| 45 | Intermediate S | (1S,4R)-4-[3-((S)-1,2-Dimethyl-pyrrolidin-2-yl)-[1,2,4]triazolo[4,3-a]pyridin-6-yloxy]-1,2,3,4-tetrahydro-naphthalen-1-ylamine (WO 2013/083604, which is incorporated herein by reference) | N-[3-tert-Butyl-5-(3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido)-benzyl]-methanesulfonamide | ¹H NMR (400 MHz, d-₆-DMSO): 1.27 (9H, s), 1.52 (3H, s), 1.80-2.23 (11H, m), 2.66 (1H, q, J = 8.6 Hz), 2.84 (3H, s), 3.14-3.19 (1H, m), 4.10 (2H, d, J = 6.4 Hz), 4.88-4.94 (1H, m), 5.35 (1H, t, J = 4.0 Hz), 6.60 (1H, d, J = 8.7 Hz), 6.96 (1H, br s), 7.25-7.43 (7H, m), 7.52 (1H, t, J = 6.4 Hz), 7.76 (1H, dd, J = 9.9, 0.6 Hz), 8.42 (1H, br s), 8.47 (1H, d, J = 1.5 Hz) | (Method 3): Rt 3.48 min, m/z 660 [MH⁺] |

TABLE 5-continued

| Ex. | Intermediate | Amine | Structure | NMR (400 MHz) δ | LC-MS |
|---|---|---|---|---|---|
| 46 | Intermediate T | (1S,4R)-4-[3-((S)-1,2-Dimethyl-pyrrolidin-2-yl)-[1,2,4]triazolo[4,3-a]pyridin-6-yloxy]-1,2,3,4-tetrahydro-naphthalen-1-ylamine (WO 2013/083604, which is incorporated herein by reference) | [3-tert-Butyl-5-(3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido)-phenyl]-carbamic acid methyl ester | $^1$H NMR (400 MHz, d-$_6$-DMSO): 1.24 (9H, s), 1.52 (3H, s), 1.79-2.23 (11H, m), 2.66 (1H, q, J = 9.0 Hz), 3.14-3.20 (1H, m), 3.64 (3H, s), 4.89-4.93 (1H, m), 5.35 (1H, t, J = 3.9 Hz), 6.54 (1H, d, J = 8.7 Hz), 7.09 (1H, br s), 7.23 (1H, t, J = 1.8 Hz), 7.27-7.43 (6H, m), 7.76 (1H, dd, J = 9.9, 0.6 Hz), 8.39 (1H, br s), 8.46 (1H, d, J = 1.7 Hz), 9.47 (1H, br s) | (Method 3): Rt 3.61 min, m/z 626 [MH$^+$] |
| 47 | Intermediate U | (1S,4R)-4-[3-((S)-1,2-Dimethyl-pyrrolidin-2-yl)-[1,2,4]triazolo[4,3-a]pyridin-6-yloxy]-1,2,3,4-tetrahydro-naphthalen-1-ylamine (WO 2013/083604, which is incorporated herein by reference) | 1-(3-tert-Butyl-5-methanesulfonyl-phenyl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea | $^1$H NMR (400 MHz, d-$_6$-DMSO): 1.31 (9H, s), 1.52 (3H, s), 1.80-2.24 (11H, m), 2.66 (1H, q, J = 8.6 Hz), 3.14-3.19 (4H, m), 4.90-4.96 (1H, m), 5.35 (1H, t, J = 4.0 Hz), 6.79 (1H, d, J = 8.8 Hz), 7.27-7.43 (5H, m), 7.45 (1H, t, J = 1.6 Hz), 7.68 (1H, t, J = 1.9 Hz), 7.77 (1H, dd, J = 9.8, 0.6 Hz), 8.00 (1H, t, J = 1.8 Hz), 8.47 (1H, d, J = 1.6 Hz), 8.83 (1H, s) | (Method 3): Rt 3.52 min, m/z 631 [MH$^+$] |
| 48 | Intermediate V | (1S,4R)-4-[3-((S)-1,2-Dimethyl-pyrrolidin-2-yl)-[1,2,4]triazolo[4,3-a]pyridin-6-yloxy]-1,2,3,4-tetrahydro-naphthalen-1-ylamine (WO 2013/083604, which is incorporated herein by reference) | 1-(3-tert-Butyl-5-morpholin-4-yl-phenyl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea | $^1$H NMR (400 MHz, d-$_6$-DMSO): 1.24 (9H, s), 1.52 (3H, s), 1.80-2.23 (11H, m), 2.66 (1H, q, J = 8.6 Hz), 3.06 (4H, t, J = 4.6 Hz), 3.14-3.19 (1H, m), 3.73 (4H, t, J = 4.6 Hz), 4.86-4.92 (1H, m), 5.35 (1H, t, J = 3.9 Hz), 6.54-6.57 (2H, m), 6.84 (1H, br s), 7.01 (1H, t, J = 1.8 Hz), 7.27-7.42 (5H, m), 7.76 (1H, dd, J = 9.8, 0.5 Hz), 8.28 (1H, s), 8.47 (1H, d, J = 1.6 Hz) | (Method 3): Rt 3.61 min, m/z 638 [MH$^+$] |

Example 49. 1-(3-tert-Butyl-5-hydroxymethyl-phenyl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea

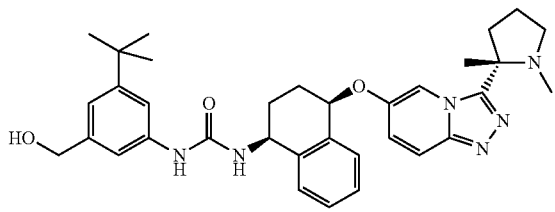 [SMILES: CN1CCC[C@@]1(C)c1nnc2ccc(O[C@@H]3CC[C@H](NC(=O)Nc4cc(CO)cc(C(C)(C)C)c4)c4ccccc43)cn12]

a. (3-Bromo-5-tert-butyl-benzyloxy)-tert-butyl-dimethyl-silane (Intermediate 49a)

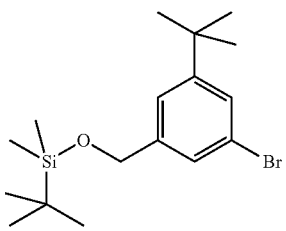 [SMILES: CC(C)(C)c1cc(Br)cc(CO[Si](C)(C)C(C)(C)C)c1]

A solution of (3-bromo-5-tert-butyl-phenyl)-methanol (WO 2011/140936, which is incorporated herein by reference in its entirety, 500 mg, 2.06 mmol) and imidazole (421 mg, 6.18 mmol) in DCM (8 ml) at 0° C. was treated with tert-butyldimethylsilyl chloride (466 mg, 3.09 mmol) and the resulting mixture was stirred at 0° C. for 5 minutes and at RT for 2 hours. The reaction mixture was partitioned between DCM and H$_2$O and the two phases were separated. The aqueous phase was extracted with DCM (×3) and the combined organic phases were washed with brine, dried with Na$_2$SO$_4$ and the solvent was removed under reduced pressure. Purification by FCC, eluting with 0-10% EtOAc/cyclohexane to afford the title compound (571 mg, 78%).

$^1$H NMR (300 MHz, CDCl$_3$): 0.10 (6H, s), 0.95 (9H, s), 1.30 (9H, s), 4.70 (2H, s), 7.26-7.28 (2H, m), 7.36-7.38 (1H, m).

b. [3-tert-Butyl-5-(tert-butyl-dimethyl-silanyloxymethyl)-phenyl]-carbamic acid tert-butyl ester (Intermediate 49b)

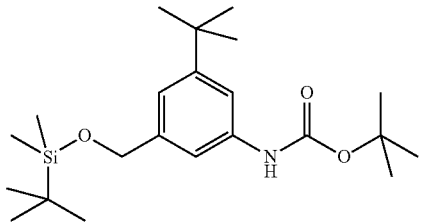 [SMILES: CC(C)(C)OC(=O)Nc1cc(CO[Si](C)(C)C(C)(C)C)cc(C(C)(C)C)c1]

The title compound (192 mg, 35%) was prepared starting from Intermediate 49a (500 mg, 1.40 mmol) using the procedure described to make Intermediate Qb.

$^1$H NMR (300 MHz, CDCl$_3$): 0.09 (6H, s), 0.94 (9H, s), 1.30 (9H, s), 1.43 (9H, s), 4.71 (2H, s), 6.42 (1H, br s), 7.07 (1H, br s), 7.11 (1H, br s), 7.24 (1H, br s).

c. 3-tert-Butyl-5-(tert-butyl-dimethyl-silanyloxymethyl)-phenylamine (Intermediate 49c)

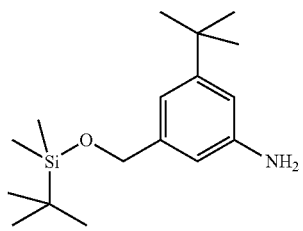 [SMILES: CC(C)(C)c1cc(N)cc(CO[Si](C)(C)C(C)(C)C)c1]

Intermediate 49b (250 mg, 0.64 mmol) was dissolved in DCM (3 ml) and TFA (3 ml) and the reaction mixture was stirred at RT for 1 hour. The solvent was removed under reduced pressure and the residue was dissolved in DCM and a saturated aqueous NaHCO$_3$ solution. The two phases were separated and the aqueous phase was extracted with DCM (×2). The combined organic phases were dried with Na$_2$SO$_4$ and the solvent was removed under reduced pressure. The residue (185 mg) was dissolved in DCM and cooled at 0° C. Imidazole (140 mg, 2.06 mmol) and tert-butyldimethylsilyl chloride (155 mg, 1.03 mmol) were added and the reaction mixture was stirred at 0° C. for 5 minutes and at RT for 4 hours. The reaction mixture was partitioned between DCM and H$_2$O and the two phases were separated. The aqueous phase was extracted with DCM (×3) and the combined organic phases were washed with brine, dried with Na$_2$SO$_4$ and the solvent was removed under reduced pressure. Purification by FCC, eluting with 0-15% EtOAc/cyclohexane afforded the title compound (120 mg, 64%).

$^1$H NMR (300 MHz, CDCl$_3$): 0.09 (6H, s), 0.94 (9H, s), 1.30 (9H, s), 3.48 (2H, br s), 4.66 (2H, s), 6.50 (1H, br s), 6.60 (1H, br s), 6.76 (1H, br s).

d. tert-Butyl-(3-tert-butyl-5-isocyanato-benzyloxy)-dimethyl-silane (Intermediate 49d)

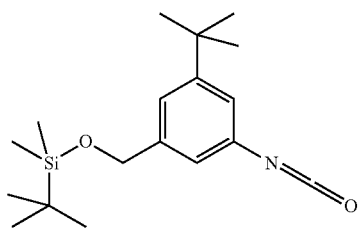 [SMILES: CC(C)(C)c1cc(CO[Si](C)(C)C(C)(C)C)cc(N=CC=O)c1]

The title compound (140 mg, quant.) was prepared starting from Intermediate 49c (120 mg, 0.41 mmol) using the procedure described to make Intermediate A.

$^1$H NMR (300 MHz, CDCl$_3$): 0.09 (6H, s), 0.95 (9H, s), 1.30 (9H, s), 4.68 (2H, s), 6.85 (1H, br s), 6.94 (1H, br s), 7.18 (1H, br s).

e. 1-[3-tert-Butyl-5-(tert-butyl-dimethyl-silany-loxymethyl)-phenyl]-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea (Intermediate 49e)

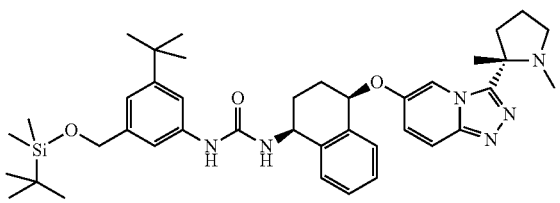 [SMILES: CN1CCC[C@@]1(C)c1nnc2ccc(O[C@@H]3CC[C@H](NC(=O)Nc4cc(CO[Si](C)(C)C(C)(C)C)cc(C(C)(C)C)c4)c4ccccc43)cn12]

The title compound (182 g, 69%) was prepared starting from (1S,4R)-4-[3-(S)-1,2-dimethyl-pyrrolidin-2-yl)-[1,2,4]triazolo[4,3-a]pyridin-6-yloxy]-1,2,3,4-tetrahydro-naphthalen-1-ylamine (WO 2013/083604, 143 mg, 0.38 mmol) and Intermediate 49d (140 mg, 0.44 mmol) using the procedure described to make Example 18.

$^1$H NMR (300 MHz, CDCl$_3$): 0.08 (6H, s), 0.93 (9H, s), 1.30 (9H, s), 1.57 (3H, s), 1.77-2.32 (1H, m), 2.71 (1H, q, J=8.7 Hz), 3.11-3.18 (1H, m), 4.70 (2H, s), 5.12-5.23 (2H, m), 6.34 (1H, d, J=8.6 Hz), 6.92 (1H, dd, J=9.9, 2.3 Hz), 7.07-7.65 (9H, m), 8.56 (1H, d, J=1.6 Hz).

f. Example 49

The title compound was prepared starting from Intermediate 49e (182 mg, 0.26 mmol) using the procedure described to make Example 31. The crude was purified by FCC, 0-8% 2M NH$_3$ in MeOH/DCM, followed by a further HPLC (X-Bridge 18, 25-65% MeCN in H$_2$O, 0.1% NH$_4$OH, 18 ml/min) to afford the title compound (23 mg, 15%).

LCMS (Method 3): Rt 3.37 min, m/z 583 [MH$^+$]. $^1$H NMR (400 MHz, d-$_6$-DMSO): 1.26 (9H, s), 1.51 (3H, s), 1.78-2.01 (5H, m), 2.03 (3H, s), 2.05-2.24 (3H, m), 2.65 (1H, q, J=8.9 Hz), 3.12-3.20 (1H, m), 4.43 (2H, s), 4.86-4.94 (1H, m), 5.10 (1H, br), 5.34 (1H, t, J=5.3 Hz), 6.61 (1H, d, J=8.7 Hz), 6.91 (1H, s), 7.23 (1H, s), 7.25-7.44 (6H, m), 7.76 (1H, d, J=9.8 Hz), 8.38 (1H, s), 8.46 (1H, d, J=1.7 Hz).

Example 50. 3-tert-Butyl-N-(2-hydroxy-ethyl)-5-(3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-ureido)-benzamide

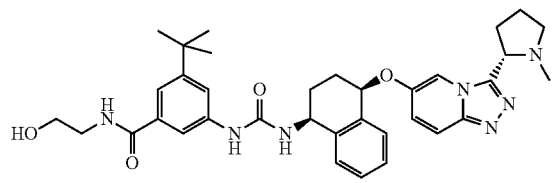 [SMILES: CN1CCC[C@H]1c1nnc2ccc(O[C@@H]3CC[C@H](NC(=O)Nc4cc(C(=O)NCCO)cc(C(C)(C)C)c4)c4ccccc43)cn12]

To a stirred solution of Example 40 (61.9 mg, 0.10 mmol) in MeOH (0.5 ml) was added Na$_2$CO$_3$ (13 mg, 0.12 mmol) and 2-amino-ethanol (8 µl, 0.12 mmol). The reaction mixture was stirred at RT for 18 hours and then another aliquot of 2-amino-ethanol (25 µl, 0.41 mmol) was added. The resulting mixture was heated at 45° C. for 2 days. Additional aliquots of 2-amino-ethanol (30 µl, 0.50 mmol) and methanol (0.5 ml) were added, the reaction mixture was stirred at 45° C. for 24 hours and then partitioned between EtOAc and H$_2$O. The two phases were separated and the aqueous phase was extracted with EtOAc (×2). The combined organic phases were washes with brine, dried with a phase separator and the solvent was removed under reduced pressure. Purification by MDAP (Method 7) afforded the title compound (18 mg, 28%).

LCMS (Method 3): Rt 3.08 min, m/z 626 [MH$^+$]. $^1$H NMR (400 MHz, d-$_6$-DMSO): 1.29 (9H, s), 1.87-2.11 (5H, m), 2.13 (3H, s), 2.16-2.26 (2H, m), 2.31-2.39 (1H, m), 3.10-3.19 (1H, m), 3.26-3.35 (2H, m), 3.50 (2H, q, J=5.7 Hz), 3.99 (1H, t, J=8.0 Hz), 4.72 (1H, t, J=5.6 Hz), 4.88-4.95 (1H, m), 5.42 (1H, t, J=4.0 Hz), 6.72 (1H, d, J=8.6 Hz), 7.26-7.45 (5H, m), 7.64 (1H, t, J=1.8 Hz), 7.69 (1H, t, J=1.8 Hz), 7.76 (1H, dd, J=9.9, 0.6 Hz), 8.27 (1H, d, J=2 Hz), 8.35 (1H, t, J=5.5 Hz), 8.55 (1H, s) plus two protons not observed.

Example 51. 3-tert-Butyl-5-(3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido)-N-(2-hydroxy-ethyl)-benzamide

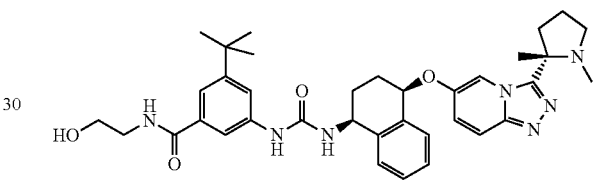

The title compound was prepared starting from Example 41 (119 mg, 0.20 mmol) using the procedure described to make Example 50. The crude was purified by MDAP (Method 7) to afford the title compound (76 mg, 59%).

LCMS (Method 3): Rt 3.14 min, m/z 640 [MH$^+$]. $^1$H NMR (400 MHz, d-$_6$-DMSO): 1.30 (9H, s), 1.52 (3H, s), 1.80-2.24 (10H, m), 2.66 (1H, q, J=8.3 Hz), 3.14-3.20 (1H, m), 3.51 (2H, q, J=6.3 Hz), 4.72 (1H, t, J=5.4 Hz), 4.89-4.95 (1H, m), 5.35 (1H, t, J=4.0 Hz), 6.69 (1H, d, J=8.7 Hz), 7.27-7.44 (6H, m), 7.64 (1H, t, J=1.9 Hz), 7.69 (1H, t, J=1.7 Hz), 7.76 (1H, dd, J=9.9, 0.7 Hz), 8.36 (1H, t, J 5.6 Hz), 8.47 (1H, d, J=1.6 Hz), 8.52 (1H, s) plus three protons under the solvent signals.

Example 52. 3-tert-Butyl-5-(3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-ureido)-benzamide

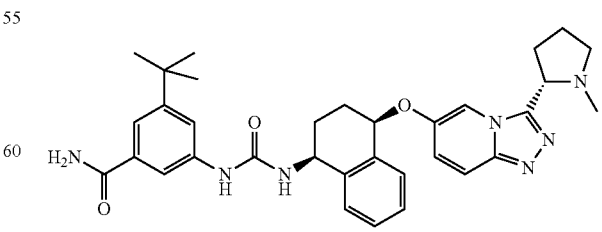

A solution of Example 40 (75 mg, 0.126 mmol) and NH$_3$ (7N in MeOH, 7 ml) was stirred at 60° C. in a sealed pressure vessel for 3 days. Another aliquot of NH$_3$ (7N in MeOH, 2 ml) was added and the reaction mixture was stirred at 60° C. for 24 hours. The volatiles were removed under reduced pressure and the residue was partitioned between EtOAc and a saturated aqueous NaHCO₃ solution. The aqueous phase was extracted with EtOAc (×2) and the combined organic phases were washed with brine, dried with a phase separator and the solvent was removed under reduced pressure. Purification by MDAP (Method 7) afforded the title compound (20 mg, 27%).

LCMS (Method 3): Rt 3.13 min, m/z 582 [MH⁺]. ¹H NMR (400 MHz, d-₆-DMSO): 1.29 (9H, s), 1.88-2.25 (10H, m), 2.36 (1H, q, J=8.5 Hz), 3.13-3.28 (1H, m), 4.00 (1H, q, J=8.1 Hz), 4.89-4.95 (1H, m), 5.43 (1H, t, J=4.0 Hz), 6.73 (1H, d, J=8.8 Hz), 7.24-7.46 (7H, m), 7.67-7.69 (2H, m), 7.77 (1H, dd, J=9.9, 0.6 Hz), 7.91 (1H, br s), 8.27 (1H, d, J=1.4 Hz), 8.52 (1H, s) plus one proton not observed.

Example 53. 3-tert-Butyl-5-(3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido)-benzamide

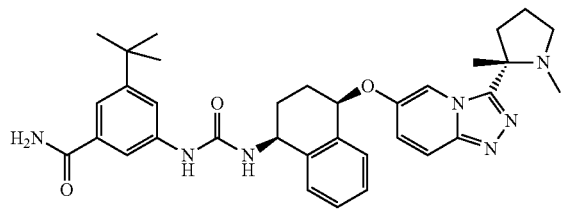 [SMILES: CN1CCC[C@@]1(C)c1nnc2ccc(O[C@@H]3CC[C@H](NC(=O)Nc4cc(C(N)=O)cc(C(C)(C)C)c4)c4ccccc43)cn12]

The title compound was prepared starting from Example 41 (160 mg, 0.27 mmol) using the procedure described to make Example 52. The crude was purified by MDAP (Method 7) to afford the title compound (40 mg, 25%).

LCMS (Method 3): Rt 3.19 min, m/z 596 [MH⁺]. ¹H NMR (400 MHz, d₆-DMSO): 1.29 (9H, s), 1.51 (3H, s), 1.77-2.06 (5H, m), 2.03 (3H, s), 2.05-2.25 (3H, m), 2.60-2.70 (1H, m), 3.12-3.20 (1H, m), 4.87-4.95 (1H, m), 5.35 (1H, t, J=4.0 Hz), 6.72 (1H, d, J=8.8 Hz), 7.20-7.47 (7H, m), 7.66-7.69 (2H, m), 7.76 (1H, dd, J=9.9, 0.6 Hz), 7.91 (1H, br s), 8.45-8.48 (1H, m), 8.51 (1H, s).

Example 54. 3-tert-Butyl-N-methyl-5-(3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-ureido)-benzamide

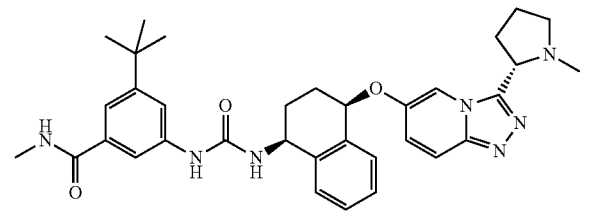

A solution of Example 40 (60 mg, 0.10 mmol), methylamine (2M in THF, 1.5 ml) and methylamine (40% in H₂O, 1.5 ml) was stirred at RT for 3 days. The volatiles were removed under reduced pressure and the crude was purified by MDAP (Method 7) to give the title compound (31 mg, 52%).

LCMS (Method 3): Rt 3.27 min, m/z 596.5 [MH⁺]. ¹H NMR (400 MHz, d₆-DMSO): 1.29 (9H, s), 1.84-2.12 (6H, m), 2.14 (3H, s), 2.16-2.27 (2H, m), 2.30-2.40 (1H, m), 2.77 (3H, d, J=4.6 Hz), 3.11-3.18 (1H, m), 3.99 (1H, t, J=8.2 Hz), 4.87-4.96 (1H, m), 5.42 (1H, t, J=4.0 Hz), 6.71 (1H, d, J=8.7 Hz), 7.25-7.45 (6H, m), 7.60-7.70 (2H, m), 7.76 (1H, dd, J=9.9, 0.6 Hz), 8.25-8.29 (1H, m), 8.31-8.37 (1H, m), 8.53 (1H, br s).

Example 55. 3-tert-Butyl-5-(3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido)-N-methyl-benzamide

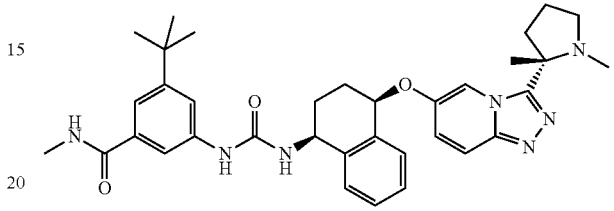

The title compound was prepared starting from Example 41 (159 mg, 0.27 mmol) using the procedure described to make Example 54. The crude was purified by MDAP (Method 7) to afford the title compound (87 mg, 53%).

LCMS (Method 3): Rt 3.31 min, m/z 610 [MH⁺]. ¹H NMR (400 MHz, d₆-DMSO): 1.29 (9H, s), 1.51 (3H, s), 1.78-2.06 (5H, m), 2.03 (3H, s), 2.06-2.25 (3H, m), 2.61-2.70 (1H, m), 2.77 (3H, d, J=4.6 Hz), 3.13-3.20 (1H, m), 4.87-4.96 (1H, m), 5.35 (1H, t, J=4.0 Hz), 6.69 (1H, d, J=8.7 Hz), 7.26-7.70 (5H, m), 7.62-7.64 (1H, m), 7.67-7.70 (1H, m), 7.76 (1H, dd, J=9.8, 0.6 Hz), 8.31-8.37 (1H, m), 8.45-8.48 (1H, m), 8.52 (1H, br s), plus one proton not observed.

Example 56. N-[5-tert-Butyl-3-(3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido)-2-methyl-phenyl]-methanesulfonamide

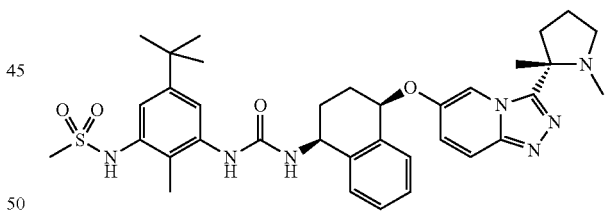

a. N-(5-tert-Butyl-3-isocyanato-2-methyl-phenyl)-methanesulfonamide (Intermediate 56a)

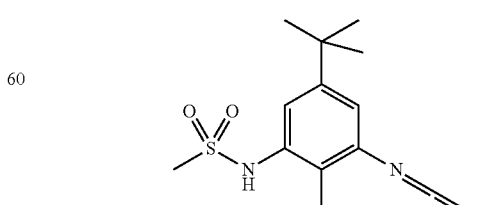

The title compound (220 mg, quant.) was prepared starting from N-(3-amino-5-(tert-butyl)-2-methylphenyl)methanesulfonamide (WO 2005/090333, which is incorporated herein by reference in its entirety, 200 mg, 0.78 mmol) using the procedure described to make Intermediate A.

¹H NMR (300 MHz, CDCl₃): 1.30 (9H, s), 2.27 (3H, s), 3.01 (3H, s), 6.21 (1H, br s), 7.02 (1H, d, J=2.0 Hz), 7.33 (1H, d, J=2.0 Hz).

b. Example 56

The title compound was prepared starting from (1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-ylamine (WO 2013/083604, which is incorporated herein by reference in its entirety, 268 mg, 0.71 mmol) and Intermediate 56a (220 mg, 0.78 mmol) using the procedure described to make Example 18. The crude was purified by FCC, eluting with 0-7% 2N NH₃ in MeOH/DCM, followed by MDAP (Method 7) to afford the title compound (180 mg, 38%).

LCMS (Method 3): Rt 3.37 min, m/z 660 [MH⁺]. ¹H NMR (400 MHz, d₆-DMSO): 1.26 (9H, s), 1.52 (3H, s), 1.80-2.23 (14H, m), 2.66 (1H, q, J=8.6 Hz), 2.90 (3H, s), 3.14-3.19 (1H, m), 4.88-4.94 (1H, m), 5.36 (1H, t, J=4.2 Hz), 6.96 (1H, d, J=2.0 Hz), 7.07 (1H, d, J=8.7 Hz), 7.28-7.45 (5H, m), 7.64 (1H, s), 7.76 (1H, dd, J=9.9, 0.6 Hz), 7.88 (1H, br s), 8.47 (1H, d, J=1.6 Hz), 8.98 (1H, br s).

Example 57. N-[5-tert-Butyl-2-methyl-3-(3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-ureido)-phenyl]-methanesulfonamide

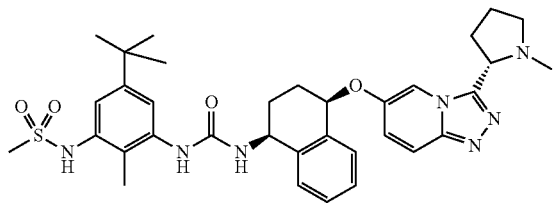

A solution of Intermediate 56a (133 mg, 0.47 mmol) in 2-methyltetrahydrofuran (6 ml) was treated with (1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-ylamine (WO 2014/195402, which is incorporated herein by reference in its entirety, 149 mg, 0.41 mmol) and the mixture was stirred at RT for 18 hours. The mixture was concentrated to approximately half volume and Et₂O was added to precipitate a solid. The solid was filtered and purified using FCC, eluting with 0-4% 2M NH3 in MeOH/DCM. Further purification by MDAP (Method 7) followed by MDAP (Method 6) gave product as a formate salt. This was dissolved in DCM, washed with saturated NaHCO₃ solution, dried (Na₂SO₄) and evaporated. The obtained solid was dissolved in MeCN (1 ml) and H₂O (1 ml). The mixture was lyophilised to afford the title compound (35.9 mg, 14%).

LCMS (Method 3): Rt 3.27 min, m/z 646 [MH⁺]. ¹H NMR (400 MHz, d₆-DMSO): 1.26 (9H, s), 1.84-2.30 (14H, m), 2.36 (1H, q, J=8.0 Hz), 2.93 (3H, s), 3.11-3.19 (1H, m), 4.00 (1H, t, J=8.0 Hz), 4.87-4.96 (1H, m), 5.43 (1H, t, J=4.3 Hz), 6.95 (1H, d, J=1.9 Hz), 7.11 (1H, d, J=8.6 Hz), 7.27-7.46 (5H, m), 7.66 (1H, br s), 7.77 (1H, dd, J=9.8, 0.6 Hz), 7.94 (1H, d, J=1.7 Hz), 8.28 (1H, d, J=1.7 Hz), 8.97 (1H, br s).

Example 58. 1-(3-tert-Butyl-5-morpholin-4-yl-phenyl)-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea

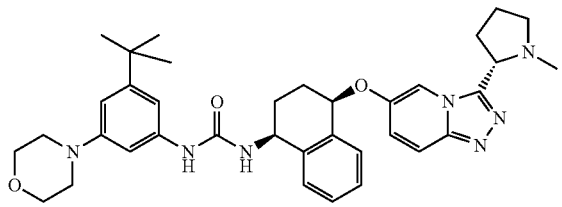 [SMILES: CN1CCC[C@H]1c1nnc2ccc(O[C@@H]3CC[C@H](NC(=O)Nc4cc(N5CCOCC5)cc(C(C)(C)C)c4)c4ccccc43)cn12]

A solution of Intermediate V (58 mg, 0.22 mmol) in 2-methyltetrahydrofuran (4 ml) was treated with (1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-ylamine (WO 2014/195402, which is incorporated herein by reference in its entirety) (70 mg, 0.19 mmol). The reaction mixture was stirred at RT for 48 hours. The reaction mixture was diluted with 2N NH₃ in MeOH/DCM (ratio 1:9) and filtered through a pad of silica gel. Purification by HPLC (XBridge C18, 10-95% MeCN in H₂O, 0.1% NH₄OH, 20 ml/min) afforded the title compound (43 mg, 36%).

LCMS (Method 3): Rt 3.53 min, m/z 624 [MH⁺]. ¹H NMR (400 MHz, d₆-DMSO): 1.24 (9H, s), 1.85-2.24 (10H, m), 2.36 (1H, q, J=9.0 Hz), 3.06 (4H, t, J=4.8 HZ), 3.13-3.17 (1H, m), 3.73 (4H, t, J=4.8 Hz), 4.00 (1H, t, J=8.0 Hz), 4.86-4.92 (1H, m), 5.42 (1H, t, J=4.2 Hz), 6.54 (1H, t, J=1.8 Hz), 6.60 (1H, d, J=8.6 Hz), 6.84 (1H, t, J=1.5 Hz), 7.01 (1H, t, J=1.9 Hz), 7.26-7.42 (5H, m), 7.77 (1H, d, J=9.8 Hz), 8.27 (1H, d, J=1.4 Hz), 8.32 (1H, br s), plus one proton obscured by solvent peak.

Example 59. 1-(5-tert-Butyl-2-hydroxymethyl-phenyl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}1-urea

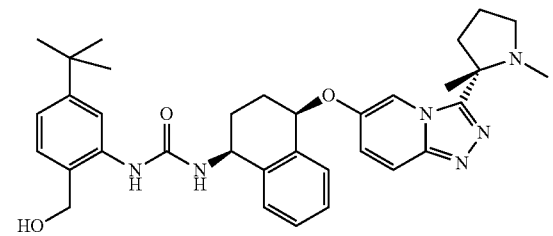 [SMILES: CN1CCC[C@@]1(C)c1nnc2ccc(O[C@@H]3CC[C@H](NC(=O)Nc4cc(C(C)(C)C)ccc4CO)c4ccccc43)cn12]

a. Acetic acid 2-bromo-4-tert-butyl-benzyl ester (Intermediate 59a)

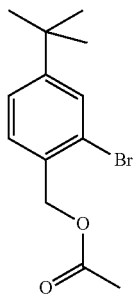 [SMILES: CC(=O)OCc1ccc(C(C)(C)C)cc1Br]

A stirred solution of 2-bromo-1-(bromomethyl)-4-(tert-butyl)benzene (*J. Med. Chem.*, 2005, 48, 71-90, which is incorporated herein by reference in its entirety, 500 mg, 1.63 mmol) and sodium acetate (802 mg, 8.17 mmol) in dimethylformamide (7.5 mL) was warmed to 70° C. for 18 hours. The reaction mixture was cooled to RT and partitioned between water and EtOAc. The two phases were separated and the aqueous phase was extracted with EtOAc (×2). The combined organic phases were passed through a phase separator and the solvent was removed under reduced pressure to afford the title compound (470 mg, quantitative).

$^1$H NMR (300 MHz, CDCl$_3$): 1.30 (9H, s), 2.12 (3H, s), 5.16 (2H, s), 7.32 (2H, d, J=1.1 Hz), 7.58 (1H, s).

b. (2-Bromo-4-tert-butyl)-methanol (Intermediate 59b)

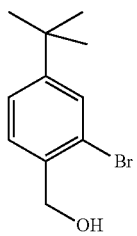

To a stirred solution of Intermediate 59a (950 mg, 3.33 mmol) in methanol (25 mL) was added sodium hydroxide (666 mg, 16.65 mmol) in water (7.5 mL). The reaction mixture was heated at 90° C. for 2 hours and then cooled to RT. The methanol was removed under reduced pressure and the residue was partitioned between an aqueous 1M HCl solution and EtOAc. The two phases were separated and the aqueous phase was extracted with EtOAc (×2). The combined organic layers were dried with sodium sulphate and the solvent was removed under reduced pressure. This product was purified by FCC, eluting with 0-50% ethylacetate in cyclohexane to afford the title compound (695 mg, 86%).

$^1$H NMR (300 MHz, CDCl$_3$): 1.30 (9H, s), 4.71 (2H, s), 7.33 (1H, dd, J=8.0, 1.8 Hz), 7.39 (1H, d, J=8.0 Hz), 7.55 (1H, d, J=1.8 Hz).

c. (2-Bromo-4-tert-butyl-benzyloxy)-tetra-butyl-dimethyl-silane (Intermediate 59c)

To a stirred solution of Intermediate 59b (695 mg, 2.86 mmol) in DCM (10 mL) at 0° C. was added 1H-imidazole (390 mg, 5.72 mmol) and tert-butyl-dimethylsilyl chloride (647 mg, 4.29 mmol). The reaction mixture was stirred at RT for 3 hours. The mixture was partitioned between water and DCM and the two phases were separated. The aqueous phase was extracted with DCM (×2) and the combined organic phases were washed with brine, dried with sodium sulphate and the solvent was removed under reduced pressure. Purification by FCC, eluting with 0-100% ethyl acetate in cyclohexane afforded the title compound (945 mg, 92%).

$^1$H NMR (300 MHz, CDCl$_3$): 0.84 (9H, s), 1.17 (9H, s), 1.30 (6H, s), 4.58 (2H, s), 7.21 (1H, dd, J=8.1, 1.9 Hz), 7.32-7.38 (2H, m).

d. {(1S,4R)-4-[3-((S)-1,2-Dimethyl-pyrrolidin-2-yl)-[1,2,4]triazolo[4,3-a]pyridin-6-yloxy]-1,2,3,4-tetrahydro-naphthalen-1-yl}-urea (Intermediate 59d)

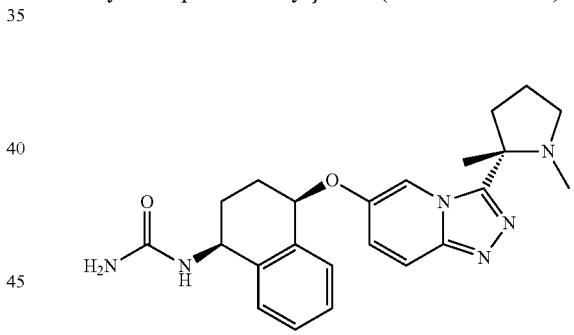

To a stirred solution of triphosgene (2.22 g, 7.49 mmol) in DCM (40 ml) at −10° C. was added slowly a solution of (1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-ylamine (WO 2013/083604, which is incorporated herein by reference in its entirety, 2.57 g, 6.81 mmol) and TEA (3.8 ml, 27.2 mmol). The reaction mixture was stirred at 0° C. for 1 hour and then added to a solution of NH$_3$ in MeOH (2M, 250 ml, 511 mmol) pre-cooled at 0° C. The resulting mixture was stirred at 0° C. for 30 minutes and then the volatiles were removed under reduced pressure. The residue was dissolved in DCM and H$_2$O and the two phases were separated. The aqueous phase was extracted with DCM and the combined organic phases were washed with brine (×2), passed through a phase separator and the solvent was removed under reduced pressure. Purification by FCC, eluting with 0-10% 2N NH$_3$ in MeOH/DCM afforded the title compound (2.08 g, 73%).

LCMS (Method 1): Rt 0.36 min, m/z 443 [MNa$^+$].

e. 1-[5-tert-Butyl-2-(tert-butyl-dimethyl-silanyloxymethyl)-phenyl]-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea (Intermediate 59e)

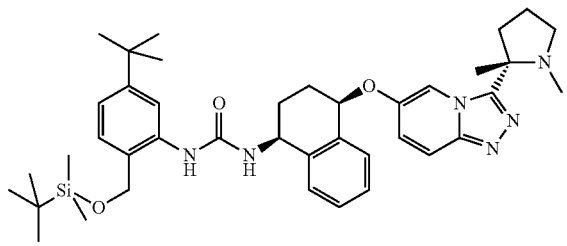 [SMILES: CN1CCC[C@@]1(C)c1nnc2ccc(O[C@@H]3CC[C@H](NC(=O)Nc4cc(C(C)(C)C)ccc4CO[Si](C)(C)C(C)(C)C)c4ccccc43)cn12]

A solution of Intermediate 59c (500 mg, 1.40 mmol) in dioxane (7 ml) was treated with Intermediate 59d (590 mg, 1.40 mmol), Pd(OAc)₂ (16 mg, 0.07 mmol), XPhos (67 mg, 0.14 mmol) and Cs₂CO₃ (613 mg, 1.88 mmol). The reaction mixture was purged with nitrogen and then heated at 95° C. for 18 hours. The reaction mixture was cooled at RT and Pd(OAc)₂ (16 mg, 0.07 mmol) and Xantphos (81 mg, 0.14 mmol) were added. The reaction mixture was heated at 90° C. for 72 hours and cooled at RT. Other aliquots of Pd(OAc)₂ (16 mg, 0.07 mmol) and XPhos (67 mg, 0.14 mmol) were added and the mixture was heated at 90° C. for 20 hours. The reaction mixture was cooled at RT, diluted with DCM and filtered through a pad of Celite®. The solvents were removed under reduced pressure and the crude was purified by FCC, eluting with 0-10% 2N NH₃ in MeOH/DCM to give the title compound (187 mg, 19%).

LCMS (Method 1): Rt 3.69 min, m/z 697 [MH⁺].

f. 1-(5-tert-Butyl-2-hydroxymethyl-phenyl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea (Example 59)

A solution of Intermediate 59e (187 mg, 0.27 mmol) in THF (4 ml) was treated with 1N TBAF in THF (0.8 ml) and the reaction mixture was stirred at room temperature for 3 h. The reaction mixture was partitioned between Et₂O, EtOAc and saturated NH₄Cl solution and the two phases were separated. The organic phase was washed with saturated NH₄Cl solution (×2) and the solvent was removed under reduced pressure. Purification by MDAP (Method 7) afforded the title compound (49 mg, 31%).

LCMS (Method 3): Rt 3.53 min, m/z 583 [MH⁺]. ¹H NMR (400 MHz, d-₆-DMSO): 1.26 (9H, s), 1.51 (3H, s), 1.79-2.23 (11H, m), 2.66 (1H, q, J=8.7 Hz), 3.14-3.19 (1H, m), 4.44 (2H, s), 4.88-4.94 (1H, m), 5.15 (1H, br s), 5.34 (1H, t, J=4.2 Hz), 6.97 (1H, dd, J=8.0, 2.0 Hz), 7.18 (1H, d, J=8.0 Hz), 7.26-7.43 (6H, m), 7.76 (1H, dd, J=9.9, 0.6 Hz), 7.85 (1H, br s), 8.03 (1H, d, J=1.9 Hz). 8.47 (1H, d, J=1.6 Hz).

Example 60. N-(5-tert-Butyl-2-methoxy-3-{3-[(1S,4R)-4-(3-piperidin-1-yl-[1,2,4]triazolo[4,3-a]pyridin-6-yloxy)-1,2,3,4-tetrahydro-naphthalen-1-yl]-ureido}-phenyl-N-(2-dimethylamino-ethyl)-methanesulfonamide formate salt

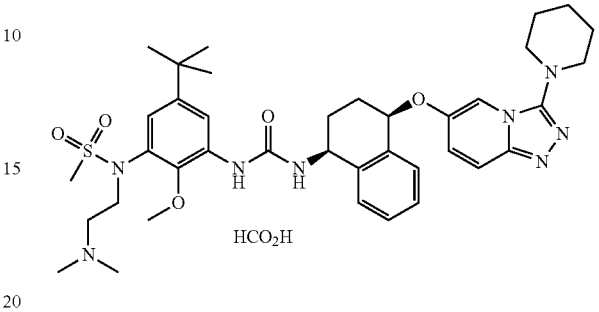

A solution of N-(5-tert-butyl-2-methoxy-3-{3-[(1S,4R)-4-(3-piperidin-1-yl-[1,2,4]triazolo[4,3-a]pyridin-6-yloxy)-1,2,3,4-tetrahydro-naphthalen-1-yl]-ureido}-phenyl)-methanesulfonamide (WO 2013/083604, which is incorporated herein by reference in its entirety, 50 mg, 0.076 mmol) in dry DMF (0.5 ml) was treated with (2-bromoethyl)-dimethylamine hydrobromide (18 mg, 0.076 mmol) and K₂CO₃ (31 mg, 0.23 mmol). The reaction mixture was heated at 80° C. for 18 hours. A further aliquot of (2-bromoethyl)-dimethylamine hydrobromide (9 mg, 0.039 mmol) was added and the mixture stirred at 80° C. for a further 18 hours. The reaction mixture was cooled to RT, diluted with EtOAc and washed with water, brine and dried (MgSO₄). The aqueous phase was further extracted with DCM (×3) and the combined organic phases dried (MgSO₄) and evaporated. Purification by MDAP (Method 6) afforded the title compound (5 mg, 9%) as formate salt.

LCMS (Method 4): Rt 3.47 min, m/z 733 [MH⁺]. ¹H NMR (400 MHz, d-₆-DMSO): 1.24 (9H, s), 1.53-2.18 (16H, m), 2.24 (2H, t, J=6.4 Hz), 3.11 (2H, t, J=5.2 Hz), 3.16 (3H, s), 3.75 (3H, s), 4.84-4.94 (1H, m), 5.55 (1H, t, J=4.5 Hz), 6.87 (1H, d, J=2.2 Hz), 7.15 (1H, dd, J=9.8, 2.2 Hz), 7.24-7.42 (5H, m), 7.56-7.64 (2H, m), 8.05 (1H, s), 8.31 (1H, d, J=2.4 Hz), 4 protons not observed. Plus signals at 8.16 (1.5H, s) and large broad signal 2.8-4.0 for formate.

Intermediate W. (1S,4R)-4-{3-[1-Methyl-1-(4-methyl-piperazin-1-yl)-ethyl]-[1,2,4]triazolo[4,3-a]pyridin-6-yloxy}-1,2,3,4-tetrahydro-naphthalen-1-ylamine

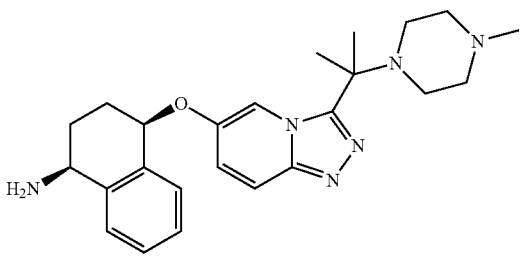 [SMILES: CN1CCN(C(C)(C)c2nnc3ccc(O[C@@H]4CC[C@H](N)c5ccccc54)cn23)CC1]

a. 2-Methyl-2-(4methyl-piperazin-1-yl)-propionic acid N'-(5-fluoro-pyridin-2-yl)-hydrazide (Intermediate Wa)

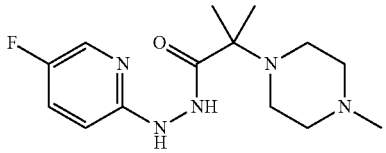 [SMILES: CN1CCN(C(C)(C)C(=O)NNc2ccc(F)cn2)CC1]

A solution of (5-fluoro-2-pyridyl) hydrazine (935 mg, 7.36 mmol) in DCM (25 ml) was treated with 2-methyl-2-(4-4-methylpiperazin-1-yl) propanoic acid dihydrobromide (2.5 g, 7.18 mmol), DIPEA (2.5 ml, 14.4 mmol), HOBt.xH$_2$O (97 mg, 0.72 mmol) and finally EDCI (1.7 g, 8.85 mmol). The mixture was stirred at RT overnight. The reaction mixture was washed with water and the aqueous phase was extracted with DCM (×3). The combined organic phases were passed through a phase separator and evaporated under reduced pressure. The crude mixture was purified by FCC, eluting with 0-8% 2M NH$_3$ in MeOH/DCM to afford the title compound (1.29 g, 61%).

$^1$H NMR (300 MHz, CDCl$_3$): 1.27 (6H, s), 2.32 (3H, s), 2.35-2.78 (8H, br m), 6.53 (1H, br d, J=4.0 Hz), 6.61 (1H, dd, J=8.9, 3.5 Hz), 7.22-7.32 (1H, m), 8.01 (1H, d, J=2.8 Hz), 9.09 (1H, br d, J=3.5 Hz).

b. 6-Fluoro-3-[1-methyl-1-(4-methylpiperazin-1-yl)-ethyl]-[1,2,4]triazolo[4,3,a]pyridine (Intermediate Wb)

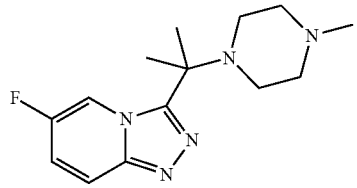 [SMILES: CN1CCN(C(C)(C)c2nnc3ccc(F)cn23)CC1]

A solution of Intermediate Wa (1.21g, 4.10 mmol) in THF was treated with triethylamine (4.57 ml, 32.8 mmol) and triphenylphosphine (2.15g, 8.20 mmol). The mixture was treated portionwise with hexachloroethane (1.94g, 8.20 mmol) and stirred at RT for 5 hours. The reaction mixture was filtered and evaporated under reduced pressure. The residue was partitioned between DCM and an aqueous 1M HCl solution and the two phases were separated. The organic layer was further extracted with an aqueous 1M HCl solution (×3). The combined aqueous layers were washed with Et$_2$O and then basified with solid Na$_2$CO$_3$ and extracted with DCM (×4). The combined DCM layers were passed through a phase separator and evaporated under reduced pressure to give the title compound (1.08g, 95%).

$^1$H NMR (300 MHz, CDCl$_3$): 1.63 (6H, s), 2.29 (3H, d, s), 2.33-2.59 (8H, br m), 7.17 (1H, ddd, J=10.0, 10.0, 2.4 Hz), 7.73 (1H, ddd, J=10.0, 5.0, 0.8 Hz), 8.94 (1H, ddd, J=4.5, 2.5, 0.8 Hz).

4-{3-[1-Methyl-1-(4-methyl-piperazin-1-yl)-ethyl]-[1,2,4]triazolo[4,3-a]pyridin-6-yloxy}-1,2,3,4-tetrahydro-naphthalen-1-ylamine (Intermediate W)

A solution of Intermediate Wb (225 mg, 0.81 mmol) in 2-methyltetrahydrofuran (5 ml) was treated with (1R,4S)-4-amino-1,2,3,4-tetrahydronaphthalen-1-ol (WO 2014/195402, which is incorporated herein by reference in its entirety, 132 mg, 0.81 mmol) and 18-crown-6 (106 mg, 0.4 mmol) and the flask was evacuated and purged with argon. The mixture was treated with KO$^t$Bu (136 mg, 1.22 mmol) and stirred at RT overnight under argon. The reaction was quenched with water and the aqueous phase extracted with 2-methyltetrahydrofuran and DCM. The combined organic layers were dried (Na$_2$SO$_4$) and evaporated. The residue was purified by FCC, eluting with 0-10% 2M NH$_3$ in MeOH/DCM to afford the title compound (69 mg, 20%).

$^1$H NMR (300 MHz, CDCl$_3$): 1.63 (6H, s), 1.87-2.64 (16H, m), 3.63-3.77 (1H, m), 3.96-4.04 (1H, m), 5.22 (1H, t, J=4.1 Hz), 7.11 (1H, dd, J=10.0, 2.2 Hz), 7.21-7.31 (5H, m), 8.72 (1H, d, J=1.8 Hz).

Intermediate WW. (1S,4R)-4-[3-((S)-1-Methyl-azetidin-2-yl)-[1,2,4]triazolo[4,3-a]pyridin-6-yloxy]-1,2,3,4-tetrahydro-naphthalen-1-ylamine

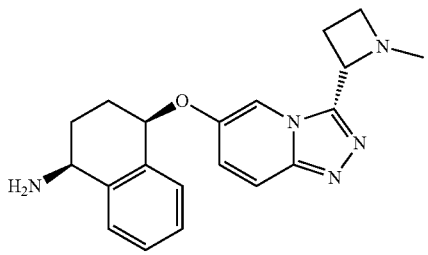

a. (S)-2-[N'-(5-Fluoro-pyridin-2-yl)-hydrazinocarbonyl]-azetidine-1-carboxylic acid tert-butyl ester (Intermediate WWa)

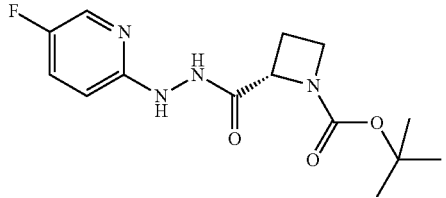 [SMILES: CC(C)(C)OC(=O)N1CC[C@H]1C(=O)NNc1ccc(F)cn1]

A solution of (S)-azetidine-1,2-dicarboxylic acid 1-tert-butyl ester (5.0 g, 24.90 mmol) and (5-fluoro-pyridin-2-yl)-hydrazine (WO 2014/195402, which is incorporated herein by reference in its entirety, 3.16 g, 24.90 mmol) in DCM (50 ml) was treated with EDC (4.76 g, 24.90 mmol) and HOBt (380 mg, 2.50 mmol). The reaction mixture was stirred for 1 h at RT. The reaction mixture was quenched with H$_2$O and the two phases were separated. The aqueous phase was extracted with DCM (×2) and the combined organic phases were washed with a saturated aqueous NaHCO$_3$ solution and brine, dried with Na$_2$SO$_4$ and the solvent was removed under reduced pressure to give the title compound (7.0 g, 91%).

$^1$H NMR (400 MHz, CDCl$_3$): 1.45 (9H, s), 2.32-2.7 (2H, m), 3.78-4.10 (2H, m), 4.64-4.91 (1H, m), 6.53-6.79 (2H, m), 7.27-7.38 (1H, m), 8.04 (1H, s), 9.17 (1H, bs).

b. (S)-2-(6-Fluoro-[1,2,4]triazolo[4,3-a]pyridin-3-yl)-azetidine-1-carboxylic acid tert-butyl ester (Intermediate WWb)

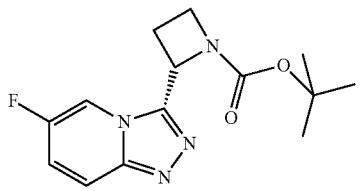

Hexachloroethane (10.70 g, 45.20 mmol) was added portion-wise to an ice cold stirred solution of Intermediate WWa (7 g, 22.6 mmol), triphenylphosphine (11.8 g, 45.20 mmol) and TEA (12.60 ml, 90.30 mmol) in anhydrous Me-THF (100 ml) and the reaction mixture was stirred at RT for 1 h. The reaction was partitioned with $H_2O$ and diluted with EtOAc. The two phases were separated and the organic phase was extracted with HCl 1M; the acidic layer washed with $Et_2O$, basified with solid $K_2CO_3$ and then extracted with DCM (×2). The combined organic phases were washed with a saturated $NaHCO_3$ aqueous solution and brine, dried with $Na_2SO_4$ and the solvent was removed under reduced pressure. Purification by FCC, eluting with MeOH/DCM 0-10% afforded the title compound (3.83 g, 58%).

$^1$H NMR (400 MHz, $CDCl_3$): 1.25 (9H, s), 2.68-2.87 (1H, m), 3.16-3.53 (1H, bs), 3.98-4.23 (2H, m), 5.57 (1H, bs), 7.15-7.25 (1H, m), 7.69-7.85 (1H, m), 8.55-8.91 (1H, bs).

c. 3-(S)-Azetidin-2-yl-6-fluoro-[1,2,4]triazolo[4,3-a]pyridine (Intermediate WWc)

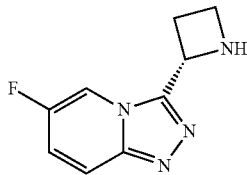 [SMILES: Fc1ccc2nnc([C@@H]3CCN3)n2c1]

A solution of Intermediate WWb (3.8 g, 13.00 mmol) in DCM (20 mL) was treated with TFA (20 mL) and the reaction mixture was stirred at RT for 1 h. The solvent was evaporated under reduced pressure and the residue was taken up in MeOH and applied to a SCX-2 cartridge eluting with MeOH followed by 2M NH3 in MeOH. The relevant fractions were combined and evaporated under reduced pressure to give the title compound (2.45 g, 98%).

$^1$H NMR (400 MHz, $CDCl_3$): 2.61-2.76 (1H, m), 2.76-2.91 (1H, m), 3.64-3.75 (1H, m), 3.91 (1H, q, J=8.66 Hz), 5.66 (1H, t, J=8.66 Hz), 7.15-7.25 (1H, m), 7.69-7.78 (1H, m), 8.89-8.97 (1H, m).

d. 6-Fluoro-3-((S)-1-methyl-azetidin-2-yl)-[1,2,4]triazolo[4,3-a]pyridine (Intermediate WWd)

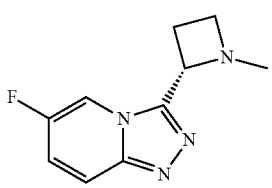

A solution of Intermediate WWc (2.45 g, 12.8 mmol) in DBE (50 mL) was treated with formaldehyde 37% in $H_2O$ (2.59 ml, 31.9 mmol). The reaction mixture was stirred at RT for 3 h and then treated with $Na(OAc)_3BH$. The resulting reaction mixture was stirred at RT for 1 h. The reaction mixture was evaporated and the residue partitioned between $H_2O$ and 2-methyltetrahydrofuran. The aqueous phase was carefully basified by addition of solid $K_2CO_3$ and the organic layer was washed with $H_2O$, extracted into HCl 1M and the aqueous layer washed with $Et_2O$. The aqueous was basified by addition of solid $K_2CO_3$ and then extracted with 2-methyltetrahydrofuran (×2). The combined organic phases were removed under reduced pressure to afforded the title compound (1.45 g, 55%).

$^1$H NMR (400 MHz, $CDCl_3$): 2.27 (3H, s), 2.28-2.37 (1H, m), 2.38-2.55 (1H, m), 2.93-3.06 (1H, m), 3.47-3.58 (1H, m), 4.71 (1H, t, J=8.94 Hz), 7.09-7.19 (1H, m), 7.62-7.72 (1H, m), 8.99-9.04 (1H, m).

e. (1S,4R)-4-[3-((S)-1-Methyl-azetidin-2-yl)-[1,2,4]triazolo[4,3-a]pyridin-6-yloxy]-1,2,3,4-tetrahydro-naphthalen-1-ylamine (Intermediate WW)

To a solution of Intermediate WWd (1.45 g, 7.00 mmol), (1R,4S)-4-amino-1,2,3,4-tetrahydro-naphthalen-1-ol (WO 2014/195402, 1.16 g, 7.1 mmol) and 18-crown-6 (186 mg, 0.7 mmol) in 2-methyltetrahydrofuran (15 ml) at 0° C. under nitrogen was added potassium tert-butoxide (907 mg, 17.50 mmol). The reaction mixture was warmed at RT and stirred for 23 h and then diluted with $H_2O$. The two phases were separated and the aqueous phase was extracted with 2-methyltetrahydrofuran (×2). The combined organic phases were washed with a saturated aqueous $NaHCO_3$ solution and brine, dried with $Na_2SO_4$ and the solvent was removed under reduced pressure. Purification by FCC, eluting with 0-4% 2M $NH_3$ in MeOH/DCM afforded the title compound (1.22 g, 50%).

$^1$H NMR (400 MHz, $CDCl_3$): 1.89-2.02 (1H, m), 2.02-2.15 (2H, m), 2.34 (3H, s), 2.35-2.45 (2H, m), 2.44-2.57 (1H, m), 2.96-3.08 (1H, m), 3.43-3.54 (1H, m), 3.95-4.04 (1H, m), 4.74 (1H, t, J=8.45 Hz), 5.26-5.33 (1H, m), 7.10-7.19 (1H, m), 7.27-7.32 (1H, m), 7.35-7.44 (2H, m), 7.61 (1H, d, J=7.9 Hz), 7.68 (1H, dd, J=10.0, 1.2 Hz), 8.65-8.70 (1H, m), plus two protons not observed.

Examples 61-63

General Procedure for the Examples 61-63

A solution of Intermediate K (22.8 mmol) and an appropriate amine (see Table 6) (22.8 mmol) in 2-methyltetrahydrofuran (100 ml) was stirred at RT for 4 hours. The volatiles were removed under reduced pressure and the residue was purified by FCC, eluting with 0-10% 2M $NH_3$ in MeOH/DCM or MDAP (Method 6) or MDAP (Method 7) or HPLC (Gemini C18, 5-95% MeCN in $H_2O$, 0.1% $HCO_2H$, 18 ml/min) or SFC (LUX CELLULOSE-3 10/90 MeOH (0.1% DEA)/CO2, 100 ml/min, 120 bar, 40° C., GLS 40 psi, SYSTEM 3150 PSI, DROP 94 Bar, DAD 220 nm) afforded the title compounds (39-77%).

TABLE 6

| | | | | |
|---|---|---|---|---|
| 61 | (1S,4R)-4-[3-((S)-1-methyl-piperidin-2-yl)-[1,2,4]triazolo[4,3-a]pyridin-6-yloxy]-1,2,3,4-tetrahydro-naphthalen-1-ylamine (WO 2013/083604, which is incorporated herein by reference in its entirety) | 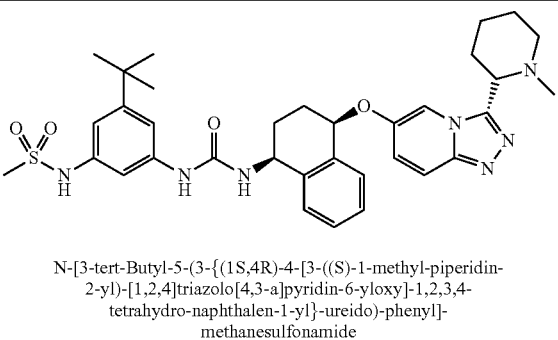<br>N-[3-tert-Butyl-5-(3-{(1S,4R)-4-[3-((S)-1-methyl-piperidin-2-yl)-[1,2,4]triazolo[4,3-a]pyridin-6-yloxy]-1,2,3,4-tetrahydro-naphthalen-1-yl}-ureido)-phenyl]-methanesulfonamide | $^1$H NMR (400 MHz, d-$_6$-DMSO): 1.24 (9H, s), 1.33-2.26 (15H, m), 2.96 (3H, s), 2.97-3.03 (1H, m), 3.79 (1H, dd, J = 10.5, 2.6 Hz), 4.83-4.95 (1H, m), 5.42 (1H, t, J = 4.1 Hz), 6.57 (1H, d, J = 8.7 Hz), 6.81 (1H, t, J = 1.8 Hz), 7.20 (1H, t, J = 1.8 Hz), 7.27-7.44 (5H, m), 7.76 (1H, dd, J = 10.0, 0.5 Hz), 8.42 (1H, d, J = 1.5 Hz), 8.48 (1H, s), 9.56 (1H, s). | (Method 3): Rt 3.40 min, m/z 646 [MH$^+$]. |
| 62 | Intermediate W | 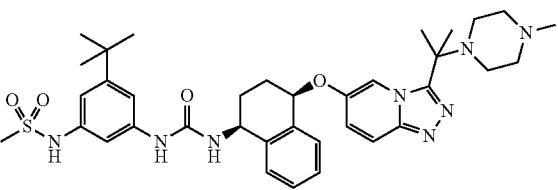<br>N-{3-tert-Butyl-5-[3-((1S,4R)-4-{3-[1-methyl-1-(4-methyl-piperazin-1-yl)-ethyl]-[1,2,4]triazolo[4,3-a]pyridin-6-yloxy}-1,2,3,4-tetrahydro-naphthalen-1-yl)-ureido]-phenyl}-methanesulfonamide | $^1$H NMR (400 MHz, d-$_6$-DMSO): 1.24 (9H, s), 1.54 (3H, s), 1.55 (3H, s), 1.89-2.07 (2H, m), 2.11 (3H, s), 2.17-2.48 (8H, m), 2.96 (3H, s), 3.36-3.42 (2H, m, partially covered by solvent peak), 4.90-4.95 (1H, m), 5.47 (1H, t, J = 4.4 Hz), 6.59 (1H, d, J = 8.6 Hz), 6.81 (1H, t, J = 1.8 Hz), 7.19 (1H, t, J = 1.8 Hz), 7.26 (1H, t, J = 1.8 Hz), 7.29-7.48 (5H, m), 7.74 (1H, d, J = 9.8 Hz), 8.47 (1H, bs s), 8.73 (1H, d, J = 1.6 Hz), 9.55 (1H, br s). | (Method 2): Rt 3.35 min, m/z 689 [MH$^+$]. |
| 63 | Intermediate WW | 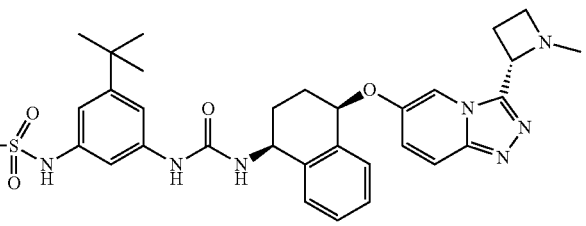<br>N-[3-tert-Butyl-5-(3-{(1S,4R)-4-[3-((S)-1-methyl-azetidin-2-yl)-[1,2,4]triazolo[4,3-a]pyridin-6-yloxy]-1,2,3,4-tetrahydro-naphthalen-1-yl}-ureido)-phenyl]-methanesulfonamide | $^1$H NMR (400 MHz, d$_6$-DMSO): 1.25 (9H, s), 1.83-1.96 (1H, m), 1.97-2.06 (1H, m), 2.07-2.24 (2H, m), 2.28 (3H, s), 2.30-2.39 (1H, m), 2.56-2.69 (1H, m), 2.94 (3H, s), 2.96-3.04 (1H, m), 3.16 (3H, d, J = 5.2 Hz), 3.47 (1H, t, J = 8.7 Hz), 4.08 (1H, q, J = 5.06 Hz), 4.69 (1H, t, J = 7.96 Hz), 4.86-4.94 (1H, m), 6.53-6.60 (1H, m), 6.80 (1H, s), 7.19 (1H, s), 7.26 (1H, s), 7.27-7.34 (1H, m), 7.37-7.45 (3H, m), 7.77 (1H, d, J = 7.75 Hz), 9.55 (1H, bs). | (Method 3): Rt 4.10 min, m/z 618 [MH$^+$]. |

Example 64. 1-(3-tert-Butyl-5-piperazin-1-yl-phenyl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea b. 4-(3-Benzyloxycarbonylamino-5-tert-butyl-phenyl)-piperazine-1-carboxylic acid tert-butyl ester (Intermediate 64a)

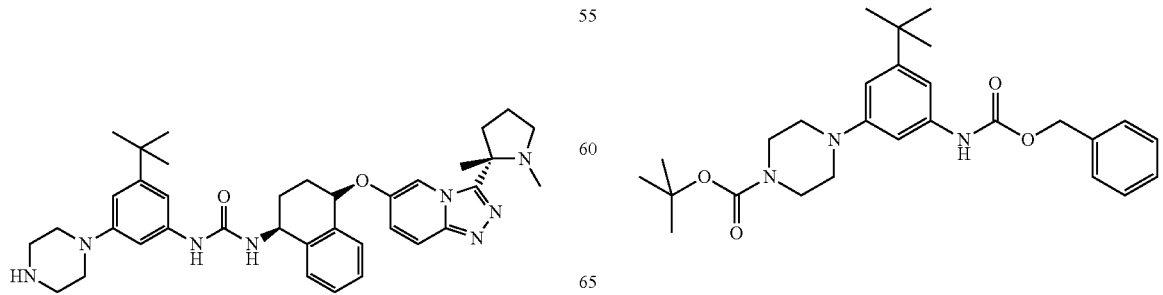

The title compound (346 mg, 67%) was prepared starting from Intermediate Ua (400 mg, 1.10 mmol) and 1-Bocpiperazine (310 mg, 1.66 mmol) using the procedure described to make Intermediate Va.

¹H NMR (300 MHz, CDCl₃): 1.28 (9H, s), 1.48 (9H, s), 3.10-3.14 (4H, m), 3.54-3.58 (4H, m), 5.19 (2H, s), 6.63 (1H, br s), 6.67 (1H, t, J=2.4 Hz), 6.76 (1H, t, J=2.4 Hz), 7.03 (1H, br s), 7.30-7.41 (5H, m).

b. (3-tert-Butyl-5-piperazin-1-yl-phenyl)-carbamic acid benzyl ester (Intermediate 64b)

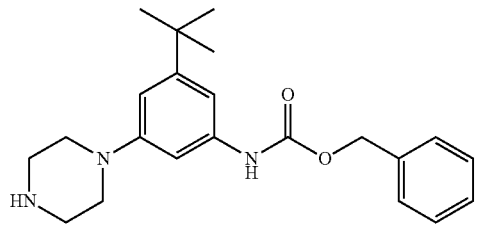 [SMILES: CC(C)(C)c1cc(NC(=O)OCc2ccccc2)cc(N2CCNCC2)c1]

Intermediate 64a (302 mg, 0.63 mmol) was dissolved in DCM (3 ml) and TFA (3 ml) and the reaction mixture was stirred at RT for 6 hours. The reaction mixture was diluted with DCM and H₂O and solid K₂CO₃ was carefully added. The two phases were separated and the aqueous phase was extracted with DCM (×2). The combined organic phases were washed with water, dried with Na₂SO₄ and the solvent was removed under reduced pressure to afford the title compound (210 mg, 70%).

¹H NMR (300 MHz, CDCl₃): 1.28 (9H, s), 3.01-3.18 (8H, m), 5.19 (2H, s), 6.61 (1H, br s), 6.68 (1H, t, J=2.5 Hz), 6.74-6.77 (1H, m), 7.00 (1H, br s), 7.32-7.42 (5H, m).

c. {3-tert-Butyl-5-[4-(2,2,2-trifluoro-acetyl)-piperazin-1-yl]-phenyl}-carbamic acid benzyl ester (Intermediate 64c)

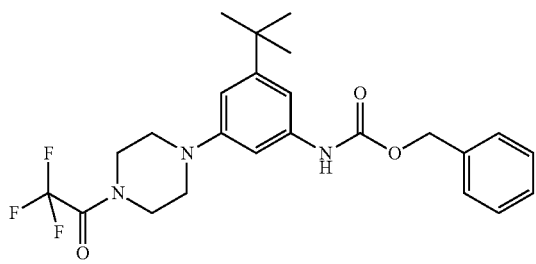 [SMILES: CC(C)(C)c1cc(NC(=O)OCc2ccccc2)cc(N2CCN(C(=O)C(F)(F)F)CC2)c1]

A stirred solution of Intermediate 64b (150 mg, 0.40 mmol) and TEA (70 µl, 0.48 mmol) in DCM (4 ml) at 0° C. was treated with TFAA (67 µl, 0.48 mmol). The reaction mixture was warmed at RT and stirred for 20 hours. The solvent was removed under reduced pressure and the residue was partitioned between EtOAc and an aqueous 0.5M HCl solution. The two phases were separated and the aqueous phase was extracted with EtOAc (×2). The combined organic phases were washed with a saturated aqueous NaHCO₃ solution and brine. The organic phases were passed through a phase separator and the solvent was removed under reduced pressure to afford the title compound (210 mg, quant.).

¹H NMR (300 MHz, CDCl₃): 1.21 (9H, s), 3.16 (4H, t, J=6.8 Hz), 3.68 (2H, t, J=7.0 Hz), 3.76 (2H, t, J=6.8 Hz), 5.12 (2H, s), 6.60-6.70 (3H, m), 7.04 (1H, br s), 7.25-7.33 (5H, m).

d. 1-[4-(3-Amino-5-tert-butyl-phenyl)-piperazin-1-yl]-2,2,2-trifluoro-ethanone (Intermediate 64d)

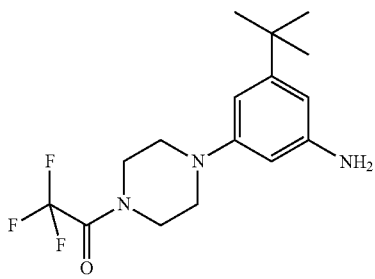 [SMILES: CC(C)(C)c1cc(N)cc(N2CCN(C(=O)C(F)(F)F)CC2)c1]

To a solution of Intermediate 64c (213 mg, 0.46 mmol) in EtOAc (8 ml) was added palladium on carbon (10% Pd, 53 mg). The vessel was evacuated and purged with nitrogen (×3) and then it was evacuated and filled with hydrogen (×3). The reaction mixture was stirred at RT under hydrogen for 48 hours. The reaction mixture was filtered through a pad of Celite® and the solvent was removed under reduced pressure to give the title compound (155 mg, quant., purity ~70%).

¹H NMR (300 MHz, CDCl₃): 1.20 (9H, s), 3.11-3.17 (4H, m), 3.66-3.79 (4H, m), 6.04 (1H, br s), 6.29 (1H, br s), 6.34 (1H, br s), plus two protons not observed.

e. 1-[4-(3-tert-Butyl-5-isocyanato-phenyl)-piperazin-1-yl]-2,2,2-trifluoro-ethanone (Intermediate 64e)

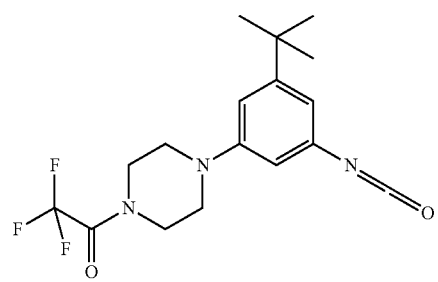 [SMILES: CC(C)(C)c1cc(N=CC=O)cc(N2CCN(C(=O)C(F)(F)F)CC2)c1]

The title compound (165 mg, quant., purity ~60%) was prepared starting from Intermediate 64d (155 mg, 0.46 mmol, purity ~70%) using the procedure described to make Intermediate A.

¹H NMR (300 MHz, CDCl₃): 1.22 (9H, s), 3.13-3.17 (4H, m), 3.67-3.79 (4H, m), 6.37 (1H, t, J=2.8 Hz), 6.62 (1H, t, J=2.5 Hz), 6.70 (1H, t, J=2.5 Hz).

f. 1-{3-tert-Butyl-5-[4-(2,2,2-trifluoro-acetyl)-piperazin-1-yl]-phenyl}-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea (Intermediate 64f)

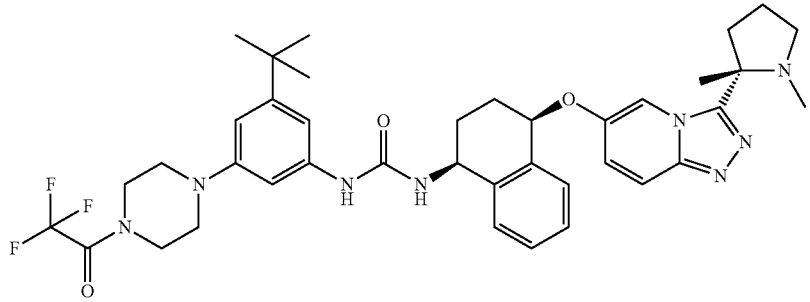 [SMILES: CN1CCC[C@@]1(C)c1nnc2ccc(O[C@@H]3CC[C@H](NC(=O)Nc4cc(N5CCN(C(=O)C(F)(F)F)CC5)cc(C(C)(C)C)c4)c4ccccc43)cn12]

A solution of Intermediate 64e (165 mg, 0.46 mmol, purity—60%) in 2-methyltetrahydrofuran (4 ml) was treated with (1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-ylamine (WO 2013/083604, which is incorporated herein by reference in its entirety, 110 mg, 0.29 mmol). The reaction mixture was stirred at RT for 20 hours and diluted with 2-methyltetrahydrofuran and H$_2$O. The two phases were separated and the aqueous phase was extracted with 2-methyltetrahydrofuran (×2). The combined organic phases were dried with Na$_2$SO$_4$ and the solvent was removed under reduced pressure. Purification by FCC, eluting with 0-5% 2N NH$_3$ in MeOH/DCM afforded the title compound (127 mg, 60%).

LCMS (Method 1): Rt 3.09 min, m/z 733 [MH$^+$].

g. 1-(3-tert-Butyl-5-piperazin-1-yl-phenyl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea (Example 64)

A solution of Intermediate 64f (127 mg, 0.17 mmol) in methanol (5.6 ml) and H$_2$O (0.4 ml) was treated with K$_2$CO$_3$ (25 mg, 0.17 mmol). The reaction mixture was heated at reflux for 18 hours. The reaction mixture was cooled at RT and the solvents were removed under reduced pressure. Purification by FCC, eluting with 0-10% 2N NH$_3$ in MeOH/DCM, followed by followed by titration with Et$_2$O afforded the title compound (23 mg, 21%).

LCMS (Method 3): Rt 2.73 min, m/z 637 [MH$^+$]. $^1$H NMR (400 MHz, d-$_6$-DMSO): 1.24 (9H, s), 1.52 (3H, s), 1.80-2.23 (11H, m), 2.66 (1H, q, J=8.7 Hz), 2.81-2.84 (4H, m), 2.97-3.00 (4H, m), 3.14-3.20 (1H, m), 4.86-4.92 (1H, m), 5.34 (1H, t, J=4.1 Hz), 6.51-6.55 (2H, m), 6.80 (1H, t, J=1.7 Hz), 6.98 (1H, t, J=1.7 Hz), 7.26-7.43 (5H, m), 7.76 (1H, d, J=9.8 Hz), 8.25 (1H, br s), 8.47 (1H, d, J=1.6 Hz), plus one proton not observed.

Intermediate X.
(3-Bromo-5-tert-butyl-benzyl)-dimethyl-amine

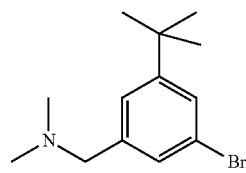

a. Methanesulfonic acid 3-bromo-5-tert-butyl-benzyl ester (Intermediate Xa)

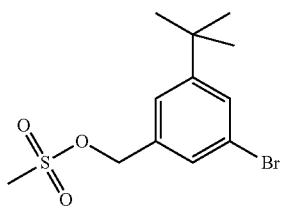 [SMILES: CC(C)(C)c1cc(Br)cc(COS(C)(=O)=O)c1]

To a stirred solution of (3-bromo-5-tert-butyl-phenyl)-methanol (WO 2011/140936, which is incorporated herein by reference in its entirety, 250 mg, 1.03 mmol) in DCM (3 ml) at 0° C. was added triethylamine (105 µl, 1.34 mmol) and methanesulfonylchloride (430 µl, 3.09 mmol). The reaction mixture was stirred at 0° C. for 20 min and at room temperature for 1 h. The reaction mixture was quenched with an aqueous 0.2 N HCl solution and diluted with DCM. The two phases were separated and the aqueous phase was extracted with DCM (×3). The combined organic phases were washed with H$_2$O, dried over Na$_2$SO$_4$, filtered and the solvent was removed under reduced pressure. The crude mixture was purified by FCC, eluting with 0-20% EtOAc/cyclohexane to afford the title compound (124 mg, 37%).

$^1$H NMR (300 MHz, CDCl$_3$): 1.31 (9H, s), 2.96 (3H, s), 5.18 (2H, s), 7.33 (1H, t, J=1.6 Hz), 7.38 (1H, t, J=1.6 Hz) 7.53 (1H, t, J=1.8 Hz)

b. (3-Bromo-5-tert-butyl-benzyl)-dimethyl-amine (Intermediate X)

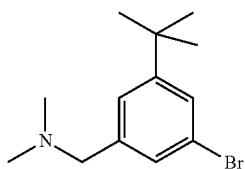

To a solution of Intermediate Xa (124 mg, 0.39 mmol) in THF (4 ml) was added a solution of dimethylamine in THF (2.0M, 0.8 μl, 1.56 mmol) and K$_2$CO$_3$ (54 mg, 0.39 mmol). The reaction mixture was heated at reflux overnight. The reaction mixture was cooled to room temperature and diluted with saturated NH$_4$Cl solution and EtOAc. The two phases were separated and the aqueous phase was extracted with EtOAc (×2). The combined organic phases were washed with brine, dried over Na$_2$SO$_4$, filtered and the solvent was removed under reduced pressure to afford the title compound (98 mg, 92%).

$^1$H NMR (300 MHz, CDCl$_3$): 1.30 (9H, s), 2.30 (6H, s), 3.47 (2H, s), 7.29-7.34 (2H, m), 7.38 (1H, t, J=1.6 Hz).

Intermediate Y. 2-[(3-Bromo-5-tert-butyl-benzyl)-methyl-amino]-ethanol

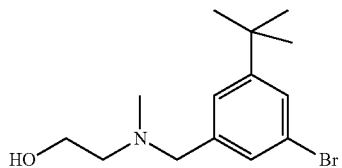 [SMILES: CN(CCO)Cc1cc(Br)cc(C(C)(C)C)c1]

The title compound (223 mg, 100%) was prepared starting from Intermediate Xa (195 mg, 0.74 mmol) and 2-(methylamino)ethanol (180 μl, 2.22 mmol) using the procedure described to make Intermediate X.

$^1$H NMR (300 MHz, CDCl$_3$): 1.22 (9H, s), 2.16 (3H, s), 2.51 (2H, t, J=5.5 Hz), 3.45 (2H, s), 3.56 (2H, t, J=5.5 Hz), 7.14 (1H, s), 7.19 (1H, s), 7.33 (1H, t, J=1.8 Hz), plus one proton not observed.

Intermediate Z. [2-(3-Bromo-5-tert-butyl-benzyloxy)-ethyl]-dimethyl-amine

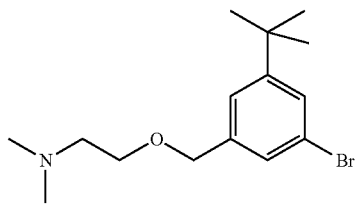 [SMILES: CN(C)CCOCc1cc(Br)cc(C(C)(C)C)c1]

To a stirred suspension of sodium hydride (60% in mineral oil, 176 mg, 4.41 mmol) in DMF (4 ml) at 0° C. was added (3-bromo-5-tert-butyl-phenyl)-methanol (WO 2011/140936, which is incorporated herein by reference in its entirety, 120 mg, 0.49 mmol). The reaction mixture was stirred at 0° C. for 5 minutes and at RT for 60 minutes. (2-Bromoethyl)-dimethylamine hydrobromide (230 mg, 0.99 mmol) was added and the reaction mixture was stirred at RT for 1 hour and at 60° C. for 20 hours. The resulting mixture was cooled at RT, quenched with a saturated aqueous NH$_4$Cl solution and DCM and the two phases were separated. The aqueous phase was extracted with DCM (×2) and the combined organic phases were washed with brine, dried with Na$_2$SO$_4$ and the solvent was removed under reduced pressure. Purification by FCC, eluting with 0-10% 2N NH$_3$ in MeOH/DCM afforded the title compound (94 mg, 61%).

$^1$H NMR (300 MHz, CDCl$_3$): 1.30 (9H, s), 2.27 (6H, s), 2.54 (2H, t, J=5.8 Hz), 3.55 (2H, t, J=5.8 Hz), 4.49 (2H, s), 7.26-7.32 (2H, m), 7.41 (1H, t, J=1.8 Hz).

Intermediate AA. 1-[2-(3-Bromo-5-tert-butyl-benzyloxy)-ethyl]-piperidine

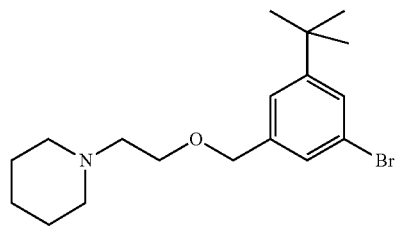 [SMILES: CC(C)(C)c1cc(Br)cc(COCCN2CCCCC2)c1]

The title compound (87 mg, 40%) was prepared starting from (3-bromo-5-tert-butyl-phenyl)-methanol (WO 2011/140936, which is incorporated herein by reference in its entirety, 150 mg, 0.62 mmol) and 1-(2-chloroethyl)piperidine.HCl (226 mg, 1.23 mmol) using the procedure described to make Intermediate Z.

$^1$H NMR (300 MHz, CDCl$_3$): 1.26 (9H, s), 1.40-1.46 (2H, m), 1.59 (4H, q, J=5.0 Hz), 2.43 (4H, t, J=5.0 Hz), 2.59 (2H, t, J=6.0 Hz), 3.58 (2H, t, J=6.0 Hz), 4.48 (2H, s), 7.29-7.30 (2H, m) 7.41 (1H, t, J=1.8 Hz).

Intermediate AB. 4-[2-(3-Bromo-5-tert-butyl-benzyloxy)-ethyl]-morpholine

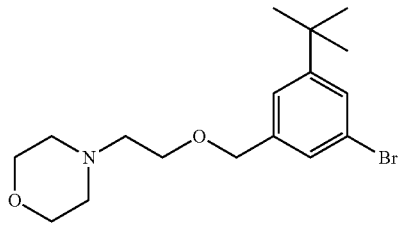 [SMILES: CC(C)(C)c1cc(Br)cc(COCCN2CCOCC2)c1]

The title compound (77 mg, 27%) was prepared starting from (3-bromo-5-tert-butyl-phenyl)-methanol (WO 2011/140936, which is incorporated herein by reference in its entirety, 197 mg, 0.81 mmol) and 4-(2-chloroethyl)morpholine.HCl (301 mg, 1.62 mmol) using the procedure described to make Intermediate Z.

$^1$H NMR (300 MHz, CDCl$_3$): 1.26 (9H, s), 2.48-2.52 (4H, m), 2.61 (2H, t, J=5.7 Hz), 3.58 (2H, t, J=5.7 Hz), 3.54-3.70 (4H, m), 4.49 (2H, s), 7.24-7.25 (1H, m), 7.30-7.31 (1H, m), 7.41 (1H, t, J=1.8 Hz).

Intermediate AC.
4-(2-Bromo-4-tert-butyl-benzyl)-morpholine

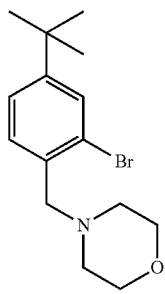 [SMILES: CC(C)(C)c1ccc(CN2CCOCC2)c(Br)c1]

A stirred solution of 2-bromo-1-(bromomethyl)-4-(tert-butyl)benzene (*J. Med. Chem.*, 2005, 48, 71-90, which is incorporated herein by reference in its entirety, 400 mg, 1.31 mmol), potassium carbonate (181 mg, 1.31 mmol) and morpholine (230 µL, 2.62 mmol) in tetrahydrofuran (12 mL) was heated at 70° C. for 18 hours. The reaction mixture was allowed to cool to RT and partitioned between a saturated aqueous NH$_4$Cl solution and EtOAc. The two phases were separated and the aqueous phase was extracted with EtOAc (×2). The combined organic phases were washed with brine and passed through a phase separator. The solvent was removed under reduced pressure to afford the title compound (430 mg, quantitative).

$^1$H NMR (300 MHz, CDCl$_3$): 1.22 (9H, s), 2.44 (4H, t, J=4.7 Hz), 3.49 (2H, s), 3.64 (4H, t, J=4.6 Hz), 7.21 (1H, dd, J=8.1, 1.9 Hz), 7.29 (1H, d, J=8.1 Hz), 7.47 (1H, d, J=1.9 Hz).

Intermediate AD. {(1S,4R)-4-[3-((S)-2-Methyl-piperidin-1-yl)-[1,2,4]triazolo[4,3-a]pyridin-6-yloxy]-1,2,3,4-tetrahydro-naphthalen-1-yl}-urea

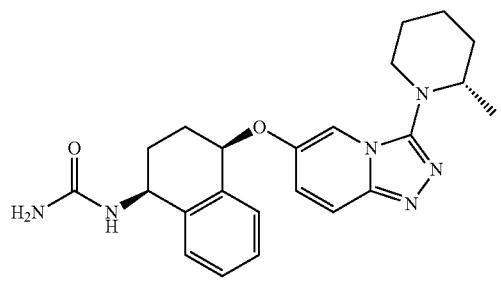 [SMILES: C[C@H]1CCCCN1c1nnc2ccc(O[C@@H]3CC[C@H](NC(N)=O)c4ccccc43)cn12]

A solution of triphosgene (4.32g, 14.57 mmol) in DCM (80 ml) was cooled to -10° C. and treated portion-wise with a solution of (1S,4R)-4-[3-((S)-2-methyl-piperidin-1-yl)-[1,2,4]triazolo[4,3-a]pyridin-6-yloxy]-1,2,3,4-tetrahydro-naphthalen-1-ylamine (WO2014/194956, which is incorporated herein by reference in its entirety, 5.0g, 13.25 mmol) and trimethylamine (5.35g, 52.98 mmol) in DCM (80 ml) maintaining the temperature between -5 and -10° C. The resulting mixture was stirred at -10° C. for 1 hour and then added to a solution of 2M NH$_3$ in MeOH (300 ml) pre-cooled to -10° C. The resulting mixture was allowed to reach RT over ca. 1.5 hours and then evaporated under reduced pressure. The residue was partitioned between DCM and H$_2$O and the two phases were separated. The aqueous phase was further extracted with DCM. The combined organic layers were washed with brine, passed through a phase separator and evaporated under reduced pressure. The crude mixture was purified by FCC, eluting with 0-10% 2M NH$_3$ in MeOH/DCM to afford the title compound (4.18 g, 75%).

$^1$H NMR (300 MHz, CDCl$_3$): 0.94 (3H, br d, J=6.0 Hz), 1.40-2.36 (1H, br m), 2.93-3.16 (2H, br m), 3.27-3.42 (1H, br m), 4.72 (2H, br s), 5.00-5.13 (1H, br m), 5.29 (1H, br s), 5.53 (1H, br d, J=8.3 Hz), 6.98 (1H, br d, J=9.8 Hz), 7.21-7.56 (6H, br m).

Examples 65-74

General Procedure for the Examples 65-74

A solution of an appropriate arylbromide (see Table 7) (0.36 mmol) in dioxane (2 ml) was treated with an appropriate urea (see Table 7) (0.36 mmol), Pd(OAc)$_2$ (0.02 mmol), XPhos (0.04 mmol) and Cs$_2$CO$_3$ (0.50 mmol). The reaction mixture was purged with nitrogen and then heated at 95° C. for 18 hours. The reaction mixture was cooled at RT, diluted with MeOH and filtered through a pad of Celite®. Purification by FCC, eluting with 0-9% 2N NH$_3$ in MeOH/DCM or MDAP (Method 6) or MDAP (Method 7) or HPLC (X-Bridge 18, 30-75% MeCN in H$_2$O, 0.1% NH$_4$OH, 18 ml/min) or titration with cyclohexane afforded the title compounds (13-60%).

TABLE 7

| Ex. | Intermediate | Urea | Structure | NMR (400 MHz) δ | LC-MS |
|---|---|---|---|---|---|
| 65 | Intermediate X | Intermediate 59d | 1-(3-tert-Butyl-5-dimethylaminomethyl-phenyl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea | $^1$H NMR (400 MHz, d-$_6$-DMSO): 1.26 (9H, s), 1.52 (3H, s), 1.76-2.55 (18H, m), 2.66 (1H, q, J = 8.5 Hz), 3.13-3.20 (1H, m), 4.85-4.94 (1H, m), 5.35 (1H, t, J = 4.1 Hz), 6.57 (1H, d, J = 8.7 Hz), 6.87 (1H, s), 7.23 (1H, s), 7.25-7.45 (6H, m), 7.76 (1H, dd, J = 9.9 Hz), 8.36 (1H, s), 8.46 (1H, d, J = 1.6 Hz) plus one proton not observed. | (Method 3): Rt 2.72 min, m/z 610 [MH$^+$]. |

TABLE 7-continued

| Ex. | Intermediate | Urea | Structure | NMR (400 MHz) δ | LC-MS |
|---|---|---|---|---|---|
| 66 | Intermediate X | Intermediate AD | 1-(3-tert-Butyl-5-dimethylaminomethyl-phenyl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea | $^1$H NMR (400 MHz, d-$_6$-DMSO): 0.91 (3H, d, J = 6.3 Hz), 1.25 (10H, s), 1.42-1.58 (2H, m), 1.59-1.73 (2H, m), 1.74-1.86 (2H, m), 1.87-2.11 (4H, m), 2.19-2.25 (8H, m), 2.85-2.95 (1H, m), 3.12-3.21 (1H, m), 4.84-4.94 (1H, m), 5.54 (1H, t, J = 4.0 Hz), 6.55 (1H, d, J = 8.7 Hz), 6.86 (1H, s), 7.20-7.25 (2H, m), 7.26-7.33 (2H, m), 7.34-7.44 (3H, m), 7.65 (1H, d, J = 9.8 Hz), 7.71 (1H, d, J = 1.4 Hz), 8.36 (1H, s). | (Method 3): Rt 3.59 min, m/z 610 [MH$^+$]. |
| 67 | Intermediate Y | Intermediate 59d | 1-(3-tert-Butyl-5-{[(2-hydroxy-ethyl)-methyl-amino]-methyl}-phenyl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea | $^1$H NMR (400 MHz, d-$_6$-DMSO): 1.26 (9H, s), 1.52 (3H, s), 1.79-2.22 (14H, m), 2.42 (2H, q, J = 6.6 Hz), 2.66 (1H, q, J = 8.6 Hz), 3.14-3.20 (1H, m), 3.44 (2H, s), 3.48-3.53 (2H, m), 4.37 (1H, br s), 4.87-4.93 (1H, m), 5.35 (1H, t, J = 4.3 Hz), 6.56 (1H, t, J = 8.8 Hz), 6.89 (1H, s), 7.21 (1H, s), 7.26-7.43 (6H, m), 7.76 (1H, d, J = 10.0 Hz), 8.36 (1H, bs s), 8.47 (1H, d, J = 1.6 Hz). | (Method 3): Rt 2.71 min, m/z 640 [MH$^+$]. |
| 68 | Intermediate Y | Intermediate AD | 1-(3-tert-Butyl-5-{[(2-hydroxy-ethyl)-methyl-amino]-methyl}-phenyl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea | $^1$H NMR (400 MHz, d-$_6$-DMSO): 0.91 (3H, d, J = 6.3 Hz), 1.25 (9H, s), 1.43-2.12 (9H, m), 2.16 (3H, s), 2.17-2.23 (1H, m), 2.41 (2H, t, J = 6.5 Hz), 2.86-2.95 (1H, m), 3.12-3.21 (1H, m), 3.43 (2H, s), 3.51 (2H, br s), 4.36 (1H, br s), 4.85-4.94 (1H, m), 5.54 (1H, t, J = 4.0 Hz), 6.57 (1H, d, J = 8.7 Hz), 6.88 (1H, s), 7.19-7.25 (2H, m), 7.25-7.32 (1H, m), 7.33-7.44 (4H, m), 7.65 (1H, d, J = 9.8 Hz), 7.71 (1H, d, J = 1.4 Hz), 8.38 (1H, s). | (Method 3): Rt 3.56 min, m/z 640 [MH$^+$]. |
| 69 | Intermediate Z | Intermediate 59d | 1-[3-tert-Butyl-5-(2-dimethylamino-ethoxymethyl)-phenyl]-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea | $^1$H NMR (400 MHz, d-$_6$-DMSO): 1.26 (9H, s), 1.51 (3H, s), 1.79-2.23 (16H, m), 2.44 (2H, t, J = 6.0 Hz), 2.66 (1H, q, J = 9.0 Hz), 3.14-3.19 (1H, m), 3.51 (2H, t, J = 6.0 Hz), 4.41 (2H, s), 4.87-4.94 (1H, m), 5.35 (1H, t, J = 4.1 Hz), 6.61 (1H, d, J = 8.7 Hz), 6.91 (1H, br s), 7.25 (1H, br s), 7.27-7.43 (6H, m), 7.76 (1H, dd, J = 9.9, 0.7 Hz), 8.41 (1H, br s), 8.46 (1H, d, J = 1.6 Hz) plus one proton not observed. | (Method 3): Rt 2.85 min, m/z 654 [MH+]. |

TABLE 7-continued

| Ex. | Intermediate | Urea | Structure | NMR (400 MHz) δ | LC-MS |
|---|---|---|---|---|---|
| 70 | Intermediate Z | Intermediate AD | 1-[3-tert-Butyl-5-(2-dimethylamino-ethoxymethyl)-phenyl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea | $^1$H NMR (400 MHz, d-$_6$-DMSO): 0.92 (3H, d, J = 6.2 Hz), 1.26 (9H, s), 1.45-2.13 (12H, m), 2.15 (6H, s), 2.44 (2H, t, J = 5.9 Hz), 2.86-2.96 (1H, m), 3.13-3.21 (1H, m), 3.50 (2H, t, J = 5.9 Hz), 4.41 (2H, s), 4.85-4.94 (1H, m), 5.54 (1H, t, J = 4.1 Hz), 6.59 (1H, d, J = 8.7 Hz), 6.91 (1H, s), 7.20-7.44 (6H, m), 7.65 (1H, dd, J = 9.8, 0.7 Hz), 7.72 (1H, d, J = 1.4 Hz), 8.41 (1H, br s). | (Method 3): Rt 3.67 min, m/z 654 [MH$^+$]. |
| 71 | Intermediate AA | Intermediate 59d | 1-[3-tert-Butyl-5-(2-piperidin-1-yl-ethoxymethyl)-phenyl]-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea | $^1$H NMR (400 MHz, d-$_6$-DMSO): 1.26 (9H, s), 1.32-1.49 (8H, m), 1.52 (3H, s), 1.80-2.22 (9H, m), 2.36 (4H, br s), 2.45-2.48 (2H, m), 2.66 (1H, q, J = 9.3 Hz), 3.14-3.19 (1H, m), 3.51 (2H, t, J = 5.9 Hz), 4.41 (2H, s), 4.87-4.94 (1H, m), 5.35 (1H, t, J = 4.4 Hz), 6.59 (1H, d, J = 8.8 Hz), 6.91 (1H, br s), 7.25-7.43 (7H, m), 7.76 (1H, d, J = 9.9 Hz), 8.39 (1H, d, J = 1.7 Hz), plus one proton not observed | (Method 3): Rt 2.95 min, m/z 695 [MH$^+$]. |
| 72 | Intermediate AB | Intermediate 59d | 1-[3-tert-Butyl-5-(2-morpholin-4-yl-ethoxymethyl)-phenyl]-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea | 1H NMR(400 MHz, d-$_6$-DMSO): 1.26 (9H, s), 1.51 (3H, s), 1.76-2.01 (5H m), 2.02-2.05 (3H, s), 2.06-2.25 (4H, m), 2.40 (4H, t, J = 4.5 Hz), 2.52 (1H, s), 2.65 (1H, q, J = 8.4 Hz), 3.12-3.20 (1H, m), 3.50-3.59 (6H, m), 4.41 (2H, s), 4.85-4.94 (1H, m), 5.31-5.37 (1H, t, J = 4.1 Hz), 6.62 (1H, d, J = 8.7 Hz), 6.90 (1H, s), 7.23-7.44 (7H, m), 7.79 (1H, d, J = 9.9 Hz), 8.44 (2H, d, J = 1.5 Hz), plus one proton not observed. | (Method 3): Rt 2.91 min, m/z 696 [MH$^+$]. |
| 73 | Intermediate AC | Intermediate 59d | 1-(5-tert-Butyl-2-morpholin-4-ylmethyl-phenyl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea | $^1$H NMR(400 MHz, d-$_6$-DMSO): 1.26 (9H, s), 1.52 (3H, s), 1.80-2.36 (15H, m), 2.66 (1H, q, J = 8.7 Hz), 3.14-3.19 (1H, m), 3.44 (2H, s), 3.58 (4H, m), 4.94 (1H, q, J = 7.8 Hz), 5.35 (1H, t, J = 3.6 Hz), 6.92 (1H, dd, J = 7.9, 2.0 Hz), 7.06 (1H, d, J = 8.0 Hz), 7.26-7.45 (6H, m), 7.76 (1H, d, J = 9.9 Hz), 8.17 (1H, d, J = 2.0 Hz), 8.47 (1H, d, J = 2.0 Hz), 8.60 (1H, s). | (Method 3): Rt 2.98 min, m/z 652 [MH$^+$]. |

| Ex. | Intermediate | Urea | Structure | NMR (400 MHz) δ | LC-MS |
|---|---|---|---|---|---|
| 74 | Intermediate AC | Intermediate AD | 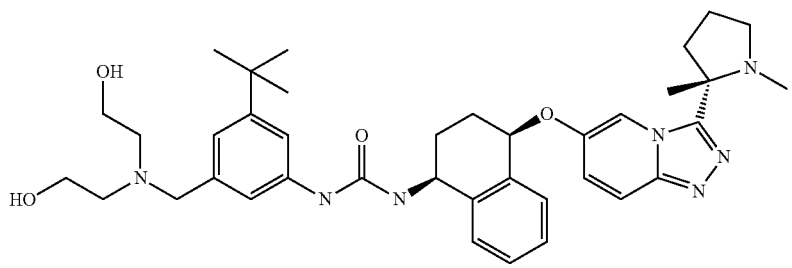 [SMILES: CN1CCC[C@@]1(C)c1nnc2ccc(O[C@@H]3CC[C@H](NC(=O)Nc4cc(CN(CCO)CCO)cc(C(C)(C)C)c4)c4ccccc43)cn12]

1-(5-tert-Butyl-2-morpholin-4-ylmethyl-phenyl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea | $^1$HNMR (400 MHz, d$_6$-DMSO): 0.92 (3H, d, J = 6.3 Hz), 1.26 (9H, s), 1.43-1.58 (2H, m), 1.60-1.73 (2H, m), 1.74-1.88 (5H, m), 2.20-2.40 (5H, m), 2.85-2.98 (1.5H, m), 3.12-3.22 (1.5H, m), 3.44 (2H, s), 3.58 (4H, br s), 4.88-4.97 (1H, m), 5.55 (1H, br s), 6.92 (1H, dd, J = 7.9, 2.0 Hz), 7.06 (1H, d, J = 8.0 Hz), 7.19 (1H, dd, J = 9.8, 2.2 Hz), 7.25-7.32 (1H, m), 7.35-7.47 (4H, m), 7.65 (1H, d, J = 9.8 Hz), 7.71 (1H, br s), 8.17 (1H, d, J = 2.0 Hz), 8.60 (1H, br s). | (Method 3): Rt 4.17 min, m/z 652 [MH$^+$]. |

Example 75. 1-(3-{[Bis-(2-hydroxy-ethyl)-amino]-methyl}-5-tert-butyl-phenyl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea a. 2-[(3-Bromo-5-tert-butyl-benzyl)-(2-hydroxy-ethyl)-amino]-ethanol (Intermediate 75a)

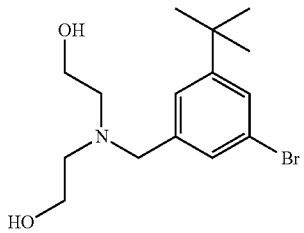 [SMILES: CC(C)(C)c1cc(Br)cc(CN(CCO)CCO)c1]

The title compound (440 mg, quant.) was prepared starting from Intermediate Xa (391 mg, 1.22 mmol) and diethanolamine (226 mg, 1.23 mmol) using the procedure described to make Intermediate X.

$^1$H NMR (300 MHz, CDCl$_3$): 1.29 (9H, s), 2.71 (4H, t, J=5.5 Hz), 3.63 (4H, t, J=5.5 Hz) 3.67 (2H, s), 7.26-7.27 (2H, m), 7.40 (1H, t, J=1.8 Hz) plus two protons not observed.

b. (3-Bromo-5-tert-butyl-benzyl)-bis-[2-(tert-butyl-dimethyl-silanyloxy)-ethyl]-amine (Intermediate 75b)

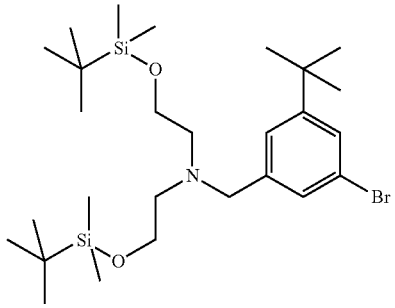 [SMILES: CC(C)(C)c1cc(Br)cc(CN(CCO[Si](C)(C)C(C)(C)C)CCO[Si](C)(C)C(C)(C)C)c1]

To a stirred solution of Intermediate 75a (440 mg, 1.33 mmol) in DCM (5 mL) at 0° C. was added 1H-imidazole (543 mg, 7.98 mmol) and tert-butyl-dimethylsilyl chloride (601 mg, 3.99 mmol). The reaction mixture was stirred at 0° C. for 15 minutes and at RT for 4 hours. The mixture was partitioned between water and DCM and the two phases were separated. The aqueous phase was extracted with DCM (×2) and the combined organic phases were washed with brine, passed through a phase separator and the solvent was removed under reduced pressure. Purification by FCC, eluting with 0-40% EtOAc/cyclohexane afforded the title compound (576 mg, 77%).

$^1$H NMR (300 MHz, CDCl$_3$): 0.02 (12H, s), 0.87 (18H, s), 1.29 (9H, s), 2.66 (4H, t, J=6.7 Hz), 3.62-3.67 (6H, m), 7.23-7.25 (1H, m), 7.31-7.37 (2H, m).

c. 1-[3-({Bis-[2-(tert-butyl-dimethyl-silanyloxy)-ethyl]-amino}-methyl)-5-tert-butyl-phenyl]-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea (Intermediate 75c)

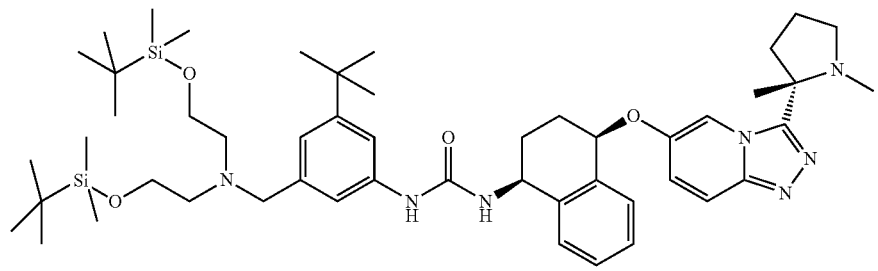 [SMILES: CN1CCC[C@@]1(C)c1nnc2ccc(O[C@@H]3CC[C@H](NC(=O)Nc4cc(CN(CCO[Si](C)(C)C(C)(C)C)CCO[Si](C)(C)C(C)(C)C)cc(C(C)(C)C)c4)c4ccccc43)cn12]

A solution of Intermediate 75b (180 mg, 0.32 mmol) in dioxane (2 ml) was treated with Intermediate 59d (135 mg, 0.32 mmol), Pd(OAc)$_2$ (5.0 mg, 0.02 mmol), XPhos (15 mg, 0.03 mmol) and Cs$_2$CO$_3$ (140 mg, 0.43 mmol). The reaction mixture was purged with nitrogen and then heated at 95° C. for 18 hours. The reaction mixture was cooled at RT, diluted with MeOH and filtered through a pad of Celite®. The solvents were removed under reduced pressure. Purification by FCC, eluting with 0-6% 2N NH$_3$ in MeOH/DCM afforded the title compound (247 mg, 86%).

LCMS (Method 1): Rt 3.21 min, m/z 898 [MH$^+$].

d. 1-(3-{[Bis-(2-hydroxy-ethyl)-amino]-methyl}-5-tert-butyl-phenyl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea (Example 75)

A solution of Intermediate 75c (247 mg, 0.27 mmol) in THF (4 ml) was treated with 1N TBAF in THF (1.6 ml) and the reaction mixture was stirred at room temperature overnight. The reaction mixture was diluted with 2-methyltetrahydrofuran and H$_2$O and the two phases were separarted. The aqueous phase was extracted with 2-methyltetrahydrofuran (×2) and the combined organic phases were dried over Na$_2$SO$_4$, filtered and the solvent was removed under reduced pressure. This was purified by MDAP (Method 7) followed by further purification by FCC, eluting with 0-8% 2N NH$_3$ in MeOH/DCM. The isolated residue was dissolved in DCM, washed with a saturated aqueous NH$_4$Cl solution (×2) and the solvent was removed under reduced presssure to afford the title compound (130 mg, 31%).

LCMS (Method 3): Rt 2.68 min, m/z 670 [MH$^+$]. $^1$H NMR (400 MHz, d-$_6$-DMSO): 1.26 (9H, s), 1.51 (3H, s), 1.79-2.23 (11H, m), 2.54 (3H, m), 2.66 (1H, q, J=8.7 Hz), 3.14-3.19 (1H, m), 3.45 (4H, m), 3.58 (2H, s), 4.33 (2H, s), 4.87-4.93 (1H, m), 5.34 (1H, t, J=4.1 Hz), 6.56 (1H, d, J=8.7 Hz), 6.92 (1H, s), 7.18 (1H, s), 7.26-7.42 (6H, m), 7.76 (1H, dd, J=9.9, 0.4 Hz), 8.35 (1H, s), 8.46 (1H, d, J=1.6 Hz), plus one proton not observed.

Example 76. 1-(3-{[Bis-(2-hydroxy-ethyl)-amino]-methyl}-5-tert-butyl-phenyl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea

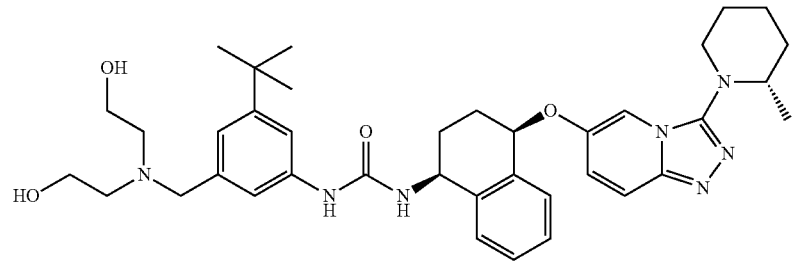 [SMILES: C[C@H]1CCCCN1c1nnc2ccc(O[C@@H]3CC[C@H](NC(=O)Nc4cc(CN(CCO)CCO)cc(C(C)(C)C)c4)c4ccccc43)cn12]

a. 1-[3-({Bis-[2-(tert-butyl-dimethyl-silanyloxy)-ethyl]-amino}-methyl)-5-tert-butyl-phenyl]-3-{(1S,4R)-4-[3-(S)-2-methyl-piperidin-1-yl)-[1,2,4]triazolo[4,3-a]pyridin-6-yloxy]-1,2,3,4-tetrahydro-naphthalen-1-yl}-urea (Intermediate 76a)

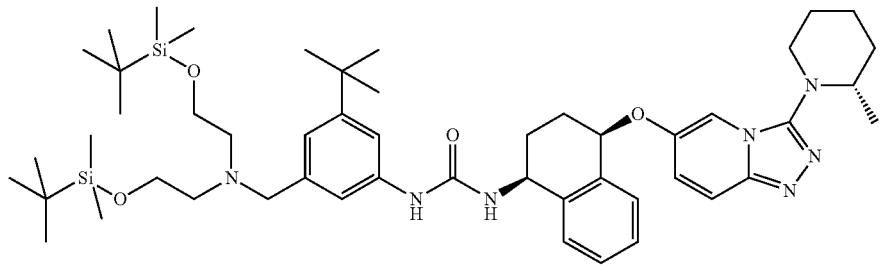 [SMILES: C[C@H]1CCCCN1c1nnc2ccc(O[C@@H]3CC[C@H](NC(=O)Nc4cc(CN(CCO[Si](C)(C)C(C)(C)C)CCO[Si](C)(C)C(C)(C)C)cc(C(C)(C)C)c4)c4ccccc43)cn12]

The title compound (182 mg, 63%) was prepared starting from Intermediate 75b (180 mg, 0.32 mmol) and Intermediate AD (135 mg, 0.32 mmol) using the procedure described to make Intermediate 75c.

LCMS (Method 1): Rt 3.86 min, m/z 899 [MH$^+$].

b. 1-(3-{[Bis-(2-hydroxy-ethyl)-amino]-methyl}-5-tert-butyl-phenyl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea (Example 76)

A solution of Intermediate 76a (182 mg, 0.20 mmol) in THF (4 ml) was treated with 1N TBAF in THF (1.2 ml) and the reaction mixture was stirred at RT overnight.

The reaction mixture was diluted with 2-methyltetrahydrofuran and H$_2$O and the two phases were separated. The aqueous phase was extracted with 2-methyltetrahydrofuran (×2) and the combined organic phases were dried over Na$_2$SO$_4$, filtered and the solvent was removed under reduced pressure. Purification by MDAP (Method 7) afforded the title compound (89 mg, 66%).

LCMS (Method 3): Rt 3.59 min, m/z 670 [MH$^+$]. $^1$H NMR (400 MHz, d$_6$-DMSO): 0.91 (3H, d, J=6.3 Hz), 1.25 (9H, s), 1.49-2.20 (11H, m), 2.54 (4H, t, J=6.5 Hz), 2.88-2.94 (1H, m), 3.14-3.19 (1H, m), 3.45 (4H, q, J=6.0 Hz), 3.58 (2H, s), 4.33 (2H, t, J=5.0 Hz), 4.88-4.92 (1H, m), 5.54 (1H, t, J=4.1 Hz), 6.57 (1H, d, J=8.7 Hz), 6.92 (1H, s), 7.18 (1H, s), 7.21-7.42 (6H, m), 7.76 (1H, dd, J=9.9, 0.7 Hz), 7.72 (1H, d, J=1.4 Hz), 8.37 (1H, s).

Biological Assays
P38alpha Enzyme Inhibition Assay

The inhibitory activity of compounds was determined using an Alphascreen® (Perkin Elmer) based kinase activity assay. Kinase reactions consisted of 25 mM HEPES pH 7.5, 10 mM MgCl$_2$, 100 µM Na$_3$VO$_4$, 2 mM DTT, 0.05 mg/ml Tween 20, 100 µM p38alpha (Invitrogen, PV3304), 1% DMSO and 0.3 µg/ml ATF-2 fusion protein (New England Biolabs, 9224). Compounds were incubated under these conditions for 2 hours, at 25° C., prior to the initiation of the kinase activity by the addition of the 250 µM ATP. Reaction volumes were 20 uL. After 1 hr at 25° C. reactions were stopped by the adding 10 uL of 25 mM HEPES pH 7.5 containing 62.5 mM EDTA, 0.05% Triton X-100, 10% BSA and 0.83 ng/uL anti-phospho-ATF2 antibody (Abcam, ab28812). Detection was performed by measuring luminescence following the addition of Alphascreen Donor beads (Perkin Elmer 6765300) and Protein A Alphascreen Acceptor beads (Perkin Elmer 6760137), both at a final concentration of 20 ug/ml. IC$_{50}$ values were determined from concentration-response curves.

Results are shown in the following Table.

| Example numbers | p38α inhibition |
| --- | --- |
| 10, 5, 9, 8, 6, 14, 13, 15, 23, 30, 37, 26, 41, 46, 17, 16, 58, 60, 63, 73, 74 | + |
| 1, 2, 7, 11, 3, 4, 19, 12, 24, 16, 34, 20, 21, 22, 40, 36, 38, 42, 31, 39, 50, 49, 25, 33, 51, 43, 44, 52, 54, 53, 35, 55, 27, 45, 56, 47, 32, 29, 28, 48, 57, 59, 61, 62, 64, 65, 66, 67, 68, 69, 70, 71, 72, 75, 76 | ++ |

In the table above, p38a potencies (IC$_{50}$ values) are indicated as follows:
1-10 nM '+';
<1 nM '++'

LPS-Stimulated PBMC TNFα Release Assay

Peripheral Blood Mononuclear Cells (PBMCs) were isolated from healthy human volunteer blood using a standard density gradient centrifugation technique. Citrated blood was placed onto Histopaque™ and centrifuged. The PBMCs were removed from the density gradient interface and washed in phosphate buffered saline (PBS). The PBMCs were suspended in RPMI 1640 medium (without serum), dispensed into a 96-well plate and incubated at 37° C. for 3 h in a humidified incubator. After incubation, the medium was replaced (with medium containing 1% foetal bovine serum) and the plate incubated at 37° C., for 1 h, in the presence of test compound or the appropriate vehicle. LPS (10 ng/ml), or an appropriate vehicle control, was then added to the cells and the plate returned to the incubator for 18 h. Cell-free supernatants were removed and assayed for TNFα levels using MSD plates on the Sector Imager 6000 (MesoScale).

A dose response curve to each test compound was performed and the effect of compound in each experiment was expressed as a percentage inhibition of the control TNFα release. Dose response curves were plotted and compound potency (IC$_{50}$) was determined. Compounds were tested in at least three separate experiments.

Results are shown in the following Table.

| Example numbers | LPS-stimulated PBMC TNFα release inhibition |
|---|---|
| 23, 30, 31, 50, 25, 17, 58, 60, 62, 63, 64, 67, 68, 69, 70, 72, 73, 74 | + |
| 12, 16, 21, 22, 40, 36, 38, 26, 43, 52, 54, 35, 32, 29, 28, 57, 61, 65, 66, 71, 75, 76 | ++ |
| 1, 2, 7, 11, 3, 10, 4, 19, 5, 9, 8, 6, 24, 14, 13, 15, 34, 20, 37, 42, 39, 49, 33, 44, 53, 55, 27, 45, 46, 56, 47, 48, 51, 59 | +++ |

In the table above, human PBMC potencies (IC$_{50}$ values) are indicated as follows:
>5 nM '+';
1-5 nM '++';
<1 nM '+++'

The compounds of the invention show human PBMC potencies (IC50 values)<20 nM.

TNFα-Stimulated BEAS-2B IL-8 Release Assay

Human bronchial epithelial cell line BEAS-2B was purchased from Sigma (St. Louis, Mo.). BEAS-2B cells were cultured in Bronchial Epithelial cell Growth Medium (BEGM), prepared by supplementing Bronchial Epithelial Basal Medium with SingleQuotes™ (Lonza, Switzerland), which contains retinoic acid, epidermal growth factor, epinephrine, transferrin, triiodothyronin, insulin, hydrocortisone, antimicrobial agents, and bovine pituitary extract. In addition, BEGM medium was supplemented with 2 mM glutamine, 100 U penicillin and 100 µg/ml streptomycin (Life Technologies), in an atmosphere of 95% air and 5% CO2 at 37° C.

BEAS-2B were seeded in 48-well plates at the density of 3×104 cells per well, grown to approximately 80-90% confluence. Cells were pre-incubated with p38 inhibitors for 1 hour and then stimulated with TNF-α (10 ng/ml) for 18 h at 37° C. with 5% CO2. Subsequently, supernatants were collected and used for measuring IL-8 levels using a paired antibody quantitative ELISA kit purchased from Life Technologies (detection limit: 5 µg/ml). All the treatments were performed at least in quadruplicate.

A concentration-response curve to each test compound was performed and the effect of compound in each experiment was expressed as a percentage inhibition of the control IL-8 release. Compound potency (IC50) was calculated by the analysis of the sigmoidal dose-response curve (variable slope) elaborated by Graph Pad PRISM4 program.

Results are shown in the following Table.

| Example numbers | TNFα-stimulated BEAS-2B IL-8 release inhibition |
|---|---|
| 11, 31, 25, 54, 57, 61-64, 68, 75, 76 | + |
| 7, 12, 21, 38, 33, 51, 16, 36, 58, 65, 67, 70-74 | ++ |
| 1, 2, 3, 5, 24, 10, 20 ,4, 39, 19, 9, 8, 6, 14, 13, 15, 37, 42, 43, 49 ,44, 53, 55, 27, 41, 35, 45, 46, 56, 47, 59, 66, 69 | +++ |

In the table above, BEAS-2B potencies (IC$_{50}$ values) are indicated as follows:
>1 nM '+';
0.3-1 nM '++';
<0.3 nM '+++'

Anti-inflammatory activity of P38alpha inhibitors in a LPS-challenge model in rat Twelve hours after compound/vehicle administration, rats are challenged intratracheally with LPS. Four hours later, rats are sacrificed, bronchoalveolar lavage fluid (BALF) collected and the total cell number and neutrophil numbers determined. Anti-inflammatory activity is represented by a reduction in the number of neutrophils as compared to a vehicle-treated control group.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound of formula (I)

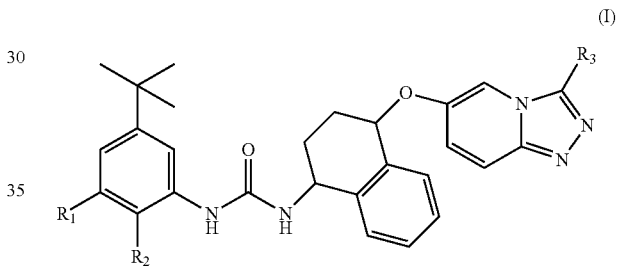

wherein:
R$_1$ is H or selected from the group consisting of (C$_1$-C$_4$) alkyl-, (C$_3$-C$_7$)cycloalkyl-, (C$_4$-C$_7$)heterocycloalkyl-, R$^A$O—, (R$^A$R$^B$)NC(O)—, R$^C$CO(R$^A$)N—, R$^A$O(C$_1$-C$_4$)alkylene-, (R$^A$R$^B$)N—, R$^C$O(O)C—, (R$^A$R$^B$)NSO$_2$—, R$^C$SO$_2$(C$_1$-C$_4$)alkylene-, R$^C$(O)CO(C$_1$-C$_4$)alkylene-, R$^C$OC(O)(R$^A$)N—, (R$^A$R$^B$)NCO(R$^D$)N—, and (R$^A$R$^B$)N(C$_1$-C$_6$)alkylene-, wherein any of said alkyl, alkylene, cycloalkyl, heterocycloalkyl or heteroaryl may be optionally substituted by one or more groups selected from the group consisting of (C$_1$-C$_3$) alkyl, (C$_3$-C$_6$)cycloalkyl, (C$_4$-C$_7$)heterocycloalkyl, —OR$^A$, halo, and CN;
R$_2$ is H or selected from the group consisting of halo, (C$_1$-C$_6$)alkyl, R$^A$O—, (R$^A$R$^B$)N(C$_1$-C$_6$)alkylene-, and R$^A$O(C$_1$-C$_4$)alkylene-;
R$^A$ and R$^B$ are at each occurrence independently H or selected from the group consisting of (C$_1$-C$_4$)alkyl-, (C$_3$-C$_7$)cycloalkyl-, and (C$_4$-C$_7$)heterocycloalkyl-, wherein any of said alkyl, cycloalkyl, or heterocycloalkyl may be optionally substituted;
or R$^A$ and R$^B$ may form together with the nitrogen atom to which they are attached an optionally substituted 5-11-membered saturated heterocyclic monocyclic ring system optionally containing a further heteroatom which is oxygen or nitrogen;
R$^C$ is selected from the group consisting of (C$_1$-C$_4$)alkyl-, (C$_3$-C$_7$)cycloalkyl-, and (C$_4$-C$_7$)heterocycloalkyl-, wherein any of said alkyl, cycloalkyl, or heterocycloalkyl may be optionally substituted;

R$^D$ is I-1 or is selected from the group consisting of (C$_1$-C$_4$)alkyl-, (C$_3$-C$_7$)cycloalkyl-, and (C$_4$-C$_7$)heterocycloalkyl-, wherein any of said alkyl, cycloalkyl, or heterocycloalkyl may be optionally substituted;

R$_3$ is a group of one of formula (IIa) to (IIf):

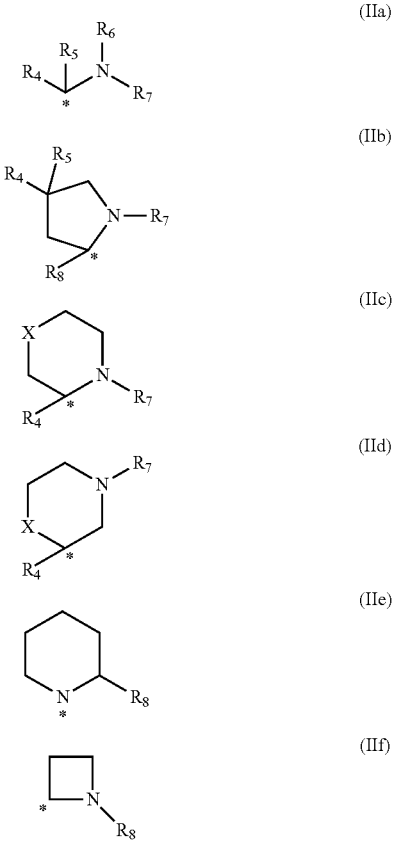

R$_4$ and R$_5$ are at each occurrence independently H or optionally substituted (C$_1$-C$_4$)alkyl-; or R$_4$ and R$_5$ may form together with the carbon atom to which they are attached an optionally substituted 3-6-membered saturated heterocyclic monocyclic ring system;

R$_6$ and R$_7$ are at each occurrence independently H or optionally substituted (C$_1$-C$_4$)alkyl-;

or R$_5$ and R$_6$ may form together with the carbon or nitrogen atom to which they are attached 4-6-membered saturated heterocyclic monocyclic ring system;

or R$_6$ and R$_7$ may form together with the nitrogen atom to which they are attached an optionally substituted 4-6-membered saturated heterocyclic monocyclic ring system optionally containing a further heteroatom which is oxygen or nitrogen wherein said nitrogen may be optionally substituted with (C$_1$-C$_6$)alkyl-;

R$_8$ is H or optionally substituted (C$_1$-C$_4$)alkyl-;

X is —CH$_2$—, —O—, or —NR$_8$;

wherein "optionally substituted" means substitution by one or more groups selected from the group consisting of (C$_1$-C$_3$)alkyl, (C$_3$-C$_6$)cycloalkyl, (C$_4$-C$_7$)heterocycloalkyl, OH, (C$_1$-C$_6$)alkyl-O, —NH$_2$, (C$_1$-C$_4$)HN—,
(C$_1$-C$_4$)alkyl(C$_1$-C$_4$)alkyl(N)—, halo, and CN;

with the proviso that— when R$_1$ is H, then R$_2$ is not H, halo or CH$_3$;

or a pharmaceutically acceptable salt thereof.

2. A compound or pharmaceutically acceptable salt according to claim 1, which is a compound of formula (Ia) wherein a carbon stereogenic centers on the cycloalkylene portion linked to group —NH and —O— and identified, respectively, with numbers (1) and (2), have the absolute configuration shown below

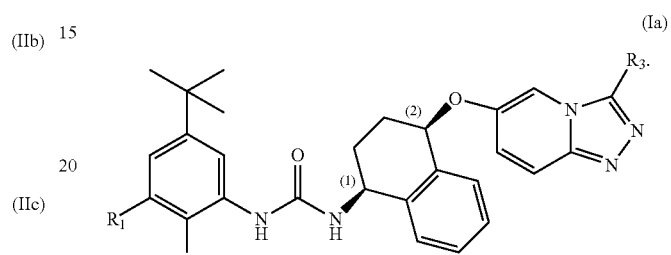

3. A compound or pharmaceutically acceptable salt according to claim 1, wherein R$_1$ is H or is selected from the group consisting of (C$_1$-C$_4$)alkyl-, R$^C$SO$_2$—, (R$^A$R$^B$)NCO—, R$^C$CO(R$^A$)N—, R$^A$O(C$_1$-C$_4$)alkylene-, (R$^A$R$^B$)N—, R$^C$O(O)C—, (R$^A$R$^B$)NSO$_2$—, R$^C$SO$_2$(C$_1$-C$_4$)alkylene-, R$^C$(O)CO(C$_1$-C$_4$)alkylene-, and R$^C$OC(O)(R$^A$)N—, wherein any of said alkyl or alkylene may be optionally substituted by one or more groups —OR$^A$; wherein R$^A$ and R$^B$ are at each occurrence independently H or (C$_1$-C$_4$)alkyl-, which may be optionally substituted by —OH or R$^A$ and R$^B$ may form together with the nitrogen atom to which they are attached an optionally substituted 6 membered saturated heterocyclic monocyclic ring system optionally containing a further heteroatom which is oxygen; R$^C$ is selected from the group consisting of (C$_1$-C$_4$)alkyl- and (C$_3$-C$_7$)cycloalkyl-, wherein any of such alkyl or cycloalkyl may be optionally substituted by one or more groups selected from the group consisting of (C$_1$-C$_6$)alkyl-O— and halo.

4. A compound or pharmaceutically acceptable salt according to claim 1, wherein R$_2$ is H or selected from the group consisting of (C$_1$-C$_6$)alkyl and R$^A$O—; wherein R$^A$ is H or (C$_1$-C$_4$)alkyl-.

5. A compound or pharmaceutically acceptable salt according to claim 1, wherein R$_3$ is a group of formula (IIb)

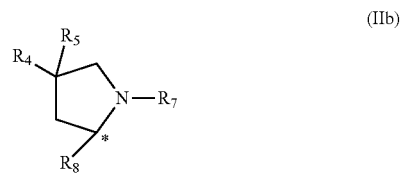

wherein R$_4$ and R$_5$ are at each occurrence independently H or (C$_1$-C$_4$)alkyl- optionally substituted by —OH; R$_7$ is H or (C$_1$-C$_4$)alkyl-; R$_8$ is H or (C$_1$-C$_4$)alkyl- optionally substituted by —OH.

6. A compound or pharmaceutically acceptable salt according to claim 1, wherein R$_3$ is a group of formula (IIa):

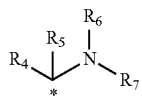
(IIa)

wherein $R_4$ and $R_5$ are $(C_1-C_4)$alkyl-; and $R_6$ and $R_7$ are $(C_1-C_4)$alkyl-.

7. A compound or pharmaceutically acceptable salt according to claim 1, wherein
- $R_1$ is H or selected from the group consisting of $(C_1-C_4)$ alkyl-, $R^CSO_2$—, $(R^AR^B)NC(O)$—, $R^CCO(R^A)N$—, $(R^AR^B)N$—, $R^CO(O)C$—, $(R^AR^B)NSO_2$—, $R^CSO_2(C_1-C_4)$alkylene-, $R^C(O)CO(C_1-C_4)$alkylene-, $R^COC(O)(R^A)N$—, and $(R^AR^B)N(C_1-C_6)$alkylene- wherein any of said alkyl or alkylene may be optionally substituted by one or more groups —$OR^A$;
- $R_2$ is H or selected from the group consisting of $(C_1-C_6)$ alkyl-, $R^AO$—, and $R^AO(C_1-C_4)$alkylene-;
- wherein $R^A$ and $R^B$ are at each occurrence independently H or $(C_1-C_4)$alkyl-, wherein any of such alkyl may be optionally substituted by $(C_1-C_4)$alkyl$(C_1-C_4)$alkyl(N)—;
- $R^C$ is selected from the group consisting of $(C_1-C_4)$alkyl- and $(C_3-C_7)$cycloalkyl-, wherein any of such alkyl may be optionally substituted by $(C_1-C_6)$alkylO—;
- $R_3$ is a group of formulae (IIa), (III)), (IIc), or (IIe)

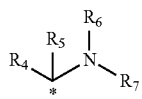
(IIa)

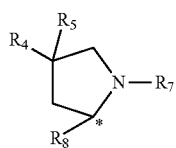
(IIb)

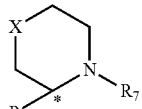
(IIc)

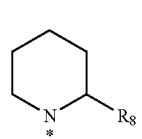
(IIe)

wherein X is —$CH_2$,
$R_4$ and $R_5$ are at each occurrence independently H or $(C_1-C_4)$alkyl-;
$R_6$ and $R_7$ are at each occurrence $(C_1-C_4)$alkyl-;
$R_8$ is H or $(C_1-C_4)$alkyl-.

8. A compound selected from the group consisting of
1-(5-tert-butyl-2-methyl-2H-pyrazol-3-yl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea hydrochloride salt;
1-(5-tert-butyl-3-hydroxymethyl-2-methoxy-phenyl)-3-{(1S,4R)-4-[-3-((S)-1-methyl-pyrrolidin-2-yl)-[1,2,4]triazolo[4,3-a]pyridin-6-yloxy]-1,2,3,4-tetrahydro-naphthalen-1-yl}-urea;
1-(5-tert-butyl-3-hydroxymethyl-2-methoxy-phenyl)-3-{(1S,4R)-4-[-3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea hydrochloride salt;
1-(5-tert-butyl-3-hydroxymethyl-2-methoxy-phenyl)-3-{(1S,4R)-4-[3-(1-dimethylamino-1-methyl-ethyl)-[1,2,4]triazolo[4,3-a]pyridin-6-yloxy]-1,2,3,4-tetrahydro-naphthalen-1-yl}-urea hydrochloride salt;
1-(5-tert-butyl-3-hydroxymethyl-2-methoxy-phenyl)-3-{(1S,4R)-4-[3-((S)-1-methyl-piperidin-2-yl)-[1,2,4]triazolo[4,3-a]pyridin-6-yloxy]-1,2,3,4-tetrahydro-naphthalen-1-yl}-urea;
1-(5-tert-butyl-3-hydroxymethyl-2-methoxy-phenyl)-3-{(1S,4R)-4-[3-((S)-1-isopropyl-pyrrolidin-2-yl)-[1,2,4]triazolo[4,3-a]pyridin-6-yloxy]-1,2,3,4-tetrahydro-naphthalen-1-yl}-urea;
5-tert-butyl-2-methoxy-N-methyl-3-(3-{(1S,4R)-4-[-3-((S)-1-methyl-pyrrolidin-2-yl)-[1,2,4]triazolo[4,3-a]pyridin-6-yloxy]-1,2,3,4-tetrahydro-naphthalen-1-yl}-ureido)-benzamide hydrochloride salt;
N-[5-tert-butyl-3-(3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido)-2-methoxy-phenyl]-acetamide;
N-[5-tert-butyl-3-(3-{(1S,4R)-4-[3-((S)-1-isopropyl-pyrrolidin-2-yl)-[1,2,4]triazolo[4,3-a]pyridin-6-yloxy]-1,2,3,4-tetrahydro-naphthalen-1-yl}-ureido)-2-methoxy-phenyl]-acetamide;
N-[5-tert-butyl-3-(3-{(1S,4R)-4-[3-(1-dimethylamino-1-methyl-ethyl)-[1,2,4]triazolo[4,3-a]pyridin-6-yloxy]-1,2,3,4-tetrahydro-naphthalen-1-yl}-ureido)-2-methoxy-phenyl]-acetamide;
N-[5-tert-butyl-2-methoxy-3-(3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-ureido)-phenyl]-acetamide;
N-[5-tert-butyl-2-methoxy-3-(3-{(1S,4R)-4-[3-((S)-1-methyl-piperidin-2-yl)-[1,2,4]triazolo[4,3-a]pyridin-6-yloxy]-1,2,3,4-tetrahydro-naphthalen-1-yl}-ureido)-phenyl]-acetamide;
1-(3-amino-5-tert-butyl-2-methoxyphenyl-3-{(1S,4R)-4-[3-(1-dimethylamino-1-methyl-ethyl)-[1,2,4]triazolo[4,3-a]pyridin-6-yloxy]-1,2,3,4-tetrahydro-naphthalen-1-yl}-urea;
1-(3-amino-5-tert-butyl-2-methoxyphenyl-3-{(1S,4R)-4-[3-(1-dimethylamino-1-methyl-ethyl)-[1,2,4]triazolo[4,3-a]pyridin-6-yloxy]-1,2,3,4-tetrahydro-naphthalen-1-yl}-urea;
1-(3-amino-5-tert-butyl-phenyl-3-{(1S,4R)-4-[3-(1-dimethylamino-1-methyl-ethyl)-[1,2,4]triazolo[4,3-a]pyridin-6-yloxy]-1,2,3,4-tetrahydro-naphthalen-1-yl}-urea;
1-(3-amino-5-tert-butyl-phenyl-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea;
3-tert-butyl-N-methyl-5-(3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-ureido)-benzenesulfonamide;
3-tert-butyl-5-(3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido)-N-methyl-benzenesulfonamide;

3-tert-butyl-5-(3-{(1S,4R)-4-[3((S)-1-methyl-pyrrolidin-2-yl)-[1,2,4]triazolo[4,3-a]pyridin-6-yloxy]-1,2,3,4-tetrahydro-naphthalen-1-yl}-ureido)-benzoic acid methyl ester;

3-tert-butyl-5-(3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido)-benzoic acid methyl ester;

1-(3-tert-butyl-5-methanesulfonylmethyl-phenyl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea;

acetic acid 3-tert-butyl-5-(3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-ureido)-benzyl ester;

acetic acid 3-tert-butyl-5-(3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido)-benzyl ester;

N-[3-tert-butyl-5-(3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido)-benzyl]-methanesulfonamide;

[3-tert-butyl-5-(3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido)-phenyl]-carbamic acid methyl ester;

1-(3-tert-butyl-5-methanesulfonyl-phenyl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea;

1-(3-tert-butyl-5-morpholin-4-yl-phenyl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea;

1-(3-tert-butyl-5-hydroxymethyl-phenyl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea;

3-tert-butyl-N-(2-hydroxy-ethyl)-5-(3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-ureido)-benzamide;

3-tert-butyl-5-(3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido)-N-(2-hydroxy-ethyl)-benzamide;

3-tert-butyl-5-(3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-ureido)-benzamide;

3-tert-butyl-5-(3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido)-benzamide;

3-tert-butyl-N-methyl-5-(3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-ureido)-benzamide;

3-tert-butyl-5-(3-{(1 S, 4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-ureido)-N-methyl-benzamide;

1-(3-tert-butyl-5-morpholin-4-yl-phenyl)-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea;

1-(5-tert-butyl-2-hydroxymethyl-phenyl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea;

1-(3-tert-butyl-5-piperazin-1-yl-phenyl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea;

1-(3-tert-butyl-5-dimethylaminomethyl-phenyl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea;

1-(3-tert-butyl-5-dimethylaminomethyl-phenyl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-(3-tert-butyl-5-{[(2-hydroxy-ethyl)-methyl-amino]-methyl}-phenyl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea;

1-(3-tert-butyl-5-{[(2-hydroxy-ethyl)-methyl-amino]-methyl}-phenyl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-[3-tert-butyl-5-(2-dimethylamino-ethoxymethyl)-phenyl]-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea;

1-[3-tert-butyl-5-(2-dimethylamino-ethoxymethyl)-phenyl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-[3-tert-butyl-5-(2-piperidin-1-yl-ethoxymethyl)-phenyl]-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea;

1-[3-tert-butyl-5-(2-morpholin-4-yl-ethoxymethyl)-phenyl]-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea;

1-(5-tert-butyl-2-morpholin-4-ylmethyl-phenyl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea;

1-(5-tert-butyl-2-morpholin-4-ylmethyl-phenyl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-(3-{bis-(2-hydroxy-ethyl)-amino]-methyl}-5-tert-butyl-phenyl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea;

1-(3-{[bis-(2-hydroxy-ethyl)-amino]-methyl}-5-tert-butyl-phenyl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

or a pharmaceutically acceptable salt of said compound.

9. A pharmaceutical composition, comprising a compound or pharmaceutically acceptable salt according to claim 1 and one or more pharmaceutically acceptable carriers.

10. A method of treating a disease or condition selected from the group consisting of chronic eosinophilic pneumonia, asthma, chronic obstructive pulmonary disease, adult respiratory distress syndrome, exacerbation of airways hyper-reactivity consequent to other drug therapy, or airways disease that is associated with pulmonary hypertension in a human subject, comprising administering to a subject in need thereof an effective amount a compound or pharmaceutically acceptable salt according to claim 1.

11. A method according to claim 10, wherein the disease or condition is chronic eosinophilic pneumonia.

12. A method according to claim 10, wherein the disease or condition is asthma.

13. A method according to claim 10, wherein the disease or condition is chronic obstructive pulmonary disease.

14. A method according to claim 10, wherein the disease or condition is adult respiratory distress syndrome.

15. A method according to claim 10, wherein the disease or condition is exacerbation of airways hyper-reactivity consequent to other drug therapy.

16. A method according to claim 10, wherein the disease or condition is airways disease that is associated with pulmonary hypertension.

\* \* \* \* \*